(12) United States Patent
Bacon et al.

(10) Patent No.: US 7,981,907 B2
(45) Date of Patent: Jul. 19, 2011

(54) THIO-SUBSTITUTED BIARYLMETHANESULFINYL DERIVATIVES

(75) Inventors: Edward R. Bacon, Audubon, PA (US); Sankar Chatterjee, Wynnewood, PA (US); Derek Dunn, Coatesville, PA (US); Marie-Edith Gourdel, Savigny le Temple (FR); Greg Hostetler, Newark, DE (US); Mohamed Iqbal, Malvern, PA (US); Brigitte Lesur, Champs sur Marne (FR); Philippe Louvet, Montegeron (FR); Eric Riguet, Bonneville (FR); Dominique Schweizer, Paris (FR); Christophe Yue, Vincennes (FR)

(73) Assignees: Cephalon, Inc., Frazer, PA (US); Cephalon France, Maisons-Alfort Cedex (FR)

( * ) Notice: Subject to any disclaimer, the term of this patent is extended or adjusted under 35 U.S.C. 154(b) by 215 days.

(21) Appl. No.: 12/199,167

(22) Filed: Aug. 27, 2008

(65) Prior Publication Data
US 2009/0062284 A1 Mar. 5, 2009

Related U.S. Application Data

(62) Division of application No. 11/104,091, filed on Apr. 12, 2005, now Pat. No. 7,449,481.

(60) Provisional application No. 60/569,153, filed on May 7, 2004.

(30) Foreign Application Priority Data

Apr. 13, 2004 (EP) ..................... 04290982

(51) Int. Cl.
*A61K 31/445* (2006.01)
(52) U.S. Cl. .................. 514/317; 514/252.13; 514/414; 514/438
(58) Field of Classification Search .................. 514/317, 514/252.13, 414, 438
See application file for complete search history.

(56) References Cited

U.S. PATENT DOCUMENTS

| | | | |
|---|---|---|---|
| 3,894,034 A | 7/1975 | Gassman et al. |
| 3,993,683 A | 11/1976 | Nickl et al. |
| 4,062,973 A | 12/1977 | Nickl et al. |
| 4,066,686 A | 1/1978 | Lafon |
| 4,120,692 A | 10/1978 | Plant et al. |
| 4,177,290 A | 12/1979 | Lafon |
| 4,191,776 A | 3/1980 | Nickl et al. |
| 4,216,160 A | 8/1980 | Dorn et al. |
| 4,329,363 A | 5/1982 | Dorn et al. |
| 4,582,837 A | 4/1986 | Hauel et al. |
| 4,696,931 A | 9/1987 | Hauel et al. |
| 4,744,812 A | 5/1988 | Parg et al. |
| 4,846,875 A | 7/1989 | Chang |
| 4,846,882 A | 7/1989 | Chang |
| 4,927,855 A | 5/1990 | Lafon |
| 4,935,240 A | 6/1990 | Nakai et al. |
| 4,959,385 A | 9/1990 | Cook et al. |
| 4,980,372 A | 12/1990 | Nakai et al. |
| 5,105,017 A | 4/1992 | Dillard |
| 5,180,745 A | 1/1993 | Lafon |
| 5,258,433 A | 11/1993 | Meier et al. |
| 5,391,576 A | 2/1995 | Lafon |
| 5,393,768 A | 2/1995 | Dillard |
| 5,401,776 A | 3/1995 | Laurent |
| 5,585,359 A | 12/1996 | Breslin et al. |
| 5,612,379 A | 3/1997 | Laurent |
| 5,719,168 A | 2/1998 | Laurent |
| 5,763,539 A | 6/1998 | Stern et al. |
| 6,346,548 B1 | 2/2002 | Miller et al. |
| 6,455,588 B1 | 9/2002 | Scammell et al. |
| 6,472,414 B1 | 10/2002 | Biller et al. |
| 6,488,164 B2 | 12/2002 | Miller et al. |
| 6,492,362 B1 | 12/2002 | Graupe et al. |
| 6,492,396 B2 | 12/2002 | Bacon et al. |
| 6,566,404 B2 | 5/2003 | Esteve et al. |
| 6,670,358 B2 | 12/2003 | Bacon et al. |
| 6,919,367 B2 | 7/2005 | Bacon et al. |
| 6,924,314 B2 | 8/2005 | Sharma et al. |
| 7,119,214 B2 | 10/2006 | Lesur et al. |
| 7,132,443 B2 | 11/2006 | Haffner et al. |
| 7,157,463 B2 | 1/2007 | Backer et al. |
| 7,268,132 B2 | 9/2007 | Bacon et al. |

(Continued)

FOREIGN PATENT DOCUMENTS

DE 25 45 947 4/1977

(Continued)

OTHER PUBLICATIONS

Augeri, et al., Journal of Medicinal Chemistry, vol. 41, No. 22, 1998, pp. 4288-4300.

(Continued)

*Primary Examiner* — Rei-tsang Shiao

(57) ABSTRACT

The present invention is related to chemical compositions, processes for the preparation thereof and uses of the composition. Particularly, the present invention relates to compositions that include substituted biaryl-methanesulfinyl acetamides of Formula (I):

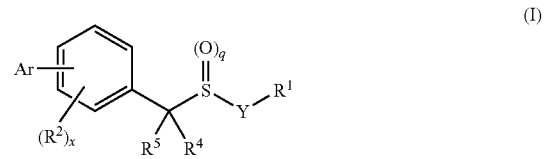

(I)

wherein Ar, Y, $R^1$, $R^2$, $R^4$, $R^5$, q and x are as defined herein; and their use in the treatment of diseases, including treatment of sleepiness associated with narcolepsy, obstructive sleep apnea, or shift work disorder; Parkinson's disease; Alzheimer's disease; attention deficit disorder; attention deficit hyperactivity disorder; depression; or fatigue associated with a neurological disease; as well as the promotion of wakefulness.

6 Claims, No Drawings

U.S. PATENT DOCUMENTS

| | | | |
|---|---|---|---|
| 7,297,817 | B2 | 11/2007 | Lesur et al. |
| 7,314,875 | B2 | 1/2008 | Bacon et al. |
| 7,423,176 | B2 | 9/2008 | Bacon et al. |
| 7,449,481 | B2 | 11/2008 | Bacon et al. |
| 7,476,690 | B2 | 1/2009 | Lesur et al. |
| 7,759,356 | B2 * | 7/2010 | Heintzelman et al. ........ 514/267 |
| 2003/0100548 | A1 | 5/2003 | Barlaam et al. |
| 2003/0113751 | A1 | 6/2003 | Sem et al. |
| 2008/0027228 | A1 | 1/2008 | Bacon et al. |
| 2008/0070956 | A1 | 3/2008 | Bacon et al. |
| 2009/0018143 | A1 | 1/2009 | Lesur et al. |
| 2009/0042907 | A1 | 2/2009 | Bacon et al. |
| 2009/0105241 | A1 | 4/2009 | Lesur et al. |

FOREIGN PATENT DOCUMENTS

| | | |
|---|---|---|
| EP | 0 001 989 | 10/1978 |
| GB | 1 140 748 | 1/1969 |
| GB | 1 178 279 | 1/1970 |
| GB | 1 570 982 | 3/1976 |
| GB | 1 469 083 | 3/1977 |
| GB | 1 600 840 | 5/1978 |
| JP | 45-28989 | 9/1970 |
| JP | 04-059754 | 2/1992 |
| WO | WO 87/04049 | 7/1987 |
| WO | WO 87/07602 | 12/1987 |
| WO | WO 91/17162 | 11/1991 |
| WO | WO 95/01171 | 1/1995 |
| WO | WO 96/09836 | 4/1996 |
| WO | WO 97/15555 | 5/1997 |
| WO | WO 98/08941 | 3/1998 |
| WO | WO 98/23588 | 6/1998 |
| WO | WO 99/25329 | 5/1999 |
| WO | WO 01/19796 | 3/2001 |
| WO | WO 01/87830 | 11/2001 |
| WO | WO 02/10125 | 2/2002 |
| WO | WO 02/069901 | 9/2002 |
| WO | WO 02/070469 | 9/2002 |
| WO | WO 03/037853 | 10/2002 |
| WO | WO 03/002531 | 1/2003 |
| WO | WO 03/023392 | 3/2003 |
| WO | WO 03/072561 | 9/2003 |

OTHER PUBLICATIONS

Boeckmann, et al., Chemische Berichte, vol. 114, No. 3, 1981, pp. 1048-1064.
Bradbury, et al., Journal of Medicinal Chemistry, vol. 35, No. 22, 1992 pp. 4027-4038.
Breslin, et al., Bioorganic & Medicinal Chemistry Letters, 8, 1998, pp. 3311-3316.
Brown, et al., Journal of Medicinal Chemistry, vol. 35, No. 20, 1992, pp. 3613-3624.
Costero, et al., Journal of Chemical Research, No. 4, 1994, pp. 761-769.
El Sakka et al., Arch. Pharm. , 327, 1994, pp. 133-135.
El-Zohry, Phosphorus, Sulfur, and Silicon, vol. 66, No. 14, 1992, pp. 311-319.
Faucher et al., J. Med. Chem, 47, 2004, pp. 18-21.
Graybill, et al., Tetrahedron Letters, vol. 43, No. 30, 2002, pp. 5305-5309.
Han et al., J. Org. Chem., 62, 1997, pp. 3841-3848.
Hermant et al., Psychipharmacaology, 103, 1991, pp. 28-32.
Iqbal et al., Drug Development Research, vol. 51, 2000, pp. 177-186.
Le Diguarher, et al., Journal of Medicinal Chemistry, vol. 46, No. 18, 2003, pp. 3840-3852.
McConachie, et al., Tetrahedron Letters, vol. 41, No. 30, 2002, pp. 5637-5641.
Nishikawa, et al., Takeda Kenkyusho Ho, Journal of the Takeda Research Laboratories, vol. 31, No. 3, 1972, pp. 331-348.
Nugent, et al., Journal of Medicinal Chemistry, vol. 41, No. 20, 1998, pp. 3793-3803.
Panckeri et al., Sleep, 19(8), 1996, pp. 626-631.
Picard, et al., Heterocycles, vol. 38, No. 8, 1994 pp. 1775-1789.
Segarra, et al., Bioorganic & Medicinal Chemistry Letters, vol. 8, No. 5, 1998, pp. 505-510.
Shelton et al., Sleep, 18(10), 1995, pp. 817-826.
Shiotsuki et al., Pesticide Biochemistry and Physiology, 37, 1990, pp. 121-129.
Sucholeiki, Tetrahedron Letters, vol. 35, No. 40, 1994, pp. 7307-7310.
Takeuchi, et al., Journal of Chemical Research, Miniprint, No. 12, 1991, pp. 3156-3188.
Touret et al., Neuroscience Letters, 189, 1995, pp. 43-46.
Suzuki et al., Toyobo Fiber Laboratory, May 4, 1967, pp. 583-587.
Dostert P. and Jalfre M., *Eur. J. Med. Chem*., 1974, 9(3), 259-262.
Saenz R.V. and Sowell J.W., *J. Pharm. Sci.*, 1972, 61(6), 978-980.
Portevin, B. et al., *J. Med. Chem.*, 1996, 39, 2379-2391.

* cited by examiner

THIO-SUBSTITUTED BIARYLMETHANESULFINYL DERIVATIVES

REFERENCE TO RELATED APPLICATIONS

The present application is a divisional of U.S. application Ser. No. 11/104,091 filed Apr. 12, 2005, which claims priority to U.S. Provisional Application Ser. No. 60/569,153, filed May 7, 2004 and European Patent Application No. 04290982.0, filed Apr. 13, 2004. The disclosure of each of these applications is incorporated herein by reference in its entirety.

FIELD OF THE INVENTION

The present invention is related to chemical compositions, processes for the preparation thereof and uses of the composition. Particularly, the present invention relates to compositions that include substituted biaryl-methanesulfinyl acetamides of Formula (I):

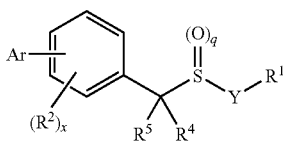

wherein Ar, Y, $R^1$, $R^2$, $R^4$, $R^5$, q and x are as defined herein; and their use in the treatment of diseases, including treatment of sleepiness associated with narcolepsy, obstructive sleep apnea, or shift work disorder; Parkinson's disease; Alzheimer's disease; attention deficit disorder; attention deficit hyperactivity disorder; depression; or fatigue associated with a neurological disease; as well as the promotion of wakefulness.

BACKGROUND OF THE INVENTION

The compounds disclosed herein are related to the biological and chemical analogs of modafinil. Modafinil, $C_{15}H_{15}NO_2S$, also known as 2-(benzhydrylsulfinyl)acetamide, or 2-[(diphenylmethyl)sulfinyl]acetamide, a synthetic acetamide derivative with wake-promoting activity, has been described in French Patent No. 78 05 510 and in U.S. Pat. No. 4,177,290 ("the '290 patent"). It has been approved by the United States Food and Drug Administration for use in the treatment of excessive daytime sleepiness associated with narcolepsy. Methods for preparing modafinil and several derivatives are described in the '290 patent. The levorotatory isomer of modafinil, along with additional modafinil derivatives are described in U.S. Pat. No. 4,927,855, and are reported to be useful for treatment of hypersomnia, depression, Alzheimer's disease and to have activity towards the symptoms of dementia and loss of memory, especially in the elderly.

Modafinil has also been described as a useful agent in the treatment of Parkinson's disease (U.S. Pat. No. 5,180,745); in the protection of cerebral tissue from ischemia (U.S. Pat. No. 5,391,576); in the treatment of urinary and fecal incontinence (U.S. Pat. No. 5,401,776); and in the treatment of sleep apneas and disorders of central origin (U.S. Pat. No. 5,612,379). In addition, modafinil may be used in the treatment of eating disorders, or to promote weight gain or stimulate appetite in humans or animals (U.S. Pat. No. 6,455,588), or in the treatment of attention deficit hyperactivity disorder (U.S. Pat. No. 6,346,548), or fatigue, especially fatigue associated with multiple sclerosis (U.S. Pat. No. 6,488,164). U.S. Pat. No. 4,066,686 describes various benzhydrylsulphinyl derivatives as being useful in therapy for treating disturbances of the central nervous system.

Several published patent applications describe derivative forms of modafinil and the use of modafinil derivatives in the treatment of various disorders. For example, PCT publication WO 99/25329 describes various substituted phenyl analogs of modafinil as being useful for treating drug-induced sleepiness, especially sleepiness associated with administration of morphine to cancer patients. U.S. Pat. No. 5,719,168 and PCT Publication No. 95/01171 describes modafinil derivatives that are useful for modifying feeding behavior. PCT Publication No. 02/10125 describes several modafinil derivatives of modafinil, along with various polymorphic forms of modafinil.

Additional publications describing modafinil derivatives include U.S. Pat. No. 6,492,396, and PCT Publ. No. WO 02/10125.

Terauchi, H, et al. described nicotinamide derivatives useful as ATP-ase inhibitors (Terauchi, H, et al, *J. Med. Chem.*, 1997, 40, 313-321). In particular, several N-alkyl substituted 2-(Benzhydrylsulfinyl)nicotinamides are described.

U.S. Pat. Nos. 4,980,372 and 4,935,240 describe benzoylaminophenoxybutanoic acid derivatives. In particular, sulfide derivatives of modafinil containing a phenyl and substituted phenyl linker between the sulfide and carbonyl, and a substituted aryl in the terminal amide position, are disclosed.

Other modafinil derivatives have been disclosed wherein the terminal phenyl groups are constrained by a linking group. For example, in U.S. Pat. No. 5,563,169, certain xanthenyl and thiaxanthenyl derivatives having a substituted aryl in the terminal amide position are reported.

Other xanthenyl and thiaxanthenyl derivatives are disclosed in Annis, I; Barany, G. *Pept. Proc. Am. Pept. Symp.* 15th (Meeting Date 1997) 343-344, 1999 (preparation of a xanthenyl derivative of Ellman's Reagent, useful as a reagent in peptide synthesis); Han, Y.; Barany, G. *J. Org. Chem.*, 1997, 62, 3841-3848 (preparation of S-xanthenyl protected cysteine derivatives, useful as a reagent in peptide synthesis); and El-Sakka, I. A., et al. *Arch. Pharm.* (*Weinheim*), 1994, 327, 133-135 (thiaxanthenol derivatives of thioglycolic acid).

Thus, there is a need for novel classes of compounds that possess the beneficial properties. It has been discovered that a class of compounds, referred to herein as substituted biaryl-methanesulfinyl acetamides, are useful as agents for treating or preventing various diseases or disorders disclosed herein.

SUMMARY OF THE INVENTION

The present invention in one aspect is directed to various novel compounds of structure:

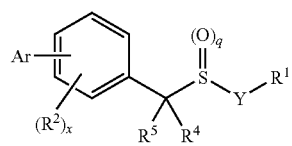

wherein Ar, Y, $R^1$, $R^2$, $R^4$, $R^5$, q and x are as defined herein; and its stereoisomeric forms, mixtures of stereoisomeric forms, or pharmaceutically acceptable salt forms thereof, wherein the constituent members are defined infra.

Another object of the present invention is to provide pharmaceutical compositions comprising the compounds of the present invention wherein the compositions comprise one or more pharmaceutically acceptable excipients and a therapeutically effective amount of at least one of the compounds of the present invention, or a pharmaceutically acceptable salt or ester form thereof.

Another object of the present invention is to provide methods of treating or preventing diseases or disorders, including treatment of sleepiness, promotion of wakefulness, treatment of Parkinson's disease, cerebral ischemia, stroke, sleep apneas, eating disorders, stimulation of appetite and weight gain, treatment of attention deficit hyperactivity disorder (ADHD), enhancing function in disorders associated with hypofunctionality of the cerebral cortex, including, but not limited to, depression, schizophrenia, fatigue, in particular, fatigue associated with neurologic disease, such as multiple sclerosis, chronic fatigue syndrome, and improvement of cognitive dysfunction.

These and other objects, features and advantages of the substituted benzylthioalkyl will be disclosed in the following detailed description of the patent disclosure.

DETAILED DESCRIPTION OF THE INVENTION

In a first embodiment, the present invention provides novel compounds of Formula (I):

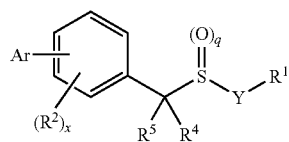

and stereoisomeric forms, mixtures of stereoisomeric forms or pharmaceutically acceptable salt forms thereof,
wherein:

Ar is $C_6$-$C_{10}$ aryl substituted by 0-5 $R^3$;
  $C_5$-$C_{10}$ cycloalkenyl substituted by 0-5 $R^3$; or
  5 to 14 membered heteroaryl group substituted by 0-5 $R^3$, wherein said heteroaryl group comprises one, two, or three heteroatoms selected from N, O, S or Se;

Y is $C_1$-$C_6$ alkylene substituted with 0-3 $R^{20A}$;
  $C_1$-$C_4$ alkylene-$Z^1$—($C_1$-$C_4$ alkylene)$_n$ substituted with 0-3 $R^{20A}$; or
  ($C_1$-$C_4$ alkylene)$_m$-$Z^2$—($C_1$-$C_4$ alkylene)$_n$ substituted with 0-3 $R^{20A}$;

$Z^1$ is O, $NR^{10}$, S, S(=O), or S(=O)$_2$;

$Z^2$ is $CR^{21}$=$CR^{21}$, C≡C, $C_6$-$C_{10}$ arylene substituted with 0-3 $R^{20}$; 5-10 membered heteroarylene substituted with 0-3 $R^{20}$; $C_3$-$C_6$ cycloalkylene substituted with 0-3 $R^{20}$; or 3-6 membered heterocycloalkylene substituted with 0-3 $R^{20}$;

$R^1$ is selected from H, C(=O)$NR^{12}R^{13}$, C(=N)$NR^{12}R^{13}$, OC(=O)$NR^{12}R^{13}$, $NR^{21}$C(=O)$NR^{12}R^{13}$, $NR^{21}$S(=O)$_2$$NR^{12}R^{13}$, —($C_6$-$C_{10}$ aryl)-$NR^{12}R^{13}$ wherein said aryl is substituted with 0-3 $R^{20}$; $NR^{21}$C(=O)$R^{14}$, C(=O)$R^{14}$, C(=O)$OR^{11}$, OC(=O)$R^{11}$, and $NR^{21}$S(=O)$_2$$R^{11}$;

$R^2$ is selected from H, F, Cl, Br, I, $OR^{16}$, $OR^{25}$, $NR^{17}R^{18}$, NHOH, $NO_2$, CN, $CF_3$, $C_1$-$C_6$ alkyl, $C_2$-$C_6$ alkenyl, $C_2$-$C_6$ alkynyl, C(=O)$R^{16}$, C(=O)$OR^{16}$, OC(=O)$R^{16}$, C(=O)$NR^{17}R^{18}$, $NR^{15}$C(=O)$R^{16}$, $NR^{15}$CO$_2$$R^{16}$, OC(=O)$NR^{17}R^{18}$, $NR^{15}$C(=S)$R^{16}$, $SR^{16}$; S(=O)$R^{16}$; and S(=O)$_2$$R^{16}$;

alternatively, two $R^2$ groups may be combined to form a methylenedioxy group, an ethylenedioxy group, or a propylenedioxy group;

$R^3$ is selected from H, F, Cl, Br, I, $OR^{16}$, $OCF_3$, $OR^{25}$, $NR^{17}R^{18}$, NHOH, $NO_2$, CN, $CF_3$, $CH_2OR^{16}$, $C_6$-$C_6$ alkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, $C_7$-$C_{10}$ arylalkyl, C(=O)$R^{16}$, C(=O)$OR^{16}$, OC(=O)$R^{16}$, C(=O)$NR^{17}R^{18}$, $NR^{15}$C(=O)$R^{16}$, $NR^{15}$CO$_2$$R^{16}$, OC(=O)$NR^{17}R^{18}$, $NR^{15}$C(=S)$R^{16}$, $SR^{16}$; S(=O)$R^{16}$; S(=O)$_2$$R^{16}$, and $NR^{15}$S(=O)$_2$$R^{16}$;

alternatively, two $R^3$ groups may be combined to form a methylenedioxy group, an ethylenedioxy group, or a propylenedioxy group;

$R^4$ and $R^5$ at each occurrence are independently selected from H, $C_1$-$C_6$ alkyl, $C_2$-$C_6$ alkenyl, and $C_2$-$C_6$ alkynyl;

alternatively, $R^4$ and $R^5$, together with the carbon atom to which they are attached, form a 3-7 membered spirocyclic ring;

$R^{10}$ is selected from H, $C_1$-$C_6$ alkyl substituted with 0-3 $R^{20}$; $C_6$-$C_{10}$ aryl substituted with 0-3 $R^{20}$; C(=O)$R^{14}$, $SR^{14}$, S(=O)$R^{14}$, and S(=O)$_2$$R^{14}$;

$R^{11}$ at each occurrence is independently selected from H, $C_1$-$C_6$ alkyl substituted with 0-3 $R^{20}$; and $C_6$-$C_{10}$ aryl substituted with 0-3 $R^{20}$;

$R^{12}$ and $R^{13}$ at each occurrence are each independently selected from H, $C_1$-$C_6$ alkyl substituted with 0-3 $R^{20}$; and $C_6$-$C_{10}$ aryl substituted with 0-3 $R^{20}$;

alternatively, $R^{12}$ and $R^{13}$ together with the nitrogen to which they are attached, form a 3-7 membered heterocyclic ring substituted with 0-3 $R^{20}$;

$R^{14}$ at each occurrence is independently selected from $C_1$-$C_6$ alkyl substituted with 0-3 $R^{20}$; $C_6$-$C_{10}$ aryl substituted with 0-3 $R^{20}$; and $C_7$-$C_{10}$ arylalkyl substituted with 0-3 $R^{20}$;

$R^{15}$ at each occurrence is independently selected from H and $C_1$-$C_6$ alkyl;

$R^{16}$ at each occurrence is independently selected from H, $C_1$-$C_6$ alkyl, and $C_6$-$C_{10}$ aryl;

$R^{17}$ and $R^{18}$ at each occurrence are each independently selected from H, $C_1$-$C_6$ alkyl, and $C_6$-$C_{10}$ aryl, or alternatively, $R^{17}$ and $R^{18}$, together with the nitrogen to which they are attached, form a 3-7 membered heterocyclic ring, wherein said 3-7 membered heterocyclic ring is substituted with 0-2 oxo groups;

$R^{20}$ at each occurrence is independently selected from F, Cl, Br, I, OH, $OR^{22}$, $OR^{25}$, $NR^{23}R^{24}$, NHOH, $NO_2$, CN, $CF_3$, $C_2$-$C_6$ alkyl, $C_1$-$C_6$ alkyl-OH, $C_2$-$C_6$ alkenyl, $C_2$-$C_6$ alkynyl, $C_3$-$C_7$ cycloalkyl, 3-7 membered heterocycloalkyl, phenyl substituted by 0-1 $R^{26}$; 5 or 6 membered heteroaryl, $C_7$-$C_{10}$ arylalkyl, =O, C(=O)$R^{22}$, C(=O)$OR^{22}$, OC(=O)$R^{22}$, C(=O)$NR^{23}R^{24}$, $NR^{21}$C(=O)$R^{22}$, $NR^{21}$CO$_2$$R^{22}$, OC(=O)$NR^{23}R^{24}$, $NR^{21}$C(=S)$R^{22}$, $SR^{22}$; S(=O)$R^{22}$; and S(=O)$_2$$R^{22}$;

$R^{20A}$ at each occurrence is independently selected from F, Cl, Br, OH, $OR^{22}$, NHOH, $NO_2$, CN, $CF_3$, $C_1$-$C_6$ alkyl, $C_1$-$C_6$ alkyl-OH, $C_2$-$C_6$ alkenyl, $C_2$-$C_6$ alkynyl, $C_3$-$C_7$ cycloalkyl, 3-7 membered heterocycloalkyl, phenyl substituted by 0-1 $R^{26}$; 5 or 6 membered heteroaryl, and $C_7$-$C_{10}$ arylalkyl;

$R^{21}$ at each occurrence is independently selected from H and $C_1$-$C_6$ alkyl;

$R^{22}$ at each occurrence is independently selected from H, an $C_1$-$C_6$ alkyl-OH, and $C_6$-$C_{10}$ aryl;

$R^{23}$ and $R^{24}$ at each occurrence are each independently selected from H, $C_1$-$C_6$ alkyl, and $C_6$-$C_{10}$ aryl, or alternatively, $R^{23}$ and $R^{24}$, together with the nitrogen to which they are attached, form a 3-7 membered heterocyclic ring;

$R^{25}$ at each occurrence is independently the residue of an amino acid after the hydroxyl group of the carboxyl group is removed;

$R^{26}$ at each occurrence is independently selected from H, F, Cl, Br, $C_1$-$C_6$ alkyl, and $C_1$-$C_6$ alkoxy;

m is 0 or 1;

n is 0 or 1;

x is 0, 1, 2, 3, or 4; and q is 0, 1, or 2;

provided, (i) when Y is —$CH_2$—, Ar is phenyl substituted by 0-5 $R^3$, and —$C(R^4)(R^5)$— is —$CH(C_1$-$C_3$ alkyl)-, then Ar is in the ortho or meta position to the —$C(R^4)(R^5)$— substituent on the core phenyl ring;

(ii) when Y is —$CH_2$—, $R^1$ is H, $C(=O)OR^{11}$, or $C(=O)NR^{12}R^{13}$; Ar is phenyl substituted by 0-2 $R^3$, and $R^3$ is H, F, Cl, Br, I, $CH_3$, $OCH_3$, $SCH_3$, CN, $NO_2$, or methylendioxyphenyl; then Ar is in the ortho or meta position to the —$C(R^4)(R^5)$— substituent on the core phenyl ring;

(iii) when Ar is imidazopyridine substituted by 0-5 $R^3$, Ar is in the ortho or meta position to the —$C(R^4)(R^5)$— substituent on the core phenyl ring;

(iv) when Ar is benzotriazolyl in the meta position to the —$C(R^4)(R^5)$— substituent on the core phenyl ring, then $R^1$ is not H;

(v) when Ar is in the meta position to the —$C(R^4)(R^5)$— substituent on the core phenyl ring and Ar is a heteroaryl group attached to the phenyl ring through a nitrogen atom, then Ar is pyrrolyl, indolyl, imidazolyl, benzimidazolyl, benzotriazolyl, triazolyl, or 1,3-dihydroisoindolyl;

(vi) when Y is —$CH_2$— and Ar is pyridyl substituted by a nitro, a methyl, a second methyl, and a $C(=O)OC_3H_7$ group, then $R^1$ is not H;

(vii) when Y is —$CH_2$— and Ar is a purine, imidazopyridine, dihydro-imidazopyridine or benzimidazole, substituted by 0-5 $R^3$, then $R^1$ is not H;

(viii) when Ar is triazolinonyl substituted by 0-2 $R^3$; then $R^1$ is not H;

(ix) when q is 0, Y is —$CH_2$—, and Ar is phenyl, substituted by 0-5 $R^3$, in the meta position to the —$C(R^4)(R^5)$— substituent on the core phenyl ring, then neither $R^{12}$ nor $R^{13}$ is phenyl;

(x) when q is 0, $R^{20}$ is cyano, and Ar is phenyl, substituted by 0-5 $R^3$, in the para position to the —$C(R^4)(R^5)$— substituent on the core phenyl ring, then $R^3$ is not piperazinyl;

(xi) when q is 0, and Ar is imidazolyl attached to the phenyl ring through a nitrogen atom, then $R^1$ is not H, $C(=O)OR^{11}$, $C(=O)R^{14}$, or $C(=O)NHCH_3$;

(xii) when q is 0 or 1, Y is butylene and Ar is phenyl, substituted by 0-5 $R^3$, in the para position to the —$C(R^4)(R^5)$— substituent on the core phenyl ring, then $R^1$ is not H;

(xiii) when q is 0 or 1, Y is —$CH_2$—, —$CH_2CH_2$—, or phenylene, and Ar is pyrrolyl in the ortho position to the —$C(R^4)(R^5)$— substituent on the core phenyl ring; then $R^1$ is not H;

(xiv) when q is 0 or 1, $R^2$ is OH, and Ar is phenyl or cycloalkenyl; then $R^1$ is not H or $C(=O)OR^{11}$;

(xv) when q is 1, Y is —$CH_2$—, $R^4$ is H, $R^5$ is H, and Ar is phenyl in the ortho position to the —$C(R^4)(R^5)$— substituent on the core phenyl ring, then $R^1$ is not H;

(xvi) when q is 1 or 2, and Ar is imidazolyl attached to the phenyl ring through a nitrogen atom, then $R^1$ is not H;

(xvii) when q is 2, then Ar is in the ortho or meta position to the —$C(R^4)(R^5)$— substituent on the core phenyl ring;

(xviii) when q is 2, Y is —$CH_2$—, $R^4$ is H, $R^5$ is H, and Ar is 1,2-(methylenedioxy)-phenyl, then Ar is in the ortho position to the —$C(R^4)(R^5)$— substituent on the core phenyl ring;

(xix) when q is 2, and Ar is phenyl in the ortho position to the —$C(R^4)(R^5)$— substituent on the core phenyl ring, then $R^1$ is not H; and (xx) when q is 0, and Ar is phenyl in the meta position to the —$C(R^4)(R^5)$— substituent on the core phenyl ring, then $R^1$ is not H.

In a preferred embodiment, the present invention provides novel compounds of Formula (I):

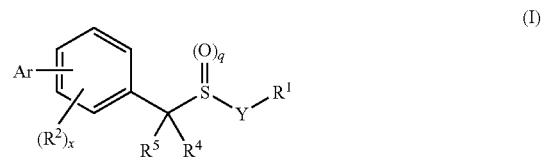

(I)

and stereoisomeric forms, mixtures of stereoisomeric forms or pharmaceutically acceptable salt forms thereof, wherein:

Ar is $C_6$-$C_{10}$ aryl substituted by 0-5 $R^3$;
$C_5$-$C_{10}$ cycloalkenyl substituted by 0-5 $R^3$; or
5 to 14 membered heteroaryl group substituted by 0-5 $R^3$, wherein said heteroaryl group comprises one, two, or three heteroatoms selected from N, O, S or Se;

Y is $C_1$-$C_6$ alkylene substituted with 0-3 $R^{20A}$;

$R^1$ is selected from H, $C(=O)NR^{12}R^{13}$, $C(=N)NR^{12}R^{13}$, $OC(=O)NR^{12}R^{13}$, $NR^{21}C(=O)NR^{12}R^{13}$, $NR^{21}S(=O)_2NR^{12}R^{13}$, —($C_6$-$C_{10}$ aryl)-$NR^{12}R^{13}$ wherein said aryl is substituted with 0-3 $R^{20}$; $NR^{21}C(=O)R^{14}$, $C(=O)R^{14}$, $C(=O)OR^{11}$, $OC(=O)R^{11}$, and $NR^{21}S(=O)_2R^{11}$;

$R^2$ is selected from H, F, Cl, Br, I, $OR^{16}$, $OR^{25}$, $NR^{17}R^{18}$, NHOH, $NO_2$, CN, $CF_3$, $C_1$-$C_6$ alkyl, $C_2$-$C_6$ alkenyl, $C_2$-$C_6$ alkynyl, $C(=O)R^{16}$, $C(=O)OR^{16}$, $OC(=O)R^{16}$, $C(=O)NR^{17}R^{18}$, $NR^{15}C(=O)R^{16}$, $NR^{15}CO_2R^{16}$, $OC(=O)NR^{17}R^{18}$, $NR^{15}C(=S)R^{16}$, $SR^{16}$; $S(=O)R^{16}$; and $S(=O)_2R^{16}$;

alternatively, two $R^2$ groups may be combined to form a methylenedioxy group, an ethylenedioxy group, or a propylenedioxy group;

$R^3$ is selected from H, F, Cl, Br, I, $OR^{16}$, $OCF_3$, $OR^{25}$, $NR^{17}R^{18}$, NHOH, $NO_2$, CN, $CF_3$, $CH_2OR^{16}$, $C_6$-$C_6$ alkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, $C_7$-$C_{10}$ arylalkyl, $C(=O)R^{16}$, $C(=O)OR^{16}$, $OC(=O)R^{16}$, $C(=O)NR^{17}R^{18}$, $NR^{15}C(=O)R^{16}$, $NR^{15}CO_2R^{16}$, $OC(=O)NR^{17}R^{18}$, $NR^{15}C(=S)R^{16}$, $SR^{16}$; $S(=O)R^{16}$; $S(=O)_2R^{16}$, and $NR^{15}S(=O)_2R^{16}$;

alternatively, two $R^3$ groups may be combined to form a methylenedioxy group, an ethylenedioxy group, or a propylenedioxy group;

$R^4$ and $R^5$ at each occurrence are independently selected from H, $C_1$-$C_6$ alkyl, $C_2$-$C_6$ alkenyl, and $C_2$-$C_6$ alkynyl;

alternatively, $R^4$ and $R^5$, together with the carbon atom to which they are attached, form a 3-7 membered spirocyclic ring;

$R^{11}$ at each occurrence is independently selected from H, $C_1$-$C_6$ alkyl substituted with 0-3 $R^{20}$; and $C_6$-$C_{10}$ aryl substituted with 0-3 $R^{20}$;

$R^{12}$ and $R^{13}$ at each occurrence are each independently selected from H, $C_1$-$C_6$ alkyl substituted with 0-3 $R^{20}$ and $C_6$-$C_{10}$ aryl substituted with 0-3 $R^{20}$;

alternatively, $R^{12}$ and $R^{13}$ together with the nitrogen to which they are attached, form a 3-7 membered heterocyclic ring substituted with 0-3 $R^{20}$;

$R^{14}$ at each occurrence is independently selected from $C_1$-$C_6$ alkyl substituted with 0-3 $R^{20}$; $C_6$-$C_{10}$ aryl substituted with 0-3 $R^{20}$; and $C_7$-$C_{10}$ arylalkyl substituted with 0-3 $R^{20}$;

$R^{15}$ at each occurrence is independently selected from H and $C_1$-$C_6$ alkyl;

$R^{16}$ at each occurrence is independently selected from H, $C_1$-$C_6$ alkyl, and $C_6$-$C_{10}$ aryl;

$R^{17}$ and $R^{18}$ at each occurrence are each independently selected from H, $C_1$-$C_6$ alkyl, and $C_6$-$C_{10}$ aryl, or alternatively, $R^{17}$ and $R^{18}$, together with the nitrogen to which they are attached, form a 3-7 membered heterocyclic ring, wherein said 3-7 membered heterocyclic ring is substituted with 0-2 oxo groups;

$R^{20}$ at each occurrence is independently selected from F, Cl, Br, I, OH, $OR^{22}$, $OR^{25}$, $NR^{23}R^{24}$, NHOH, $NO_2$, CN, $CF_3$, $C_1$-$C_6$ alkyl, $C_1$-$C_6$ alkyl-OH, $C_2$-$C_6$ alkenyl, $C_2$-$C_6$ alkynyl, $C_3$-$C_7$ cycloalkyl, 3-7 membered heterocycloalkyl, phenyl substituted by 0-1 $R^{26}$; 5 or 6 membered heteroaryl, $C_7$-$C_{10}$ arylalkyl, =O, $C(=O)R^{22}$, $C(O)OR^{22}$, $OC(=O)R^{22}$, $C(=O)NR^{23}R^{24}$, $NR^{21}C(=O)R^{22}$, $N^{21}CO_2R^{22}$, $OC(=O)NR^{23}R^{24}$, $NR^{21}C(=S)R^{22}$, $SR^{22}$; $S(=O)R^{22}$; and $S(=O)_2R^{22}$;

$R^{20A}$ at each occurrence is independently selected from F, Cl, OH, $C_1$-$C_4$ alkoxy, $CF_3$, $C_1$-$C_4$ alkyl, $C_1$-$C_4$ alkyl-OH, $C_2$-$C_4$ alkenyl, $C_2$-$C_4$ alkynyl, and $C_3$-$C_5$ cycloalkyl;

$R^{21}$ at each occurrence is independently selected from H and $C_1$-$C_6$ alkyl;

$R^{22}$ at each occurrence is independently selected from H, $C_1$-$C_6$ alkyl, $C_1$-$C_6$ alkyl-OH, and $C_6$-$C_{10}$ aryl;

$R^{23}$ and $R^{24}$ at each occurrence are each independently selected from H, $C_1$-$C_6$ alkyl, and $C_6$-$C_{10}$ aryl, or alternatively, $R^{23}$ and $R^{24}$ together with the nitrogen to which they are attached, form a 3-7 membered heterocyclic ring;

$R^{25}$ at each occurrence is independently the residue of an amino acid after the hydroxyl group of the carboxyl group is removed;

$R^{26}$ at each occurrence is independently selected from H, F, Cl, Br, $C_1$-$C_6$ alkyl, and $C_1$-$C_6$ alkoxy;

x is 0, 1, 2, 3, or 4; and q is 1 or 2;

provided, (i) when Y is —$CH_2$—, Ar is phenyl substituted by 0-5 $R^3$, and —$C(R^4)(R^5)$— is —$CH(C_1$-$C_3$ alkyl)-, then Ar is in the ortho or meta position to the —$C(R^4)(R^5)$— substituent on the core phenyl ring;

(ii) when Y is —$CH_2$—, $R^1$ is H, $C(=O)OR^{11}$, or $C(=O)NR^{12}R^{13}$; Ar is phenyl substituted by 0-2 $R^3$, and $R^3$ is H, F, Cl, Br, I, $CH_3$, $OCH_3$, $SCH_3$, CN, $NO_2$, or methylendioxyphenyl; then Ar is in the ortho or meta position to the —$C(R^4)(R^5)$— substituent on the core phenyl ring;

(iii) when Ar is imidazopyridine substituted by 0-5 $R^3$, Ar is in the ortho or meta position to the —$C(R^4)(R^5)$— substituent on the core phenyl ring;

(iv) when Ar is benzotriazolyl in the meta position to the —$C(R^4)(R^5)$— substituent on the core phenyl ring, then $R^1$ is not H;

(v) when Ar is in the meta position to the —$C(R^4)(R^5)$— substituent on the core phenyl ring and Ar is a heteroaryl group attached to the phenyl ring through a nitrogen atom, then Ar is pyrrolyl, indolyl, imidazolyl, benzimidazolyl, benzotriazolyl, triazolyl, or 1,3-dihydroisoindolyl;

(vi) when Y is —$CH_2$— and Ar is pyridyl substituted by a nitro, a methyl, a second methyl, and a $C(=O)OC_3H_7$ group, then $R^1$ is not H;

(vii) when Y is —$CH_2$— and Ar is a purine, imidazopyridine, dihydro-imidazopyridine or benzimidazole, substituted by 0-5 $R^3$, then $R^1$ is not H;

(viii) when Ar is triazolinonyl substituted by 0-2 $R^3$; then $R^1$ is not H;

(ix) when q is 0, Y is —$CH_2$—, and Ar is phenyl, substituted by 0-5 $R^3$, in the meta position to the —$C(R^4)(R^5)$— substituent on the core phenyl ring, then neither $R^{12}$ nor $R^{13}$ is phenyl;

(x) when q is 0, $R^{20}$ is cyano, and Ar is phenyl, substituted by 0-5 $R^3$, in the para position to the —$C(R^4)(R^5)$— substituent on the core phenyl ring, then $R^3$ is not piperazinyl;

(xi) when q is 0, and Ar is imidazolyl attached to the phenyl ring through a nitrogen atom, then $R^1$ is not H, $C(=O)OR^{11}$, $C(=O)R^{14}$, or $C(=O)NHCH_3$;

(xii) when q is 0 or 1, Y is butylene and Ar is phenyl, substituted by 0-5 $R^3$, in the para position to the —$C(R^4)(R^5)$— substituent on the core phenyl ring, then $R^1$ is not H;

(xiii) when q is 0 or 1, Y is —$CH_2$— or —$CH_2CH_2$—, and Ar is pyrrolyl in the ortho position to the —$C(R^4)(R^5)$— substituent on the core phenyl ring; then $R^1$ is not H;

(xiv) when q is 0 or 1, $R^2$ is OH, and Ar is phenyl or cycloalkenyl; then $R^1$ is not H or $C(=O)OR^{11}$;

(xv) when q is 1, Y is —$CH_2$—, $R^4$ is H, $R^5$ is H, and Ar is phenyl in the ortho position to the —$C(R^4)(R^5)$— substituent on the core phenyl ring, then $R^1$ is not H;

(xvi) when q is 1 or 2, and Ar is imidazolyl attached to the phenyl ring through a nitrogen atom, then $R^1$ is not H;

(xvii) when q is 2, then Ar is in the ortho or meta position to the —$C(R^4)(R^5)$— substituent on the core phenyl ring;

(xviii) when q is 2, Y is —$CH_2$—, $R^4$ is H, $R^5$ is H, and Ar is 1,2-(methylenedioxy)-phenyl, then Ar is in the ortho position to the —$C(R^4)(R^5)$— substituent on the core phenyl ring;

(xix) when q is 2, and Ar is phenyl in the ortho position to the —$C(R^4)(R^5)$— substituent on the core phenyl ring, then $R^1$ is not H; and (xx) when q is 0, and Ar is phenyl in the meta position to the —$C(R^4)(R^5)$— substituent on the core phenyl ring, then $R^1$ is not H.

In a preferred embodiment q is 1.

In a preferred embodiment $R^1$ is H.

In a preferred embodiment $R^1$ is $C(=O)NR^{12}R^{13}$.

In a preferred embodiment $R^{12}$ and $R^{13}$ are each independently selected from H and $C_1$-$C_6$ alkyl substituted with 0-3 $R^{20}$.

In a preferred embodiment $R^{12}$ and $R^{13}$ together with the nitrogen to which they are attached form a 3-7 membered heterocyclic ring substituted with 0-3 $R^{20}$.

In a preferred embodiment Y is —$CH_2$—.

In a preferred embodiment Y is —$CH_2CH_2$—.

In a preferred embodiment $R^4$ and $R^5$ are H.

In a preferred embodiment Ar is phenyl substituted by 0-5 $R^3$.

In a preferred embodiment Ar is $C_5$-$C_{10}$ cycloalkenyl substituted by 0-5 $R^3$.

In a preferred embodiment Ar is a 5 to 14 membered heteroaryl group substituted by 0-5 $R^3$, wherein said heteroaryl group comprises one, two, or three heteroatoms selected from N, O, S or Se.

In a preferred embodiment Ar is a 5 to 14 membered heteroaryl group substituted by 0-5 $R^3$, wherein said heteroaryl group comprises one, two, or three heteroatoms selected from N, O, S or Se; wherein said 5 to 14 membered heteroaryl group is selected from phenoxathiinyl, quinolinyl, isoxazolyl, thienyl, benzothienyl, (1,1-dioxo)-benzothienyl, indolyl, furyl, benzofuryl, pyridyl, seleninyl, 1,3-dihydro-isoindolyl, pyrrolyl, and 2-benzo[1,4]dioxine.

In a preferred embodiment Ar is in the ortho position to the —$C(R^4)(R^5)$— substituent on the core phenyl ring.

In a preferred embodiment Ar is in the meta position to the —$C(R^4)(R^5)$— substituent on the core phenyl ring.

In a preferred embodiment Ar is in the para position to the —$C(R^4)(R^5)$— substituent on the core phenyl ring.

In another preferred embodiment, the present invention provides novel compounds of Formula (Ia):

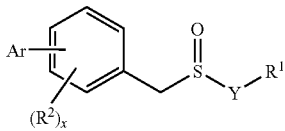

and stereoisomeric forms, mixtures of stereoisomeric forms or pharmaceutically acceptable salt forms thereof.

In another preferred embodiment, the present invention provides novel compounds of Formula (Ib):

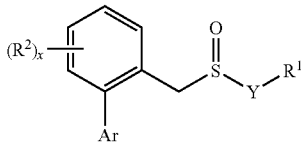

and stereoisomeric forms, mixtures of stereoisomeric forms or pharmaceutically acceptable salt forms thereof.

In another preferred embodiment, the present invention provides novel compounds of Formula (Ic):

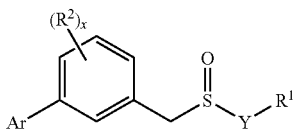

and stereoisomeric forms, mixtures of stereoisomeric forms or pharmaceutically acceptable salt forms thereof.

In another preferred embodiment, the present invention provides novel compounds of Formula (Id):

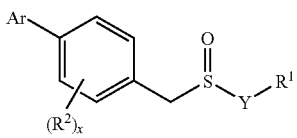

and stereoisomeric forms, mixtures of stereoisomeric forms or pharmaceutically acceptable salt forms thereof.

In another preferred embodiment, the present invention provides novel compounds of Formula (Ie):

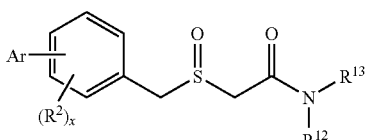

and stereoisomeric forms, mixtures of stereoisomeric forms or pharmaceutically acceptable salt forms thereof, wherein:
Ar is $C_6$-$C_{10}$ aryl substituted by 0-5 $R^3$;
$C_5$-$C_{10}$ cycloalkenyl substituted by 0-5 $R^3$; or
5 to 14 membered heteroaryl group substituted by 0-5 $R^3$, wherein said heteroaryl group comprises one, two, or three heteroatoms selected from N, O, S or Se;
$R^2$ is selected from H, F, Cl, Br, I, $OR^{16}$, $NR^{17}R^{18}$, NHOH, $NO_2$, CN, $CF_3$, $C_1$-$C_6$ alkyl, $C_2$-$C_6$ alkenyl, $C_2$-$C_6$ alkynyl, $C(=O)R^{16}$, $C(=O)OR^{16}$, $OC(=O)R^{16}$, $C(=O)NR^{17}R^{18}$, $NHC(=O)R^{16}$, $NHCO_2R^{16}$, $OC(=O)NR^{17}R^{18}$, $NHC(=S)R^{16}$, $SR^{16}$; $S(=O)R^{16}$; and $S(=O)_2R^{16}$;
alternatively, two $R^2$ groups may be combined to form a methylenedioxy group, an ethylenedioxy group, or a propylenedioxy group;
$R^3$ is selected from H, F, Cl, Br, I, $OR^{16}$, $OCF_3$, $NR^{17}R^{18}$, NHOH, $NO_2$, CN, $CF_3$, $CH_2OR^{16}$, $C_1$-$C_6$ alkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, $C_7$-$C_{10}$ arylalkyl, $C(=O)R^{16}$, $C(=O)OR^{16}$, $OC(=O)R^{16}$, $C(=O)NR^{17}R^{18}$, $NHC(=O)R^{16}$, $NHCO_2R^{16}$, $OC(=O)NR^{17}R^{18}$, $NHC(=S)R^{16}$, $SR^{16}$; $S(=O)R^{16}$; $S(=O)_2R^{16}$, and $NHS(=O)_2R^{16}$;
alternatively, two $R^3$ groups may be combined to form a methylenedioxy group, an ethylenedioxy group, or a propylenedioxy group;
$R^{12}$ and $R^{13}$ at each occurrence are each independently selected from H, $C_1$-$C_6$ alkyl substituted with 0-3 $R^{20}$ and $C_6$-$C_{10}$ aryl substituted with 0-3 $R^{20}$;
alternatively, $R^{12}$ and $R^{13}$ together with the nitrogen to which they are attached, form a 3-7 membered heterocyclic ring substituted with 0-3 $R^{20}$;
$R^{16}$ at each occurrence is independently selected from H, $C_1$-$C_6$ alkyl, and $C_6$-$C_{10}$ aryl;
$R^{17}$ and $R^{18}$ at each occurrence are each independently selected from H, $C_1$-$C_6$ alkyl, and $C_6$-$C_{10}$ aryl, or
alternatively, $R^{17}$ and $R^{18}$, together with the nitrogen to which they are attached, form a 3-7 membered heterocyclic ring, wherein said 3-7 membered heterocyclic ring is substituted with 0-2 oxo groups;
$R^{20}$ at each occurrence is independently selected from F, Cl, Br, I, OH, $OR^{22}$, $NR^{23}R^{24}$, NHOH, $NO_2$, CN, $CF_3$, $C_1$-$C_6$ alkyl, $C_1$-$C_6$ alkyl-OH, $C_2$-$C_6$ alkenyl, $C_2$-$C_6$ alkynyl, $C_3$-$C_7$ cycloalkyl, 3-7 membered heterocycloalkyl, phenyl substituted by 0-1 $R^{26}$; 5 or 6 membered heteroaryl, $C_7$-$C_{10}$ arylalkyl, =O, $C(=O)R^{22}$, $C(=O)OR^{22}$, $OC(=O)R^{22}$, $C(=O)NR^{23}R^{24}$, $NHC(=O)R^{22}$, $NHCO_2R^{22}$, $OC(=O)NR^{23}R^{24}$, $NHC(=S)R^{22}$, $SR^{22}$; $S(=O)R^{22}$; and $S(=O)_2R^{22}$;
$R^{22}$ at each occurrence is independently selected from H, $C_1$-$C_4$ alkyl, $C_1$-$C_4$ alkyl-OH, and $C_6$-$C_{10}$ aryl;
$R^{23}$ and $R^{24}$ at each occurrence are each independently selected from H, $C_1$-$C_4$ alkyl, and $C_6$-$C_{10}$ aryl, or
alternatively, $R^{23}$ and $R^{24}$ together with the nitrogen to which they are attached, form a 3-7 membered heterocyclic ring;
$R^{26}$ at each occurrence is independently selected from H, F, Cl, Br, $C_1$-$C_4$ alkyl, and $C_1$-$C_4$ alkoxy; and
x is 0, 1, 2, 3, or 4;
provided,
(ii) when Ar is phenyl substituted by 0-2 $R^3$, and $R^3$ is H, F, Cl, Br, I, $CH_3$, $OCH_3$, $SCH_3$, CN, $NO_2$, or methylendioxyphenyl; then Ar is in the ortho or meta position to the —$C(R^4)(R^5)$— substituent on the core phenyl ring;
(iii) when Ar is imidazopyridine substituted by 0-5 $R^3$, Ar is in the ortho or meta position to the —$C(R^4)(R^5)$— substituent on the core phenyl ring; and (v) when Ar is in the meta position to the —C(R⁴)(R⁵)— substituent on the core phenyl ring and Ar is a heteroaryl group attached to the phenyl ring through a nitrogen atom, then Ar is pyrrolyl, indolyl, imidazolyl, benzimidazolyl, benzotriazolyl, triazolyl, or 1,3-dihydroisoindolyl.

In another preferred embodiment $R^{12}$ and $R^{13}$ are each independently selected from H and $C_1$-$C_6$ alkyl substituted with 0-3 $R^{20}$.

In another preferred embodiment $R^{12}$ and $R^{13}$ together with the nitrogen to which they are attached form a 3-7 membered heterocyclic ring substituted with 0-3 $R^{20}$.

In another preferred embodiment Ar is phenyl substituted by 0-5 $R^3$.

In another preferred embodiment Ar is phenyl substituted by 0-5 $R^3$, in the ortho or meta position to the —C(R⁴)(R⁵)— substituent on the core phenyl ring.

In another preferred embodiment Ar is phenyl substituted by 0-5 $R^3$, in the ortho position to the —C(R⁴)(R⁵)— substituent on the core phenyl ring.

In another preferred embodiment Ar is phenyl substituted by 0-5 $R^3$, in the meta position to the —C(R⁴)(R⁵)— substituent on the core phenyl ring.

In another preferred embodiment Ar is $C_5$-$C_{10}$ cycloalkenyl substituted by 0-5 $R^3$ In another preferred embodiment Ar is $C_5$-$C_{10}$ cycloalkenyl substituted by 0-5 $R^3$, in the ortho or meta position to the —C(R⁴)(R⁵)— substituent on the core phenyl ring.

In another preferred embodiment Ar is $C_5$-$C_{10}$ cycloalkenyl substituted by 0-5 $R^3$, in the ortho position to the —C(R⁴)(R⁵)— substituent on the core phenyl ring.

In another preferred embodiment Ar is $C_5$-$C_{10}$ cycloalkenyl substituted by 0-5 $R^3$, in the meta position to the —C(R⁴)(R⁵)— substituent on the core phenyl ring.

In another preferred embodiment Ar is a 5 to 14 membered heteroaryl group substituted by 0-5 $R^3$, wherein said heteroaryl group comprises one, two, or three heteroatoms selected from N, O, S or Se; wherein said 5 to 14 membered heteroaryl group is selected from phenoxathiinyl, quinolinyl, isoxazolyl, thienyl, benzothienyl, (1,1-dioxo)-benzothienyl, indolyl, furyl, benzofuryl, pyridyl, seleninyl, 1,3-dihydroisoindolyl, pyrrolyl, and 2-benzo[1,4]dioxine.

In another preferred embodiment Ar is a 5 to 14 membered heteroaryl group substituted by 0-5 $R^3$, wherein said heteroaryl group comprises one, two, or three heteroatoms selected from N, O, S or Se; in the ortho position to the —C(R⁴)(R⁵)— substituent on the core phenyl ring.

In another preferred embodiment Ar is a 5 to 14 membered heteroaryl group substituted by 0-5 $R^3$, wherein said heteroaryl group comprises one, two, or three heteroatoms selected from N, O, S or Se; in the meta position to the —C(R⁴)(R⁵)— substituent on the core phenyl ring.

In another preferred embodiment a compound of Formula (If):

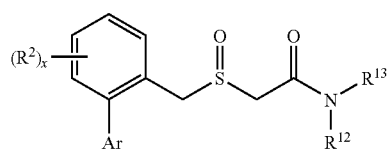

and stereoisomeric forms, mixtures of stereoisomeric forms or pharmaceutically acceptable salt forms thereof.

In another preferred embodiment a compound of Formula (Ig):

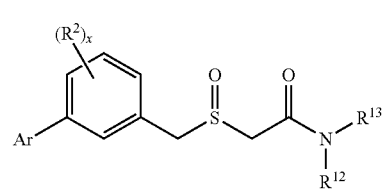

and stereoisomeric forms, mixtures of stereoisomeric forms or pharmaceutically acceptable salt forms thereof.

In another preferred embodiment a compound of Formula (Ih):

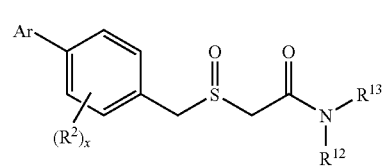

and stereoisomeric forms, mixtures of stereoisomeric forms or pharmaceutically acceptable salt forms thereof.

In another preferred embodiment, the present invention provides novel compounds of Formula (Ie) wherein Ar is phenyl substituted by 0-5 $R^3$, and wherein said Ar group is in the ortho position to the —C(R⁴)(R⁵)— substituent on the core phenyl ring.

In another preferred embodiment, the present invention provides novel compounds of Formula (I):

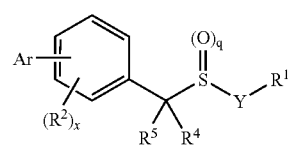

and stereoisomeric forms, mixtures of stereoisomeric forms or pharmaceutically acceptable salt forms thereof,
wherein:
Ar is $C_6$-$C_{10}$ aryl substituted by 0-5 $R^3$;
  $C_5$-$C_{10}$ cycloalkenyl substituted by 0-5 $R^3$; or a
  5 to 10 membered heteroaryl group substituted by 0-5 $R^3$, wherein said heteroaryl group comprises one, two, or three heteroatoms selected from N, O, or S; wherein said 5 to 10 membered heteroaryl group is selected from quinolinyl, isoxazolyl, thienyl, benzothienyl, (1,1-dioxo)-benzothienyl, indolyl, furyl, benzofuryl, pyridyl, seleninyl, 1,3-dihydro-isoindolyl, pyrrolyl, and 2-benzo[1,4]dioxine;
Y is $C_1$-$C_3$ alkylene substituted with 0-1 $R^{20A}$;
$R^1$ is selected from H, C(=O)NR¹²R¹³, and C(=O)OR¹¹;
$R^2$ is selected from H, F, Cl, Br, $C_1$-$C_4$ alkoxy, CN, CF₃, $C_1$-$C_4$ alkyl;
alternatively, two $R^2$ groups may be combined to form a methylenedioxy group, an ethylenedioxy group, or a propylenedioxy group;
$R^3$ is selected from H, F, Cl, Br, OR¹⁶, OCF₃, NR¹⁷R¹⁸, NHOH, NO₂, CN, CF₃, CH₂OR¹⁶, $C_1$-$C_6$ alkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, $C_7$-$C_{10}$ arylalkyl, C(=O)$R^{16}$, C(=O)O$R^{16}$, OC(=O)$R^{16}$, C(=O)N$R^{17}R^{18}$, NHC(=O)$R^{16}$, NHCO$_2R^{16}$, OC(=O) N$R^{17}R^{18}$, NHC(=S)$R^{16}$, S$R^{16}$, S(=O)$R^{16}$; S(=O)$_2R^{16}$, and NHS(=O)$_2R^{16}$;

alternatively, two $R^3$ groups may be combined to form a methylenedioxy group, an ethylenedioxy group, or a propylenedioxy group;

$R^4$ and $R^5$ at each occurrence are independently selected from H, methyl, and ethyl;

$R^{11}$ at each occurrence is independently selected from H, $C_1$-$C_6$ alkyl substituted with 0-3 $R^{20}$; and $C_6$-$C_{10}$ aryl substituted with 0-3 $R^{20}$;

$R^{12}$ and $R^{13}$ at each occurrence are each independently selected from H, $C_1$-$C_6$ alkyl substituted with 0-3 $R^{20}$ and $C_6$-$C_{10}$ aryl substituted with 0-3 $R^{20}$;

alternatively, $R^{12}$ and $R^{13}$, together with the nitrogen to which they are attached, form a 3-7 membered heterocyclic ring substituted with 0-3 $R^{20}$;

$R^{16}$ at each occurrence is independently selected from H, $C_1$-$C_6$ alkyl, and $C_6$-$C_{10}$ aryl;

$R^{17}$ and $R^{18}$ at each occurrence are each independently selected from H, $C_1$-$C_6$ alkyl, and $C_6$-$C_{10}$ aryl, or alternatively, $R^{17}$ and $R^{18}$, together with the nitrogen to which they are attached, form a 3-7 membered heterocyclic ring, wherein said 3-7 membered heterocyclic ring is substituted with 0-2 oxo groups;

$R^{20}$ at each occurrence is independently selected from F, Cl, Br, OH, O$R^{22}$, N$R^{23}R^{24}$, NHOH, NO$_2$, CN, CF$_3$, $C_1$-$C_6$ alkyl, $C_1$-$C_6$ alkyl-OH, $C_2$-$C_6$ alkenyl, $C_2$-$C_6$ alkynyl, $C_3$-$C_7$ cycloalkyl, 3-7 membered heterocycloalkyl, phenyl substituted by 0-1 $R^{26}$; 5 or 6 membered heteroaryl, $C_7$-$C_{10}$ arylalkyl, =O, C(=O)$R^{22}$, C(=O)O$R^{22}$, OC(=O)$R^{22}$, C(=O)N$R^{23}R^{24}$, NHC(=O)$R^{22}$, NHCO$_2R^{22}$, OC(=O) N$R^{23}R^{24}$, NHC(=S)$R^{22}$, S$R^{22}$; S(=O)$R^{22}$; and S(=O)$_2R^{22}$;

$R^{20A}$ at each occurrence is independently selected from F, Cl, OH, methoxy, ethoxy, methyl, and ethyl;

$R^{22}$ at each occurrence is independently selected from H, $C_1$-$C_6$ alkyl, $C_1$-$C_6$ alkyl-OH, and $C_6$-$C_{10}$ aryl;

$R^{23}$ and $R^{24}$ at each occurrence are each independently selected from H, $C_1$-$C_6$ alkyl, and $C_6$-$C_{10}$ aryl, or alternatively, $R^{23}$ and $R^{24}$, together with the nitrogen to which they are attached, form a 3-7 membered heterocyclic ring;

$R^{26}$ at each occurrence is independently selected from H, F, $C_1$-$C_6$ alkyl, and $C_1$-$C_6$ alkoxy;

x is 0, 1, 2, 3, or 4; and q is 1 or 2;

provided, (i) when Y is —CH$_2$—, Ar is phenyl substituted by 0-5 $R^3$, and —C($R^4$)($R^5$)— is —CH($C_1$-$C_3$ alkyl)-, then Ar is in the ortho or meta position to the —C($R^4$)($R^5$)— substituent on the core phenyl ring;

(ii) when Y is —CH$_2$—, $R^1$ is H, C(=O)O$R^{11}$, or C(=O) N$R^{12}R^{13}$; Ar is phenyl substituted by 0-2 $R^3$, and $R^3$ is H, F, Cl, Br, I, CH$_3$, OCH$_3$, SCH$_3$, CN, NO$_2$, or methylendioxyphenyl; then Ar is in the ortho or meta position to the —C($R^4$)($R^5$)— substituent on the core phenyl ring;

(v) when Ar is in the meta position to the —C($R^4$)($R^5$)— substituent on the core phenyl ring and Ar is a heteroaryl group attached to the phenyl ring through a nitrogen atom, then Ar is pyrrolyl, indolyl, imidazolyl, benzimidazolyl, benzotriazolyl, triazolyl, or 1,3-dihydroisoindolyl;

(vi) when Y is —CH$_2$— and Ar is pyridyl substituted by a nitro, a methyl, a second methyl, and a C(=O)OC$_3$H$_7$ group, then $R^1$ is not H;

(xiii) when q is 1, Y is —CH$_2$— or —CH$_2$CH$_2$—, and Ar is pyrrolyl in the ortho position to the —C($R^4$)($R^5$)— substituent on the core phenyl ring; then $R^1$ is not H;

(xv) when q is 1, Y is —CH$_2$—, $R^4$ is H, $R^5$ is H, and Ar is phenyl in the ortho position to the —C($R^4$)($R^5$)— substituent on the core phenyl ring, then $R^1$ is not H; and (xvii) when q is 2, then Ar is in the ortho or meta position to the —C($R^4$)($R^5$)— substituent on the core phenyl ring;

(xviii) when q is 2, Y is —CH$_2$—, $R^4$ is H, $R^5$ is H, and Ar is 1,2-(methylenedioxy)-phenyl, then Ar is in the ortho position to the —C($R^4$)($R^5$)— substituent on the core phenyl ring; and (xix) when q is 2, and Ar is phenyl in the ortho position to the —C($R^4$)($R^5$)— substituent on the core phenyl ring, then $R^1$ is not H.

In another preferred embodiment, the present invention provides novel compounds of Formula (I) wherein q is 1.

In another preferred embodiment, the present invention provides novel compounds of Formula (I) wherein q is 1; and Y is —CH$_2$—, —CH(OCH$_3$)—, or —CH$_2$CH$_2$—.

In another preferred embodiment, the present invention provides novel compounds of Formula (I) wherein q is 1; Y is —CH$_2$—, —CH(OCH$_3$)—, or —CH$_2$CH$_2$—; and $R^1$ is C(=O)N$R^{12}R^{13}$.

In another preferred embodiment, the present invention provides novel compounds of Formula (I) wherein q is 1; Y is —CH$_2$—, —CH(OCH$_3$)—, or —CH$_2$CH$_2$—; and $R^1$ is C(=O)NH$_2$.

In another preferred embodiment, the present invention provides novel compounds of Formula (I) wherein: the Ar group is in the ortho position to the —C($R^4$)($R^5$)— substituent on the core phenyl ring;

Ar is $C_6$-$C_{10}$ aryl substituted by 0-5 $R^3$;

$C_5$-$C_{10}$ cycloalkenyl substituted by 0-5 $R^3$; or a 5 to 10 membered heteroaryl group substituted by 0-5 $R^3$, wherein said aryl, cycloalkenyl, or heteroaryl group is selected from phenyl, cyclopentenyl, cyclohexenyl, cycloheptenyl, naphthyl, quinolinyl, isoxazolyl, thienyl, benzothienyl, (1,1-dioxo)-benzothienyl, indolyl, furyl, benzofuryl, pyridyl, seleninyl, 1,3-dihydro-isoindolyl, or 2-benzo[1,4]dioxine;

$R^1$ is C(=O)N$R^{12}R^{13}$;

and pharmaceutically acceptable salt forms thereof.

In another preferred embodiment, the present invention provides novel compounds of Formula (I) wherein the Ar group is in the ortho position to the —C($R^4$)($R^5$)— substituent on the core phenyl ring; and q is 1.

In another preferred embodiment, the present invention provides novel compounds of Formula (I) wherein the Ar group is in the ortho position to the —C($R^4$)($R^5$)— substituent on the core phenyl ring; q is 1; and Ar is phenyl substituted by 0-5 $R^3$.

In another preferred embodiment, the present invention provides novel compounds of Formula (I) wherein the Ar group is in the ortho position to the —C($R^4$)($R^5$)— substituent on the core phenyl ring; q is 1; Ar is phenyl substituted by 0-5 $R^3$; and Y is —CH$_2$—, —CH(OCH$_3$)—, or —CH$_2$CH$_2$—.

In another preferred embodiment, the present invention provides novel compounds of Formula (I) wherein the Ar group is in the ortho position to the —C($R^4$)($R^5$)— substituent on the core phenyl ring; q is 1; Y is —CH$_2$—, —CH(OCH$_3$)—, or —CH$_2$CH$_2$—; Ar is phenyl substituted by 0-3 $R^3$; and $R^3$ is selected from F, Cl, and Br.

In another preferred embodiment, the present invention provides novel compounds of Formula (I) wherein the Ar group is in the ortho position to the —C($R^4$)($R^5$)— substituent on the core phenyl ring; q is 1; Y is —CH$_2$—, —CH(OCH$_3$)—, or —CH$_2$CH$_2$—; Ar is phenyl substituted by 0-3 R$^3$; R$^3$ is selected from F, Cl, and Br; and R$^1$ is C(=O)NH$_2$.

In another preferred embodiment, the present invention provides novel compounds of Formula (I) wherein: the Ar group is in the meta position to the —C(R$^4$)(R$^5$)— substituent on the core phenyl ring;
Ar is C$_6$-C$_{10}$ aryl substituted by 0-5 R$^3$;
  C$_5$-C$_{10}$ cycloalkenyl substituted by 0-5 R$^3$; or a
  5 to 10 membered heteroaryl group substituted by 0-5 R$^3$,
    wherein said aryl, cycloalkenyl, and heteroaryl group is selected from phenyl, cyclopentenyl, cyclohexenyl, cycloheptenyl, naphthyl, quinolinyl, isoxazolyl, thienyl, benzothienyl, (1,1-dioxo)-benzothienyl, indolyl, furyl, benzofuryl, pyridyl, seleninyl, 1,3-dihydro-isoindolyl, pyrrolyl, or 2-benzo[1,4]dioxine;
R$^1$ is H or C(=O)NR$^{12}$R$^{13}$;
and pharmaceutically acceptable salt forms thereof.

In another preferred embodiment, the present invention provides novel compounds of Formula (I) wherein: the Ar group is in the meta position to the —C(R$^4$)(R$^5$)— substituent on the core phenyl ring; q is 1; and R$^1$ is C(=O)NR$^{12}$R$^{13}$.

In another preferred embodiment, the present invention provides novel compounds of Formula (I) wherein: the Ar group is in the meta position to the —C(R$^4$)(R$^5$)— substituent on the core phenyl ring; q is 1; Ar is phenyl substituted by 0-5 R$^3$; and R$^1$ is C(=O)NR$^{12}$R$^{13}$.

In another preferred embodiment, the present invention provides novel compounds of Formula (I) wherein: the Ar group is in the meta position to the —C(R$^4$)(R$^5$)— substituent on the core phenyl ring; q is 1; Ar is phenyl substituted by 0-5 R$^3$; Y is —CH$_2$—, —CH(OCH$_3$)—, or —CH$_2$CH$_2$—; and R$^1$ is C(=O)NR$^{12}$R$^{13}$.

In another preferred embodiment, the present invention provides novel compounds of Formula (I) wherein: the Ar group is in the meta position to the —C(R$^4$)(R$^5$)— substituent on the core phenyl ring; q is 1; Y is —CH$_2$—, —CH(OCH$_3$)—, or —CH$_2$CH$_2$—; Ar is phenyl substituted by 0-3 R$^3$; R$^3$ is selected from F, Cl, and Br; and R$^1$ is C(=O)NR$^{12}$R$^{13}$.

In another preferred embodiment, the present invention provides novel compounds of Formula (I) wherein: the Ar group is in the meta position to the —C(R$^4$)(R$^5$)— substituent on the core phenyl ring; q is 1; Y is —CH$_2$—, —CH(OCH$_3$)—, or —CH$_2$CH$_2$—; Ar is phenyl substituted by 0-3 R$^3$; R$^3$ is selected from F, Cl, and Br; and R$^1$ is C(=O)NH$_2$.

In another preferred embodiment, the present invention provides novel compounds of Formula (I):

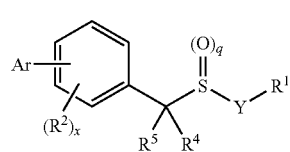

(I)

and stereoisomeric forms, mixtures of stereoisomeric forms or pharmaceutically acceptable salt forms thereof,
wherein:
Ar is C$_6$-C$_{10}$ aryl substituted by 0-3 R$^3$;
  C$_5$-C$_{10}$ cycloalkenyl substituted by 0-3 R$^3$; or a
  5 to 10 membered heteroaryl group substituted by 0-1 R$^3$;
    wherein said aryl, cycloalkenyl, or heteroaryl group is selected from phenyl, cyclopentenyl, cyclohexenyl, cycloheptenyl, naphthyl, quinolinyl, isoxazolyl, thienyl, benzothienyl, (1,1-dioxo)-benzothienyl, indolyl, furyl, benzofuryl, pyridyl, seleninyl, 1,3-dihydro-isoindolyl, pyrrolyl, and 2-benzo[1,4]dioxine;
Y is —CH$_2$—, —CH(OCH$_3$)—, or —CH$_2$CH$_2$—;
R$^1$ is selected from H, C(=O)NR$^{12}$R$^{13}$, and C(=O)OR$^{11}$;
R$^2$ is selected from H, Cl, F, methoxy, ethoxy, methyl, ethyl, and propyl;
alternatively, two R$^2$ groups may be combined to form a methylenedioxy group;
R$^3$ is selected from H, F, Cl, Br, CF$_3$, cyano, OCF$_3$, NO$_2$, OH, phenyl, cyclopropyl, cyclobutyl, cyclopentyl, cyclohexyl, methyl, ethyl, propyl, i-propyl, n-butyl, i-butyl, s-butyl, t-butyl, CH$_2$=CH$_2$, morpholinyl, OR$^{16}$, NR$^{17}$R$^{18}$, CH$_2$OR$^{16}$, C(=O)R$^{16}$, C(=O)OR$^{16}$, C(=O)NR$^{17}$R$^{18}$, SR$^{16}$; S(=O)R$^{16}$; S(=O)$_2$R$^{16}$, and NHS(=O)$_2$R$^{16}$;
alternatively, two R$^3$ groups may be combined to form a methylenedioxy group, an ethylenedioxy group, or a propylenedioxy group;
R$^4$ is H;
R$^5$ is H;
R$^{11}$ at each occurrence is independently selected from H and C$_1$-C$_6$ alkyl substituted with 0-3 R$^{20}$;
R$^{12}$ and R$^{13}$ at each occurrence are each independently selected from H, and C$_1$-C$_3$ alkyl substituted with 0-1 R$^{20}$; wherein said alkyl is methyl, ethyl, n-propyl or i-propyl;
alternatively, R$^{12}$ and R$^{13}$, together with the nitrogen to which they are attached, form a 3-7 membered heterocyclic ring substituted with 0-3 R$^{20}$; wherein said 3-7 membered heterocyclic ring is selected from morpholinyl, piperazinyl, azetidinyl, piperidinyl, and pyrrolidinyl;
R$^{16}$ at each occurrence is independently selected from H, methyl, ethyl, propyl, butyl, and phenyl;
R$^{17}$ and R$^{18}$ at each occurrence are each independently selected from H, methyl, and ethyl; or
alternatively, R$^{17}$ and R$^{18}$, together with the nitrogen to which they are attached, form a 3-7 membered heterocyclic ring selected from piperidinyl, (4-oxo)-piperidinyl and morpholinyl;
R$^{20}$ at each occurrence is independently selected from F, Cl, OH, CN, CF$_3$, methyl, ethyl, propyl, i-propyl, n-butyl, i-butyl, s-butyl, t-butyl, CH$_2$CH$_2$OH, cyclopropyl, cyclobutyl, cyclopentyl, cyclohexyl, pyridyl, and pyrrolidinyl, OR$^{22}$, N$^{23}$R$^{24}$, C(=O)R$^{22}$, C(=O)OR$^{22}$, C(=O)NR$^{23}$R$^{24}$, and phenyl substituted by 0-1 R$^{26}$;
R$^{22}$ at each occurrence is independently selected from H, methyl, ethyl, propyl, butyl, and CH$_2$CH$_2$OH;
R$^{23}$ and R$^{24}$ at each occurrence are each independently selected from H, methyl, ethyl, propyl, butyl, and phenyl;
R$^{26}$ at each occurrence is independently selected from H, F, methyl, ethyl, propyl, methoxy, and ethoxy;
x is 0, 1, or 2; and
q is 1 or 2;
provided,
(ii) when Y is —CH$_2$—, R$^1$ is H, C(=O)OR$^{11}$, or C(=O)NR$^{12}$R$^{13}$; Ar is phenyl substituted by 0-2 R$^3$, and R$^3$ is H, F, Cl, Br, I, CH$_3$, OCH$_3$, SCH$_3$, CN, NO$_2$, or methylendioxyphenyl; then Ar is in the ortho or meta position to the —C(R$^4$)(R$^5$)— substituent on the core phenyl ring;
(v) when Ar is in the meta position to the —C(R$^4$)(R$^5$)— substituent on the core phenyl ring and Ar is a heteroaryl group attached to the phenyl ring through a nitrogen atom, then Ar is pyrrolyl, indolyl, imidazolyl, benzimidazolyl, benzotriazolyl, triazolyl, or 1,3-dihydroisoindolyl;
(vi) when Y is —CH$_2$— and Ar is pyridyl substituted by a nitro, a methyl, a second methyl, and a C(=O)OC$_3$H$_7$ group, then R$^1$ is not H;

(xiii) when q is 1, Y is —CH$_2$— or —CH$_2$CH$_2$—, and Ar is pyrrolyl in the ortho position to the —C(R$^4$)(R$^5$)— substituent on the core phenyl ring; then R$^1$ is not H;

(xv) when q is 1, Y is —CH$_2$—, R$^4$ is H, R$^5$ is H, and Ar is phenyl in the ortho position to the —C(R$^4$)(R$^5$)— substituent on the core phenyl ring, then R$^1$ is not H;

(xvii) when q is 2, then Ar is in the ortho or meta position to the —C(R$^4$)(R$^5$)— substituent on the core phenyl ring;

(xviii) when q is 2, Y is —CH$_2$—, R$^4$ is H, R$^5$ is H, and Ar is 1,2-(methylenedioxy)-phenyl, then Ar is in the ortho position to the —C(R$^4$)(R$^5$)— substituent on the core phenyl ring; and (xix) when q is 2, and Ar is phenyl in the ortho position to the —C(R$^4$)(R$^5$)— substituent on the core phenyl ring, then R$^1$ is not H.

In another preferred embodiment, the present invention provides novel compounds of Formula (I) wherein: the Ar group is in the ortho position to the —C(R$^4$)(R$^5$)— substituent on the core phenyl ring; q is 1; Ar is phenyl substituted by 0-3 R$^3$; and R$^1$ is C(=O)NR$^{12}$R$^{13}$; and pharmaceutically acceptable salt forms thereof.

In another preferred embodiment, the present invention provides novel compounds of Formula (I) wherein: the Ar group is in the ortho position to the —C(R$^4$)(R$^5$)— substituent on the core phenyl ring; q is 1; Y is —CH$_2$—; Ar is phenyl substituted by 0-3 R$^3$; R$^1$ is C(=O)NR$^{12}$R$^{13}$; and R$^3$ is selected from F, Cl, and Br; and pharmaceutically acceptable salt forms thereof.

In another preferred embodiment, the present invention provides novel compounds of Formula (I) wherein: the Ar group is in the meta position to the —C(R$^4$)(R$^5$)— substituent on the core phenyl ring; q is 1; Ar is phenyl substituted by 0-3 R$^3$; and R$^1$ is C(=O)NR$^{12}$R$^{13}$; and pharmaceutically acceptable salt forms thereof.

In another preferred embodiment, the present invention provides novel compounds of Formula (I) wherein: the Ar group is in the meta position to the —C(R$^4$)(R$^5$)— substituent on the core phenyl ring; q is 1; Y is —CH$_2$—; Ar is phenyl substituted by 0-3 R$^3$; R$^1$ is C(=O)NR$^{12}$R$^{13}$; and R$^3$ is selected from F, Cl, and Br; and pharmaceutically acceptable salt forms thereof.

In another preferred embodiment, the present invention provides novel compounds of Formula (I) selected from the following Examples:

|  |  |  |  |
|---|---|---|---|
|  | Example 1 | Example 2 | Example 3 |
| Example 4 | Example 5 | Example 6 | Example 7 |
| Example 8 | Example 9 | Example 10 | Example 11 |
| Example 12 | Example 13 | Example 14 | Example 15 |
| Example 16 | Example 17 | Example 18 | Example 19 |
| Example 20 | Example 21 | Example 22 | Example 23 |
| Example 24 | Example 25 | Example 26 | Example 27 |
| Example 28 | Example 29 | Example 30 | Example 31 |
| Example 32 | Example 33 | Example 34 | Example 35 |
| Example 36 | Example 37 | Example 38 | Example 39 |
| Example 40 | Example 41 | Example 42 | Example 43 |
| Example 44 | Example 45 | Example 46 | Example 47 |
| Example 48 | Example 49 | Example 50 | Example 51 |
| Example 52 | Example 53 | Example 54 | Example 55 |
| Example 56 | Example 57 | Example 58 | Example 59 |
| Example 60 | Example 61 | Example 62 | Example 63 |
| Example 64 | Example 65 | Example 66 | Example 67 |
| Example 68 | Example 69 | Example 70 | Example 71 |
| Example 72 | Example 73 | Example 74 | Example 75 |
| Example 76 | Example 77 | Example 78 | Example 79 |
| Example 80 | Example 81 | Example 82 | Example 83 |
| Example 84 | Example 85 | Example 86 | Example 87 |
| Example 88 | Example 89 | Example 90 | Example 91 |
| Example 92 | Example 93 | Example 94 | Example 95 |
| Example 96 | Example 97 | Example 98 | Example 99 |
| Example 100 | Example 101 | Example 102 | Example 103 |
| Example 104 | Example 105 | Example 106 | Example 107 |
| Example 108 | Example 109 | Example 110 | Example 111 |
| Example 112 | Example 113 | Example 114 | Example 115 |
| Example 116 | Example 117 | Example 118 | Example 119 |
| Example 120 | Example 121 | Example 122 | Example 123 |
| Example 124 | Example 125 | Example 126 | Example 127 |
| Example 128 | Example 129 | Example 130 | Example 131 |
| Example 132 | Example 133 | Example 134 | Example 135 |
| Example 136 | Example 137 | Example 138 | Example 139 |
| Example 140 | Example 141 | Example 142 | Example 143 |
| Example 144 | Example 145 | Example 146 | Example 147 |
| Example 148 | Example 149 | Example 150 | Example 151 |
| Example 152 | Example 153 | Example 154 | Example 155 |
| Example 156 | Example 157 | Example 158 | Example 159 |
| Example 160 | Example 161 | Example 162 | Example 163 |
| Example 164 | Example 165 | Example 166 | Example 167 |
| Example 168 | Example 169 | Example 170 | Example 171 |
| Example 172 | Example 173 | Example 174 | Example 175 |
| Example 176 | Example 177 | Example 178 | Example 179 |
| Example 180 | Example 181 | Example 182 | Example 183 |
| Example 184 | Example 185 | Example 186 | Example 187 |
| Example 188 | Example 189 | Example 190 | Example 191 |
| Example 192 | Example 193 | Example 194 | Example 195 |
| Example 196 | Example 197 | Example 198 | Example 199 |
| Example 200 | Example 201 | Example 202 | Example 203 |
| Example 204 | Example 205 | Example 206 | Example 207 |
| Example 208 | Example 209 | Example 210 | Example 211 |
| Example 212 | Example 213 | Example 214 | Example 215 |
| Example 216 | Example 217 | Example 218 | Example 219 |
| Example 220 | Example 221 | Example 222 | Example 223 |
| Example 224 | Example 225 | Example 226 | Example 227 |
| Example 228 | Example 229 | Example 230 | Example 231 |
| Example 232 | Example 233 | Example 234 | Example 235 |
| Example 236 | Example 237 | Example 238 | Example 239 |
| Example 240 | Example 241 | Example 242 | Example 243 |
| Example 244 | Example 245 | Example 246 | Example 247 |
| Example 248 | Example 249 | Example 250 | Example 251 |
| Example 252 | Example 253 | Example 254 | Example 255 |
| Example 256 | Example 257 | Example 258 | Example 259 |
| Example 260 | Example 261 | Example 262 | Example 263 |
| Example 264 | Example 265 | Example 266 | Example 267 |
| Example 268 | Example 269 | Example 270 | Example 271 |
| Example 272 | Example 273 | Example 274 | Example 275 |
| Example 276 | Example 277 | Example 278 | Example 279 |
| Example 280 | Example 281 | Example 282 | Example 283 |
| Example 284 | Example 285 | Example 286 | Example 287 |
| Example 288 | Example 289 | Example 290 | Example 291 |
| Example 292 | Example 293 | Example 294 | Example 295 |
| Example 296 | Example 297 | Example 298 | Example 299 |
| Example 300 | Example 301 | Example 302 | Example 303 |
| Example 304 | Example 305 | Example 306 | Example 307 |
| Example 308 | Example 309 | Example 310 | Example 311 |
| Example 312 | Example 313 | Example 314 | Example 315 |
| Example 316 | Example 317 | Example 318 | Example 319 |
| Example 320 | Example 321 | Example 322 | Example 323 |
| Example 324 | Example 325 | Example 326 | Example 327 |
| Example 328 | Example 329 | Example 330 | Example 331 |
| Example 332 | Example 333 | Example 334 | Example 335 |
| Example 336 | Example 337 | Example 338 | Example 339 |
| Example 340 | Example 341 | Example 342 | Example 343 |
| Example 344 | Example 345 | Example 346 | Example 347 |
| Example 348 | Example 349 | Example 350 | Example 351 |
| Example 352 | Example 353 | Example 354 | Example 355 |
| Example 356 | Example 357 | Example 358 | Example 359 |
| Example 360 | Example 361 | Example 362 | Example 363 |
| Example 364 | Example 365 | Example 366 | Example 367 |
| Example 368 | Example 369 | Example 370 | Example 371 |
| Example 372 | Example 373 | Example 374 | Example 375 |
| Example 376 | Example 377 | Example 378 | Example 379 |
| Example 380 | Example 381 | Example 382 | Example 383 |
| Example 384 | Example 385 | Example 386 | Example 387 |
| Example 388 | Example 389 | Example 390 | Example 391 |
| Example 392 | Example 393 | Example 394 | Example 395 |
| Example 396 | Example 397 | Example 398 | Example 399 |
| Example 400 | Example 401 | Example 402 | Example 403 |
| Example 404 | Example 405 | Example 406 | Example 407 |
| Example 408 | Example 409 | Example 410 | Example 411 |
| Example 412 | Example 413 | Example 414 | Example 415 |
| Example 416 | Example 417 | Example 418 | Example 419 |
| Example 420 | Example 421 | Example 422 | Example 423 |

| | | | |
|---|---|---|---|
| Example 424 | Example 425 | Example 426 | Example 427 |
| Example 428 | Example 429 | Example 430 | Example 431 |
| Example 432 | Example 433 | and | Example 434 | and pharmaceutically acceptable salt forms thereof.

In another preferred embodiment, the present invention provides novel compounds of Formula (I) selected from the following Examples:

| | | | |
|---|---|---|---|
| Example 436; | Example 437; | Example 438; | Example 439; |
| Example 440; | Example 441; | Example 442; | Example 443; |
| Example 444; | Example 445; | Example 446; | and |
| Example 447; | | | | and pharmaceutically acceptable salt forms thereof.

In another preferred embodiment, the present invention provides novel compounds of Formula (I) selected from Examples wherein Ar is substituted or unsubstituted phenyl.

In another preferred embodiment, the present invention provides novel compounds of Formula (I) selected from Examples wherein Ar is substituted or unsubstituted cycloalkenyl.

In another preferred embodiment, the present invention provides novel compounds of Formula (I) selected from Examples wherein Ar is substituted or unsubstituted heteroaryl.

In another preferred embodiment, the present invention provides novel compounds of Formula (I) selected from Examples wherein Ar is substituted or unsubstituted heteroaryl; wherein heteroaryl is one of quinolinyl, isoxazolyl, thienyl, benzothienyl, (1,1-dioxo)-benzothienyl, indolyl, furyl, benzofuryl, pyridyl, seleninyl, 1,3-dihydro-isoindolyl, pyrrolyl, or 2-benzo[1,4]dioxine.

In a second embodiment, the present invention provides a method for treatment of diseases comprising administering to a subject in need thereof a therapeutically effective amount of a compound of Formula (I), or a pharmaceutically acceptable salt thereof. In a preferred embodiment, the present invention provides a method of treating or preventing diseases or disorders, including treatment of sleepiness, promotion of wakefulness, treatment of Parkinson's disease, cerebral ischemia, stroke, sleep apneas, eating disorders, stimulation of appetite and weight gain, treatment of attention deficit hyperactivity disorder, enhancing function in disorders associated with hypofunctionality of the cerebral cortex, including, but not limited to, depression, schizophrenia, fatigue, in particular, fatigue associated with neurologic disease, such as multiple sclerosis, chronic fatigue syndrome, and improvement of cognitive dysfunction.

In a preferred second embodiment the present invention provides a method of treating sleepiness associated with narcolepsy, obstructive sleep apnea, or shift work disorder; Parkinson's disease; Alzheimer's disease; attention deficit disorder; attention deficit hyperactivity disorder; depression; or fatigue in a mammal comprising administering to said mammal a therapeutically effective amount of a compound of Formula (I).

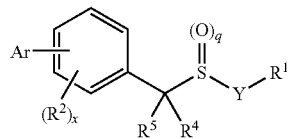

(I)

and stereoisomeric forms, mixtures of stereoisomeric forms or pharmaceutically acceptable salt forms thereof, wherein:

Ar is $C_6$-$C_{10}$ aryl substituted by 0-5 $R^3$;
$C_5$-$C_{10}$ cycloalkenyl substituted by 0-5 $R^3$; or
5 to 14 membered heteroaryl group substituted by 0-5 $R^3$, wherein said heteroaryl group comprises one, two, or three heteroatoms selected from N, O, S or Se;

Y is $C_1$-$C_6$ alkylene substituted with 0-3 $R^{20A}$;
$C_1$-$C_4$ alkylene-$Z^1$—($C_1$-$C_4$ alkylene)$_n$ substituted with 0-3 $R^{20A}$; or
($C_1$-$C_4$ alkylene)$_m$-$Z^2$—($C_1$-$C_4$ alkylene)$_n$ substituted with 0-3 $R^{20A}$;

$Z^1$ is O, $NR^{10}$, S, S(=O), or S(=O)$_2$;

$Z^2$ is $CR^{21}$=$CR^{21}$, C≡C, $C_6$-$C_{10}$ arylene substituted with 0-3 $R^{20}$; 5-10 membered heteroarylene substituted with 0-3 $R^{20}$; $C_3$-$C_6$ cycloalkylene substituted with 0-3 $R^{20}$; or 3-6 membered heterocycloalkylene substituted with 0-3 $R^{20}$;

$R^1$ is selected from H, C(=O)$NR^{12}R^{13}$, C(=N)$NR^{12}R^{13}$, OC(=O)$NR^{12}R^{13}$, $NR^{21}$C(=O)$NR^{12}R^{13}$, $NR^{21}$S(=O)$_2$$NR^{12}R^{13}$, —($C_6$-$C_{10}$ aryl)-$NR^{12}R^{13}$ wherein said aryl is substituted with 0-3 $R^{20}$; $NR^{21}$C(=O)$R^{14}$, C(=O)$R^{14}$, C(=O)$OR^{11}$, OC(=O)$R^{11}$, and $NR^{21}$S(=O)$_2$$R^{11}$;

$R^2$ is selected from H, F, Cl, Br, I, $OR^{16}$, $OR^{25}$, $NR^{17}R^{18}$, NHOH, NO$_2$, CN, CF$_3$, $C_1$-$C_6$ alkyl, $C_2$-$C_6$ alkenyl, $C_2$-$C_6$ alkynyl, C(=O)$R^{16}$, C(=O)$OR^{16}$, OC(=O)$R^{16}$, C(=O)$NR^{17}R^{18}$, $NR^{15}$C(=O)$R^{16}$, $NR^{15}$CO$_2$$R^{16}$, OC(=O)$NR^{17}R^{18}$, $NR^{15}$C(=S)$R^{16}$, $SR^{16}$; S(=O)$R^{16}$; and S(=O)$_2$$R^{16}$;

alternatively, two $R^2$ groups may be combined to form a methylenedioxy group, an ethylenedioxy group, or a propylenedioxy group;

$R^3$ is selected from H, F, Cl, Br, I, $OR^{16}$, OCF$_3$, $OR^{25}$, $NR^{17}R^{18}$, NHOH, NO$_2$, CN, CF$_3$, CH$_2$$OR^{16}$, $C_1$-$C_6$ alkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, $C_7$-$C_{10}$ arylalkyl, C(=O)$R^{16}$, C(=O)$OR^{16}$, OC(=O)$R^{16}$, C(=O)$NR^{17}R^{18}$, $NR^{15}$C(=O)$R^{16}$, $NR^{15}$CO$_2$$R^{16}$, OC(=O)$NR^{17}R^{18}$, $NR^{15}$C(=S)$R^{16}$, $SR^{16}$; S(=O)$R^{16}$; S(=O)$_2$$R^{16}$ and $NR^{15}$S(=O)$_2$$R^{16}$;

alternatively, two $R^3$ groups may be combined to form a methylenedioxy group, an ethylenedioxy group, or a propylenedioxy group;

$R^4$ and $R^5$ at each occurrence are independently selected from H, $C_1$-$C_6$ alkyl, $C_2$-$C_6$ alkenyl, and $C_2$-$C_6$ alkynyl;

alternatively, $R^4$ and $R^5$ together with the carbon atom to which they are attached, form a 3-7 membered spirocyclic ring;

$R^{10}$ is selected from H, $C_1$-$C_6$ alkyl substituted with 0-3 $R^{20}$; $C_6$-$C_{10}$ aryl substituted with 0-3 $R^{10}$; C(=O)$R^{14}$, $SR^{14}$, S(=O)$R^{14}$, and S(=O)$_2$$R^{14}$;

$R^{11}$ at each occurrence is independently selected from H, $C_1$-$C_6$ alkyl substituted with 0-3 $R^{20}$; and $C_6$-$C_{10}$ aryl substituted with 0-3 $R^{20}$;

$R^{12}$ and $R^{13}$ at each occurrence are each independently selected from H, $C_1$-$C_6$ alkyl substituted with 0-3 $R^{20}$; and $C_6$-$C_{10}$ aryl substituted with 0-3 $R^{20}$;

alternatively, $R^{12}$ and $R^{13}$, together with the nitrogen to which they are attached, form a 3-7 membered heterocyclic ring substituted with 0-3 $R^{20}$;

$R^{14}$ at each occurrence is independently selected from $C_1$-$C_6$ alkyl substituted with 0-3 $R^{20}$; $C_6$-$C_{10}$ aryl substituted with 0-3 $R^{20}$; and $C_7$-$C_{10}$ arylalkyl substituted with 0-3 $R^{20}$;

$R^{15}$ at each occurrence is independently selected from H and $C_1$-$C_6$ alkyl;

$R^{16}$ at each occurrence is independently selected from H, $C_1$-$C_6$ alkyl, and $C_6$-$C_{10}$ aryl;

$R^{17}$ and $R^{18}$ at each occurrence are each independently selected from H, $C_1$-$C_6$ alkyl, and $C_6$-$C_{10}$ aryl, or alternatively, $R^{17}$ and $R^{18}$, together with the nitrogen to which they are attached, form a 3-7 membered heterocyclic ring, wherein said 3-7 membered heterocyclic ring is substituted with 0-2 oxo groups;

$R^{20}$ at each occurrence is independently selected from F, Cl, Br, I, OH, $OR^{22}$, $OR^{25}$, $NR^{23}R^{24}$, NHOH, $NO_2$, CN, $CF_3$, $C_1$-$C_6$ alkyl, $C_1$-$C_6$ alkyl-OH, $C_2$-$C_6$ alkenyl, $C_2$-$C_6$ alkynyl, $C_3$-$C_7$ cycloalkyl, 3-7 membered heterocycloalkyl, phenyl substituted by 0-1 $R^{26}$; 5 or 6 membered heteroaryl, $C_7$-$C_{10}$ arylalkyl, =O, C(=O)$R^{22}$, C(=O)$OR^{22}$, OC(=O)$R^{22}$, C(=O)$NR^{23}R^{24}$, $NR^{21}$C(=O)$R^{22}$, $NR^{21}CO_2R^{22}$, OC(=O)$NR^{23}R^{24}$, $NR^{21}$C(=S)$R^{22}$, $SR^{22}$; S(=O)$R^{22}$; and S(=O)$_2R^{22}$;

$R^{20A}$ at each occurrence is independently selected from F, Cl, Br, OH, $OR^{22}$, NHOH, $NO_2$, CN, $CF_3$, $C_1$-$C_6$ alkyl, $C_1$-$C_6$ alkyl-OH, $C_2$-$C_6$ alkenyl, $C_2$-$C_6$ alkynyl, $C_3$-$C_7$ cycloalkyl, 3-7 membered heterocycloalkyl, phenyl substituted by 0-1 $R^{26}$; 5 or 6 membered heteroaryl, and $C_7$-$C_{10}$ arylalkyl;

$R^{21}$ at each occurrence is independently selected from H and $C_1$-$C_6$ alkyl;

$R^{22}$ at each occurrence is independently selected from H, $C_1$-$C_6$ alkyl, $C_1$-$C_6$ alkyl-OH, and $C_6$-$C_{10}$ aryl;

$R^{23}$ and $R^{24}$ at each occurrence are each independently selected from H, $C_1$-$C_6$ alkyl, and $C_6$-$C_{10}$ aryl, or alternatively, $R^{23}$ and $R^{24}$ together with the nitrogen to which they are attached, form a 3-7 membered heterocyclic ring;

$R^{25}$ at each occurrence is independently the residue of an amino acid after the hydroxyl group of the carboxyl group is removed;

$R^{26}$ at each occurrence is independently selected from H, F, Cl, Br, $C_1$-$C_6$ alkyl, and $C_1$-$C_6$ alkoxy;

m is 0 or 1;

n is 0 or 1;

x is 0, 1, 2, 3, or 4; and q is 0, 1, or 2.

In another preferred second embodiment the present invention provides a method of treating a sleep affecting disease or disorder in a mammal comprising administering to said mammal a therapeutically effective amount of a compound of Formula (I) in order to promote wakefulness.

In another preferred second embodiment the present invention provides a method for the treatment of a neurological disease or disorder in a mammal comprising administering to said mammal a therapeutically effective amount of a compound of Formula (I), wherein said neurological disease or disorder is selected from Parkinson's disease; Alzheimer's disease; attention deficit disorder; attention deficit hyperactivity disorder; depression; and fatigue associated with a neurological disease or disorder.

In another preferred second embodiment the present invention provides a method wherein the compound is administered for the treatment of sleepiness associated with narcolepsy.

In a third embodiment, the present invention provides a pharmaceutical composition comprising a compound of Formula (I), or a pharmaceutically acceptable salt or ester form thereof, and one or more pharmaceutically acceptable excipients.

In a preferred third embodiment, the present invention provides a pharmaceutical composition comprising a therapeutically effective amount of compound of Formula (I), or a pharmaceutically acceptable salt or ester form thereof, and one or more pharmaceutically acceptable excipients.

In a fourth embodiment, the present invention provides for the use of compounds of formula (I) or pharmaceutically acceptable salts thereof for the manufacture of a medicament for the treatment of a disease or disorder.

These and other objects, features and advantages of the substituted biaryl-methanesulfinyl acetamides derivatives will be disclosed in the following detailed description of the patent disclosure.

DEFINITIONS

The following terms and expressions contained herein are defined as follows:

As used herein, the term "about" refers to a range of values from ±10% of a specified value. For example, the phrase "about 50 mg" includes ±10% of 50, or from 45 to 55 mg.

As used herein, a range of values in the form "x-y" or "x to y", or "x through y", include integers x, y, and the integers therebetween. For example, the phrases "1-6", or "1 to 6" or "1 through 6" are intended to include the integers 1, 2, 3, 4, 5, and 6. Preferred embodiments include each individual integer in the range, as well as any subcombination of integers. For example, preferred integers for "1-6" can include 1, 2, 3, 4, 5, 6, 1-2, 1-3, 1-4, 1-5, 2-3, 2-4, 2-5, or 2-6, etc.

As used herein "stable compound" or "stable structure" refers to a compound that is sufficiently robust to survive isolation to a useful degree of purity from a reaction mixture, and preferably capable of formulation into an efficacious therapeutic agent. The present invention is directed only to stable compounds.

As used herein, the term "alkyl" refers to a straight-chain, or branched, alkyl group having 1 to 6 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, etc. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons, such as methyl, ethyl, propyl, isopropyl, butyl, isobutyl, sec-butyl, and tert-butyl. A designation such as "$C_1$-$C_4$ alkyl" refers to an alkyl radical containing from 1 to 4 carbon atoms.

As used herein, the term "alkenyl" refers to a straight-chain, or branched, hydrocarbon group of 2 to 6 carbon atoms having at least one carbon-carbon double bond. A designation "$C_2$-$C_6$ alkenyl" refers to an alkenyl radical containing from 2 to 6 carbon atoms. Examples of alkenyl groups include, but are not limited to, ethenyl, propenyl, isopropenyl, butenyl, pentenyl, 2,4-pentadienyl, etc. Preferred alkenyl groups include ethenyl and propenyl.

As used herein, the term "alkynyl" refers to a straight chain, or branched hydrocarbon chains of 2 to 6 carbon atoms having at least one carbon-carbon triple bond. A designation "$C_2$-$C_6$ alkynyl" refers to an alkynyl radical containing from 2 to 6 carbon atoms. Examples include, but are not limited to, ethynyl, propynyl, isopropynyl, 3,5-hexadiynyl, etc.

As used herein, the term "alkylene" refers to a substituted or unsubstituted, branched or straight chained hydrocarbon of 1 to 6 carbon atoms, which is formed by the removal of two hydrogen atoms. A designation such as "$C_1$-$C_4$ alkylene" refers to an alkylene radical containing from 1 to 4 carbon atoms. Examples include, but are not limited to, methylene (—$CH_2$—), ethylene (—$CH_2CH_2$—), ethylidene (—CH($CH_3$)—), propylene (—$CH_2CH_2CH_2$—), iso-propylene (—CH($CH_3$)$CH_2$—), propylidene (—CH($CH_2CH_3$)—), butylene (—$CH_2CH_2CH_2CH_2$—), etc.

As used herein, the term "cycloalkylene" refers to a saturated or partially saturated mono- or bicyclic alkyl ring system containing 3 to 10 carbon atoms, which is formed by the removal of two hydrogen atoms. A designation such as "$C_3$-

$C_6$ cycloalkylene" refers to a cycloalkyl radical containing from 3 to 6 ring carbon atoms. Preferred cycloalkylene groups include those containing 3, 4, 5, or 6 ring carbon atoms. Examples of cycloalkylene groups include such groups as cyclopropylene (—$C_3H_4$—), cyclobutylene (—$C_4H_6$—), cyclopentylene (—$C_5H_8$—), cyclopentenylene (—$C_5H_6$—), cyclohexylene (—$C_6H_{10}$—), and cyclohexenylene (—$C_6H_8$—).

As used herein, the term "phenylene" refers to a phenyl group with an additional hydrogen atom removed, i.e. a moiety with the structure of (—$C_6H_4$—).

As used herein, the terms "carbocycle", "carbocyclic" or "carbocyclyl" refer to a substituted or unsubstituted, stable monocyclic or bicyclic hydrocarbon ring system which is saturated, partially saturated or unsaturated, and contains from 3 to 10 ring carbon atoms. Accordingly the carbocyclic group may be aromatic or non-aromatic, and includes the cycloalkyl and aryl compounds defined herein. The bonds connecting the endocyclic carbon atoms of a carbocyclic group may be single, double, triple, or part of a fused aromatic moiety.

As used herein, the term "cycloalkyl" refers to a saturated or partially saturated mono- or bicyclic alkyl ring system containing 3 to 10 carbon atoms. A designation such as "$C_3$-$C_7$ cycloalkyl" refers to a cycloalkyl radical containing from 3 to 7 ring carbon atoms. Preferred cycloalkyl groups include those containing 3, 4, 5, 6, or 7 ring carbon atoms. More preferred cycloalkyl groups include those containing 3, 4, 5, or 6 ring carbon atoms. Examples of cycloalkyl groups include such groups as cyclopropyl, cyclobutyl, cyclopentyl, cyclohexl, cycloheptyl, cyclooctyl, pinenyl, and adamantanyl.

As used herein, the term "cycloalkenyl" refers to partially unsaturated mono- or bicyclic alkenyl ring system containing 5 to 10 carbon atoms. A designation such as "$C_5$-$C_{10}$ cycloalkenyl" refers to a cycloalkenyl radical containing from 5 to 10 ring carbon atoms and one or more double bonds. Preferred cycloalkenyl groups include those containing 5 or 7 ring carbon atoms. Examples of cycloalkenyl groups include such groups as cyclopentenyl, cyclohexenyl, and cycloheptenyl.

As used herein, the term "aryl" refers to a substituted or unsubstituted, mono- or bicyclic hydrocarbon aromatic ring system having 6 to 10 ring carbon atoms. Examples include phenyl and naphthyl. Preferred aryl groups include unsubstituted or substituted phenyl and naphthyl groups. Included within the definition of "aryl" are fused ring systems, including, for example, ring systems in which an aromatic ring is fused to a cycloalkyl ring. Examples of such fused ring systems include, for example, indane, indene, and tetrahydronaphthalene.

As used herein, the term "arylene" refers to an aryl group with an additional hydrogen atom removed, i.e. an aryl group bonded through two carbon atoms, for example phenylene.

As used herein, the term "heteroarylene" refers to a heteroaryl group with an additional hydrogen atom removed, i.e. a heteroaryl group bonded through two carbon atoms, for example furan-2,5-diyl; or a heteroaryl group bonded through a carbon atom and a nitrogen atom, for example pyrrol-1,2-diyl.

As used herein, the term "heterocycloalkylene" refers to a heterocycloalkyl group with an additional hydrogen atom removed, i.e. a heterocycloalkyl group bonded through two carbon atoms or a heterocycloalkyl group bonded through a carbon atom and a nitrogen atom.

As used herein, the terms "heterocycle", "heterocyclic" or "heterocyclyl" refer to a substituted or unsubstituted carbocyclic group in which the ring portion includes at least one to four heteroatoms, such as O, N, or S. The nitrogen and sulfur heteroatoms may be optionally oxidized, and the nitrogen may be optionally substituted in non-aromatic rings. Heterocycles are intended to include heteroaryl and heterocycloalkyl groups. Examples of heterocyclic groups include pyrrolyl, furanyl, thienyl, pyrazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl, as well as, pyrrolidinyl, pyrrolinyl, imidazolidinyl, imidazolinyl, pyrazolidinyl, pyrazolinyl, pyrazalinyl, piperidyl, piperazinyl, morpholinyl, thiomorpholinyl, tetrahydrofuranyl, dithiolyl, oxathiolyl, dioxazolyl, oxathiazolyl, pyranyl, oxazinyl, oxathiazinyl, and oxadiazinyl. Examples of 3 to 7 membered heterocyclic groups include pyrrolyl, furanyl, thienyl, pyrazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, and triazinyl, as well as, pyrrolidinyl, pyrrolinyl, imidazolidinyl, imidazolinyl, pyrazolidinyl, pyrazolinyl, pyrazalinyl, piperidyl, piperazinyl, morpholinyl, thiomorpholinyl, tetrahydrofuranyl, dithiolyl, oxathiolyl, dioxazolyl, oxathiazolyl, pyranyl, oxathiazinyl, and oxadiazinyl.

As used herein, the term "heterocycloalkyl" refers to a 3 to 7 membered cycloalkyl group in which one, two or three ring carbon atoms are replaced by a heteroatom such as —O—, —N—, or —S—. Examples of heterocycloalkyl groups include pyrrolidinyl, pyrrolinyl, imidazolidinyl, imidazolinyl, pirazolidinyl, pirazolinyl, pyrazalinyl, piperidyl, piperazinyl, morpholinyl, thiomorpholinyl, tetrahydrofuranyl, dithiolyl, oxathiolyl, dioxazolyl, oxathiazolyl, pyranyl, oxathiazinyl, and oxadiazinyl.

As used herein, the term "heteroaryl" refers to an aromatic group containing 5 to 14 ring carbon atoms in which one, two three, or four ring carbon atoms are replaced by a heteroatom such as —O—, —N—, —S—, or —Se—. Examples of heteroaryl groups include pyrrolyl, furanyl, thienyl, pyrazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, picolinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl. Included within the definition of "heteroaryl" are fused ring systems, including, for example, ring systems in which an aromatic ring is fused to a heterocycloalkyl ring. Examples of such fused ring systems include, for example, phthalamide, phthalic anhydride, indoline, isoindoline, tetrahydroisoquinoline, chroman, isochroman, chromene, and isochromene.

As used herein, the term "arylalkyl" refers to an alkyl group that is substituted with an aryl group. A designation "$C_7$-$C_{10}$ arylalkyl" refers to an alkyl group that is substituted with an aryl group with the combination thereof containing from 7 to 10 carbon atoms. Examples of arylalkyl groups include, but are not limited to, benzyl, phenethyl, phenpropyl, phenbutyl, diphenylmethyl, triphenylmethyl, diphenylethyl, naphthylmethyl, etc. Preferred examples of arylalkyl groups include, but are not limited to, benzyl and phenethyl.

As used herein, the term "amino acid" refers to a group containing both an amino group and a carboxyl group. Embodiments of amino acids include α-amino, β-amino, γ-amino acids. The α-amino acids have a general formula HOOC—CH (side chain)-$NH_2$. In certain embodiments, substituent groups for the compounds of the present invention include the residue of an amino acid after removal of the hydroxyl moiety of the carboxyl group thereof, i.e., groups of formula —C(═O)CH(NH$_2$)-(side chain). The amino acids can be in their D, L or racemic configurations. The amino acids include naturally-occurring and non-naturally occurring moieties. The naturally-occurring amino acids include the standard 20α-amino acids found in proteins, such as glycine, serine, tyrosine, proline, histidine, glutamine, etc. Naturally-occurring amino acids can also include non-α-amino acids (such as β-alanine, γ-aminobutyric acid, homocysteine, etc.), rare amino acids (such as 4-hydroxyproline, 5-hydroxylysine, 3-methylhistidine, etc.) and non-protein amino acids (such as citrulline, ornithine, canavanine, etc.). Non-naturally occurring amino acids are well-known in the art, and include analogs of natural amino acids. See Lehninger, A. L. Biochemistry, 2$^{nd}$ ed.; Worth Publishers New York, 1975; 71-77, the disclosure of which is incorporated herein by reference. Non-naturally occurring amino acids also include α-amino acids wherein the side chains are replaced with synthetic derivatives. Representative side chains of naturally occurring and non-naturally occurring α-amino acids are shown below in Table A.

TABLE A

| | | |
|---|---|---|
| H | CH$_3$ | CH(CH$_3$)$_2$ |
| CH$_2$CH(CH$_3$)$_2$ | CH(CH$_3$)CH$_2$CH$_3$ | CH$_2$OH |
| CH$_2$SH | CH(OH)CH$_3$ | CH$_2$CH$_2$SCH$_3$ |
| CH$_2$C$_6$H$_5$ | (CH$_2$)$_4$NH$_2$ | (CH$_2$)$_3$NHC(═NH)NH$_2$ |
| CH$_2$COOH | CH$_2$CH$_2$COOH | CH$_2$CONH$_2$ |
| CH$_2$CH$_2$CONH$_2$ | CH$_2$CH$_3$ | CH$_2$CH$_2$CH$_3$ |
| CH$_2$CH$_2$CH$_2$CH$_3$ | CH$_2$CH$_2$SH | CH$_2$CH$_2$OH |
| CH$_2$CH$_2$SCH$_3$ | (CH$_2$)$_3$NH$_2$ | (CH$_2$)$_2$CH(OH)CH$_2$NH$_2$ |
| (CH$_2$)$_3$NHC(═O)NH$_2$ | (CH$_2$)$_2$ONHC(═NH)NH$_2$ | CH$_2$C(═O)NHCH$_2$COOH |

As used herein, the term "residue of an amino acid after the hydroxyl group of the carboxyl group is removed" refers to that moiety of an amino acid group less the hydroxyl group. Examples of the residue of an amino acid after the hydroxyl group of the carboxyl group is removed include, but are not limited to, H$_2$N—CH$_2$—C(═O)— of glycine; H$_2$N—CH(CH$_2$OH)—C(═O)— of serine; and H$_2$N—CH((CH$_2$)$_4$NH$_2$)—C(═O)— of lysine.

As used herein, the term "subject" or "mammal" refers to a warm blooded animal such as a mammal, preferably a human, or a human child, which is afflicted with, or has the potential to be afflicted with, one or more diseases and conditions described herein.

As used herein, a "therapeutically effective amount" refers to an amount of a compound of the present invention effective to prevent or treat the symptoms of particular disorder. Such disorders include, but are not limited to, those pathological and neurological disorders associated with the aberrant activity of the receptors described herein, wherein the treatment or prevention comprises inhibiting, inducing, or enhancing the activity thereof by contacting the receptor with a compound of the present invention.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, the term "unit dose" refers to a single dose which is capable of being administered to a patient, and which can be readily handled and packaged, remaining as a physically and chemically stable unit dose comprising either the active compound itself, or as a pharmaceutically acceptable composition, as described hereinafter.

All other terms used in the description of the present invention have their meanings as is well known in the art.

In another aspect, the present invention is directed to pharmaceutically acceptable salts of the compounds described above. As used herein, "pharmaceutically acceptable salts" includes salts of compounds of the present invention derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, para-toluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

In addition to pharmaceutically-acceptable salts, other salts are included in the invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent. Such solvates are within the scope of the present invention.

The present invention also encompasses the pharmaceutically acceptable prodrugs of the compounds disclosed herein. As used herein, "prodrug" is intended to include any compounds which are converted by metabolic processes within the body of a subject to an active agent that has a formula within the scope of the present invention. Since prodrugs are known to enhance numerous desirable qualities of pharmaceuticals (e.g., solubility, bioavailability, manufacturing, etc.) the compounds of the present invention may be delivered in prodrug form. Conventional procedures for the selection and preparation of suitable prodrug derivatives are described, for example, in *Prodrugs*, Sloane, K. B., Ed.; Marcel Dekker: New York, 1992, incorporated by reference herein in its entirety It is recognized that compounds of the present invention may exist in various stereoisomeric forms. As such, the compounds of the present invention include both diastereomers and enantiomers. The compounds are normally prepared as racemates and can conveniently be used as such, but individual enantiomers can be isolated or synthesized by conventional techniques if so desired. Such racemates and individual enantiomers and mixtures thereof form part of the present invention.

It is well known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. *Stereochemistry of Organic Compounds*; Wiley: New York, 1994, and Jacques, J, et al. *Enantiomers, Racemates, and Resolutions*; Wiley: New York, 1981, each incorporated by reference herein in their entireties.

It is further recognized that functional groups present on the compounds of Formula (I) may contain protecting groups. For example, the amino acid side chain substituents of the compounds of Formula (I) can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl (Cbz; Z) group and the tert-butyloxycarbonyl (Boc) group. Other preferred protecting groups according to the invention may be found in Greene, T. W. and Wuts, P. G. M., "Protective Groups in Organic Synthesis" 2d. Ed., Wiley & Sons, 1991.

Synthesis

The compounds of the present invention may be prepared in a number of methods well known to those skilled in the art, including, but not limited to those described below, or through modifications of these methods by applying standard techniques known to those skilled in the art of organic synthesis. All processes disclosed in association with the present invention are contemplated to be practiced on any scale, including milligram, gram, multigram, kilogram, multikilogram or commercial industrial scale.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from active starting materials or by deliberate chiral synthesis of target centers.

As will be readily understood, functional groups present on the compounds of Formula (I) may contain protecting groups. For example, the amino acid side chain substituents of the compounds of Formula (I) can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl (Cbz; Z) group and the tert-butyloxycarbonyl (Boc) group. Other preferred protecting groups according to the invention may be found in Greene, T. W. and Wuts, P. G. M., "Protective Groups in Organic Synthesis" 2d. Ed., Wiley & Sons, 1991.

General routes to prepare the Examples of the present invention are shown in the Schemes and examples that follow. The reagents and starting materials are commercially available and/or, using well-known techniques, can be readily synthesized by one of ordinary skill in the art. All substituents in the synthetic Schemes, unless otherwise indicated, are as previously defined.

Compounds of invention can be synthesized following various generic synthetic schemes. Thus, in one variation, as shown in the following Scheme 1, compound of general structure 1.1 in a polar solvent, e.g. water could be treated with thiourea in presence of an acid, e.g. HBr to generate corresponding thiouronium compound 1.2. Compound 1.2 could then be hydrolyzed to corresponding carboxylic acid 1.3 in presence of a base, e.g. NaOH. Amidation of compound 1.3 with an amine in presence of a coupling reagent, e.g. 2-(1H-benzotriazol-1-yl)-1,1,3,3-tetramethyluronium tetrafluoroborate (TBTU), and a base generates compound 1.4. Oxidation of 1.4 by proper choice of an oxidizing agent, e.g. aqueous hydrogen peroxide in glacial acetic acid or m-chloroperbenzoic acid in a halogenated organic solvent, produces compound 1.5. Compound 1.5 can be further oxidized to the corresponding sulfone.

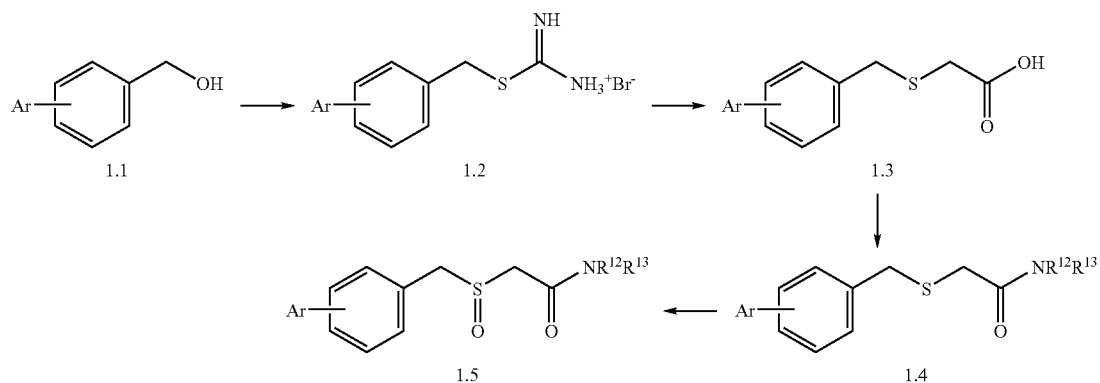

In an alternate variation, as shown in the Scheme 2, compound 2.1 (X=Br, I) can be converted to compound 2.2 via the thiouronium route, as described before. Following the same protocol as described previously, amidation of compound 2.2 generates compound 2.3 that, on oxidation, produces compound 2.4. Suzuki-coupling of compound 2.4 with an appropriately substituted aryl boronic acid, in presence of a catalyst, generates compound 2.5.

Compounds Prepared According to Scheme A

The following Scheme A corresponds to the synthesis of compounds of general structure wherein $R^1$ is C(=O)$NR^{12}R^{13}$.

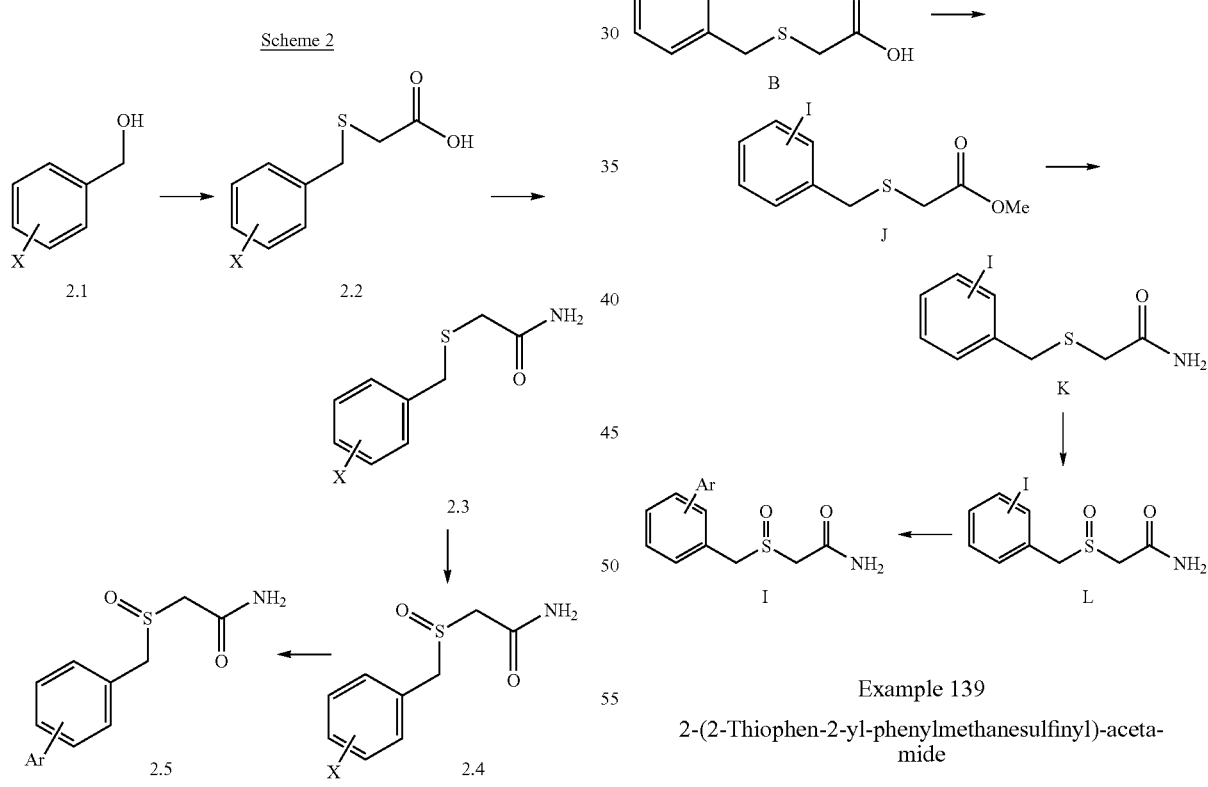

Example 139

2-(2-Thiophen-2-yl-phenylmethanesulfinyl)-acetamide

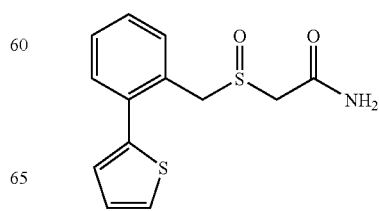

EXAMPLES

Other features of the invention will become apparent in the course of the following descriptions of exemplary embodiments. These examples are given for illustration of the invention and are not intended to be limiting thereof.

Synthesis of Compound I Wherein Ar=ortho-thien-2-yl

Compound B (ortho): (2-iodo-benzylsulfanyl)-acetic acid

To a solution of thiourea (12.16 g, 160 mmol) in 80 mL of water at 60° C. was added 2-iodobenzyl bromide (47.52 g, 160 mmol) in one portion. The reaction mixture was then heated to reflux for ½ h, cooled at 60° C. and was added dropwise a solution of sodium hydroxide in pellets (25.6 g, 640 mmol) in 40 mL of water. The reaction mixture was then heated to reflux 5 nm, cooled and at 60° C. was added slowly a solution of sodium chloroacetate (224 mmol) in 160 mL of water. The reaction mixture was then heated at 110° C. for 1 h, cooled, diluted with ice-water, and acidified with hydrochloric acid (pH~2). The resultant acidic mixture was extracted into diethyl ether (750 ml), the organic layer was washed with a solution of NaOH, the aqueous layer was acidified again (pH~2), extracted into diethyl ether (750 ml), dried over $Na_2SO_4$. On concentration, the solution generated a yellow oil that crystallized slowly to give 48 g of compound B (Yield=97%).

$^1$H-NMR (DMSO) δ (ppm): 7.85 (d, 1H), 7.4 (m, 2H), 7 (dd, 1H), 3.9 (s, 2H), 3.2 (s, 2H).

Compound J (ortho): (2-iodo-benzylsulfanyl)-acetic acid methyl ester

A mixture of compound B (ortho) (18.48 g, 60 mmol) in methanol (150 mL) and sulfuric acid (2.2 mL) was heated to reflux for 4 h, cooled and the solvent evaporated. The residue was diluted with diethyl ether (500 ml) and washed with water (150 ml), aqueous $NaHCO_3$ and water (150 ml), dried over $MgSO_4$ and concentrated to give 14.20 g of compound J as a yellow oil (Yield=73.44%).

$R_f(CH_2Cl_2/CH_3OH\ 9/1)=0.90$

Compound K (ortho): 2-(2-iodo-benzylsulfanyl)-acetamide

A mixture of compound J (ortho) (14.20 g, 44.20 mmol) in methanol (163 mL) and 28% $NH_4OH$ (124 mL) was stirred overnight at room temperature. On concentration, the solution generated a white solid that was filtered, washed with water (3×50 ml) and dried in vacuo to give 12.45 g of compound K (Yield=83%).

$R_f(CH_2Cl_2/CH_3OH\ 9.5/0.5)=0.40$

Compound L (ortho): 2-(2-iodo-phenylmethanesulfinyl)-acetamide

To a solution of compound K (ortho) (12.45 g, 40.46 mmol) in methanol was added dropwise at 0° C. a solution of $NaIO_4$ (8.77 g; 40.9 mmol) in 117 ml of water. After ½ h of stirring, the cooling bath was removed and the reaction mixture was stirred at room temperature for one night, filtered, washed with water (2×50 ml), dried in vacuo to yield compound L (12 g; white powder) (Yield=95%).

$^1$H-NMR (DMSO) δ (ppm): 7.90 (d, 1H), 7.75 (broad s, 1H), 7.45 (m, 3H), 7.12 (m, 1), 4.3 (q, 2H), 3.7 (q, 2H).

Example 139

2-(2-Thiophen-2-yl-phenylmethanesulfinyl)-acetamide

In a three neck flask, under inert atmosphere ($N_2$), is added 3 g (9.28 mmol) of L (ortho) in 35 mL of toluene. Then, 2.37 g (18.6 mmol) of 2-thienylboronic acid already dissolved in 70 mL of EtOH is added in one portion followed by 1.07 g (0.923 mmol) of Pd(PPh$_3$)$_4$. followed immediately by the addition dropwise of 7.87 g (74.3 mmol) of $Na_2CO_3$ previously dissolved in 35 ml of water. The mixture is then allowed to heat to reflux for 12 hours. The dark brown solution obtained is cooled to 10° C. and 200 mL of water is added. Extaction with AcOEt. The organic layer is dried with $MgSO_4$, filtered and concentrated under vacuum. The residue obtained is purified by column chromatography on silicagel (Eluant: 95/5 DCM/MeOH). After evaporation of the solvents a light brown precipitate is obtained. This precipitate is mixed with petroleum ether and stirred until to obtain a white solid. This solid is filtered. to get 1.96 g (yield=76%) of the title compound, Example 139.

R.M.N $^1$H (DMSO d$_6$): δ 3.55 (d, 1H, $^2J$=13.3 Hz), 3.68 (d, 1H, $^2J$=13.3 Hz), 4.20 (d, 1H, $^2J$=13.3 Hz), 4.30 (d, 1H, $^2J$=13.3 Hz), 7.18 (m, 1H$_{Ar}$), 7.28 (d, 1H$_{Ar}$), 7.30 (s, 1H$_{Ar}$), 7.50-739 (m, 4H$_{Ar}$), 7.64 (d, 1H$_{Ar}$), 7.70 (s, 1H$_{Ar}$).

Example 77

2-(2-Benzo[b]thiophen-3-yl-phenylmethanesulfinyl)-acetamide

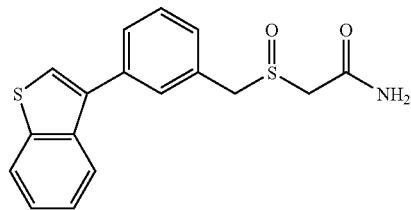

Synthesis of Compound I Wherein Ar=meta-benzothien-3-yl

Compound B (meta): (3-Iodo-benzylsulfanyl)-acetic acid

This compound was prepared, following the same procedure as described for the synthesis of compound B (ortho) except that 1-bromomethyl-3-iodo-benzene was used in place of 1-Bromomethyl-2-iodo-benzene.

$^1$H-NMR (DMSO) δ (ppm): 7.75 (s, 1H), 7.65 (d, 1H), 7.35 (d, 1H), 7.15 (t, 1H), 3.75 (s, 2H), 3.2 (s, 2H).

Compound J (meta): (3-Iodo-benzylsulfanyl)-acetic acid methyl ester

A mixture of compound B (meta) (18.48 g, 60 mmol) in methanol (150 mL) and sulfuric acid (2.2 mL) was heated to reflux for 4 h, cooled and the solvent evaporated. The residue was diluted with diethyl ether (500 ml) and washed with water (150 ml), aqueous $NaHCO_3$ and water (150 ml), dried over $Na_2SO_4$ and concentrated to give 15.74 g of compound J as a yellow oil (Yield=81.4%).

$R_f(CH_2Cl_2/CH_3OH\ 9/1)=0.95$

Compound K (meta): 2-(3-Iodo-benzylsulfanyl)-acetamide

A mixture of compound J (meta) (15.74 g, 49 mmol) in methanol (163 mL) and 28% $NH_4OH$ (124 mL) was stirred overnight at room temperature. On concentration, the solution generated a white solid that was filtered, washed with water (3×50 ml) and dried in vacuo to give 12 g of compound K (Yield=80%).

$R_f$(CH$_2$Cl$_2$/CH$_3$OH 9.5/0.5)=0.45

Compound L (meta):
2-(3-Iodo-phenylmethanesulfinyl)-acetamide

To a solution of compound K (meta) (12 g, 39 mmol) in methanol was added dropwise at 0° C. a solution of NaIO$_4$ (8.77 g; 40.9 mmol) in 117 ml of water. After ½ h of stirring, the cooling bath was removed and the reaction mixture was stirred at room temperature for one night, filtered, washed with water (2×50 ml), dried in vacuo to yield compound L (11.6 g; white powder) (Yield=92%).

$^1$H-NMR (DMSO) δ (ppm): 7.7 (m, 3H), 7.3 (d, 2H), 7.2 (t, 1), 4.15 (q, 2H), 3.5 (q, 2H).

Example 77

2-(3-Benzo[b]thiophen-3-yl-phenylmethanesulfinyl)-acetamide

To a suspension of compound L (meta) (1.93 g, 6 mmol) in toluene (24 mL) was added, under nitrogen, tetrakis(triphenylphosphine)palladium (0.693 g, 0.6 mmol), then a solution of 3-benzothiopheneboronic acid (1.6 g, 9 mmol) in ethanol (42 mL) and at last dropwise a solution of sodium carbonate (3.8 g, 36 mmol) in water (24 mL). The reaction mixture was then heated to reflux 3 h, cooled, concentrated at high vacuum, the residue was diluted with ethyl acetate (100 ml), diluted with water (50 ml) and hydrochloric acid (pH~2). The organic layer was dried over Na$_2$SO$_4$ and concentrated to yield a crude product that was purified by column chromatography (CH$_2$Cl$_2$/CH$_3$OH 9.2/0.8) to give 1.26 g of the title compound, Example 77 (pale yellow powder; yield=64%).

$^1$H-NMR (DMSO) δ (ppm): 8.15 (m, 1H), 8 (m, 1H), 7.85 (s, 1H), 7.75 (broad s, 1H), 7.65-7.5 (m, 3H), 7.45-7.35 (m, 3H), 7.3 (broad s, 1H), 4.25 (q, 2H), 3.65 (q, 2H).

Example 106

2-(2-Furan-2-yl-phenylmethanesulfinyl)-acetamide

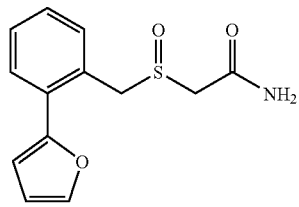

Synthesis of Compound I Wherein Ar=ortho-fur-2-yl

In a three neck flask, under inert atmosphere (N$_2$), is added 3 g (9.28 mmol) of L (ortho) in 35 mL of toluene. Then, 2.08 g (18.6 mmol) of 2-furylboronic acid already dissolved in 70 mL of EtOH is added in one portion followed by 1.07 g (0.923 mmol) of Pd(PPh$_3$)$_4$. followed immediately by the addition dropwise of 7.87 g (74.3 mmol) of Na$_2$CO$_3$ previously dissolved in 35 ml of water. The mixture is then allowed to heat to reflux for 12 hours. The dark brown solution obtained is cooled to 10° C. and 200 mL of water is added. Extaction with AcOEt. The organic layer is dried with MgSO$_4$, filtered and concentrated under vacuum. The residue obtained is purified by column chromatography on silicagel (Eluant: 95/5 DCM/MeOH). After evaporation of the solvents a light brown precipitate is obtained. This precipitate is mixed with DCM and stirred until to obtain a white solid. This solid is filtered off. to get 1.48 g (yield=61%) of the title compound Example 106.

R.M.N $^1$H (DMSO d$_6$): δ 3.55 (d, 1H, $^2$J=13.3 Hz), 3.68 (d, 1H, $^2$J=13.3 Hz), 4.20 (d, 1H, $^2$J=13.3 Hz), 4.30 (d, 1H, $^2$J=13.3 Hz), 7.18 (m, 1H$_{Ar}$), 7.28 (d, 1H$_{Ar}$), 7.30 (s, 1H$_{Ar}$), 7.50-739 (m, 4H$_{Ar}$), 7.64 (d, 1H$_{Ar}$), 7.70 (s, 1H$_{Ar}$).

Compounds Prepared According to Scheme B

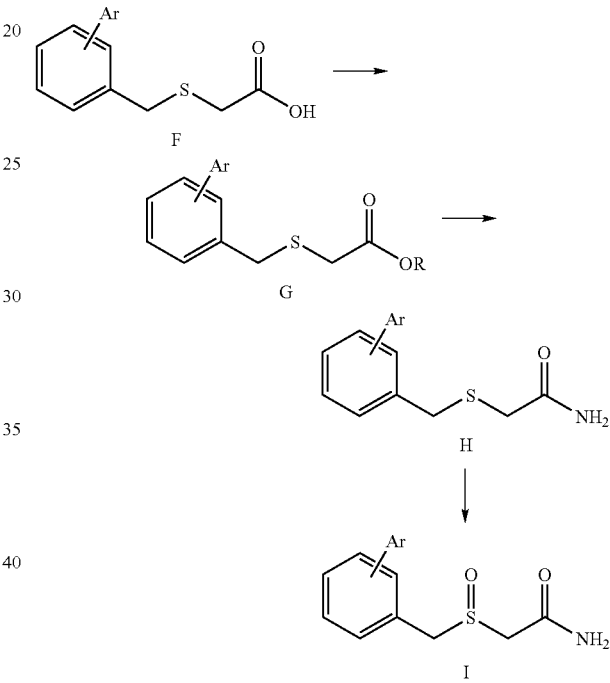

Example 47

2-(2-Benzo[b]thiophen-2-yl-phenylmethanesulfinyl)-acetamide

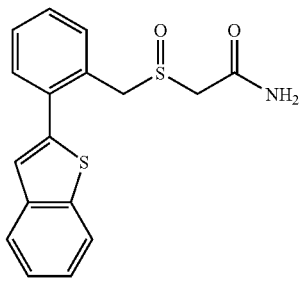

Synthesis of Compound I Wherein Ar=ortho-benzothien-2-yl

Compound F (Ar=2-benzothienyl; ortho)

To a suspension of compound B (ortho) (11.1 g, 36 mmol) in toluene (142 mL) was added under nitrogen, tetrakis(triphenylphosphine)palladium (4.16 g, 3.6 mmol), then a solution of 2-benzothiopheneboronic acid (9.6 g, 54 mmol) in ethanol (250 mL) and at last dropwise a solution of sodium carbonate (22.9 g, 216 mmol) in water (142 mL). The reaction mixture was then heated to reflux overnight, cooled, concentrated at high vacuum; the residue was diluted with ethyl acetate (500 ml), and treated with water (350 ml) and hydrochloric acid (pH~2). The organic layer was dried over $Na_2SO_4$ and concentrated to yield a crude product that was purified by trituration in cold methylene chloride to give 8.1 g of compound F as an orange solid (Yield=77%).

$^1$H-NMR (DMSO) δ (ppm): 8 (d, 1H), 7.9 (d, 1H), 7.65 (s, 1H), 7.55-7.4 (m, 4H), 4 (s, 2H), 3.25 (s, 2H).

Compound G (Ar=2-benzothienyl; ortho, R=CH₃)

A mixture of compound F (Ar=2-benzothienyl; ortho) (8.1 g, 25.8 mmol) in methanol (65 mL) and sulfuric acid (0.94 mL) was heated to reflux for 3 h, cooled, and the solvent evaporated. The residue was diluted with diethyl ether (300 ml) and washed with water (80 ml), aqueous $NaHCO_3$, water (80 ml), dried over $Na_2SO_4$ and concentrated to give 7.2 g of compound G as an orange oil (Yield=85%).

$^1$H-NMR (DMSO) δ (ppm): 8 (d, 1H), 7.85 (d, 1H), 7.65 (s, 1H), 7.55-7.4 (m, 6H), 4 (s, 2H), 3.5 (s, 3H), 3.35 (s, 2H). $R_f$ ($CH_2Cl_2$)=0.8

Compound H (Ar=2-benzothienyl; ortho; Example 54)

A mixture of compound G (Ar=2-benzothienyl; ortho, R=CH₃) (7.2 g, 21.9 mmol) in methanol (73 mL) and 28% $NH_4OH$ (55 mL) was stirred for 48 h at room temperature and filtered. The residue was washed with water (2×40 ml) and diisopropyl ether (2×30 ml), dried in vacuo to yield Example 54 (4.43 g, white solid) (Yield=65%).

$^1$H-NMR (DMSO) δ (ppm): 8 (d, 1H), 7.85 (d, 1H), 7.65 (s, 1H), 7.55-7.35 (m, 8H), 7 (broad s, 1H), 4 (s, 2H), 3.15 (s, 2H).

Synthesis of Compound Example 47

To a solution of Example 54 (Ar=2-benzothienyl; ortho) (7.2 g, 23 mmol) in glacial acetic acid (23 mL) was added 35% aqueous hydrogen peroxide (2.8 ml). The mixture was stirred until no more starting material was detected (TLC). After 4 h of stirring, the reaction mixture was concentrated, the resulting oil was diluted with water and ethyl acetate (200 ml), the organic layer was washed successively with water (100 ml), aqueous $NaHCO_3$, water (100 ml), dried over $Na_2SO_4$. On concentration, the solution generated a white solid that was filtered, washed with diisopropyl oxide and dried to give 7 g of the title compound, Example 47 (Yield=92%).

$^1$H-NMR (DMSO) δ (ppm): 8 (d, 1H), 7.85 (d, 1H), 7.7 (broad s, 1H), 7.6-7.4 (m, 7H), 7.35 (broad s, 1H), 4.4 (q, 2H), 3.6 (q, 2H).

Compounds Prepared According to Scheme C

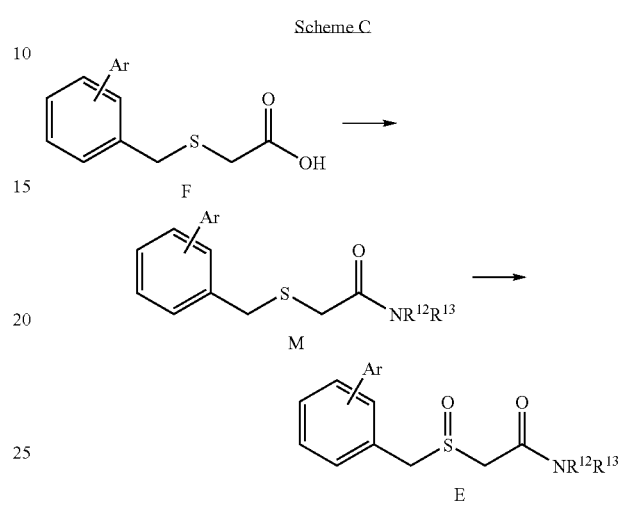

Scheme C

Example 12

1-piperazin-1-yl-2-(2-thiophen-3-yl-phenylmethanesulfinyl)-ethanone

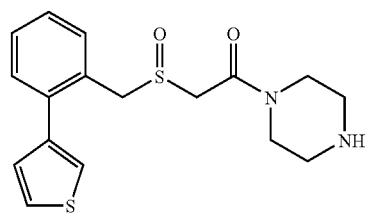

Synthesis of Compound E Wherein Ar=ortho-thien-3-yl; NR¹²R¹³=N-piperazinyl

Compound M (Ar=3-thienyl; ortho; NR¹²R¹³=N-Boc-piperazinyl)

To a cooled (ice-bath) solution of compound F (Ar=3-thienyl; ortho) (4.752 g, 18 mmol) in $CH_2Cl_2$ (100 mL), was added successively N-Boc-piperazine (3.72 g, 20 mmol), EDCI (3.83 g, 20 mmol) and HOBT (2.7 g, 20 mmol). The cooling bath was removed and the reaction mixture was stirred at room temperature for one night. It was then diluted with $CH_2Cl_2$ (120 ml), washed successively with water (100 ml), aqueous $NaHCO_3$, water (100 ml) and dried over $Na_2SO_4$. On concentration, the solution generated a crude product that was purified by column chromatography ($CH_2Cl_2/CH_3OH$ 9.7/0.3) to give 7.67 g of compound M (dark orange oil; yield ~100%).

$R_f$($CH_2Cl_2/CH_3OH$ 9/1)=0.8

Compound M (Ar=3-thienyl; ortho; NR$^{12}$R$^{13}$=N-piperazinyl)

To a solution of compound M (Ar=3-thienyl; ortho; NR$^{12}$R$^{13}$=N-Boc-piperazinyl) (7.67 g, 17.7 mmol) in ethyl acetate (67 mL) was added hydrochloric isopropanol 5N (17.7 mL). After stirring at room temperature for one night and concentrating, the residue was diluted in water (200 ml), added with sodium hydroxide (pH~10), extracted into ethyl acetate (2×150 ml) and dried over Na$_2$SO$_4$. On concentration the solution generated a crude product that was purified by column chromatography (CH$_2$Cl$_2$/CH$_3$OH 8.6/1.4) to give 4.6 g of compound M (orange oil; yield=78%).
R$_f$(CH$_2$Cl$_2$/CH$_3$OH 9/1)=0.15

Synthesis Example 12

To a solution of compound M (Ar=3-thienyl; ortho; NR$^{12}$R$^{13}$=N-piperazinyl) (1.25 g, 3.76 mmol) in methanol (30 mL) was added dropwise at 0° C. a solution of NaIO$_4$ (0.88 g; 4.14 mmol) in 11 ml of water. After ½ h of stirring, the cooling bath was removed and the reaction mixture was stirred at room temperature for three days, filtered, washed with methanol (15 ml), concentrated. The residue was diluted with CH$_2$Cl$_2$ (50 ml), washed with water (2×20 ml), the organic layer dried over Na$_2$SO$_4$. On concentration the solution generated a crude product that was purified by column chromatography (CH$_2$Cl$_2$/CH$_3$OH 8/2) to give compound E (Ar=3-thienyl; ortho; NR$^{12}$R$^{13}$=N-piperazinyl (0.595 g; white foam) (Yield=46%).
$^1$H-NMR (DMSO) δ (ppm): 7.6 (m, 2H), 7.5 (m, 1H), 7.4 (m, 3H), 7.25 (d, 1H), 4.25 (q, 2H), 4 (q, 2H), 3.5 (m, 4H), 2.8 (m, 3H), 2.45 (d, 1H).

Example 50

2-(2-Benzo[b]thiophen-2-yl-phenylmethanesulfinyl)-1-piperazin-1-yl-ethanone

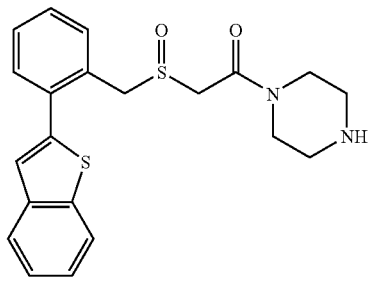

Synthesis of Compound E Wherein Ar=ortho-benzothien-2-yl; NR$^{12}$R$^{13}$=N-piperazinyl Compound M (Ar=2-benzothienyl; ortho; NR$^{12}$R$^{13}$=N-Boc-piperazinyl)

To a cooled (ice-bath) solution of compound F (Ar=2-benzothienyl; ortho) (5.65 g, 18 mmol) in CH$_2$Cl$_2$ (100 mL), was added successively N-Boc-piperazine (3.72 g, 20 mmol), EDCI (3.83 g, 20 mmol) and HOBT (2.7 g, 20 mmol). The cooling bath was removed and the mixture was stirred at room temperature for three days. It was then diluted with CH$_2$Cl$_2$ (150 ml), washed successively with water (100 ml), aqueous NaHCO$_3$, water (100 ml) and dried over Na$_2$SO$_4$. On concentration, the solution generated a crude product (viscous oil) that was directly used in the next step without any further purification.
R$_f$(CH$_2$Cl$_2$/CH$_3$OH 9/1)=0.8

Compound M (Ar=2-benzothienyl; ortho; NR$^{12}$R$^{13}$=N-piperazinyl)

To a solution of compound M (Ar=2-benzothienyl; ortho; NR$^{12}$R$^{13}$=N-Boc-piperazinyl) (8.67 g, 18 mmol) in ethyl acetate (70 mL) was added hydrochloric isopropanol 5N (18 mL). After stirring at room temperature for one night and concentrating, the residue was diluted in water (200 ml), treated with sodium hydroxide (pH~10), extracted into ethyl acetate (2×150 ml) and dried over Na$_2$SO$_4$. On concentration the solution generated a crude product that was purified by column chromatography (CH$_2$Cl$_2$/CH$_3$OH 8.6/1.4) to give 5.59 g of compound M (orange oil; yield=81%).
$^1$H-NMR (DMSO) δ (ppm): 8 (d, 1H), 7.85 (d, 1H), 7.6 (s, 1H), 7.5-7.23 (m, 6H), 3.95 (s, 2H), 3.4 (s, 2H), 3.25 (m, 4H), 2.65 (m, 2H), 2.55 (m, 2H). R$_f$(CH$_2$Cl$_2$/CH$_3$OH 9/1)=0.15

Synthesis of Example 50

To a solution of compound M (Ar=2-benzothienyl; ortho; NR$^{12}$R$^{13}$=N-piperazinyl) (1.09 g, 2.85 mmol) in glacial acetic acid (5 mL) was added 35% aqueous hydrogen peroxide (0.38 ml). The mixture was stirred until no more starting material was detected (TLC). After 3 h of stirring, the reaction mixture was concentrated at high vacuum, the residue was diluted in water, treated with sodium hydroxide (pH~10), extracted into ethyl acetate (2×50 ml) and dried over Na$_2$SO$_4$. On concentration the solution generated a crude product that was purified by column chromatography (CH$_2$Cl$_2$/CH$_3$OH 8/2) to give 0.638 g of the title compound Example 50 (white foam; yield=56%).
$^1$H-NMR (DMSO) δ (ppm): 7.9 (d, 1H), 7.75 (d, 1H), 7.5-7.25 (m, 7H), 4.25 (q, 2H), 3.9 (q, 2H), 3.2 (broad m, 4H), 2.45-2.3 (m, 4H).

Example 51

4-[2-(2-Benzo[b]thiophen-2-yl-phenylmethanesulfinyl)-acetyl]-piperazine-1-carboxylic acid amide

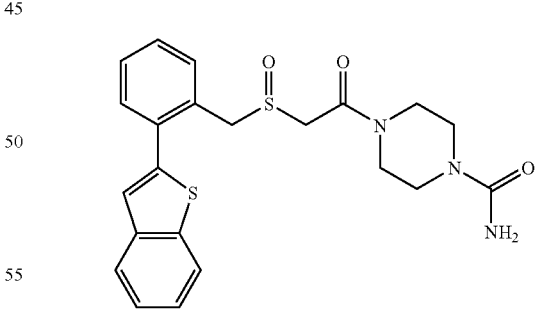

Synthesis of Compound E Wherein Ar=ortho-benzothien-2-yl; NR$^{12}$R$^{13}$=1-(4-carboxamide)-piperazinyl Compound M (Ar=2-benzothienyl; ortho; NR$^{12}$R$^{13}$=(1-(4-carboxamide)-piperazinyl)

To a solution of compound M (Ar=2-benzothienyl; ortho; NR$^{12}$R$^{13}$=N-piperazinyl) (1.45 g, 3.8 mmol) in THF (17.5 mL) was added at room temperature trimethylsilylisocyanate (0.52 ml, 3.8 mmol). After 3 h of stirring, the reaction mixture was filtered, the precipitate stirred with a solution of HCl 1N (25 ml), filtered, washed with water (2×20 ml), dried in vacuo to yield compound M (white powder; 0.9 g) (Yield=56%). $R_f$ (CH$_2$Cl$_2$/CH$_3$OH 9/1)=0.5

Synthesis of Example 51

To a solution of compound M (Ar=2-benzothienyl; ortho; NR$^{12}$R$^{13}$=(1-(4-carboxamide)-piperazinyl) (0.9 g, 2.12 mmol) in glacial acetic acid (4 mL) was added 35% aqueous hydrogen peroxide (0.27 ml). The mixture was stirred until no more starting material was detected (TLC). After 3 h of stirring, the reaction mixture was concentrated, the resulting oil was diluted with water (25 ml) and methylene chloride (50 ml), the organic layer was washed successively with water (25 ml), aqueous NaHCO$_3$, water (25 ml), dried over Na$_2$SO$_4$. On concentration, the solution generated a white solid that was filtered, washed with diisopropyl oxide and dried to give 0.44 g of the title compound Example 51 (Ar=2-benzothienyl; ortho; NR$^{12}$R$^{13}$=(1-(4-carboxamide)-piperazinyl) (Yield=47%).
$^1$H-NMR (DMSO) δ (ppm): 7.95 (d, 1H), 7.8 (d, 1H), 7.5 (s, 1H), 7.45-7.25 (m, 6H), 6 (broad s, 2H), 4.3 (q, 2H), 4 (q, 2H), 3.35 (m, 2H), 3.25 (m, 4H), 3.15 (m, 2H).

Example 52

4-[2-(2-Benzo[b]thiophen-2-yl-phenylmethanesulfinyl)-acetyl]-piperazine-1-carboxylic acid ethylamide

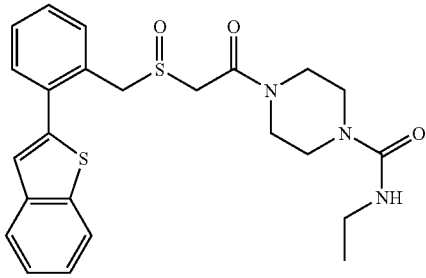

Synthesis of Compound E Wherein Ar=ortho-2-benzothienyl; NR$^{12}$R$^{13}$=(1-(4-ethylcarboxamide)-piperazinyl Compound M, (Ar=2-benzothienyl; ortho; NR$^{12}$R$^{13}$=(1-(4-ethylcarboxamide)-piperazinyl)

To a solution of compound M (Ar=2-benzothienyl; ortho; NR$^{12}$R$^{13}$=N-piperazinyl) (1.45 g, 3.8 mmol) in THF (17.5 mL) was added at room temperature ethylisocyanate (0.3 ml, 3.8 mmol). After 3 h of stirring, the reaction mixture was concentrated, the residue triturated with hexane (50 ml) to give 1.35 g of compound M as a white powder (Yield=78.5%).
$R_f$(CH$_2$Cl$_2$/CH$_3$OH 9/1)=0.75

Synthesis of Example 52

To a solution of compound M (Ar=2-benzothienyl; ortho; NR$^{12}$R$^{13}$=(1-(4-ethylcarboxamide)-piperazinyl) (1.33 g, 2.93 mmol) in glacial acetic acid (5 mL) was added 35% aqueous hydrogen peroxide (0.38 ml). The mixture was stirred until no more starting material was detected (TLC). After 3 h of stirring, the reaction mixture was concentrated, the resulting oil was diluted with water (50 ml) and ethyl acetate (100 ml), the organic layer was washed successively with water (40 ml), aqueous NaHCO$_3$, water (2×30 ml), dried over Na$_2$SO$_4$. On concentration, the residue was triturated with hexane, and generated a white solid that was filtered and dried to give 0.923 g of the title compound, Example 52 (Ar=2-benzothienyl; ortho; NR$^{12}$R$^{13}$=(1-(4-ethylcarboxamide)-piperazinyl) (Yield=67%).
$^1$H-NMR (DMSO) δ (ppm): 8.1 (d, 1H), 7.9 (d, 1H), 7.7 (s, 1H), 7.65-7.4 (m, 6H), 6.6 (t, 1H), 4.4 (q, 2H), 4.15 (q, 2H), 3.45 (m, 2H), 3.35-3.25 (m, 4H), 3.2 (m, 2H), 3.1 (q, 2H), 1.05 (t, 3H).

Compounds Prepared According to Scheme D

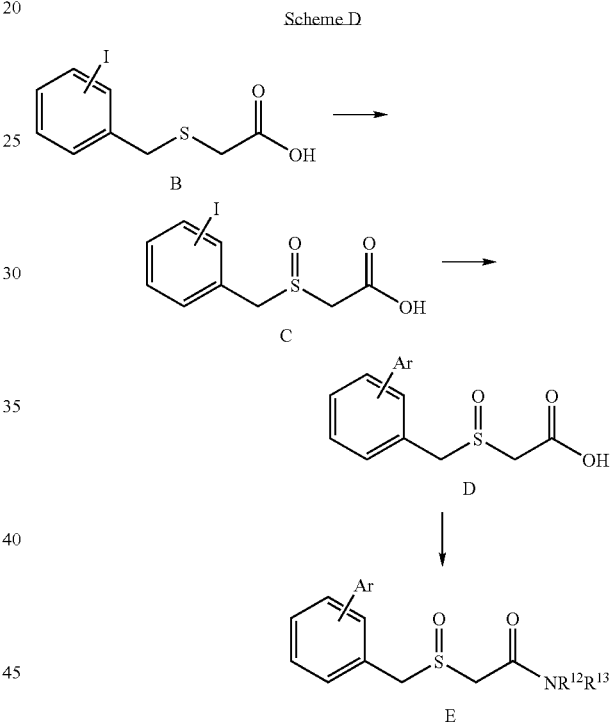

Example 7

1-(4-Hydroxy-piperidin-1-yl)-2-(2-thiophen-3-yl-phenylmethanesulfinyl)-ethanone

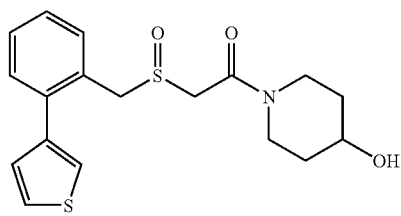

Synthesis of Compound E Wherein Ar=ortho-thien-3-yl; NR$^{12}$R$^{13}$=4-hydroxypiperidine

Compound C (ortho)

To a solution of compound B (ortho) (3.34 g, 10.84 mmol) in glacial acetic acid (10 mL) was added 35% aqueous hydrogen peroxide (1.43 ml). The mixture was stirred until no more starting material was detected. After three hours of stirring, the reaction mixture was concentrated, the resulting oil was tritured with water (100 ml) to give a white solid that, after drying, generated 2.55 g of compound C (Yield=73%).

$^1$H-NMR (DMSO) δ (ppm): 7.9 (d, 1H), 7.4 (m, 2H), 7.15 (m, 1H), 4.35 (q, 2H), 3.85 (q, 2H).

Compound D (Ar=3-thienyl; ortho)

To a suspension of compound C (ortho) (2.55 g, 7.87 mmol) in toluene (31 mL) was added, under nitrogen, tetrakis(triphenylphosphine)palladium (0.9 g, 0.787 mmol), then a solution of 3-thiopheneboronic acid (1.51 g, 11.8 mmol) in ethanol (55 mL) and at last dropwise a solution of sodium carbonate (5 g, 47.2 mmol) in water (31 mL). The reaction mixture was then heated to reflux overnight, cooled, concentrated at high vacuum, the residue was diluted with ethyl acetate (125 ml), water was added (75 ml) and hydrochloric acid (pH~2). The organic layer was dried over Na$_2$SO$_4$ and concentrated to yield compound D (2.2 g).

This compound was directly used in the next step without any further purification.

Synthesis of Example 7

To a cooled (ice-bath) solution of compound D (Ar=3-thienyl; ortho) (2.54 g, 9 mmol) in CH$_2$Cl$_2$ (54 mL), was added successively 4-hydroxypiperidine (1.01 g, 10 mmol), EDCI (1.92 g, 10 mmol) and HOBT (1.35 g, 10 mmol). The cooling bath was removed and the mixture was stirred at room temperature for one night. It was then diluted with CH$_2$Cl$_2$ (50 ml), washed successively with water (50 ml), aqueous NaHCO$_3$, water (30 ml) and dried over Na$_2$SO$_4$. On concentration, the solution generated a crude product that was purified by column chromatography (CH$_2$Cl$_2$/CH$_3$OH 9.2/0.8) to give 1.053 g of the title compound Example 7 (beige foam; yield=32%).

$^1$H-NMR (DMSO) δ (ppm): 7.6 (m, 2H), 7.45 (m, 1H), 7.35 (m, 3H), 7.25 (d, 1H), 4.75 (m, 1H), 4.2 (q, 2H), 3.95 (m, 2H), 3.8 (m, 1H), 3.7 (m, 2H), 3.2 (m, 1H), 3.1 (m, 1H), 1.7 (m, 2H), 1.4 (m, 1H), 1.25 (m, 1H).

Example 48

1-(4-Acetyl-piperazin-1-yl)-2-(2-benzo[b]thiophen-2-yl-phenylmethanesulfinyl)-ethanone

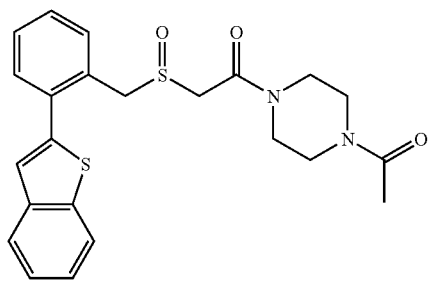

Synthesis of Compound E Wherein Ar=ortho-benzothien-2-yl; NR$^{12}$R$^{13}$=N-(4-acetyl)-piperazinyl

Synthesis of Compound D (Ar=2-benzothienyl; ortho)

To a suspension of compound C (ortho) (2.47 g, 7.6 mmol) in toluene (30 mL) was added under nitrogen, tetrakis(triphenylphosphine)palladium (0.878 g, 0.76 mmol), then a solution of 2-benzothiopheneboronic acid (2.03 g, 11.4 mmol) in ethanol (53 mL) and at last dropwise a solution of sodium carbonate (4.83 g, 45.6 mmol) in water (30 mL). The reaction mixture was then heated to reflux overnight, cooled, concentrated at high vacuum, the residue was diluted with ethyl acetate (125 ml), treated with water (75 ml) and hydrochloric acid (pH~2). The organic layer was dried over Na$_2$SO$_4$ and concentrated to yield a crude product that was purified by trituration in methylene chloride to give 2.13 g of compound D as a pink powder (Yield=84%).

R$_f$ (CH$_2$Cl$_2$/CH$_3$OH 9/1)=0.2

Synthesis of Example 48

To a cooled (ice-bath) suspension of compound D (Ar=2-benzothienyl; ortho) (1 g, 3.03 mmol) in CH$_2$Cl$_2$ (20 mL), was added successively 4-acetylpiperazine (0.439 g, 3.42 mmol), EDCI (0.655 g, 3.42 mmol) and HOBT (0.461 g, 3.42 mmol). The cooling bath was removed and the mixture was stirred at room temperature for one night. It was then diluted with CH$_2$Cl$_2$ (30 ml), washed successively with water (30 ml), aqueous NaHCO$_3$, water (30 ml) and dried over Na$_2$SO$_4$. On concentration, the solution generated a crude product that was purified by column chromatography (CH$_2$Cl$_2$/CH$_3$OH 9.2/0.8) to give 0.877 g of the title compound, Example 48 (white foam; yield=66%).

$^1$H-NMR (DMSO) δ (ppm): 8 (d, 1H), 7.85 (d, 1H), 7.6 (s, 1H), 7.55-7.4 (m, 6H), 4.45-4.3 (m, 2H), 4.1 (q, 2H), 3.5-3.25 (m, 8H).

Example 115

1-(4-Acetyl-piperazin-1-yl)-2-(3-fur-2-yl-phenyl-methanesulfinyl)-ethanone

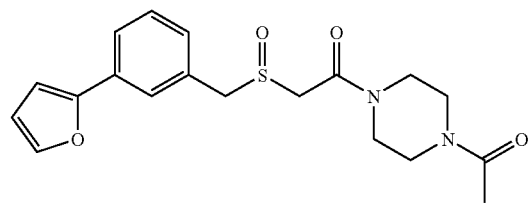

Synthesis of Compound E Wherein Ar=meta-fur-2-yl; NR$^{12}$R$^{13}$=N-(4-acetyl)-piperazinyl

Compound C (meta)

To a solution of compound B (meta) (77.80 g, 250 mmol) in MeOH (1.9 L) cooled to 0° C. was added dropwise 57.75 g (270 mmol) of NaIO$_4$ dissolved in 650 mL of water. The mixture was warmed to room temperature and stirred 12 hours. The precipitate formed was filtered and washed with water. The solid was dried under vacuum. 80.66 g (Yield=98%) of C were obtained as a white solid.

Compound D (Ar=2-furyl; meta)

In a three neck flask, under inert atmosphere (N2), is added 10 g (30.85 mmol) of C in 125 mL of toluene. Then, 5.52 g (49.36 mmol) of 2-furylboronic acid already dissolved in 250 mL of EtOH is added in one portion followed by 3.56 g (3.085 mmol) of Pd(PPh$_3$)$_4$. followed immediately by the addition dropwise of 32.70 g (308.5 mmol) of Na$_2$CO$_3$ previously dissolved in 125 ml of water. The mixture is then allowed to heat to reflux for 18 hours. The dark brown solution obtained is cooled to 10° C. and 500 mL of water is added. Extaction with AcOEt. The organic layer is dried with MgSO$_4$, filtered and concentrated under vacuum. The residue obtained is purified by column chromatography on silicagel (Eluant: 80/20 DCM/MeOH with 1 drop of NH$_4$OH). After evaporation of the solvents 7.41 g (yield=91%) of D as a light brown precipitate are obtained.

NMR $^1$H (DMSO d$_6$): δ 3.62 (d, 1H), 3.90 (d, 1H), 4.15 (d, 1H), 4.30 (d, 1H), 6.62 (t, 1H$_{Ar}$), 6.95 (d, 1H$_{Ar}$), 7.26 (d, 1H$_{Ar}$), 7.48 (t, 1H$_{Ar}$), 7.70 (m, 2H$_{Ar}$), 7.77 (d, 1H$_{Ar}$).

Synthesis of Example 115

In a three neck flask, under inert atmosphere (N$_2$), is added 7.19 g (27.2 mmol) of D in 150 ml of DCM. The mixture is cooled to 0° C. Then 5.75 g (30 mmol) of EDCI, 4.05 g (30 mmol) of HOBt and 3.85 g (30 mmol) of acetylpiperazine are added in this order. The temperature of 0° C. is maintained for 1 hour and the mixture is allowed to warm to 20° C. over 18 hours. Then 50 ml of water are added and a solution of HCl 1M is added to obtain an acidic aqueous phase. The solution is extracted with DCM. The crude product is purified by column chromatography (Eluant: 90/10 DCM/MeOH) to give 9.04 g (yield=89%) of the title compound, Example 115, as a white solid.

NMR $^1$H (DMSO d$_6$): δ 2.04 (s, 3H), 3.62-3.40 (m, 8H), 4.10-3.85 (m, 2H), 4.12 (d, 1H), 4.30 (d, 1H), 6.62 (t, 1H$_{Ar}$), 6.95 (d, 1H$_{Ar}$), 7.26 (d, 1H$_{Ar}$), 7.48 (t, 1H$_{Ar}$), 7.70 (m, 2H$_{Ar}$), 7.77 (s, 1H$_{Ar}$).

Example 120

2-(3-Furan-2-yl-phenylmethanesulfinyl)-1-[4-(2-methoxy-phenyl)-piperazin-1-yl]-ethanone

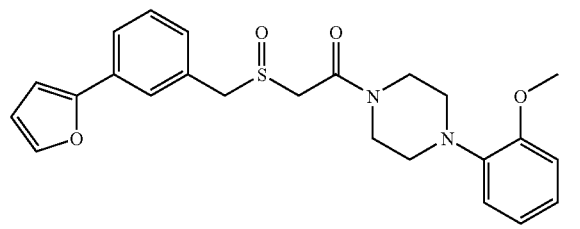

Synthesis of Compound E Wherein Ar=meta-fur-2-yl; NR$^{12}$R$^{13}$=[4-(2-methoxyphenyl)]piperazinyl In a three neck flask, under inert atmosphere (N2), is added 3.0 g (11.35 mmol) of D in 80 ml of DCM. The mixture is cooled to 0° C. Then 3.26 g (17.03 mmol) of EDCI, 2.30 g (17.03 mmol) of HOBt and 3.27 g (17.03 mmol) of 4-(2-methoxyphenyl)piperazine are added in this order. The temperature of 0° C. is maintained for 1 hour and the mixture is allowed to warm to 20° C. over 18 hours. Then 200 ml of water are added and a solution of HCl 1M is added to obtain an acidic aqueous phase. The solution is extracted with DCM. The crude product is purified by column chromatography (Eluant: 90/10 DCM/MeOH) to give 4.04 g (yield=81%) of the title compound, Example 120, as a white solid.

NMR $^1$H (DMSO d$_6$): δ 3.90 (m, 4H), 3.62 (m, 4H), 3.77 (s, 3H), 4.0 (dd, 2H), 4.20 (dd, 2H), 6.55 (t, 1H$_{Ar}$), 6.90 (m, 2H$_{Ar}$), 6.96 (m, 3H$_{Ar}$), 7.25 (d, 1H$_{Ar}$), 7.45 (t, 1H$_{Ar}$), 7.70 (m, 2H$_{Ar}$), 7.75 (d, 1H$_{Ar}$).

Compounds Prepared According to Scheme E

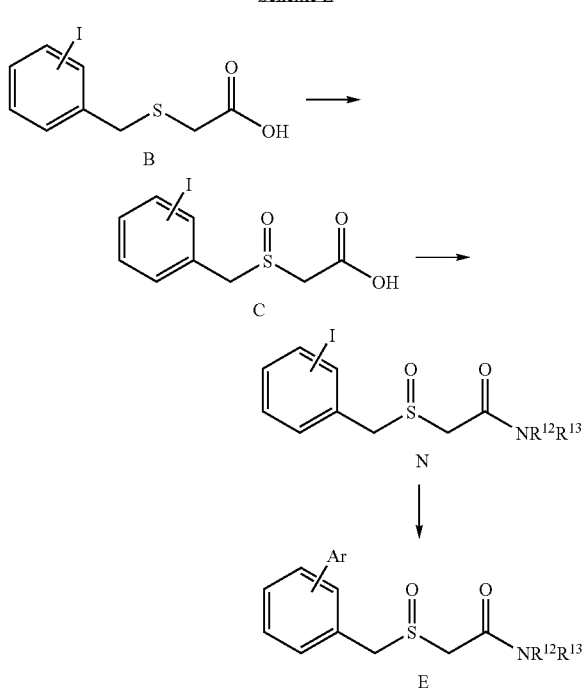

Example 149

1-(4-Acetyl-piperazin-1-yl)-2-(3-thiophen-2-yl-phenylmethanesulfinyl)-ethanone

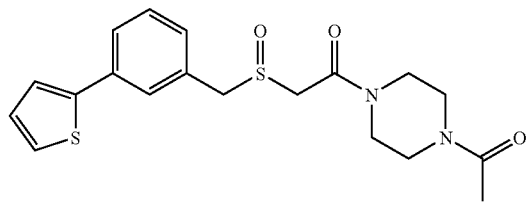

Synthesis of Compound E Wherein Ar=meta thien-2-yl and NR$^{12}$R$^{13}$=N-(4-acetyl)piperazinyl Compound N (NR$^{12}$R$^{13}$=N-(4-acetyl)piperazinyl; meta)

In a three neck flask, under inert atmosphere (N2), is added 10 g (30.85 mmol) of C in 240 ml of DCM. The mixture is cooled to 0° C. Then 6.52 g (34 mmol) of EDCI, 4.6 g (30 mmol) of HOBt and 4.6 g (36 mmol) of acetylpiperazine are added in this order. The temperature of 0° C. is maintained for 1 hour and the mixture is allowed to raise the temperature to 20° C. during 18 hours. Then 250 ml of water are added and a solution of HCl 1M is added to obtain an acidic aqueous phase. A precipitate is formed and filtered. The filtrate is extracted with DCM and the organic phase is dried with MgSO$_4$, filtered and concentrated under vacuum. 8 g (60%) of a crude product N is obtained and used to the next coupling reaction.

NMR $^1$H (DMSO d$_6$): δ 2.04 (s, 3H), 3.53-3.40 (m, 8H), 4.06-3.85 (m, 3H), 4.23 (d, 1H, $^2$J=15 Hz), 7.20 (t, 1H$_{Ar}$, $^3$J=8 Hz), 7.30 (d, 1H, $^3$J=8 Hz), 7.75-7.70 (m, 2H$_{Ar}$).

Synthesis of Example 149

In a three neck flask, under inert atmosphere (N2), is added 3 g (6.9 mmol) of N in 30 mL of toluene. Then, 1.41 g (11.04 mmol) of 2-thienylboronic acid already dissolved in 60 mL of EtOH is added in one portion followed by 0.8 g (0.69 mmol) of Pd(PPh$_3$)$_4$. followed immediately by the addition dropwise of 7.3 μg (69.0 mmol) of Na$_2$CO$_3$ previously dissolved in 30 ml of water. The mixture is then allowed to heat to reflux for 18 hours. The dark brown solution obtained is cooled to 10° C. and 200 mL of water is added. Extaction with AcOEt. The organic layer is dried with MgSO$_4$, filtered and concentrated under vacuum. The residue obtained is purified by column chromatography on silicagel (Eluant: 90/10 DCM/MeOH). After evaporation of the solvents a light brown precipitate is obtained. This precipitate is mixed with petroleum ether and stirred until a white solid was obtained. This solid is filtered. to get 1.50 g (yield=55%) of the title compound, Example 149.

NMR $^1$H (DMSO d$_6$): δ 2.04 (s, 3H), 3.53-3.40 (m, 8H), 4.10-3.85 (m, 2H), 4.12 (d, 1H), 4.30 (d, 1H), 7.15 (t, 1H$_{Ar}$), 7.27 (d, 1H$_{Ar}$), 7.44 (t, 1H$_{Ar}$), 7.52 (d, 1H$_{Ar}$).

Example 94

1-(4-Acetyl-piperazin-1-yl)-2-(3-pyridin-2-yl-phenylmethanesulfinyl)-ethanone

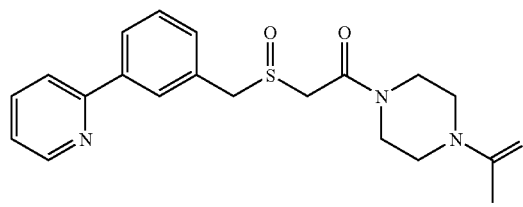

Synthesis of Compound E Wherein Ar=meta pyrid-2-yl and NR$^{12}$R$^{13}$=N-(4-acetyl)piperazinyl In a three neck flask, under inert atmosphere (N2), is added 3 g (6.9 mmol) of N in 30 mL of toluene. Then, 1.36 g (11.04 mmol) of 3-pyridylboronic acid already dissolved in 60 mL of EtOH is added in one portion followed by 0.8 g (0.69 mmol) of Pd(PPh$_3$)$_4$. followed immediately by the addition dropwise of 7.3 μg (69.0 mmol) of Na$_2$CO$_3$ previously dissolved in 30 ml of water. The mixture is then allowed to heat to reflux for 18 hours. The dark brown solution obtained is cooled to 10° C. and 200 mL of water is added. Extaction with AcOEt. The organic layer is dried with MgSO$_4$, filtered and concentrated under vacuum. The residue obtained is purified by column chromatography on silicagel (Eluant: 80/20 DCM/MeOH). After evaporation of the solvents a light brown precipitate is obtained. This precipitate is dissolved in AcOEt and a solution of HCl 6M in iPrOH is added to obtain a precipitate which is filtered off and washed with AcOEt. Evaporation of the solvent yielded 0.80 g (yield=27%) of the title compound, Example 94 are obtained.

NMR $^1$H (DMSO d$_6$): δ 2.04 (s, 3H), 3.75-3.32 (m, 8H), 4.25-4.03 (m, 3H), 4.45 (d, 1H), 7.52 (m, 1H$_{Ar}$), 7.62 (m, 1H$_{Ar}$), 7.90 (broad s, 2H$_{Ar}$), 8.90 (m, 1H$_{Ar}$), 9.28 (s, 1H).

The following Examples 1-159 in Tables 1 and 2 were prepared using appropriate starting materials and/or reagents, as determined by one skilled in the art, according to the synthetic processes disclosed in Schemes A, B, C, D, and E.

TABLE 1

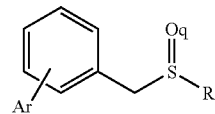

| Ex. No. | Ar | Ar Position | q | R |
|---|---|---|---|---|
| 1 | 3-thienyl | ortho | 1 | CH$_2$CONH$_2$ |
| 2 | 3-thienyl | ortho | 1 | CH$_2$CO-N-pyrrolidinyl |
| 3 | 3-thienyl | ortho | 1 | CH$_2$CONH(CH$_3$)$_2$ |
| 4 | 3-thienyl | ortho | 1 | CH$_2$CONHCH(CH$_3$)$_2$ |
| 5 | 3-thienyl | ortho | 1 | CH$_2$CO-1-(4-acetyl)-piperazinyl |
| 6 | 3-thienyl | ortho | 1 | CH$_2$CONH(CH$_2$)$_2$OH |
| 7 | 3-thienyl | ortho | 1 | CH$_2$CO-1-(4-hydroxy)-piperidinyl |
| 8 | 3-thienyl | ortho | 0 | CH—(OCH3)CONH$_2$ |
| 9 | 3-thienyl | ortho | 1 | CH$_2$CO-1-(4-ethylcarboxamide)-piperazinyl |
| 10 | 3-thienyl | ortho | 1 | CH$_2$CO-1-(4-carboxamide)-piperazinyl |
| 11 | 3-thienyl | ortho | 1 | CH$_2$CO-1-(4-phenylcarboxamide)-piperazinyl |
| 12 | 3-thienyl | ortho | 1 | CH$_2$CO-N-piperazinyl |
| 13 | 3-thienyl | ortho | 1 | CH$_2$CO-1-(4-ethylcarboxylate)-piperazinyl |
| 14 | 3-thienyl | ortho | 1 | CH$_2$CO-1-(4-methyl)-piperazinyl |
| 15 | 3-thienyl | ortho | 1 | CH$_2$COOH |
| 16 | 3-thienyl | ortho | 2 | CH$_2$CO-1-(4-acetyl)-piperazinyl |
| 17 | 5-chloro-2-thienyl | ortho | 1 | CH$_2$CONH$_2$ |
| 18 | 4-methyl-3-thienyl | ortho | 1 | CH$_2$CONH$_2$ |
| 19 | 3-thienyl | meta | 1 | CH$_2$CONH$_2$ |
| 20 | 3-thienyl | meta | 1 | CH$_2$CO-N-pyrrolidinyl |
| 21 | 3-thienyl | meta | 1 | CH$_2$CON(CH$_3$)$_2$ |
| 22 | 3-thienyl | meta | 1 | CH$_2$CONHCH(CH$_3$)$_2$ |
| 23 | 3-thienyl | meta | 1 | CH$_2$CO-1-(4-acetyl)-piperazinyl |
| 24 | 3-thienyl | meta | 1 | CH$_2$CONH(CH$_2$)$_2$OH |
| 25 | 3-thienyl | meta | 1 | CH$_2$CO-1-(4-hydroxy)-piperidinyl |
| 26 | 3-thienyl | meta | 1 | CH$_2$CO-1-(4-phenyl)-piperazinyl |
| 27 | 3-thienyl | meta | 1 | CH$_2$CO-1-(4-ethylcarboxylate)-piperazinyl |
| 28 | 3-thienyl | meta | 1 | CH$_2$CO-1-(4-methyl)-pieprazinyl |
| 29 | 3-thienyl | meta | 1 | CH$_2$CO-N-piperazinyl |
| 30 | 3-thienyl | meta | 1 | CH$_2$CO-1-(4-carboxamide)-piperazinyl |
| 31 | 3-thienyl | meta | 1 | CH$_2$CO-1-(4-propylphenyl)-piperazinyl |
| 32 | 3-thienyl | meta | 1 | CH$_2$CO-1-(4-propyl)-piperazinyl |
| 33 | 5-chloro-2-thienyl | meta | 1 | CH$_2$CONH$_2$ |
| 34 | 3-thienyl | para | 1 | CH$_2$CO-N-pyrrolidinyl |
| 35 | 3-thienyl | para | 1 | CH$_2$CONH$_2$ |
| 36 | 3-thienyl | para | 1 | CH$_2$CON(CH$_3$)$_2$ |
| 37 | 3-thienyl | para | 1 | CH$_2$CONHCH(CH$_3$)$_2$ |
| 38 | 3-thienyl | para | 1 | CH$_2$CONHCH$_2$CN |
| 39 | 3-thienyl | para | 1 | CH$_2$CO-1-(4-acetyl)-piperazinyl |

TABLE 1-continued

| Ex. No. | Ar | Ar Position | q | R |
|---|---|---|---|---|
| 40 | 3-thienyl | para | 1 | CH$_2$CO-1-(4-hydroxy)-piperidinyl |
| 41 | 3-thienyl | para | 1 | CH$_2$CO-1-(4-methyl)-piperazinyl |
| 42 | 3-thienyl | para | 1 | CH$_2$CO-1-(4-cyclohexyl)-piperazinyl |
| 43 | 3-thienyl | para | 1 | CH$_2$CO-1-(4-ethylcarboxylate)-piperazinyl |
| 44 | 3-thienyl | para | 1 | CH$_2$CO-1-(4-carboxamide)-pieprazinyl |
| 45 | 3-thienyl | para | 1 | CH$_2$CO-N-piperazinyl |
| 46 | 3-thienyl | para | 1 | CH$_2$CO-1-(4-ethylcarboxamide)-piperazinyl |
| 47 | 2-benzothienyl | ortho | 1 | CH$_2$CONH$_2$ |
| 48 | 2-benzothienyl | ortho | 1 | CH$_2$CO-1-(4-acetyl)-piperazinyl |
| 49 | 2-benzothienyl | ortho | 1 | CH$_2$CO-1-(4-ethylcarboxylate)-piperazinyl |
| 50 | 2-benzothienyl | ortho | 1 | CH$_2$CO-N-piperazinyl |
| 51 | 2-benzothienyl | ortho | 1 | CH$_2$CO-1-(4-carboxamide)-piperazinyl |
| 52 | 2-benzothienyl | ortho | 1 | CH$_2$CO-1-(4-ethylcarboxamide)-piperazinyl |
| 53 | 2-benzothienyl | ortho | 1 | CH$_2$CO-1-(4-phenylcarboxamide)-piperazinyl |
| 54 | 2-benzothienyl | ortho | 0 | CH$_2$CONH$_2$ |
| 55 | 2-benzothienyl | ortho | 1 | (CH$_2$)$_2$CONH$_2$ |
| 56 | 2-benzothienyl | ortho | 1 | (CH$_2$)$_2$CO-1-(4-methyl)-piperazinyl |
| 57 | 2-benzothienyl | ortho | 1 | CH$_2$COOH |
| 58 | 2-benzothienyl | ortho | 2 | CH$_2$CONH$_2$ |
| 59 | 2-(1,1-dioxo)benzothienyl | ortho | 2 | CH$_2$CONH$_2$ |
| 60 | 2-benzothienyl | ortho | 1 | CH$_2$CO-1-(4-methyl)-piperazinyl |
| 61 | 3-benzothienyl | ortho | 1 | CH$_2$CONH$_2$ |
| 62 | 3-benzothienyl | ortho | 0 | CH$_2$CONH$_2$ |
| 63 | 3-benzothienyl | ortho | 1 | (CH$_2$)$_2$CO-1-(4-methyl)-piperazinyl |
| 64 | 3-benzothienyl | ortho | 1 | CH$_2$CO-1-(4-acetyl)-piperazinyl |
| 65 | 3-benzothienyl | ortho | 1 | CH$_2$CO-1-(4-ethylcarboxylate)-piperazinyl |
| 66 | 3-benzothienyl | ortho | 1 | CH$_2$CO-1-(4-hydroxyethyl)-piperazinyl |
| 67 | 2-benzothienyl | meta | 1 | CH$_2$CONH$_2$ |
| 68 | 2-benzothienyl | meta | 1 | CH$_2$CO-1-(4-acetyl)-piperazinyl |
| 69 | 2-benzothienyl | meta | 1 | CH$_2$CO-1-(4-methyl)-piperazinyl |
| 70 | 2-benzothienyl | meta | 1 | CH$_2$CONHCH(CH$_3$)$_2$ |
| 71 | 2-benzothienyl | meta | 1 | CH$_2$CONH-N-morpholinyl |
| 72 | 2-benzothienyl | meta | 1 | CH$_2$CO-1-(4-ethylcarboxylate)-piperazinyl |
| 73 | 2-benzothienyl | meta | 1 | CH$_2$CON(C$_2$H$_5$)$_2$ |
| 74 | 2-benzothienyl | para | 1 | CH$_2$CONH$_2$ |
| 75 | 2-benzothienyl | para | 1 | CH$_2$CO-1-(4-acetyl)-piperazinyl |
| 76 | 2-benzothienyl | meta | 1 | CH$_2$CO-1-(4-hydroxyethyl)-piperazinyl |
| 77 | 3-benzothienyl | meta | 1 | CH$_2$CONH$_2$ |
| 78 | 3-benzothienyl | meta | 1 | CH$_2$CO-1-(4-acetyl)-piperazinyl |
| 79 | 3-benzothienyl | meta | 1 | CH$_2$CO-1-(4-methyl)-piperazinyl |
| 80 | 3-benzothienyl | meta | 1 | CH$_2$CO-1-(4-hydroxyethyl)-piperazinyl |
| 81 | 3-benzothienyl | meta | 1 | CH$_2$CO-1-(4-ethylcarboxylate)-piperazinyl |
| 82 | 2-benzothienyl | para | 1 | CH$_2$CO-1-(4-methyl)-piperazinyl |
| 83 | 2-benzothienyl | para | 1 | CH$_2$CO-1-(4-hydroxyethyl)-piperazinyl |
| 84 | 3-benzothienyl | para | 1 | CH$_2$CONH$_2$ |
| 85 | 2-indolyl | ortho | 1 | CH$_2$CONH$_2$ |
| 86 | 3-furyl | ortho | 1 | CH$_2$CO-1-(4-acetyl)-piperazinyl |
| 87 | 3-furyl | ortho | 1 | CH$_2$CO-1-(4-methyl)-piperazinyl |
| 88 | 3-furyl | ortho | 1 | CH$_2$CONH$_2$ |

TABLE 2

| Ex. No. | Ar | Ar Position | n | q | R |
|---|---|---|---|---|---|
| 89 | 3-pyridyl | ortho | 1 | 1 | CH$_2$CONH(isopropyl) |
| 90 | 3-pyridyl | ortho | 1 | 1 | CH$_2$CONH(CH$_2$)$_2$OH |
| 91 | 3-pyridyl | ortho | 1 | 1 | CH$_2$CONH$_2$ |
| 92 | 3-pyridyl | ortho | 1 | 1 | CH$_2$CONH$_2$ |
| 93 | 3-pyridyl | meta | 0 | 1 | CH$_2$CONH$_2$ |
| 94 | 3-pyridyl | meta | 1 | 1 | CH$_2$CO-1-(4-acetyl)piperazinyl |
| 95 | 3-pyridyl | meta | 1 | 1 | CH$_2$CONH(CH$_2$)$_2$OH |
| 96 | 3-pyridyl | meta | 2 | 1 | CH$_2$CO-N-piperazinyl |
| 97 | 3-pyridyl | meta | 0 | 1 | CH$_2$CONH$_2$ |
| 98 | 3-pyridyl | para | 1 | 1 | CH$_2$CONH$_2$ |
| 99 | 3-pyridyl | para | 1 | 1 | CH$_2$CO-1-(4-acetyl)piperazinyl |
| 100 | 3-pyridyl | para | 2 | 1 | CH$_2$CO-N-piperazinyl |
| 101 | 3-pyridyl | para | 1 | 1 | CH$_2$CONH(CH$_2$)$_2$OH |
| 102 | 3-pyridyl | para | 0 | 1 | CH$_2$CONH$_2$ |
| 103 | 2-furyl | ortho | 0 | 1 | CH$_2$CON(CH$_3$)$_2$ |
| 104 | 2-furyl | ortho | 0 | 1 | CH$_2$CONHCH$_2$CN |
| 105 | 2-furyl | ortho | 0 | 1 | CH$_2$CONH(isopropyl) |
| 106 | 2-furyl | ortho | 0 | 1 | CH$_2$CONH$_2$ |
| 107 | 2-furyl | ortho | 0 | 1 | CH(OCH$_3$)CONH$_2$ |
| 108 | 2-furyl | ortho | 0 | 1 | CH$_2$CONH(CH$_2$)$_2$OH |
| 109 | 2-furyl | ortho | 0 | 1 | CH$_2$CO-1-(4-acetyl)piperazinyl |
| 110 | 2-furyl | ortho | 0 | 1 | CH$_2$COOH |
| 111 | 2-furyl | meta | 0 | 1 | CH$_2$CO-N-pyrrolidinyl |
| 112 | 2-furyl | meta | 0 | 1 | CH$_2$CON(CH$_3$)$_2$ |
| 113 | 2-furyl | meta | 0 | 1 | CH$_2$CONH(isopropyl) |
| 114 | 2-furyl | meta | 0 | 1 | CH$_2$CONHCH$_2$CN |
| 115 | 2-furyl | meta | 0 | 1 | CH$_2$CO-1-(4-acetyl)piperazinyl |
| 116 | 2-furyl | meta | 0 | 1 | CH$_2$CONH(CH$_2$)$_2$OH |
| 117 | 2-furyl | meta | 0 | 1 | CH$_2$CO-N-(4-piperidinol) |
| 118 | 2-furyl | meta | 1 | 1 | CH$_2$CO-N-piperazinyl |
| 119 | 2-furyl | meta | 0 | 1 | CH$_2$CONH$_2$ |
| 120 | 2-furyl | meta | 0 | 1 | CH$_2$CO-1-[4-(2-methoxyphenyl)]piperazinyl |
| 121 | 2-furyl | meta | 0 | 1 | CH$_2$CO-1-[4-(4-fluorophenyl)]-piperazinyl |
| 122 | 2-furyl | meta | 0 | 1 | CH$_2$CO-1-(4-phenyl)piperazinyl |
| 123 | 2-furyl | meta | 0 | 1 | CH$_2$CONH$_2$ |
| 124 | 2-seleninyll | meta | 0 | 1 | CH$_2$CO-1-(4-acetyl)piperazinyl |
| 125 | 2-hydroxyphenyl | meta | 0 | 1 | CH$_2$CO-1-(4-acetyl)piperazinyl |
| 126 | 2-benzofuryl | meta | 0 | 1 | CH$_2$CO-1-(4-acetyl)piperazinyl |
| 127 | 2-benzofuryl | meta | 0 | 1 | CH$_2$CONH(CH$_2$)$_2$OH |
| 128 | 2-furyl | para | 0 | 1 | CH$_2$CONH$_2$ |
| 129 | 2-furyl | para | 0 | 1 | CH$_2$CONH(isopropyl) |
| 130 | 2-furyl | para | 0 | 1 | CH$_2$CONHCH$_2$CN |
| 131 | 2-furyl | para | 0 | 1 | CH$_2$CON(CH$_3$)$_2$ |
| 132 | 2-furyl | para | 0 | 1 | CH$_2$CO-1-(4-acetyl)piperazinyl |
| 133 | 2-furyl | para | 0 | 1 | CH$_2$CONH(CH$_2$)$_2$OH |
| 134 | 2-furyl | para | 1 | 1 | CH$_2$CO-N-piperazinyl |
| 135 | 2-thienyl | ortho | 0 | 1 | CH$_2$CO-N-pyrrolidinyl |
| 136 | 2-(5-bromo)thienyl | ortho | 0 | 1 | CH$_2$CO-N-pyrrolidinyl |
| 137 | 2-thienyl | ortho | 0 | 1 | CH$_2$CON(CH$_3$)$_2$ |
| 138 | 2-(5-bromo)thienyl | ortho | 0 | 1 | CH$_2$CON(CH$_3$)$_2$ |
| 139 | 2-thienyl | ortho | 0 | 1 | CH$_2$CONH$_2$ |
| 140 | 2-thienyl | ortho | 0 | 1 | CH$_2$CONH(CH$_2$)$_2$OH |
| 141 | 2-thienyl | ortho | 1 | 1 | CH$_2$CO-N-piperaiznyl |
| 142 | 2-thienyl | ortho | 0 | 1 | CH$_2$CO-1-(4-acetyl)piperazinyl |
| 143 | 2-thienyl | ortho | 0 | 1 | CH$_2$CONH(isopropyl) |
| 144 | 2-thienyl | meta | 0 | 1 | CH$_2$CO-N-pyrrolidinyl |
| 145 | 2-thienyl | meta | 0 | 1 | CH$_2$CON(CH$_3$)$_2$ |
| 146 | 2-thienyl | meta | 0 | 1 | CH$_2$CONH$_2$ |
| 147 | 2-thienyl | meta | 0 | 1 | CH$_2$CONH(CH$_2$)$_2$OH |
| 148 | 2-thienyl | meta | 1 | 1 | CH$_2$CO-N-piperazinyl |
| 149 | 2-thienyl | meta | 0 | 1 | CH$_2$CO-1-(4-acetyl)piperazinyl |
| 150 | 2-thienyl | para | 0 | 1 | CH$_2$CO-N-pyrrolidinyl |

TABLE 2-continued

Ar—[benzene ring]—S(=O)q—R  (HCl)n

| Ex. No. | Ar | Ar Position | n | q | R |
|---|---|---|---|---|---|
| 151 | 2-(5-bromo)thienyl | para | 0 | 1 | CH$_2$CO-N-pyrrolidinyl |
| 152 | 2-thienyl | para | 0 | 1 | CH$_2$CON(CH$_3$)$_2$ |
| 153 | 2-(5-bromo)thienyl | para | 0 | 1 | CH$_2$CON(CH$_3$)$_2$ |
| 154 | 2-thienyl | para | 0 | 1 | CH$_2$CONH$_2$ |
| 155 | 2-thienyl | para | 0 | 1 | CH$_2$CONHCH$_2$CN |
| 156 | 2-thienyl | para | 0 | 1 | CH$_2$CONH(isopropyl) |
| 157 | 2-thienyl | para | 0 | 1 | CH$_2$CO-1-(4-acetyl)piperazinyl |
| 158 | 2-thienyl | para | 0 | 1 | CH$_2$CONH(CH$_2$)$_2$OH |
| 159 | 2-thienyl | para | 1 | 1 | CH$_2$CO-N-piperazinyl |
| 436 | 2-furyl | ortho | 0 | 2 | CH$_2$CO-1-(4-acetyl)piperazinyl |

The following Table 2A demonstrates the analytical data, by each compound's mass spectrum, for Examples 1-157 and according to which synthetic process each compound was synthesized.

TABLE 2A

| Ex. No. | MF | MS | SYNTHETIC METHOD |
|---|---|---|---|
| 1 | C$_{13}$H$_{13}$NO$_2$S$_2$ | M + H = 280; M + Na = 302 | A |
| 2 | C$_{17}$H$_{19}$NO$_2$S$_2$ | M + H = 334; M + Na = 356; 2M + Na = 689 | C |
| 3 | C$_{15}$H$_{17}$NO$_2$S$_2$ | M + H = 308; M + Na = 330; 2M + Na = 637 | C |
| 4 | C$_{16}$H$_{19}$NO$_2$S$_2$ | M + H = 322; M + Na = 344 | C |
| 5 | C$_{19}$H$_{22}$N$_2$O$_3$S$_2$ | M + H = 391; M + Na = 413 | D |
| 6 | C$_{15}$H$_{17}$NO$_3$S$_2$ | M + H = 324; M + Na = 346 | D |
| 7 | C$_{18}$H$_{21}$NO$_3$S$_2$ | M + H = 364; M + Na = 386 | D |
| 8 | C$_{14}$H$_{15}$NO$_2$S$_2$ | M + NH$_4$ = 311 | A |
| 9 | C$_{20}$H$_{25}$N$_3$O$_3$S$_2$ | M + H = 420; M + Na = 442 | C |
| 10 | C$_{18}$H$_{21}$N$_3$O$_3$S$_2$ | M + H = 392; M + Na = 414 | C |
| 11 | C$_{24}$H$_{25}$N$_3$O$_3$S$_2$ | M + H = 468; M + Na = 490 | C |
| 12 | C$_{17}$H$_{20}$N$_2$O$_2$S$_2$ | M + H = 349; M + Na = 371 | C |
| 13 | C$_{20}$H$_{24}$N$_2$O$_4$S$_2$ | M + H = 421; M + Na = 443; 2M + Na = 863 | C |
| 14 | C$_{18}$H$_{22}$N$_2$O$_2$S$_2$ | M + H = 363; 2M + Na = 747 | C |
| 15 | C$_{13}$H$_{12}$O$_3$S$_2$ | M + H = 280; M + Na = 303; M + K = 319; 2M + Na = 583 | B |
| 16 | C$_{19}$H$_{22}$N$_2$O$_4$S$_2$ | M + H = 407; M + Na = 429; M + K = 445 | D |
| 17 | C$_{13}$H$_{12}$ClNO$_2$S$_2$ | M + H = 314; M + Na = 336; 2M + Na = 649 | A |
| 18 | C$_{14}$H$_{15}$NO$_2$S$_2$ | M + H = 294; M + Na = 316; 2M + Na = 609 | A |
| 19 | C$_{13}$H$_{13}$NO$_2$S$_2$ | M + H = 280; M + Na = 302 | B |
| 20 | C$_{17}$H$_{19}$NO$_2$S$_2$ | M + H = 334; M + Na = 356; 2M + Na = 689 | C |
| 21 | C$_{15}$H$_{17}$NO$_2$S$_2$ | M + H = 308; M + Na = 330; 2M + Na = 637 | C |
| 22 | C$_{16}$H$_{19}$NO$_2$S$_2$ | M + H = 322; M + Na = 344 | C |
| 23 | C$_{19}$H$_{22}$N$_2$O$_3$S$_2$ | M + H = 391; M + Na = 413 | C |
| 24 | C$_{15}$H$_{17}$NO$_3$S$_2$ | M + H = 324; M + Na = 346 | C |
| 25 | C$_{18}$H$_{21}$NO$_3$S$_2$ | M + H = 364; M + Na = 386; M + K = 402 | D |
| 26 | C$_{23}$H$_{24}$N$_2$O$_2$S$_2$ | M + H = 425; M + Na = 447 | D |
| 27 | C$_{20}$H$_{24}$N$_2$O$_4$S$_2$ | M + H = 421; M + Na = 443; M + K = 459 | D |
| 28 | C$_{18}$H$_{22}$N$_2$O$_2$S$_2$·C$_4$H$_4$O$_4$ | M + H = 363; M + Na = 385; M + K = 401 | D |
| 29 | C$_{17}$H$_{20}$N$_2$O$_2$S$_2$·HCl | M + H = 349; M + Na = 371 | C |
| 30 | C$_{18}$H$_{21}$N$_3$O$_3$S$_2$ | M + H = 392; M + Na = 414; M + K = 430 | C |
| 31 | C$_{26}$H$_{30}$N$_2$O$_2$S$_2$ | M + H = 467; M + Na = 489 | D |
| 32 | C$_{20}$H$_{26}$N$_2$O$_2$S$_2$ | M + H = 391; M + Na = 413 | D |
| 33 | C$_{13}$H$_{12}$ClNO$_2$S$_2$ | M + H = 314; M + Na = 336; 2M + Na = 649 | A |
| 34 | C$_{17}$H$_{19}$NO$_2$S$_2$ | M + H = 334; 2M + Na = 689 | C |
| 35 | C$_{13}$H$_{13}$NO$_2$S$_2$ | M + Na = 302 | B |
| 36 | C$_{15}$H$_{17}$NO$_2$S$_2$ | M + H = 308; M + Na = 330 | C |
| 37 | C$_{16}$H$_{19}$NO$_2$S$_2$ | M + H = 322; M + Na = 344 | C |
| 38 | C$_{15}$H$_{14}$N$_2$O$_2$S$_2$ | M + H = 319; M + Na = 341 | C |
| 39 | C$_{19}$H$_{22}$N$_2$O$_3$S$_2$ | M + H = 391; M + Na = 413 | C |
| 40 | C$_{18}$H$_{21}$NO$_3$S$_2$ | M + H = 364; M + Na = 386 | D |
| 41 | C$_{18}$H$_{22}$N$_2$O$_2$S$_2$ | M + H = 363; M + Na = 385; 2M + Na = 747 | D |
| 42 | C$_{23}$H$_{30}$N$_2$O$_2$S$_2$ | M + H = 431; M + Na = 453 | D |
| 43 | C$_{20}$H$_{24}$N$_2$O$_4$S$_2$ | M + H = 421; M + Na = 443 | D |
| 44 | C$_{18}$H$_{21}$N$_3$O$_3$S$_2$ | M + H = 392 | C |
| 45 | C$_{17}$H$_{20}$N$_2$O$_2$S$_2$ | M + H = 349; M + Na = 371; 2M + Na = 719 | C |
| 46 | C$_{20}$H$_{25}$N$_3$O$_3$S$_2$ | M + H = 420; M + Na = 442; M + K = 458 | C |
| 47 | C$_{17}$H$_{15}$NO$_2$S$_2$ | M + Na = 352; M + K = 368 | A or B |
| 48 | C$_{23}$H$_{24}$N$_2$O$_3$S$_2$ | M + H = 441; M + Na = 463 | D |
| 49 | C$_{24}$H$_{26}$N$_2$O$_4$S$_2$ | M + H = 471; M + Na = 493 | D |
| 50 | C$_{21}$H$_{22}$N$_2$O$_2$S$_2$ | M + H = 399; M + Na = 421 | C |
| 51 | C$_{22}$H$_{23}$N$_3$O$_3$S$_2$ | M + H = 442; M + Na = 464; M + K = 480 | C |

TABLE 2A-continued

| Ex. No. | MF | MS | SYNTHETIC METHOD |
|---|---|---|---|
| 52 | $C_{24}H_{27}N_3O_3S_2$ | M + H = 470 | C |
|  |  | M + Na = 492 |  |
|  |  | M + K = 508 |  |
| 53 | $C_{28}H_{27}N_3O_3S_2$ | M + H = 518 | C |
|  |  | M + Na = 540 |  |
|  |  | M + K = 556 |  |
| 54 | $C_{17}H_{15}NOS_2$ | M + Na = 336 | B |
| 55 | $C_{18}H_{17}NO_2S_2$ | M + H = 344 | B |
|  |  | M + Na = 366 |  |
| 56 | $C_{23}H_{26}N_2O_2S_2 \cdot C_4H_4O_4$ | M + H = 427 | C |
|  |  | M + Na = 449 |  |
|  |  | M + K = 465 |  |
| 57 | $C_{17}H_{14}O_3S_2$ | M + H = 331 | D |
|  |  | M + Na = 353 |  |
|  |  | M + K = 369 |  |
|  |  | 2M + Na = 683 |  |
| 58 | $C_{17}H_{15}NO_3S_2$ | M + H = 346 | C |
|  |  | M + Na = 368 |  |
|  |  | M + K = 384 |  |
|  |  | 2M + Na = 713 |  |
| 59 | $C_{17}H_{15}NO_5S_2$ | M + H = 378 | C |
|  |  | M + Na = 400 |  |
|  |  | M + K = 416 |  |
|  |  | 2M + Na = 777 |  |
| 60 | $C_{22}H_{24}N_2O_2S_2$ | M + H = 413 | C |
| 61 | $C_{17}H_{15}NO_2S_2$ | M + H = 330 | A or B |
|  |  | M + Na = 352 |  |
|  |  | M + K = 368 |  |
| 62 | $C_1H_{15}NOS_2$ | M + H = 314 | B |
|  |  | M + Na = 336 |  |
|  |  | M + K = 352 |  |
| 63 | $C_{22}H_{24}N_2O_4S_2$ | M + H = 413 | C |
|  |  | M + Na = 435 |  |
|  |  | 2M + Na = 847 |  |
| 64 | $C_{23}H_{24}N_2O_3S_2$ | M + H = 441 | C |
|  |  | M + Na = 463 |  |
|  |  | 2M + Na = 903 |  |
| 65 | $C_{24}H_{26}N_2O_4S_2$ | M + H = 471 | C |
|  |  | M + Na = 493 |  |
| 66 | $C_{23}H_{26}N_2O_3S_2$ | M + H = 443 | C |
|  |  | M + Na = 465 |  |
|  |  | 2M + Na = 907 |  |
| 67 | $C_{17}H_{15}NO_2S_2$ | M + H = 330 | A |
|  |  | M + Na = 352 |  |
| 68 | $C_{23}H_{24}N_2O_3S_2$ | M + Na = 463 | D |
|  |  | M + K = 479 |  |
| 69 | $C_{22}H_{24}N_2O_2S_2$ | M + H = 413 | D |
|  |  | M + Na = 435 |  |
|  |  | M + K = 451 |  |
| 70 | $C_{20}H_{21}NO_2S_2$ | M + H = 372 | D |
|  |  | M + Na = 394 |  |
|  |  | M + K = 410 |  |
| 71 | $C_{21}H_{22}N_2O_3S_2$ | M + Na = 437 | D |
|  |  | M + K = 453 |  |
| 72 | $C_{24}H_{26}N_2O_4S_2$ | M + H = 471 | D |
|  |  | M + Na = 493 |  |
|  |  | M + K = 509 |  |
| 73 | $C_{21}H_{23}NO_2S_2$ | M + H = 386 | D |
|  |  | M + Na = 408 |  |
|  |  | M + K = 424 |  |
| 74 | $C_{17}H_{15}NO_2S_2$ | M + Na = 352 | A |
|  |  | M + K = 368 |  |
| 75 | $C_{23}H_{24}N_2O_3S_2$ | M + H = 441 | D |
|  |  | M + Na = 463 |  |
| 76 | $C_{23}H_{26}N_2O_3S_2$ | M + H = 443 | D |
|  |  | M + Na = 465 |  |
| 77 | $C_{17}H_{15}NO_2S_2$ | M + Na = 352 | A |
| 78 | $C_{23}H_{24}N_2O_3S_2$ | M + H = 441 | E |
|  |  | M + Na = 463 |  |
|  |  | M + K = 479 |  |
| 79 | $C_{22}H_{24}N_2O_2S_2$ | M + H = 413 | E |
|  |  | M + Na = 435 |  |
|  |  | M + K = 451 |  |
| 80 | $C_{23}H_{26}N_2O_3S_2$ | M + H = 443 | E |
|  |  | M + Na = 465 |  |
|  |  | M + K = 481 |  |
| 81 | $C_{24}H_{26}N_2O_4S_2$ | M + H = 471 | E |
|  |  | M + Na = 493 |  |
|  |  | M + K = 509 |  |
| 82 | $C_{22}H_{24}N_2O_2S_2$ | M + H = 413 | D |
|  |  | M + Na = 435 |  |
|  |  | M + K = 451 |  |
| 83 | $C_{23}H_{26}N_2O_3S_2$ | M + H = 443 | D |
|  |  | M + Na = 465 |  |
| 84 | $C_{17}H_{15}NO_2S_2$ | M + H = 352 | A |
|  |  | M + 2Na − H = 374 |  |
| 85 | $C_{17}H_{16}N_2O_2S$ | M + H = 313 | B |
|  |  | M + Na = 335 |  |
|  |  | M + K = 351 |  |
| 86 | $C_{19}H_{22}N_2O_4S$ | M + H = 375 | C |
|  |  | M + Na = 397 |  |
|  |  | M + K = 413 |  |
| 87 | $C_{18}H_{22}N_2O_3S \cdot C_4H_4O_4$ | M + H = 347 | B |
|  |  | M + Na = 369 |  |
| 88 | $C_{13}H_{13}NO_3S$ | M + Na = 286 | A |
|  |  | 2M + Na = 549 |  |
| 89 | $C_{17}H_{21}ClN_2O_2S$ | M + H = 354 | E |
|  |  | M + Na = 376 |  |
| 90 | $C_{16}H_{19}ClN_2O_3S$ | M + H = 319 | E |
|  |  | M + Na = 341 |  |
|  |  | M + K = 357 |  |
| 91 | $C_{14}H_{15}ClN_2O_2S$ | M + H = 275 | A |
|  |  | M + Na = 297 |  |
| 92 | $C_{14}H_{15}ClN_2O_2S$ | M + H = 275 | A |
|  |  | M + Na = 297 |  |
| 93 | $C_{14}H_{14}N_2O_2S$ | M + H = 275 | A |
|  |  | M + Na = 297 |  |
| 94 | $C_{20}H_{24}N_3O_3S$ | M + H = 386 | E |
|  |  | M + Na = 408 |  |
| 95 | $C_{16}H_{19}ClN_2O_3S$ | M + H = 319 | E |
| 96 | $C_{18}H_{23}Cl_2N_3O_2S$ | M + H = 344 | E |
|  |  | M + Na = 366 |  |
|  |  | 2M + Na = 709 |  |
| 97 | $C_{14}H_{14}N_2O_2S$ | M + H = 275 | A |
|  |  | M + Na = 297 |  |
| 98 | $C_{14}H_{15}ClN_2O_2S$ | M + H = 275 | A |
|  |  | M + Na = 297 |  |
| 99 | $C_{20}H_{24}ClN_3O_3S$ | M + H = 386 | E |
|  |  | M + Na = 408 |  |
|  |  | M + K = 424 |  |
| 100 | $C_{18}H_{23}Cl_2N_3O_2S$ | M + H = 344 | E |
|  |  | M + Na = 366 |  |
|  |  | 2M + Na = 709 |  |
| 101 | $C_{16}H_{19}ClN_2O_3S$ | M + H = 319 | E |
|  |  | M + Na = 341 |  |
| 102 | $C_{14}H_{14}N_2O_2S$ | M + H = 275 | A |
|  |  | M + Na = 297 |  |
| 103 | $C_{15}H_{17}NO_3S$ | M + Na = 314 | D |
|  |  | 2M + Na = 605 |  |
| 104 | $C_{15}H_{14}N_2O_3S$ | M + Na = 325 | D |
| 105 | $C_{16}H_{19}NO_3S$ | M + Na = 328 | D |
| 106 | $C_{13}H_{13}NO_3S$ | M + H = 263 | A |
|  |  | M + Na = 286 |  |
| 107 | $C_{14}H_{15}NO_4S$ | M + H = 294 | B |
|  |  | M + Na = 316 |  |
| 108 | $C_{15}H_{17}NO_4S$ | M + H = 308 | E |
|  |  | M + Na = 330 |  |
|  |  | M + K = 346 |  |
| 109 | $C_{19}H_{22}N_2O_4S$ | M + H = 375 | E |
|  |  | M + Na = 397 |  |
|  |  | M + K = 413 |  |
| 110 | $C_{13}H_{12}O_4S$ | M − H = 263 | D |
| 111 | $C_{19}H_{19}NO_3S$ | M + H = 318 | D |
|  |  | M + Na = 340 |  |
| 112 | $C_{15}H_{17}NO_3S$ | M + H = 292 | D |
|  |  | M + Na = 314 |  |
| 113 | $C_{16}H_{19}NO_3S$ | M + H = 306 | D |
|  |  | M + Na = 328 |  |
| 114 | $C_{15}H_{14}N_2O_3S$ | M + Na = 325 | D |
| 115 | $C_{19}H_{22}N_2O_4S$ | M + H = 375 | D |
|  |  | M + Na = 397 |  |
| 116 | $C_{15}H_{17}NO_4S$ | M + H = 308 | D |
|  |  | M + Na = 330 |  |

TABLE 2A-continued

| Ex. No. | MF | MS | SYNTHETIC METHOD |
|---|---|---|---|
| 117 | $C_{18}H_{21}NO_4S$ | M + H = 348 | D |
|  |  | M + Na = 370 |  |
| 118 | $C_{17}H_{21}ClN_2O_3S$ | M + H = 333 | E |
|  |  | M + Na = 355 |  |
| 119 | $C_{13}H_{13}NO_3S$ | M + Na = 286 | A |
| 120 | $C_{24}H_{26}N_2O_4S$ | M + H = 439 | D |
|  |  | M + Na = 461 |  |
|  |  | M + K = 477 |  |
| 121 | $C_{23}H_{23}FN_2O_3S$ | M + H = 427 | D |
|  |  | M + Na = 449 |  |
|  |  | M + K = 465 |  |
| 122 | $C_{23}H_{24}N_2O_3S$ | M + H = 409 | D |
|  |  | M + Na = 431 |  |
|  |  | M + K = 447 |  |
| 123 | $C_{15}H_{16}N_2O_4S$ | M + H = 321 | D |
|  |  | M + Na = 343 |  |
| 124 | $C_{19}H_{22}N_2O_3SSe$ | M + Na = 461 | D |
|  |  | M + K = 477 |  |
| 125 | $C_{21}H_{24}N_2O_4S$ | M + Na = 423 | D |
|  |  | M + K = 439 |  |
| 126 | $C_{23}H_{24}N_2O_4S$ | M + H = 425 | D |
|  |  | M + Na = 447 |  |
|  |  | M + K = 463 |  |
| 127 | $C_{19}H_{19}NO_4S$ | M + H = 358 | D |
|  |  | M + Na = 380 |  |
|  |  | M + K = 396 |  |
| 128 | $C_{13}H_{13}NO_3S$ | M + Na = 286 | A |
| 129 | $C_{16}H_{19}NO_3S$ | M + Na = 328 | D |
| 130 | $C_{15}H_{14}N_2O_3S$ | M + Na = 325 | D |
| 131 | $C_{15}H_{17}NO_3S$ | M + Na = 314 | D |
|  |  | 2M + Na = 605 |  |
| 132 | $C_{19}H_{22}N_2O_4S$ | M + H = 375 | E |
|  |  | M + Na = 397 |  |
| 133 | $C_{15}H_{17}NO_4S$ | M + Na = 330 | E |
|  |  | M + K = 346 |  |
| 134 | $C_{17}H_{21}ClN_2O_3S$ | M + H = 333 | E |
|  |  | M + Na = 355 |  |
|  |  | 2M + Na = 687 |  |
| 135 | $C_{17}H_{19}NO_2S_2$ | M + H = 334 | C |
| 136 | $C_{17}H_{18}BrNO_2S_2$ | M + H = 412 | C |
| 137 | $C_{15}H_{17}NO_2S_2$ | M + H = 308 | C |
| 138 | $C_{15}H_{16}BrNO_2S_2$ | M + H = 386 | C |
| 139 | $C_{13}H_{13}NO_2S_2$ | M + H = 280 | A |
|  |  | M + Na = 302 |  |
| 140 | $C_{15}H_{17}NO_3S_2$ | M + Na = 346 | E |
| 141 | $C_{17}H_{20}N_2O_2S_2$ | M + H = 349 | A |
|  |  | M + Na = 371 |  |
| 142 | $C_{19}H_{22}N_2O_3S_2$ | M + H = 391 | E |
|  |  | M + Na = 413 |  |
| 143 | $C_{16}H_{19}NO_2S_2$ | M + Na = 344 | E |
| 144 | $C_{17}H_{19}NO_2S_2$ | M + H = 334 | C |
|  |  | M + Na = 356 |  |
|  |  | M + K = 372 |  |
| 145 | $C_{15}H_{17}NO_2S_2$ | M + H = 308 | B |
| 146 | $C_{13}H_{13}NO_2S_2$ | M + H = 280 | B |
|  |  | M + Na = 302 |  |
| 147 | $C_{15}H_{17}NO_3S_2$ | M + H = 324 | E |
| 148 | $C_{17}H_{20}N_2O_2S_2$ | M + H = 349 | E |
|  |  | M + Na = 371 |  |
| 149 | $C_{19}H_{22}N_2O_3S_2$ | M + H = 391 | E |
|  |  | M + Na = 413 |  |
| 150 | $C_{17}H_{19}NO_2S_2$ | M + H = 334 | C |
|  |  | M + Na = 356 |  |
|  |  | M + K = 372 |  |
|  |  | 2M + Na = 689 |  |
| 151 | $C_{17}H_{18}BrNO_2S_2$ | M + H = 412 | C |
|  |  | M + Na = 434 |  |
|  |  | M + K = 450 |  |
| 152 | $C_{15}H_{17}NO_2S_2$ | M + H = 308 | C |
|  |  | 2M + Na = 637 |  |
| 153 | $C_{15}H_{16}BrNO_2S_2$ | M + H = 386-388 | C |
|  |  | M + Na = 408-410 |  |
| 154 | $C_{13}H_{13}NO_2S_2$ | M + Na = 302 | A |
| 155 | $C_{15}H_{14}N_2O_2S_2$ | M + Na = 341 | D |
| 156 | $C_{16}H_{19}NO_2S_2$ | M + Na = 344 | D |
| 157 | $C_{19}H_{22}N_2O_3S_2$ | M + Na = 413 | D |
| 158 | $C_{15}H_{17}NO_3S_2$ | M + H = 324 | E |

TABLE 2A-continued

| Ex. No. | MF | MS | SYNTHETIC METHOD |
|---|---|---|---|
| 159 | $C_{17}H_{21}ClN_2O_2S_2$ | M + H = 349 | E |
|  |  | M + Na = 371 |  |
|  |  | 2M + Na = 719 |  |
| 436 | $C_{19}H_{22}N_2O_5S$ | M + H = 391 | E |
|  |  | M + Na = 413 |  |
|  |  | M + K = 429 |  |

Compounds Prepared According to Scheme F

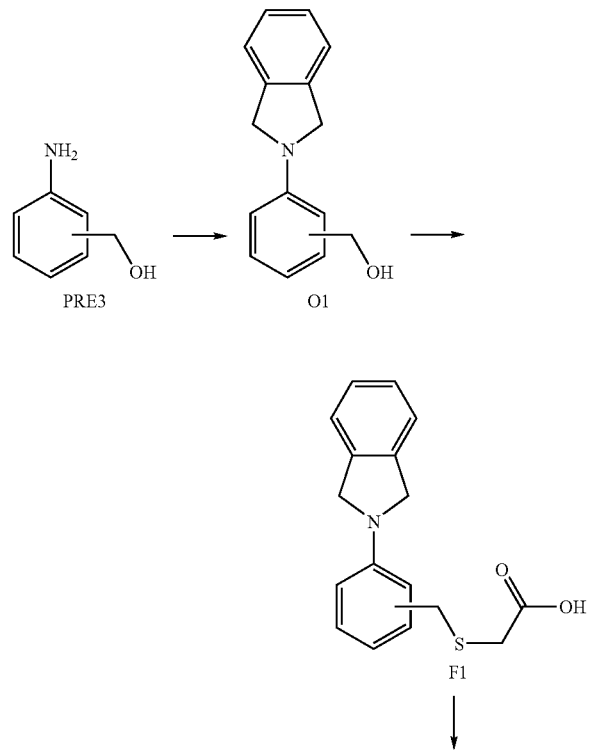

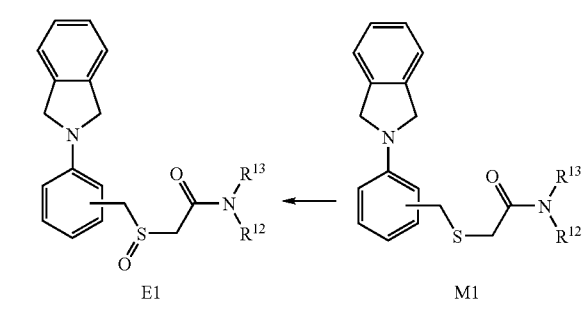

Example 161

2-[2-(1,3-Dihydro-isoindol-2-yl)-phenylmethane-sulfinyl]-N,N-dimethyl-acetamide

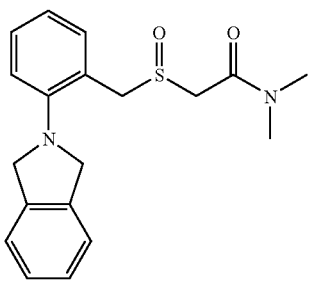

Synthesis of Compound E1 (ortho-1,3-Dihydro-isoindol-2-yl; NR$^{12}$R$^{13}$=NMe$_2$)

Compound O1 (ortho-1,3-Dihydro-isoindol-2-yl)

To a cooled solution of compound PRE3 (ortho) (12 g; 97 mmol) in DMF (100 mL) were added N,N'-diisopropylethylamine (35 mL; 200 mmol) and dibromo-o-xylene (25.6 g; 97 mmol). The reaction mixture was then heated to 75° C., maintained there for 4 hours, cooled to room temperature and diluted with water (500 mL) and brine (500 mL). The precipitate was extracted with ether (2×500 mL), the combined organic layer was washed with brine (4×200 mL), 1N HCl solution (2×300 mL), NaHCO$_3$ solution (300 mL), dried (Na$_2$SO$_4$) and concentrated. The resulting residue was purified by biotage column chromatography (cyclohexane/ethyl acetate 1:9) to furnish compound O1 (Ar=1,3-Dihydro-isoindol-2-yl; ortho) as a yellowish powder.

R$_f$=0.2 (8:2 cyclohexane/ethylacetate)
(14.6 g; 65 mmol; 67%)

Compound F1 (ortho-1,3-Dihydro-isoindol-2-yl)

To a stirred mixture of thiourea (3.25 g; 42.8 mmol), 48% HBr (19 mL) and water (3.6 mL) at 60° C. was added compound O1 (Ar=1,3-Dihydro-isoindol-2-yl; ortho) (8 g; 35.5 mmol). The reaction mixture was then heated to reflux for 5 minutes, cooled and filtered. The resulting residue was washed with water and then introduced into aqueous NaOH (32%, 14 mL). The resulting aqueous mixture was stirred and heated at 70° C., and then a solution of chloroacetic acid (3.7 g; 39 mmol) in aqueous sodium hydrogenocarbonate (9 mL) was added dropwise. The reaction mixture was then heated to reflux for one hour, cooled, diluted with water (100 mL) and filtered. The resulting powder was introduced in water (100 mL), the aqueous layer was acidified to PH 2 (4N aqueous HCl) and the precipitate was extracted into ether (150 mL). The dried organic phase was evaporated to dryness to give a residue that was triturated with cold ether to furnish compound F1 (Ar=1,3-Dihydro-isoindol-2-yl; ortho) as an off-white solid. R$_f$=0.35 (94:6 methylene chloride/methanol), (5.1 g; 17 mmol; 48%)

Compound M1 (ortho-1,3-Dihydro-isoindol-2-yl; NR$^{12}$R$^{13}$=NMe$_2$)

To a cooled solution of compound F1 (Ar=1,3-Dihydro-isoindol-2-yl; ortho) (1 g; 3.3 mmol) in THF (15 mL) was added Dimethylamine (0.8 mL; 6.3 mmol), EDCI (1.8 g; 9.4 mmol) and HOBT (0.8 g; 5.9 mmol). The reaction mixture was stirred at room temperature until no more starting material was detected. The organic layer was concentrated in vacuo and the resulting residue was taken up into ethyl acetate (150 mL). The organic layer was washed with brine (2×100 mL), aqueous ammonia solution (100 mL) and water (100 mL), dried (MgSO$_4$) and concentrated in vacuo to give compound M1 (Ar=1,3-Dihydro-isoindol-2-yl; ortho; NR$^{12}$R$^{13}$=NMe$_2$) as an oil.

R$_f$=0.31 (98:2 methylene chloride/methanol)
(1 g; 3 mmol; 91%)

Synthesis of Example 161

To a solution of compound M1 (Ar=1,3-Dihydro-isoindol-2-yl; ortho; NR$^{12}$R$^{13}$=NMe$_2$) (0.5 g; 1.5 mmol) in acetic acid (3 mL) was added a 30% by wt hydrogen peroxide solution (0.18 mL; 1.8 mmol). The mixture was stirred until no more starting material was detected and then concentrated at high vacuum. The resulting residue was taken up into ethyl acetate (100 mL), the organic layer was washed with water (3×100 mL) and concentrated in vacuo. Trituration of the resulting residue with cold Et$_2$O, filtration and drying under vacuum gave the title compound, Example 161 (Ar=1,3-Dihydro-isoindol-2-yl; ortho; NR$^{12}$R$^{13}$=NMe$_2$) as an off-white solid. (0.32 g; 0.9 mmol; 60%)

$^1$H-NMR (DMSO-d$_6$) δ: 7.3 (broad m, 7H), 7.0 (broad t, 1H), 4.6 (d, 1H), 4.5 (d, 1H) 4.4 (d, 1H), 4.25 (d, 1H), 4.0 (broad s, 2H), 3.0 (s, 3H), 2.75 (s, 3H)

The following Examples 160-165 in Table 3 were prepared using appropriate starting materials and/or reagents, as determined by one skilled in the art, according to the synthetic processes disclosed herein.

TABLE 3

| Ex. No. | Ar | Ar Position | q | R |
|---|---|---|---|---|
| 160 | 1,3-Dihydro-isoindol-2-yl | ortho | 1 | CH$_2$CO-N-pyrrolidinyl |
| 161 | 1,3-Dihydro-isoindol-2-yl | ortho | 1 | CH$_2$CONMe$_2$ |
| 162 | 1,3-Dihydro-isoindol-2-yl | meta | 1 | CH$_2$CO-N-pyrrolidinyl |
| 163 | 1,3-Dihydro-isoindol-2-yl | meta | 1 | CH$_2$CONMe$_2$ |
| 164 | 1,3-Dihydro-isoindol-2-yl | meta | 1 | CH$_2$CONHCHMe$_2$ |
| 165 | 1,3-Dihydro-isoindol-2-yl | meta | 1 | CH$_2$CONHCH$_2$CN |

The following Table 3A demonstrates the analytical data, by each compound's mass spectrum, for Examples 160-165 and according to which synthetic process each compound was synthesized.

TABLE 3A

| Ex. No. | Molecular Formula | Peak | Mass | Synthetic pathway |
|---|---|---|---|---|
| 160 | C$_{21}$H$_{24}$N$_2$O$_2$S | M + H | 369 | F |
| 161 | C$_{19}$H$_{22}$N$_2$O$_2$S | M + H | 343 | F |
| 162 | C$_{21}$H$_{24}$N$_2$O$_2$S | M + H | 369 | F |
| 163 | C$_{19}$H$_{22}$N$_2$O$_2$S | M + H | 343 | F |
| 164 | C$_{20}$H$_{24}$N$_2$O$_2$S | M + H | 357 | F |
| 165 | C$_{19}$H$_{19}$N$_3$O$_2$S | M + H | 354 | F |

Compounds prepared according by an alternative to Scheme F. (Scheme Alt-F) following the synthetic methods of Scheme F known to one skilled in the art wherein 1,3-Dihydro-isoindol-2-yl has been replaced by 2-benzofuryl are as follows:

Example 166

2-(2-Benzofuran-2-yl-phenylmethanesulfinyl)-1-piperazin-1-yl-ethanone

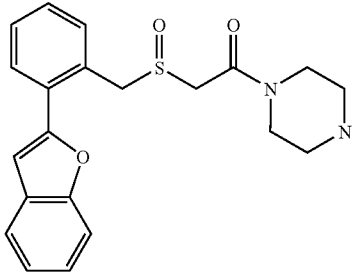

Synthesis of Compound E1 (ortho-benzofur-2-yl; $NR^{12}R^{13}$=piperazinyl)

Compound O1 (ortho-benzofur-2-yl)

To a mixture of 2-(benzofuran-2-yl)benzoic acid (22.5 g, 94.5 mmol) (J. Het. Chem. 1990, 605) in dry THF (200 ml), was added dropwise 100 ml of 1.0 M $BH_3$-THF solution at room temperature under nitrogen during 30 min. The reaction mixture was stirred at R.T. for 16 h, then quenched by brine. The organic layer was washed with brine, dried over $MgSO_4$, concentrated to give 21 g of compound O1 as a beige solid.

$^1$H-NMR (400 MHz, DMSO-$d_6$) δ 3.36 (1H, s), 4.75 (2H, d), 5.39 (1H, t), 7.3 (3H, m), 7.45 (2H, m), 7.64 (3H, m), 7.84 (1H, d).

Compound F1 (ortho-benzofur-2-yl)

To a mixture of thiourea (2.8 g, 36.8 mmol) and 48% HBr (17 ml, 158 mmol) at 70° C. was added compound O1 (Ar=benzofur-2-yl; ortho) (6.7 g, 30 mmol). The reaction mixture was heated to reflux for 1 h, then cooled and decanted twice with water to give a brown oily solid. To a mixture of this intermediate in 25 ml of 32% NaOH at 70° C. was added a solution of sodium chloroacetate (4 g, 34.3 mmol) in 20 ml of water. The resultant mixture was heated to reflux for 1 h, cooled then decanted. The oily residue was dissolved in 100 ml $CH_2Cl_2$ and washed successively with aq 4 N HCl and water, dried over $Na_2SO_4$, evaporated to yield 5.8 g of crude compound F1, (Ar=benzofur-2-yl; ortho), as a brownish solid. This acid was utilized directly in the next step without further purification (~60% purity by HPLC).

Compound M1 (ortho-benzofur-2-yl; $NR^{12}R^{13}$=1-(4-tert-butoxycarbonyl)-piperazinyl)

To a mixture of crude compound F1 (5.8 g, ~11.7 mmol), 1-(4-tert-butoxycarbonyl)piperazine (2.9 g, 15.6 mmol), HOBt (2.3 g, 17 mmol) in 200 ml of $CH_2Cl_2$ was added EDCI (3.9 g, 19.8 mmol) at room temperature. The reaction was maintained for 5 h, then washed successively with 1N HCl, water and brine, dried over $Na_2SO_4$, evaporated to give a brownish solid. The column chromatography (cyclohexane/ethyl acetate, 1/1) furnished 3.9 g of compound M1 as a brownish gum.

$^1$H-NMR (400 MHz, $CHCl_3$) δ 1.5 (9H, s), 3.25 (2H, s), 3.3 (6H, m), 4.15 (2H, s), 7.0 (1H, s), 7.25 (2H, m), 7.35 (2H, m), 7.5 (2H, m), 7.6 (1H, d), 7.75 (1H, dd).

Synthesis of Example 166 ($NR^{12}R^{13}$=piperazinyl)

To a solution of compound M1 above (2.75 g, 5.9 mmol) in 20 ml of $CH_2Cl_2$, was added trifluoroacetic acid (10 ml) at RT. The mixture was stirred for 15 minutes, then evaporated to dryness; the residue was dissolved in 50 ml of $CH_2Cl_2$, and neutralized with 1N NaOH, the organic phase was washed with water, dried over $Na_2SO_4$, evaporated to give a brownish oil.

To a solution of the above oil in acetic acid (40 ml), was added 30% $H_2O_2$. (1.1 ml). The oxidation was maintained at R.T. for 2 h, then evaporated, the residue was purified by flash chromatography ($CH_2Cl_2$/MeOH, 15/1, saturated by 28% $NH_4OH$) to furnish 1.9 g of the title compound Example 166 as a yellowish solid.

$^1$H-NMR (400 MHz, $CHCl_3$) δ 2.79 (4H, m), 3.36 (2H, m), 3.5 (2H, m), 3.63 (1H, d), 3.76 (1H, d), 4.53 (1H, d), 4.75 (1H, d), 7.03 (1H, s), 7.28 (2H, m), 7.43 (2H, m), 7.53 (2H, d), 7.59 (1H, d), 7.76 (1H, dd).

The following Examples 166-167 in Table 4 were prepared using appropriate starting materials and/or reagents, as determined by one skilled in the art, according to the synthetic processes disclosed herein.

TABLE 4

| Ex. No. | Ar | Ar Position | q | R |
|---|---|---|---|---|
| 166 | 2-Benzofuryl | ortho | 1 | $CH_2CO$-1-piperazinyl |
| 167 | 2-Benzofuryl | ortho | 1 | $CH_2CO$-1-(4-acetyl)-piperazinyl |

The following Table 4A demonstrates the analytical data, by each compound's mass spectrum, for Examples 166-167 and according to which synthetic process each compound was synthesized.

TABLE 4A

| Ex. No. | MF | MS | SYNTHETIC METHOD |
|---|---|---|---|
| 166 | $C_{21}H_{22}N_2O_3S$ | M + H = 383 | Alt-F |
| 167 | $C_{23}H_{24}N_2O_4S$ | M + H = 425 | Alt-F |
|  |  | M + Na = 447 |  |

Compounds Prepared According to Scheme G

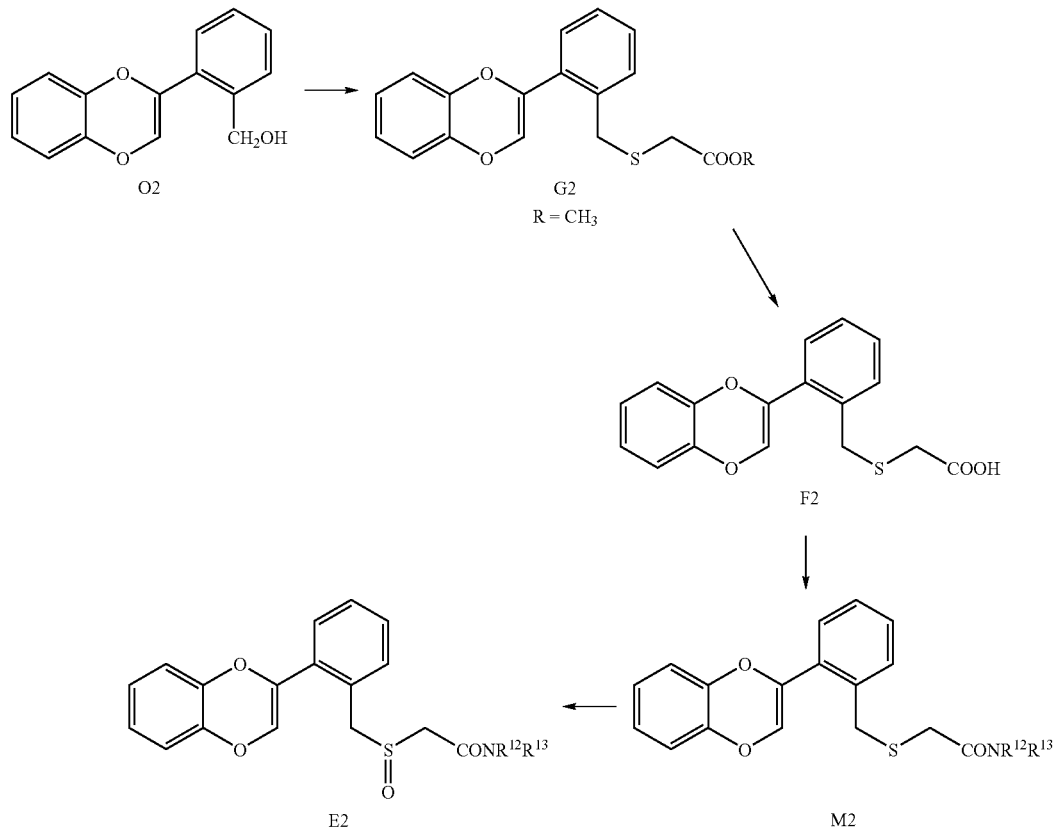

Example 168

1-(4-Acetyl-piperazin-1-yl)-2-(2-benzo[1,4]dioxin-2-yl-phenylmethanesulfinyl)-ethanone

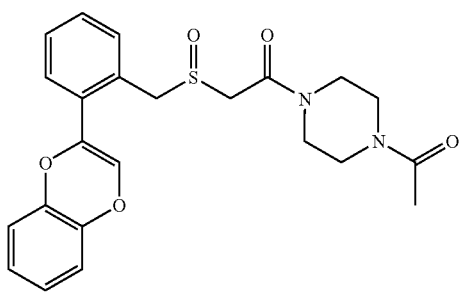

Synthesis of Compound E2 (ortho-2-benzo[1,4]dioxine; $NR^{12}R^{13}$=-(4-acetyl)-piperazinyl)

Compound F2 (ortho-2-benzo[1,4]dioxine)

To an ice/water-cooled solution of G2 (1.5 g, 4.57 mmol) in MeOH (9 mL) was added a solution of KOH (85%, 0.6 g, 9.14 mmol). The reaction mixture was stirred at RT during 1 h and concentrated. The residue was partitioned between water (60 mL) and EtOAc. The aqueous layer was acidified with 1N HCl and extracted with $Et_2O$. This organic layer was dried over $MgSO_4$ and concentrated to give F2 (1.19 g, 83%).

$^1$H-NMR ($CDCl_3$) d (ppm): 7.41 (m, 1H), 7.37 (m, 2H), 7.29 (m, 1H), 6.86 (m, 2H), 6.72 (m, 2H), 6.17 (s, 1H), 4.08 (s, 2H), 3.19 (s, 2H).

Compound M2 (ortho)

To an ice/water-cooled solution of F2 (Ar=2-benzo[1,4]dioxine; ortho) (1.19 g, 3.79 mmol) in $CH_2Cl_2$ (3 mL) was added Acetylpiperazine (572 mg, 4.17 mmol), EDCI.HCl (857 mg, 4.17 mmol) and HOBt (591 mg, 4.17 mmol). The reaction mixture was stirred at RT during 17 h, diluted with $CH_2Cl_2$, and washed with $H_2O$ (20 mL), sat. $NaHCO_3$ (20 mL) and $H_2O$ (20 mL). The organic layer was dried over $MgSO_4$ and concentrated to give an oil (1.63 g). Flash Chromatography $CH_2Cl_2$:MeOH 97:3 to 95:5) of the crude product yielded a foam (1.30 g g, 81%).

$^1$H-NMR ($CDCl_3$) d (ppm): 7.46 (m, 1H), 7.35 (m, 2H), 7.27 (m, 1H), 6.86 (m, 2H), 6.72 (m, 2H), 6.15 (s, 1H), 4.04 (s, 2H), 3.37 to 3.63 (m, 8H), 3.31 (s, 2H), 2.09 (s, 3H).

Synthesis of Example 168

To an ice/water-cooled solution of M2 (1.26, 2.97 mmol) in acetic acid (3.2 mL) was added dropwise $H_2O_2$ (0.32 mL, 3.42 mmol). The reaction mixture was stirred at RT during 5 h, then diluted with $CH_2Cl_2$ (70 mL), and washed carefully with saturated aqueous NaHCO₃ (2×70 mL). The combined organic layers were dried over MgSO₄ and concentrated to give a white foam (1.12 g).). Flash Chromatography CH$_2$Cl$_2$: MeOH 95:5) of the crude product yielded a foam (0.92 g, 71%).

¹H-NMR (CDCl$_3$) d (ppm): 7.50 (m, 1H), 7.38 (m, 3H), 6.87 (m, 2H), 6.76 (m, 1H), 6.71 (m, 1H), 6.14/6.13 (s, 1H), 4.52 (m, 1H), 4.34 (m, 1H), 3.88 (m, 1H), 3.41 to 3.71 (m, 10H), 2.10/2.09 (s, 3H).

The following Examples 168-170 in Table 5 were prepared using appropriate starting materials and/or reagents, as determined by one skilled in the art, according to the synthetic processes disclosed herein.

TABLE 5

| Ex. No. | Ar | Ar Position | q | R |
|---|---|---|---|---|
| 168 | 2-benzo[1,4]dioxine | ortho | 1 | CH$_2$CO-1-(4-acetyl)-piperazinyl |
| 169 | 2-benzo[1,4]dioxine | ortho | 1 | CH$_2$CO-1-(4-methyl)-piperazinyl |
| 170 | 2-benzo[1,4]dioxine | ortho | 1 | CH$_2$CONHCH(CH$_3$)$_2$ |

The following Table 5A demonstrates the analytical data, by each compound's mass spectrum, for Examples 168-170 and according to which synthetic process each compound was synthesized.

TABLE 5A

| Ex. No. | MF | MS | SYNTHETIC METHOD |
|---|---|---|---|
| 168 | C$_{23}$H$_{24}$N$_2$O$_5$S | M + H = 441<br>M + Na = 463 | G |
| 169 | C$_{22}$H$_{24}$N$_2$O$_4$S | M + H = 413<br>M + Na = 435 | G |
| 170 | C$_{20}$H$_{21}$NO$_4$S | M + H = 372<br>M + Na = 394 | G |

Compounds prepared according by an alternative to Scheme G. (Scheme Alt-G). following the synthetic methods of Scheme G known to one skilled in the art wherein 2-benzo[1,4]dioxine has been replaced by pyrrol-1-yl are as follows:

The following Examples 171-176 in Table 6 were prepared using appropriate starting materials and/or reagents, as determined by one skilled in the art, according to the synthetic processes disclosed herein.

TABLE 6

| Ex. No. | Ar | Ar Position | q | R |
|---|---|---|---|---|
| 171 | Pyrrol-1-yl | meta | 1 | CH$_2$CONH(CH$_2$)$_2$OH |
| 172 | Pyrrol-1-yl | meta | 1 | CH$_2$CO-1-(4-hydroxy)-piperidinyl |
| 173 | Pyrrol-1-yl | meta | 1 | CH$_2$CO-1-(4-acetyl)-piperazinyl |
| 174 | Pyrrol-1-yl | ortho | 1 | CH$_2$CONH(CH$_2$)$_2$OH |
| 175 | Pyrrol-1-yl | ortho | 1 | CH$_2$CO-1-(4-hydroxy)-piperidinyl |
| 176 | Pyrrol-1-yl | ortho | 1 | CH$_2$CONH(CH$_2$)$_2$O(CH2)$_2$OH |

The following Table 6A demonstrates the analytical data, by each compound's mass spectrum, for Examples 171-176 and according to which synthetic process each compound was synthesized.

TABLE 6A

| Ex. No. | Molecular Formula | Peak | Mass | Synthetic pathway |
|---|---|---|---|---|
| 171 | C$_{15}$H$_{18}$N$_2$O$_3$S | M + H | 307 | Alt-G |
| 172 | C$_{18}$H$_{22}$N$_2$O$_3$S | M + H | 347 | Alt-G |
| 173 | C$_{19}$H$_{23}$N$_3$O$_3$S | M + H | 374 | Alt-G |
| 174 | C$_{15}$H$_{18}$N$_2$O$_3$S | M + Na | 329 | Alt-G |
| 175 | C$_{18}$H$_{22}$N$_2$O$_3$S | M + H | 347 | Alt-G |
| 176 | C$_{17}$H$_{22}$N$_2$O$_4$S | M + Na | 373 | Alt-G |

Compounds Prepared According to Scheme H

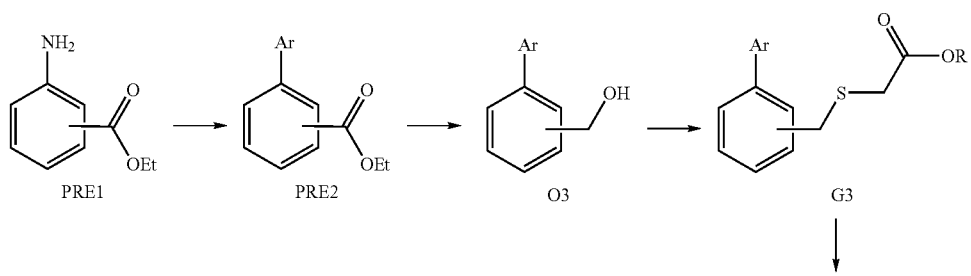

Scheme H

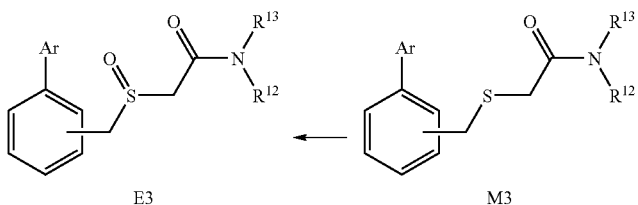

E3 ← M3

Example 177

1-Pyrrolidin-1-yl-2-(2-pyrrol-1-yl-phenylmethane-sulfinyl)-ethanone

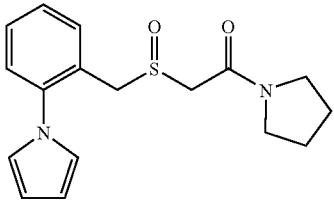

Synthesis of Compound E3 Wherein (Ar=Pyrrol-1-yl; ortho; $NR^{12}R^{13}$=N-pyrrolidinyl)

Compound PRE2 (Ar=pyrrol-1-yl; ortho)

To a stirred solution of 2-amino benzoic acid ethyl ester (20 g; 121 mmol) in acetic acid (35 mL) was added 2,5-dimethoxytetrahydrofuran (19 g; 174 mmol). The reaction mixture was stirred for two hours at reflux. After evaporation of the solvent, the crude product was purified by flash column chromatography (methylene chloride) to give compound 2-pyrrol-1-yl-benzoic acid ethyl ester as a yellow oil.

$R_f$=0.63 (methylene chloride); (22.2 g; 103 mmol; 85%)

Compound O3 (Ar=pyrrol-1-yl; ortho)

To a stirred solution of 2-pyrrol-1-yl-benzoic acid ethyl ester (22.2 g; 103 mmo) in toluene (140 mL) warmed to 35° C. was added gently sodium bis(2-ethoxymethoxy)aluminium hydride in toluene (70% wt; 32 mL; 115 mmol) while the temperature was maintained under 45° C. After one hour of stirring at 45° C., the reaction mixture was cooled to 0° C. and was quenched carefully with slow addition of 4N HCl solution and water (75 mL). The resulting organic layer was washed with a saturated solution of sodium bicarbonate (75 mL) and dried over magnesium sulfate. The solvent was removed under vacuum to give compound O3 (Ar=Pyrrol-1-yl; ortho) as a yellowish oil. $R_f$=0.56 (97:3 methylene chloride/methanol); (16.8 g; 97 mmol; 94%).

Compound G3 (Ar=Pyrrol-1-yl; ortho; R=Me)

To a solution of compound O3 (Ar=Pyrrol-1-yl; ortho) (14.7 g; 85 mmol) and triethylamine (26 mL; 184 mmol) in methylene chloride (150 mL) was added gently methanesulfonylchloride (7.35 mL; 95 mmol) while the temperature was maintained under 8° C. After one hour of stirring at 5° C., methylthioglycolate (6 mL; 67 mmol) was added and the mixture was stirred at room temperature for two days. Water (150 mL) was added, the organic layer was separated, dried over magnesium sulfate and concentrated in vacuo. The resulting oil was purified by two successive column chromatographies (cyclohexane/ethyl acetate 9/1; $R_f$=0.61) and (methylene chloride;

$R_f$=0.54) to furnish compound G3 (Ar=Pyrrol-1-yl; ortho; R=Me) as an oil.

$R_f$=0.54 (methylene chloride); (6.7 g; 26 mmol; 31%).

Compound M3 (Ar=Pyrrol-1-yl; ortho; $NR^{12}R^{13}$=N-pyrrolidinyl)

To a stirred solution of compound G3 (Ar=Pyrrol-1-yl; ortho; R=Me) (1 g; 3.8 mmol) in methylene chloride (20 mL) was added pyrrolidine (0.45 mL; 5.4 mmol) and a 2M solution of trimethyl aluminium hydride in toluene (2.7 mL; 5.4 mmol). After two days of stirring at room temperature, methylene chloride (50 mL) was added to the mixture followed by a 1N HCl solution (dropwise; 35 mL). The organic layer was collected and evaporated. The crude material was purified by biotage column chromatography (methylene chloride/methanol 98/2) to give compound M3 (Ar=Pyrrol-1-yl; ortho; $NR^{12}R^{13}$=N-pyrrolidinyl). $R_f$=0.25 (98:2 methylene chloride/methanol)

(0.96 g; 3.2 mmol; 84%).

Compound Example 177

To a stirred solution of compound M3 (Ar=Pyrrol-1-yl; ortho; $NR^{12}R^{13}$=N-pyrrolidinyl) (0.96 g; 3.2 mmol) in acetic acid (7 mL) was added a 30% by wt hydrogen peroxide solution (0.39 mL; 3.4 mmol). After one hour of stirring, the solvent was removed in vacuo and the resulting oil was purified by biotage column chromatography (methylene chloride/methanol 97/3) to give an oil which was triturated in diethylether to furnish the title compound, Example 177, as a powder.

(0.66 g; 2 mmol; 63%).

$^1$H-NMR (DMSO-$d_6$) δ: 7.55 (broad d, 1H), 7.5 (m, 2H), 7.3 (broad d, 1H), 6.95 (broad s, 2H), 6.25 (broad s, 2H), 4.05 (q, 2H), 3.8 (q, 2H), 3.45 (broad t, 2H), 3.25 (broad t, 2H), 1.8 (m, 4H)

The following Examples 177-183 in Table 7 were prepared using appropriate starting materials and/or reagents, as determined by one skilled in the art, according to the synthetic processes disclosed herein.

TABLE 7

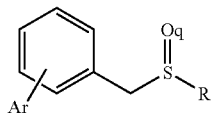

| Ex. No. | Ar | Ar Position | q | R |
|---|---|---|---|---|
| 177 | Pyrrol-1-yl | ortho | 1 | CH$_2$CO-N-pyrrolidinyl |
| 178 | Pyrrol-1-yl | ortho | 1 | CH$_2$CONMe$_2$ |
| 179 | Pyrrol-1-yl | ortho | 1 | CH$_2$CONHCHMe$_2$ |
| 180 | Pyrrol-1-yl | ortho | 1 | CH$_2$CO-1-(4-acetyl)-piperazinyl |
| 181 | Pyrrol-1-yl | meta | 1 | CH$_2$CONHCH$_2$CN |
| 182 | Pyrrol-1-yl | meta | 1 | CH$_2$CONHCHMe$_2$ |
| 183 | Pyrrol-1-yl | meta | 1 | CH$_2$CONMe$_2$ |

The following Table 7A demonstrates the analytical data, by each compound's mass spectrum, for Examples 177-183 and according to which synthetic process each compound was synthesized.

TABLE 7A

| Ex. No. | Molecular Formula | Peak | Mass | Synthetic pathway |
|---|---|---|---|---|
| 177 | C$_{17}$H$_{20}$N$_2$O$_2$S | M + H | 317 | h |
| 178 | C$_{15}$H$_{18}$N$_2$O$_2$S | M + H | 291 | h |
| 179 | C$_{16}$H$_{20}$N$_2$O$_2$S | M + H | 305 | h |
| 180 | C$_{19}$H$_{23}$N$_3$O$_3$S | M + H | 374 | h |
| 181 | C$_{15}$H$_{15}$N$_3$O$_2$S | M + H | 302 | h |
| 182 | C$_{16}$H$_{20}$N$_2$O$_2$S | M + H | 305 | h |
| 183 | C$_{15}$H$_{18}$N$_2$O$_2$S | M + H | 291 | h |

Compounds prepared according by an alternative to Scheme H (Scheme Alt-H). following the synthetic methods of Scheme H known to one skilled in the art wherein pyrrol-1-yl has been replaced by 2-benzofuryl are as follows:

Example 184

2-(2-Benzofuran-2-yl-phenylmethanesulfinyl)-N,N-dimethyl-acetamide

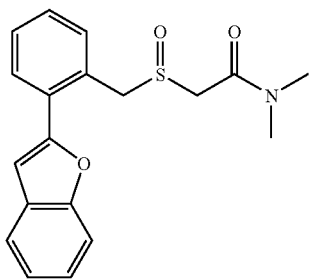

Synthesis of Compound E3 Wherein (Ar=benzofuran-2-yl; ortho; NR$^{12}$R$^{13}$=N(CH$_3$)$_2$)

Compound O3 (Ar=benzofuran-2-yl; ortho)

To a mixture of 2-(benzofuran-2-yl)benzoic acid (22.5 g, 94.5 mmol) (J. Het. Chem. 1990, 605) in dry THF (200 ml) was added drop wise 100 ml of 1.0 M BH$_3$-THF solution at R.T. under nitrogen during 30 min. The reaction mixture was stirred at R.T. for 16 h, then quenched by brine. The organic layer was washed with brine, dried over MgSO$_4$, concentrated to give 21 g of compound O, (2-(benzofuran-2-yl)-phenyl)-methanol, as a beige solid.

$^1$H-NMR (400 MHz, DMSO-d$_6$) δ 3.36 (1H, s), 4.75 (2H, d), 5.39 (1H, t), 7.3 (3H, m), 7.45 (2H, m), 7.64 (3H, m), 7.84 (1H, d).

Compound G3 (Ar=benzofuran-2-yl; ortho; R=ethyl)

To a mixture of compound O3, (2-(benzofuran-2-yl)-phenyl)-methanol, (5.2 g, 23.2 mmol), ethyl thioglycolate (2.8 g, 23.3 mmol) in 50 ml of CH$_2$Cl$_2$, ZnI$_2$ (7.5 g, 23.5 mmol) was added at R.T.; then the reaction was maintained at R.T. for 24 h. Water was added and the organic layer was washed with water, dried over MgSO$_4$ and evaporated, the residue was purified by flash chromatography three times (cyclohexane/ethyl acetate 5/1) to give 2.66 g of compound G3 a yellowish oil.

Compound M3 (Ar=benzofuran-2-yl; ortho; NR$^{12}$R$^{13}$=N(CH$_3$)$_2$)

To a mixture of compound G3 (1.7 g, 5.2 mmol) and dimethylamine hydrochloride (0.6 g, 7.36 mmol) in 50 ml of CH$_2$Cl$_2$, was added a 2M solution of trimethylaluminum in toluene (3.7 ml, 7.4 mmol) at RT. The reaction was stirred for 18 h, then quenched by water, the organic phase was dried over MgSO$_4$, evaporated, the residue was purified by flash chromatography (CH$_2$Cl$_2$/MeOH, 40/1) to furnish 0.89 g of compound M3 as an oil.

Synthesis of Example 184

To a solution of compound M3 (0.89 g, 2.7 mmol) in 10 ml of acetic acid, were added 0.4 ml of 30% H$_2$O$_2$. The oxidation was maintained at R.T. for 4 h, then evaporated, the residue was purified by flash chromatography (CH$_2$Cl$_2$/MeOH, 20/1) followed by crystallization in ethanol to yield 0.8 g of the title compound, Example 184, as a white powder.

$^1$H-NMR (400 MHz, CHCl$_3$) δ 2.8 (3H, s), 2.9 (1H, s), 3.7 (2H, q), 4.6 (2H, q), 7.05 (1H, s), 7.25 (2H, m), 7.4 (2H, m), 7.55 (2H, m), 7.65 (1H, d), 7.8 (1H, dd).

The following Examples 184-185 in Table 8 were prepared using appropriate starting materials and/or reagents, as determined by one skilled in the art, according to the synthetic processes disclosed herein.

TABLE 8

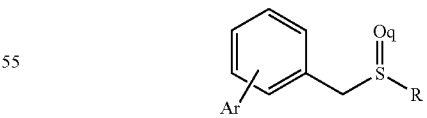

| Ex. No. | Ar | Ar Position | q | R |
|---|---|---|---|---|
| 184 | 2-Benzofuryl | ortho | 1 | CH$_2$CON(CH$_3$)$_2$ |
| 185 | 2-Benzofuryl | ortho | 1 | CH$_2$CONHCH(CH$_3$)$_2$ |

The following Table 8A demonstrates the analytical data, by each compound's mass spectrum, for Examples 184-185 and according to which synthetic process each compound was synthesized.

TABLE 8A

| Ex. No. | MF | MS | SYNTHETIC METHOD |
|---|---|---|---|
| 184 | $C_{19}H_{19}NO_3S$ | M + H = 342 | H |
| 185 | $C_{20}H_{21}NO_3S$ | M + H = 356 | H |
|  |  | M + Na = 378 |  |

Compounds Prepared According to Scheme I

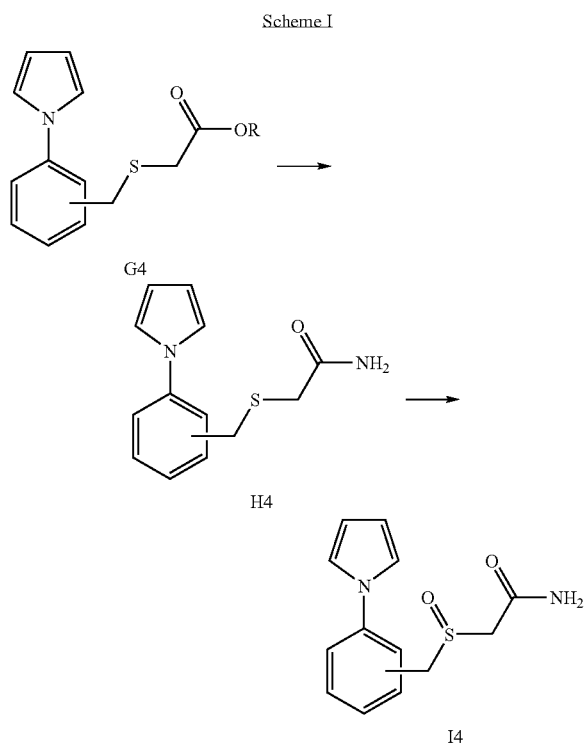

Scheme I

Example 186

2-(2-Pyrrol-1-yl-phenylmethanesulfinyl)-acetamide

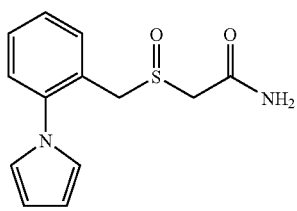

Synthesis of Compound 14 Wherein pyrrol-1-yl is ortho

Compound H4 (ortho-pyrrol-1-yl)

To a stirred solution of compound G4 (Ar=Pyrrol-1-yl; ortho; R=Me) (0.8 g; 3.1 mmol) in MeOH (30 mL) was added 28% NH$_4$OH (30 mL). The reaction mixture was stirred for two days and then the methanol was evaporated. Ethyl acetate (100 mL) was introduced into the resulting mixture, the organic layer was washed with water (2×50 mL) and dried in vacuo. Trituration of the resulting residue with Et$_2$O, filtration and drying under vacuum generate compound H4 (Ar=Pyrrol-1-yl; ortho) as an off-white powder. R$_f$=0.32 (95:5 methylene chloride/methanol); (0.47 g; 1.9 mmol; 61%)

Synthesis of Example 186

To a cooled solution of compound H4 (Ar=Pyrrol-1-yl; ortho) (0.47 g; 1.9 mmol) in methanol (15 mL) was added an aqueous solution (6 mL) of NaIO$_4$ (0.41 g; 1.9 mmol). The reaction mixture was stirred at room temperature overnight, then the methanol was removed under vacuum. The resulting residue was taken up into ethylacetate (100 mL), the organic layer was washed with water (2×50 mL), dried (MgSO$_4$) and concentrated in vacuo. Trituration of the resulting residue with cold Et$_2$O, filtration and drying under vacuum gave the title compound Example 186 (Ar=Pyrrol-1-yl; ortho) as an off-white powder. (0.32 g; 1.2 mmol; 63%)

$^1$H-NMR (DMSO-d$_6$) δ: 7.70 (broad s, 1H), 7.55 (m, 1H), 7.45 (m, 2H), 7.3 (broad s, 2H) 7.0 (broad s, 2H), 6.25 (broad s, 2H), 4.1 (d, 1H), 4.0 (d, 1H), 3.6 (d, 1H), 3.45 (d, 1H)

The following Examples 186-188 in Table 9 were prepared using appropriate starting materials and/or reagents, as determined by one skilled in the art, according to the synthetic processes disclosed herein.

TABLE 9

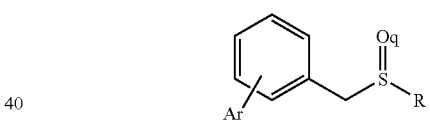

| Ex. No. | Ar | Ar Position | q | R |
|---|---|---|---|---|
| 186 | Pyrrol-1-yl | ortho | 1 | CH$_2$CONH$_2$ |
| 187 | Pyrrol-1-yl | meta | 1 | CH$_2$CONH$_2$ |
| 188 | Pyrrol-1-yl | para | 1 | CH$_2$CONH$_2$ |

The following Table 9A demonstrates the analytical data, by each compound's mass spectrum, for Examples 186-188 and according to which synthetic process each compound was synthesized.

TABLE 9A

| Ex. No. | Molecular Formula | Peak | Mass | Synthetic pathway |
|---|---|---|---|---|
| 186 | $C_{13}H_{14}N_2O_2S$ | M + H | 263 | I |
| 187 | $C_{13}H_{14}N_2O_2S$ | M + Na | 285 | I |
| 188 | $C_{13}H_{14}N_2O_2S$ | M + Na | 285 | I |

Compounds prepared according by an alternative to Scheme I (Scheme Alt-I) following the synthetic methods of Scheme I known to one skilled in the art wherein pyrrol-1-yl has been replaced by 1,4-benzodioxane are as follows:

Scheme Alt-I

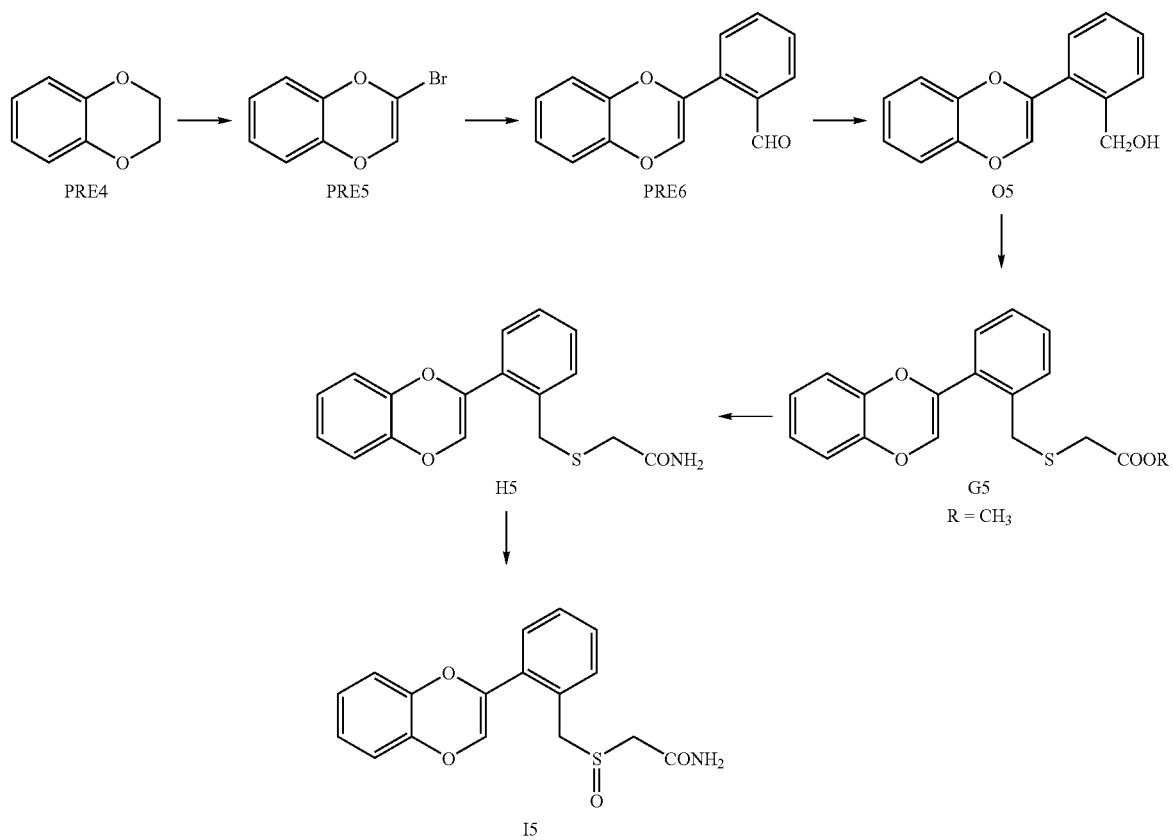

Example 190

2-(2-Benzo[1,4]dioxin-2-yl-phenylmethanesulfinyl)-acetamide

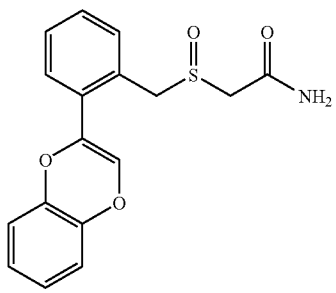

Synthesis of Compound I5

Synthesis of PRE5

To a solution of 1,4-benzodioxane (24.0 g, 176.2 mmol) in $CCl_4$ (240 mL) was added NBS (75.2 g, 422.9 mmol) and AIBN (80 mg, 0.5 mmol). The suspension was refluxed for 4 h by using a 60 W lamp then cooled. The reaction mixture was filtered. The filtrate was concentrated under reduced pressure. The residue was solubilize into $Et_2O$ (300 mL) and added dropwise during 20 min to a cooled suspension of tBuOK (30.0 g, 264.3 mmol) in $Et_2O$ (300 mL). Stirring was continued for 40 min. The reaction mixture was filtered through a pad of celite. The organic layer was then washed with water, dried over MgSO4 and concentrated. Flash chromatography (Petroleum Ether:EtOAc 9:1) of the crude product yielded a colorless oil (21.0 g, 56%).

Synthesis of PRE6

To a degassed solution of 2-bromo-1,4-benzodioxane (9.86 g, 46.3 mmol) in toluene (500 mL) was added Pd[P(Ph)$_3$]$_4$ (5.3 g, 4.6 mmol), a degassed solution of 2-formyl-boronic acid (10.3 g, 69.5 mmol) in EtOH (50 mL), then a degassed 2M aqueous solution of $Na_2CO_3$ (50 mL, 92.6 mmol). The reaction mixture was refluxed during 4 h under $N_2$ then concentrated. The residue was partitioned between EtOAc (200 mL) and water (150 mL). The organic layer was dried over $MgSO_4$ and concentrated. Flash chromatography (Petroleum ether:EtOAc 97:3 to 92:8) of the crude product yielded a yellow solid (10.41 g, 94%). mp=70° C.

$^1$H-NMR (CDCl$_3$) d (ppm): 10.42 (s, 1H), 7.96 (m, 1H), 7.60 (m, 1H), 7.51 (m, 2H), 6.88 (m, 2H), 6.76 (m, 2H), 6.11 (s, 1H).

Compound O5 (Ar=2-benzo[1,4]dioxine; ortho)

To a ice cooled suspension of PRE6 (7.0 g, 29.4 mmol) in MeOH (70 mL) was added portionwise NaBH$_4$ (0.73 g, 19.1 mmol). Stirring was continued during 1 h. The reaction was quenched with water (30 mL) and MeOH was evaporated. The aqueous residue was extracted with Et$_2$O. The organic layer was dried over MgSO$_4$ and concentrated. The crude compound (7.0 g, 99%) was used directly for the next step.

$^1$H-NMR (CDCl$_3$) d (ppm): 7.50 (m, 1H), 7.39 (m, 1H), 7.36 (broad s, 1H), 7.28 (m, 1H), 6.87 (m, 2H), 6.72 (m, 2H), 6.19 (s, 1H), 4.78 (d, 2H), 2.17 (t, 1H).

Compound G5 (Ar=2-benzo[1,4]dioxine; ortho; R=methyl)

To a solution of compound O5 (7.0, 29.1 mmol) and Et$_3$N (4.7 mL, 33.5 mmol) in THF (110 mL) at 0° C. under N$_2$ was added dropwise MsCl (2.6 mL, 33.5 mmol). After 1 h of stirring, additional Et$_3$N (0.2 mL) and MsCl (0.11 mL) were added. Stirring below 10° C. was continued during 2.5 h. The reaction mixture was filtered, and the filtrate concentrated. The residue was solubilize into MeOH (50 mL) and added to an ice cooled solution of methyl thioglycolate (3.2 mL, 35.0 mmol) and tBuOK (4.0 g, 35.0 mmol) in MeOH (100 mL). The thick reaction mixture was diluted MeOH (100 mL), stirred during 1 h, then concentrated. The residue was partitioned between EtOAc (200 mL) and saturated aqueous NH$_4$Cl (200 mL). The organic layer was dried over MgSO$_4$ and concentrated. Flash chromatography (Petroleum ether: EtOAc 96:4 to 9:1) of the crude product yielded a colorless oil (8.03 g, 84%).

$^1$H-NMR (CDCl$_3$) d (ppm): 7.42 (m, 1H), 7.35 (m, 2H), 7.27 (m, 1H), 6.86 (m, 2H), 6.72 (m, 2H), 6.17 (s, 1H), 4.05 (s, 2H), 3.67 (s, 3H), 3.18 (s, 2H).

Compound H5 (Ar=2-benzo[1,4]dioxine; ortho): Example 189

Aqueous ammonia (8 mL) was added to a solution of G5 (1.16 g, 3.53 mmol) in methanol (12 mL). The reaction mixture was stirred at RT during 17 h and concentrated. The residue was partitioned between water and CH$_2$Cl$_2$. The combined organic layers were dried over MgSO$_4$ and concentrated. Flash chromatography (CH$_2$Cl$_2$:MeOH 98:2 to 95:5) of the crude product yielded a white solid (716 mg). This product was solubilized into EtOAc and washed with 10% NaOH to remove traces of acid derivative (4%). Amide H5 white solid. mp=82-83° C.

$^1$H-NMR (CDCl$_3$) d (ppm): 7.34 (m, 3H), 7.28 (m, 1H), 6.87 (m, 2H), 6.72 (m, 2H), 6.67 (Broad s, 1H), 6.12 (s, 1H), 5.79 (Brod s, 1H), 3.98 (s, 2H), 3.17 (s, 2H).

Synthesis of Example 190: (Ar=2-benzo[1,4]dioxine; ortho)

To an ice/water-cooled solution of 189 (594 mg, 1.90 mmol) in acetic acid (2.2 mL) was added dropwise H$_2$O$_2$ (0.2 mL, 2.18 mmol). The reaction mixture was stirred at RT during 3.5 h, then diluted with CH$_2$Cl$_2$, and washed carefully with saturated aqueous NaHCO$_3$ (2×60 mL). The combined organic layers were dried over MgSO$_4$ and concentrated to give a white solid, Example 190, (511 mg, 82%) which was triturated in EtOH. mp=130-131° C.

$^1$H-NMR (CDCl$_3$) d (ppm): 7.34 to 7.43 (m, 4H), 7.08 (Broad s, 1H), 6.88 (m, 2H), 6.74 (m, 2H), 6.14 (s, 1H), 5.75 (Broad s, 1H), 4.37 (s, 2H), 3.66 (d, 1H), 3.29 (d, 1H).

The following Examples 189-190 in Table 10 were prepared using appropriate starting materials and/or reagents, as determined by one skilled in the art, according to the synthetic processes disclosed herein.

TABLE 10

| Ex. No. | Ar | Ar Position | q | R |
|---|---|---|---|---|
| 189 | 2-benzo[1,4]dioxine | ortho | 0 | CH$_2$CONH$_2$ |
| 190 | 2-benzo[1,4]dioxine | ortho | 1 | CH$_2$CONH$_2$ |

The following Table 10A demonstrates the analytical data, by each compound's mass spectrum, for Examples 189-190 and according to which synthetic process each compound was synthesized.

TABLE 10A

| Ex. No. | MF | MS | SYNTHETIC METHOD |
|---|---|---|---|
| 189 | C$_{17}$H$_{15}$NO$_3$S | M + H = 314 | I |
|  |  | M + Na = 336 |  |
| 190 | C$_{17}$H$_{15}$NO$_4$S | M + H = 330 | I |
|  |  | M + Na = 352 |  |

Compounds prepared according by an alternative to Scheme I (Scheme Alt-II) following the synthetic methods of Scheme I known to one skilled in the art wherein pyrrol-1-yl has been replaced by 2-benzofuryl are as follows:

Example 191

2-(2-Benzofuran-2-yl-phenylmethanesulfinyl)-acetamide

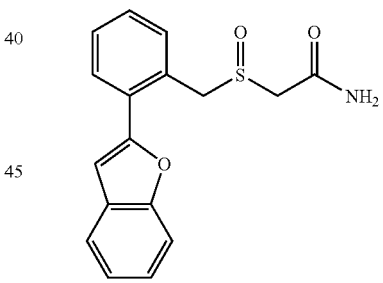

Synthesis of Compound I Wherein Ar is 2-benzofuryl

Compound H (Ar=2-benzofuryl, ortho)

Compound G (Ar=2-benzofuryl, ortho; R=ethyl) (2.66 g, 8.16 mmol) was stirred in a mixture of 50 ml ethanol and 50 ml of 28% NH$_4$OH for 18 h to give a suspension that was filtered, the crude product was purified by flash chromatography (CH$_2$Cl$_2$/MeOH, 30/1) to afford 1.3 g of compound H as a white solid.

Synthesis of Example 191 ((Ar=2-benzofuryl, ortho)

To a solution of compound H (1.3 g, 4.3 mmol) in 20 ml of acetic acid, was added 30% H$_2$O$_2$ (0.5 ml). The oxidation was maintained at R.T. for 4 h, then evaporated, the residue was recrystallized in ethanol (20 ml) to yield 1.17 g of 191 as a white powder.

$^{1}$H-NMR (400 MHz, DMSO-$d_6$) δ 3.7 (2H, q), 4.34 (1H, d), 4.69 (1H, d), 7.33 (4H, m), 7.5 (3H, m), 7.67 (2H, dd), 7.75 (1H, s), 7.86 (1H, d).

The following Example 191 in Table 11 was prepared according to the synthetic processes disclosed herein.

TABLE 11

| Ex. No. | Ar | Ar Position | q | R |
|---|---|---|---|---|
| 191 | 2-Benzofuryl | ortho | 1 | CH$_2$CONH$_2$ |

The following Table 11A demonstrates the analytical data, by the compound's mass spectrum, for Example 191 and according to which synthetic process the compound was synthesized.

TABLE 11A

| Ex. No. | MF | MS | SYNTHETIC METHOD |
|---|---|---|---|
| 191 | C$_{17}$H$_{15}$NO$_3$S | M + Na = 336 | Alt-II |

The following Examples 192-193 in Table 12 were prepared using appropriate starting materials and/or reagents, as determined by one skilled in the art, according to the synthetic processes disclosed herein.

TABLE 12

| Ex. No. | Ar | Ar Position | q | R |
|---|---|---|---|---|
| 192 | 1,3-Dihydro-isoindol-2-yl | ortho | 1 | CH$_2$CONH$_2$ |
| 193 | 1,3-Dihydro-isoindol-2-yl | meta | 1 | CH$_2$CONH$_2$ |

The following Table 12A demonstrates the analytical data, by each compound's mass spectrum, for Examples 192-193 and according to which synthetic process each compound was synthesized.

TABLE 12A

| Ex. No. | Molecular Formula | Peak | Mass | Synthetic pathway |
|---|---|---|---|---|
| 192 | C$_{17}$H$_{18}$N$_2$O$_2$S | M + H | 315 | J |
| 193 | C$_{17}$H$_{18}$N$_2$O$_2$S | M + H | 315 | J |

The following general Scheme K depicts the synthesis of various ortho-biphenyl-derived compounds as disclosed in Table 1. Members of the meta- and para-families were also synthesized following similar synthetic methods starting with appropriate starting materials.

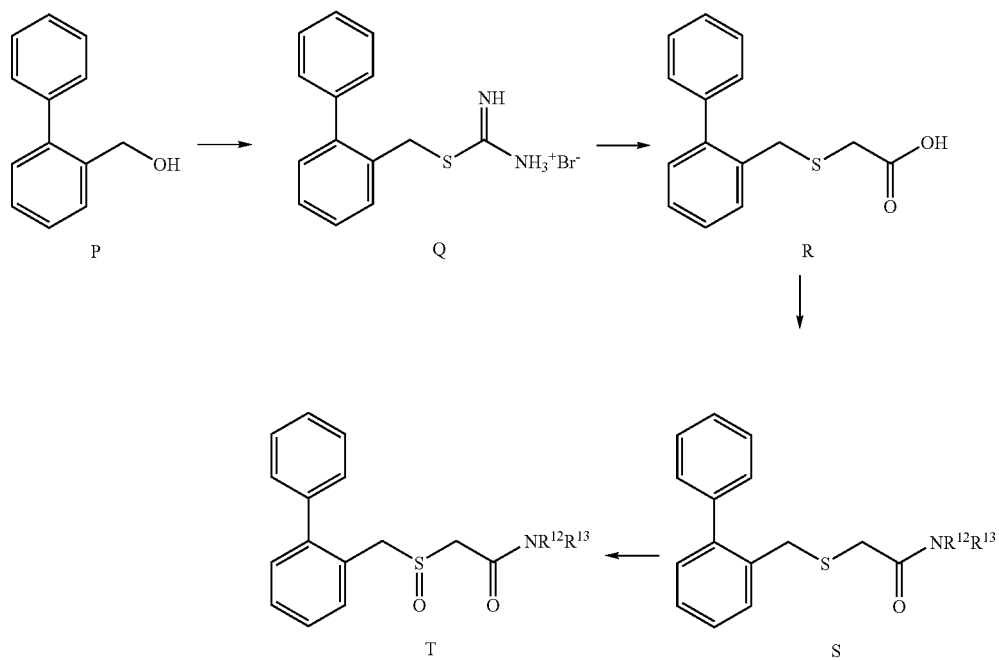

Scheme K

Example 194

2-(Biphenyl-2-ylmethanesulfinyl)-N,N-dimethyl-acetamide

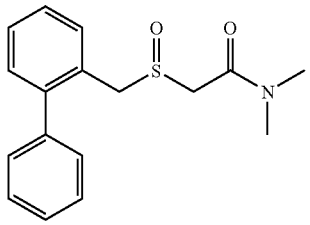

Compound R, (Biphenyl-2-ylmethylsulfanyl)-acetic acid

To a mixture of thiourea (6 g, 78 mmol) in 48% HBr (55 mL) at 60° C. was added compound P (10 g, 54 mmol) in portions. The reaction mixture was then heated to reflux for 0.5 h, cooled and filtered. The residue was washed several times with water and ether, and dried in vacuo to yield 14.8 g of compound Q (white solid) that was immediately used in the next step without any further purification. Thus, to a mixture of compound Q (7.4 g, 23 mmol) and 14% aq. NaOH (18 mL) at 70° C. was added a solution of chloroacetic acid (2.4 g, 25 mmol) in 2% aq. NaOH (2.5 mL). The reaction mixture was then heated at 110° C. for 0.5 h, cooled, diluted with ice-water, acidified (pH~2) and extracted with ethyl acetate (3×100 mL). Combined organic layer was washed with brine (1×100 mL), dried (MgSO$_4$) and concentrated to yield 5.6 g of compound R (gum) that was directly used in the next step without any further purification.

Compound S, 2-(Biphenyl-2-ylmethylsulfanyl)-N,N-dimethyl-acetamide

To a cooled (0° C.) solution of compound R (2 g, 8 mmoles) in anhyd.DMF (10 mL) was added N-methylmorpholine (2 mL, 18 mmol) followed by 2-(1H-benzotriazol-1-yl)-1,1,3,3-tetramethyluronium tetrafluoroborate (TBTU, 3.2 g, 10 mmol) The mixture was stirred for 0.5 h, treated with dimethylamine hydrochloride (0.815 g, 10 mmol, and stirred overnight at room temperature. Next day, it was diluted with ethyl acetate (100 mL), washed with water (1×50 mL), 2% aq. citric acid (2×50 mL), 2% aq. NaHCO$_3$ (2×50 mL), water (1×50 mL), and brine (1×50 mL), dried (MgSO$_4$) and concentrated to give 1.5 g of compound S(NR$^{12}$R$^{13}$=NMe$_2$) that was directly used in the next step without any further purification.

Compound T: Synthesis of Example 194; 2-(Biphenyl-2-ylmethanesulfinyl)-N,N-dimethyl-acetamide A mixture of compound S(NR$^{12}$R$^{13}$=NMe$_2$, 1.5 g, 5.3 mmol), 50% aq. H$_2$O$_2$ (0.410 mL) and gl. acetic acid (3 mL) was stirred at room temperature for 3 h, diluted with ethyl acetate (10 mL), concentrated at high vacuum and triturated with ether to give the title compound, Example 194 (NR$^{12}$R$^{13}$=NMe$_2$, 865 mg) as a white solid; $^1$H-NMR DMSO-d$_6$ δ 7.60-7.24 (m, 9H), 4.13 (q, 2H), 3.85 (q, 2H), 2.92 (s, 3H), 2.77 (s, 3H).

The following Examples 194-222 in Table 13 were prepared using appropriate starting materials and/or reagents, as determined by one skilled in the art, according to the synthetic processes disclosed according to Scheme K.

TABLE 13

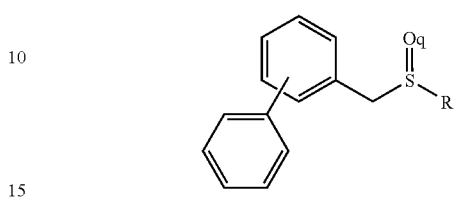

| Ex. No. | Biphenyl Isomer | q | R | MS M + H | MP ° C. |
|---|---|---|---|---|---|
| 194 | ortho | 1 | CH$_2$CON(CH$_3$)$_2$ | 302 | gum |
| 195 | ortho | 1 | CH$_2$CONH$_2$ | 274 | 140-145 |
| 196 | ortho | 1 | CH$_2$CONHCH$_3$ | 288 | 118 |
| 197 | ortho | 1 | CH$_2$CON(C$_2$H$_5$)$_2$ | 330 | 102 |
| 198 | ortho | 1 | CH$_2$CONH(CH$_2$)$_2$OH | 318 | 117-120 |
| 199 | ortho | 1 | CH$_2$CONHCH$_2$-(3-pyridyl) | 365 | 56-59 |
| 200 | ortho | 1 | CH$_2$CONH(cyclobutyl) | 328 | gum |
| 201 | ortho | 1 | CH$_2$CONH-(cyclopentyl) | 342 | gum |
| 202 | ortho | 1 | CH$_2$CO-N-pyrrolidinyl | 328 | gum |
| 203 | ortho | 1 | CH$_2$CO-N-(2-carboxamide)-pyrrolidinyl | 371 | gum |
| 204 | ortho | 1 | CH$_2$CO-N-morpholinyl | 344 | 162 |
| 205 | ortho | 1 | CH$_2$CO-N-piperazinyl | 343 | 80 |
| 206 | ortho | 1 | CH$_2$CO-N-1-(4-t-butyl-carboxylate)-piperazinyl | 443 | 58-62 |
| 207 | ortho | 1 | CH$_2$CO NHCH$_2$CN | 313 | 139 |
| 208 | ortho | 1 | CH$_2$CO NHCH$_2$CF$_3$ | 356 | 137 |
| 209 | ortho | 1 | CH$_2$CO-N-azetidinyl | 314 | gum |
| 210 | ortho | 1 | CH$_2$CONHCH(CH$_3$)$_2$ | 316 | gum |
| 211 | para | 1 | CH$_2$CO NH$_2$ | 274 | 144 |
| 212 | para | 1 | CH$_2$CO-N-pyrrolidinyl | 328 | 139-141 |
| 213 | para | 1 | CH$_2$CO N(CH$_3$)$_2$ | 302 | 75 |
| 214 | para | 1 | CH$_2$CO-N- morpholinyl | 344 | 146-147 |
| 215 | para | 1 | CH$_2$CO-N-piperidinyl | 342 | 96-100 |
| 216 | para | 1 | CH$_2$CONH(CH$_2$)$_2$-(2-pyridyl) | 379 | 182 |
| 217 | para | 1 | CH$_2$CONHCH$_2$-(3-pyridyl) | 365 | 193 |
| 218 | para | 1 | CH$_2$CONHCH(CH$_3$)$_2$ | 316 | 193 |
| 219 | meta | 1 | CH$_2$CONH$_2$ | 274 | 182 |
| 220 | meta | 1 | CH$_2$CON(CH$_3$)$_2$ | 302 | 87 |
| 221 | meta | 1 | CH$_2$CO-N-pyrroldiinyl | 328 | gum |
| 222 | meta | 1 | CH$_2$CONHCH(CH$_3$)$_2$ | 316 | 129-130 |

The following Scheme L depicts the synthesis of various ortho-biphenyl-derived compounds as disclosed in Table 14, which can be obtained through the intermediacy of compound SS. Members of the meta- and para-families were also synthesized following similar synthetic methods starting with appropriate starting materials.

Scheme L

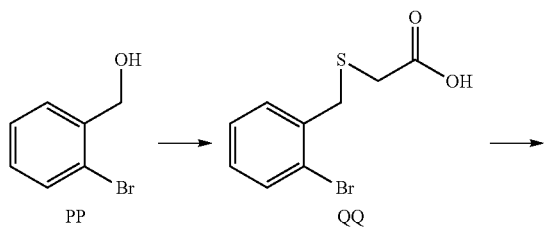

PP     QQ

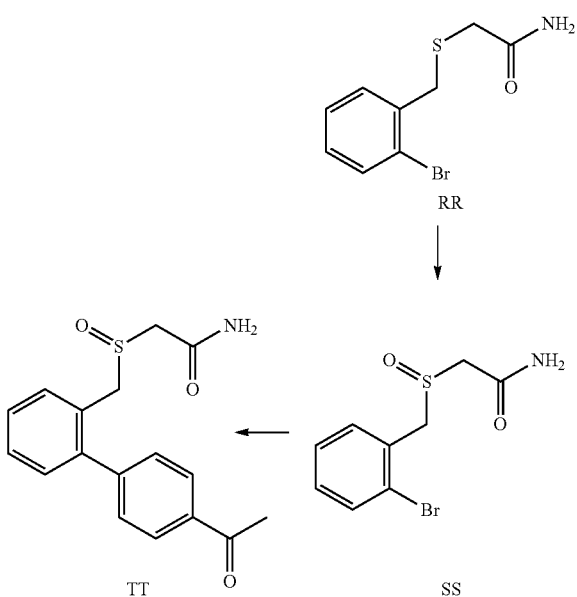

Example 223

2-(4'-Acetyl-biphenyl-2-ylmethanesulfinyl)-acetamide

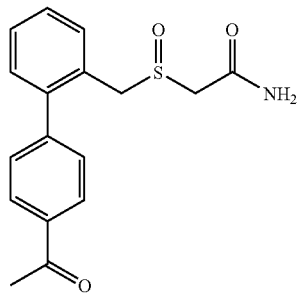

Compound QQ

To a solution of thiourea (21 g, 0.28 mol) in 48% HBr (102 mL) was added compound PP, (2-bromo-phenyl)-methanol (35 g, 0.187 mol) followed by water (20 mL). The reaction mixture was heated to 100° C. for 1 h, cooled to room temperature and filtered. Residue was washed several times with water and ether, successively and dried under vacuum to generate 39 g of the corresponding intermediate thiouronium salt; $^1$H-NMR (DMSO-d$_6$): δ 9.30 (b, 2H), 9.10 (b, 2H), 7.70 (d, 1H), 7.60 (d, 1H), 7.40 (t, 1H), 7.30 (t, 1H), 4.50 (s, 2H). Above material was then combined with material from another batch and used in the next step without any further purification.

Thus, to a mixture of the thiouronium salt (62 g) in 10 N NaOH (106 mL, 1.06 mol) and water (50 mL) at 70° C. was added chloroacetic acid (26.3 g, 0.27 mol) in water (50 mL). The reaction was then heated to 110° C., maintained there for 1 h, cooled to room temperature, diluted with water (100 mL), and washed with ether (50 mL). The aqueous basic layer was then acidified (pH~2) and extracted into ethyl acetate (3×100 mL). Combined organic layer was washed with brine (1×50 mL), dried (MgSO$_4$), and concentrated to give 50 g of compound QQ that was directly used in the next step without any further purification; $^1$H-NMR (DMSO-d$_6$): δ 12.60 (b, 1H), 7.60 (d, 1H), 7.40 (d, 1H), 7.35 (t, 1H), 7.20 (t, 1H), 3.90 (s, 2H), 3.20 (s, 2H).

Compound RR

To a solution of compound QQ (50 g, 0.192 mol) in benzene (250 mL) at 80° C. was added thionyl chloride (56 mL, 0.766 mol) dropwise. The reaction mixture was heated for another hour, cooled to room temperature, and concentrated to an oil. It was dissolved in methylene chloride (200 mL), cooled (ice bath) and treated dropwise with ammonium hydroxide (50 mL). The reaction mixture was then stirred at room temperature overnight and the layers separated. Aqueous layer was extracted with methylene chloride (2×50 mL). Combined organic layer was washed with brine (1×50 mL), dried (MgSO$_4$), and concentrated to give a residue that on trituration with ether generated 35.88 g of compound RR; $^1$H-NMR (DMSO-d$_6$): δ 7.60 (d, 1H), 7.50 (m, 2H), 7.35 (t, 1H), 7.20 (t, 1H), 7.00 (s, 1H), 3.90 (s, 2H), 3.00 (s, 2H).

Compound SS

To a solution of compound RR (25.88 g, 0.099 mol) in glacial acetic acid (100 mL) at room temperature was added 50% hydrogen peroxide (7.46 mL, 0.129 mol). The reaction was stirred for 2 h, concentrated and triturated with ether to produce 26.6 g of compound SS that served as the key building block for the compounds disclosed in Table 14; $^1$H-NMR (DMSO-d$_6$): δ 7.70 (m, 2H), 7.50-7.20 (m, 4H), 4.50 (d, 1H), 4.20 (d, 1H), 3.70 (d, 1H), 3.50 (d, 1H).

Synthesis of Compound TT; Example 223

A mixture of compound SS (2 g, 0.00725 mol), 4-acetylphenylboronic acid (2.38 g, 0.0145 mol), tetrakis (triphenylphosphine)palladium(0) (0.837 g, 0.000725 mol), aq. sodium carbonate solution (2M, 7.3 mL, 0.00145 mol), ethanol (10 mL) and toluene (10 mL) was heated to 80° C. for 1 h. The reaction mixture was then cooled, concentrated and partitioned between methylene chloride (100 mL) and water (50 mL). The organic layer was separated, washed with brine (1×50 mL), dried (MgSO$_4$) and concentrated to give a crude residue that was purified by flash chromatography (silica, eluting solvent:methanol:methylene chloride: 3:97) to give 1.66 g of the title compound Example 223; $^1$H-NMR (DMSO-d$_6$): δ 8.00 (d, 2H), 7.75-7.25 (m, 8H), 4.50-3.50 (m, 4H), 2.60 (s, 3H).

The substituted ortho-biphenyl compounds, Examples 223-352, of Table 14 were prepared by methods known to one skilled in the art following the general methods of Scheme K using the intermediate compound SS. Other members were also prepared in a similar fashion utilizing compound SS and an appropriate coupling component.

TABLE 14

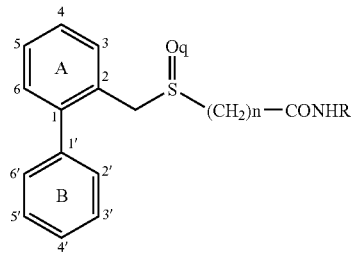
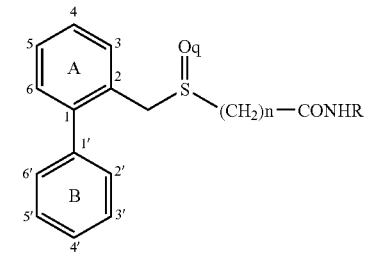

| Ex. No. | q | Substitution on Biphenyl Moiety | n | R | MS M+H | MP °C. |
|---|---|---|---|---|---|---|
| 223 | 1 | 4'-COCH₃ | 1 | H | 316 | 155-160 |
| 224 | 1 | 4'-F | 1 | H | 292 | 150 |
| 225 | 1 | 4'-CH₃ | 1 | H | 288 | 132 |
| 226 | 1 | 2'-CH₃ | 1 | H | 288 | 146 |
| 227 | 1 | 3',5'-Difluoro | 1 | H | 310 | 160 |
| 228 | 1 | 3',5'-Dimethyl | 1 | H | 302 | 138-140 |
| 229 | 1 | 3'-F | 1 | H | 292 | 134-135 |
| 230 | 1 | 2'-F | 1 | H | 292 | 140-142 |
| 231 | 1 | 2'-OEt | 1 | H | 318 | 116-119 |
| 232 | 1 | 3'-F, 4'-Ph | 1 | H | 368 | 167-173 |
| 233 | 1 | 2'-OMe, 5'-F | 1 | H | 322 | 154 |
| 234 | 1 | 4'-OMe | 1 | H | 304 | 151-154 |
| 235 | 1 | 4'-OPh | 1 | H | 366 | 30-40 |
| 236 | 1 | 3'-CN | 1 | H | 299 | 146-152 |
| 237 | 1 | 3'CONH₂ | 1 | H | 317 | 185-187 |
| 238 | 1 | 3',5'-Dichloro | 1 | H | 342 | 32-54 |
| 239 | 1 | 3'-CF₃ | 1 | H | 342 | 107-114 |
| 240 | 1 | 3'-SCH₃ | 1 | H | 320 | gum |
| 241 | 1 | 3'-SOMe | 1 | H | 336 | gum |
| 242 | 1 | 3'-OCF₃ | 1 | H | 358 | 94-95 |
| 243 | 1 | 3'-CONMe₂ | 1 | H | 345 | 32-40 |
| 244 | 1 | 4'-OCF₃ | 1 | H | 358 | 161-164 |
| 245 | 1 | 4'-CF₃ | 1 | H | 342 | 189-190 |
| 246 | 1 | 4'-SCH₃ | 1 | H | 320 | 160-172 |
| 247 | 1 | 4'-SOCH₃ | 1 | H | 336 | 169-173 |
| 248 | 1 | 2'-Cl | 1 | H | 308 | 146-149 |
| 249 | 1 | 3'-Cl | 1 | H | 308 | 142-144 |
| 250 | 1 | 4'-Cl | 1 | H | 308 | 151-154 |
| 251 | 1 | 2'-OMe | 1 | H | 304 | 129-131 |
| 252 | 1 | 3'-OMe | 1 | H | 304 | 127-129 |
| 253 | 1 | 3',4'-Dimethoxy | 1 | H | 334 | 173-177 |
| 254 | 1 | 3',4'-Methylenedioxy | 1 | H | 318 | 129-132 |
| 255 | 1 | 3',4'-Ethylenedioxy | 1 | H | 332 | 162-168 |
| 256 | 1 | 3',4'-Propylenedioxy | 1 | H | 346 | 140-143 |
| 257 | 1 | 2',6'-Dimethoxy | 1 | H | 334 | 146-149 |
| 258 | 1 | 2',5'-Dimethoxy | 1 | H | 334 | 164-165 |
| 259 | 1 | 3'-NO₂ | 1 | H | 319 | 163-166 |
| 260 | 1 | 2'-OH | 1 | H | 290 | 213-216 |
| 261 | 1 | 3'-OH | 1 | H | 290 | 157-162 |
| 262 | 1 | 4'-OH | 1 | H | 290 | 170-173 |
| 263 | 1 | 4'-CN | 1 | H | 299 | 171-174 |
| 264 | 1 | 3'-Me | 1 | H | 288 | 102-118 |
| 265 | 1 | 2'-OCF₃ | 1 | H | 358 | 151-156 |
| 266 | 1 | 3'-Me, 4'-F | 1 | H | 306 | 153-156 |
| 267 | 1 | 2'-SMe | 1 | H | 320 | 31-41 |
| 268 | 1 | 3-Cl, 4'-F | 1 | H | 326 | 162 |
| 269 | 1 | 2'-OMe, 5'-Cl | 1 | H | 338 | 167 |
| 270 | 1 | 2'-SOMe | 1 | H | 336 | 28-54 |
| 271 | 1 | 4,5-(OMe)₂ | 1 | H | 334 | 145-147 |
| 272 | 1 | 4'-Br | 1 | H | 353 | 163-175 |
| 273 | 1 | 2'-OMe, 4'-Cl | 1 | H | 338 | 174-177 |
| 274 | 1 | 2'-Me, 4'-Cl | 1 | H | 322 | 28-48 |
| 275 | 1 | 2'-Cl, 4'-Cl | 1 | H | 342 | 43-53 |
| 276 | 1 | 2'-CF₃ | 1 | H | 342 | 172-175 |
| 277 | 1 | 2'-F, 4'-Br | 1 | H | 371 | 215 |
| 278 | 2 | 4'-Cl | 1 | H | 324 | 226-230 |
| 279 | 1 | 4'-CHMe₂ | 1 | H | 316 | 173-175 |
| 280 | 1 | 4'-CMe₃ | 1 | H | 330 | 211-213 |
| 281 | 2 | 4'-Me | 1 | H | 304 | 222-225 |
| 282 | 2 | 4'-F | 1 | H | 308 | 179-181 |
| 283 | 1 | 4'-Cl | 1 | (CH₂)₂OH | 352 | 164-168 |
| 284 | 1 | 3'-Br | 1 | H | 353 | 42-56 |
| 285 | 1 | 2'-Br | 1 | H | 353 | 164-166 |
| 286 | 1 | 4'-Cl | 1 | NHR is replaced by N-pyrrolidinyl group | 362 | 39-56 |
| 287 | 1 | 4'-NMe₂ | 1 | H | 317 | 157-160 |
| 288 | 1 | 4'-CH=CH₂ | 1 | H | 300 | 162-165 |
| 289 | 1 | 4'-Cl | 1 | NHR is replaced by 4-acetylpiperazinyl group | 419 | 77-91 |
| 290 | 1 | 4'-SO₂Me | 1 | H | 352 | 199-203 |
| 291 | 1 | 3',4'-Cl₂ | 1 | H | 342 | 168-170 |
| 292 | 1 | 4'-Et | 1 | H | 302 | 137-139 |
| 293 | 1 | 4'-CH₂OMe | 1 | H | 318 | 111-115 |
| 294 | 1 | 4'-CO-N-(4-oxo)piperidinyl | 1 | H | 399 | 61-83 |
| 295 | 1 | 4'-NHSO₂Me | 1 | H | 367 | 47-74 |
| 296 | 1 | 4'-CONMe₂ | 1 | H | 345 | 64-73 |
| 297 | 1 | 4'-CO-N-morpholinyl | 1 | H | 387 | 51-77 |
| 298 | 1 | 4'-Cyclohexyl | 1 | H | 356 | 169-171 |
| 299 | 1 | 3',4'-F₂ | 1 | H | 310 | 39-41 |
| 300 | 1 | 3',4',5'-OMe₃ | 1 | H | 364 | 46-61 |
| 301 | 1 | 4'-N-morpholinyl | 1 | H | 359 | 203-204 |
| 302 | 1 | 4'-Cl | 2 | H | 322 | 132-135 |
| 303 | 1 | 3'-NMe₂ | 1 | H | 317 | 48-62 |
| 304 | 1 | 4'-CH₂CHMe₂ | 1 | H | 330 | 155-158 |
| 305 | 1 | 5-F, 4'-Cl | 1 | H | 326 | 164-165 |
| 306 | 1 | 3'-F, 4'-Cl | 1 | H | 326 | 44-56 |
| 307 | 1 | 5-F, 4'-Me | 1 | H | 306 | 161 |
| 308 | 1 | 5-F, 4'-F | 1 | H | 310 | 155 |
| 309 | 1 | 5-F, 4'-NMe₂ | 1 | H | 335 | 164 |
| 310 | 1 | 3'-OMe, 4'-Cl | 1 | H | 338 | 57-64 |
| 311 | 1 | 3',4'-F₂, 5'-OMe | 1 | H | 340 | 175-178 |
| 312 | 1 | 3'-CF₃, 4'-Cl | 1 | H | 376 | 179-182 |
| 313 | 1 | 4'-OCH₂CHMe₂ | 1 | H | 332 | 148 |
| 314 | 1 | 4'-COOMe | 1 | H | 332 | 153-155 |
| 315 | 1 | 4'-CH₂OH | 1 | H | 304 | 130-132 |
| 316 | 1 | 4'-COOtBu | 1 | H | 374 | 61-73 |
| 317 | 1 | 3',4'-Me₂ | 1 | H | 302 | 39-55 |
| 318 | 1 | 3'-CF₃, 4'-F | 1 | H | 360 | 134-138 |
| 319 | 1 | 3'-F, 4'-Me | 1 | H | 306 | 39-53 |
| 320 | 1 | 3'-Cl, 4'-Me | 1 | H | 322 | 40-60 |
| 321 | 1 | 3'-Me, 4'-Cl | 1 | H | 322 | 35-58 |
| 322 | 1 | 4,5-O—CH₂—O, 4'-Cl | 1 | H | 352 | 222 |
| 323 | 1 | 4,5-OMe₂, 4'-Cl | 1 | H | 368 | 172 |
| 324 | 1 | 4,5-O—CH₂—O, 4'-F | 1 | H | 336 | 189-191 |
| 325 | 1 | 5-F, 3',4'-F₂ | 1 | H | 328 | 145-146 |

TABLE 14-continued

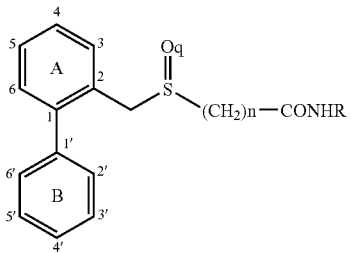

| Ex. No. | q | Substitution on Biphenyl Moiety | n | R | MS M+H | MP °C. |
|---|---|---|---|---|---|---|
| 326 | 1 | 4,5-O—CH$_2$—O, 4'-Me | 1 | H | 332 | 192-194 |
| 327 | 1 | 4,5-O—CH$_2$—O, 3',4'-F$_2$ | 1 | H | 354 | 187-189 |
| 328 | 1 | 4,5-OMe$_2$, 4'-F | 1 | H | 352 | 180-182 |
| 329 | 1 | 4,5-OMe$_2$, 4'-Me | 1 | H | 348 | 137-139 |
| 330 | 1 | 4,5-OMe$_2$, 3',4'-F$_2$ | 1 | H | 370 | 195-197 |
| 331 | 1 | 3'-Me, 4'-OMe | 1 | H | 317 | 177-180 |
| 332 | 1 | 5-Cl, 4'-Cl | 1 | H | 342 | 193-196 |
| 333 | 1 | 3',5'-Me$_2$, 4'-Cl | 1 | H | 336 | 41-67 |
| 334 | 1 | 5-Cl, 4'-F | 1 | H | 326 | 157-162 |
| 335 | 1 | 3'-CF$_3$, 4'-Me | 1 | H | 356 | 40-53 |
| 336 | 1 | 3'-NO$_2$, 4'-Cl | 1 | H | 353 | 185-188 |
| 337 | 1 | 4-F, 4'-Cl | 1 | H | 326 | 159-161 |
| 338 | 1 | 5-Cl, 3',4'-F$_2$ | 1 | H | 344 | 149-153 |
| 339 | 2 | 5-F, 4'-Cl | 1 | H | 342 | 239-240 |
| 340 | 1 | 4'-F | 2 | H | 306 | 114-118 |
| 341 | 1 | 4-F, 4'-F | 1 | H | 310 | 135-137 |
| 342 | 1 | 4-F, 4'-Me | 1 | H | 306 | 154-157 |
| 343 | 1 | 4-F, 3',4'-F$_2$ | 1 | H | 328 | 136-139 |
| 344 | 2 | 3',4'-F$_2$ | 1 | H | 326 | 172-180 |
| 345 | 1 | 5-Cl, 4'-Me | 1 | H | 322 | 145-147 |
| 346 | 1 | 4-OMe, 4'-Cl | 1 | H | 338 | 131-154 |
| 347 | 1 | 6-Me, 4'-Cl | 1 | H | 322 | 167-173 |
| 348 | 1 | 6-Me, 3',4'-Cl$_2$ | 1 | H | 357 | 50-122 |
| 349 | 1 | 4-OMe, 3',4'-Cl$_2$ | 1 | H | 373 | 173-176 |
| 350 | 1 | 4-Cl, 4'-Cl | 1 | H | 342 | 196-198 |
| 351 | 1 | 4-F, 3',4'-Cl$_2$ | 1 | H | 360 | 157-176 |
| 352 | 1 | 6-Me, 3'-F, 4'-Cl | 1 | H | 340 | 163 |

The substituted ortho-heteroaryl-phenyl or ortho-carbocyclic-phenyl compounds, Examples 353-359, of Table 14A were prepared by methods known to one skilled in the art following the general methods of Scheme K using the intermediate compound SS. Other members were also prepared in a similar fashion utilizing compound SS and an appropriate coupling component.

TABLE 14A

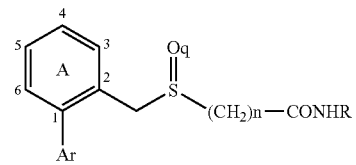

| Ex. No. | q | Ar | n | R | MS M+H | MP °C. |
|---|---|---|---|---|---|---|
| 353 | 1 | cyclohexen-1-yl | 1 | H | 278 | 146-149 |
| 354 | 1 | cyclopenten-1-yl | 1 | H | 264 | 135-136 |
| 355 | 1 | cyclohepten-1-yl | 1 | H | 292 | 136-137 |
| 356 | 1 | naphth-2-yl | 1 | H | 324 | 130-133 |
| 357 | 1 | phenoxathiin-4-yl | 1 | H | 396 | 83-84 |
| 358 | 1 | quinolin-3-yl | 1 | H | 325 | 173 |
| 359 | 1 | 3,5-dimethyl-isoxazol-4-yl | 1 | H | 293 | 40-45 |

The following Scheme M depicts the synthesis of Example 360 as disclosed in Table 15, which can be obtained through the intermediacy of compound PPP. Other meta biphenyl derived compounds were also prepared in a similar fashion utilizing appropriate starting materials and appropriate coupling components.

Scheme M

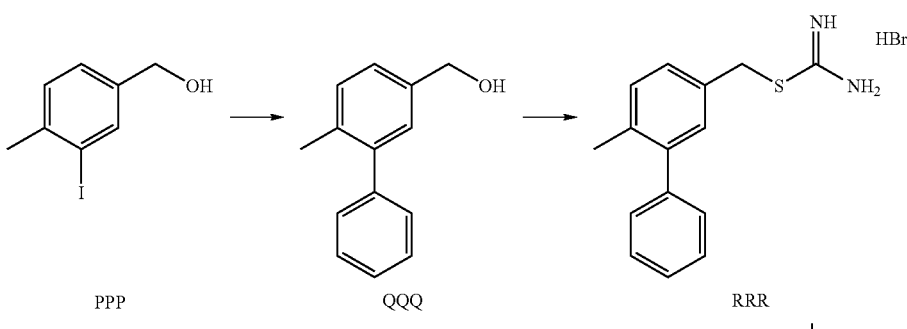

PPP      QQQ      RRR

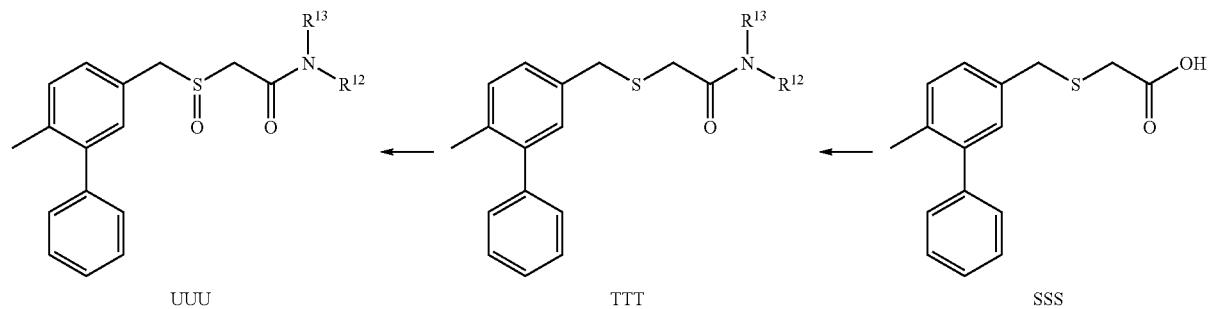

Example 360

2-(6-Methyl-biphenyl-3-ylmethanesulfinyl)-acetamide

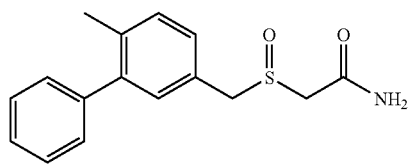

Compound QQQ:
(6-Methyl-biphenyl-3-yl)-methanol

To a mixture of compound PPP, (3-iodo-4-methyl-phenyl)-methanol, (4 g, 16.12 mmol) and phenylboronic acid (2.06 g, 16.89 mmol) in 1-propanol (30 mL) was successively added palladium(II) acetate (0.01276 g, 0.05 mmol), triphenyl phosphine (0.042 g, 0.161 mmol), aq. sodium carbonate solution (2 M, 11.44 mL, 22.88 mmol), and water (6 mL). The mixture was heated to 100° C. until reaction is complete (tlc), cooled, quenched with water (20 mL) and extracted into ethyl acetate (3×50 mL). Combined organic layer was washed with 2% aq. sodium bicarbonate (2×25 mL), brine (1×50 mL), dried (MgSO$_4$) and concentrated to yield 2.82 g of (6-methyl-biphenyl-3-yl)-methanol, compound QQQ, that was directly taken into next step without any further purification; R$_t$: 10.95 min.

Compound RRR:
2-(6-Methyl-biphenyl-3-ylmethyl)-isothiourea

To a solution of thiourea (1.57 g, 20.62 mmol) in 48% HBr in H$_2$O (15 mL, 133.67 mmol) at 60° C. was added compound QQQ (2.82 g, 14.22 mmol). The reaction was then heated to 95° C. for 0.5 h, cooled, and filtered. The residue was washed with water and ether, successively and dried under vacuum to generated 2.05 g of 2-(6-methyl-biphenyl-3-ylmethyl)-isothiourea, compound RRR, that was directly taken into next step without any further purification; R$_t$: 9.30 min.

Compound SSS

To a mixture of compound RRR (2.04 g, 6.08 mmol) in 50% aq. NaOH (1.28 mL, 24.32 mmol) and water (3.52 mL) at 70° C. was added chloroacetic acid (0.632 g, 6.69 mmol) in 50% NaOH (0.024 mL, 0.45 mmol) and water (0.627 mL). The reaction was then heated to 100° C. for 0.5 h, cooled, quenched with ice-water, acidified (pH~2) and extracted with ethyl acetate (3×50 mL). Combined organic layer was washed with water (1×50 mL), brine (1×50 mL), dried (MgSO$_4$), and concentrated to give 0.89 g of compound SSS; R$_t$: 13.06 min.

Compound TTT (Wherein NR$^{12}$R$^{13}$=NH$_2$)

A solution of compound SSS (0.89 g, 3.28 mmol), 2-(1H-Benzotriazol-1-yl)-1,1,3,3-tetra-methyluronium tetrafluoroborate (TBTU, 1.158 g, 3.608 mmol), and NMM (0.829 mL, 8.2 mmol) in DMF (10 mL) was stirred for 5 min at room temperature, treated with HOBt.NH$_3$ complex (0.748 g, 4.92 mmol) and stirred for additional 2.5 h. It was then diluted with ethyl acetate (100 mL), washed successively with water (2×50 mL), 2% aq.citric acid (2×50 mL), 2% aq. sodium bicarbonate (2×50 mL), water (1×50 mL) and brine (1×50 mL), dried (MgSO$_4$), and concentrated to give 0.35 g of compound TTT that was directly taken into next step without any further purification; R$_t$: 11.23 min.

Synthesis of Example 360 (Compound UUU Wherein NR$^{12}$R$^{13}$=NH$_2$)

To a solution of compound TTT (0.34 g, 1.29 mmol) in gl. acetic acid (1.06 mL) at room temperature was added 50% hydrogen peroxide (0.085 mL, 1.68 mmol). The reaction mixture was stirred for 0.5 h, concentrated and triturated with ether to give 0.154 g of Example 360: $^1$H-NMR (DMSO-d$_6$), δ 7.67-7.16 (m, 10H), 4.29-3.98 (dd, 2H), 3.64-3.41 (dd, 2H), 2.24 (s, 3H).

The substituted meta-biphenyl compounds, Examples 360-399, of Table 15 were prepared by methods known to one skilled in the art following the general methods of Scheme M. The Examples of Table 15 were prepared in a similar fashion utilizing appropriate reactants.

TABLE 15

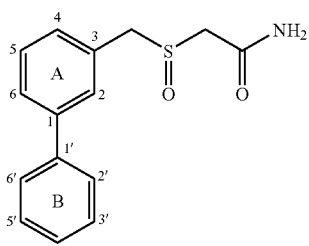

| Ex. No. | q | Substitution | MS M + H | MP ° C. |
|---|---|---|---|---|
| 360 | 1 | 6-Me | 288 | 153 |
| 361 | 1 | 2-Me | 288 | 214 |
| 362 | 1 | 4-OMe | 304 | 184-186 |
| 363 | 1 | 2'-Cl | 308 | 116-119 |
| 364 | 1 | 3'-Cl | 308 | 152-155 |
| 365 | 1 | 4'-Cl | 308 | 188-190 |
| 366 | 1 | 3',4'-(OMe)$_2$ | 334 | 131-134 |
| 367 | 1 | 2'-Me, 4'-Cl | 322 | 146-148 |
| 368 | 1 | 2'-OMe, 4'-Cl | 338 | 115-118 |
| 369 | 1 | 2'-CN | 299 | 136-139 |
| 370 | 1 | 2'-Cl, 4'-Cl | 343 | 126-129 |
| 371 | 1 | 3'-OMe | 304 | 128-130 |
| 372 | 1 | 4'-OMe | 304 | 198-200 |
| 373 | 1 | 2'-OMe | 304 | 102-104 |
| 374 | 1 | 3'-CN | 299 | 152-155 |
| 375 | 1 | 4'-CN | 299 | 169-171 |
| 376 | 1 | 2'-Me | 288 | 126-127 |
| 377 | 1 | 3'-Me | 288 | 148-152 |
| 378 | 1 | 4'-Me | 288 | 200-202 |
| 379 | 1 | 2'-F | 292 | 115-118 |
| 380 | 1 | 3'-F | 292 | 152-154 |
| 381 | 1 | 4'-F | 292 | 180-182 |
| 382 | 1 | 3',4'-Cl$_2$ | 342 | 139-142 |
| 383 | 1 | 3',4'-Me$_2$ | 302 | 169-171 |
| 384 | 1 | 4'-NMe$_2$ | 317 | 193-195 |
| 385 | 1 | 3'-NMe$_2$ | 317 | 53-60 |
| 386 | 1 | 4'-Br | 353 | 194-198 |
| 387 | 1 | 3'-CONH$_2$ | 317 | 223-227 |
| 388 | 1 | 4'-CO-N-Piperid-4-one | 399 | 69-73 |
| 389 | 1 | 3',4',5'-OMe$_3$ | 364 | 42-60 |
| 390 | 1 | 3'-CF$_3$ | 342 | 144-147 |
| 391 | 1 | 3'-NO$_2$ | 319 | 166-168 |
| 392 | 1 | 3',4'-F$_2$ | 310 | 125-127 |
| 393 | 1 | 3'-Cl, 4'-OMe | 338 | 192-197 |
| 394 | 1 | 4'-Et | 302 | 207-209 |
| 395 | 1 | 4'-OCF$_3$ | 358 | 196 |
| 396 | 1 | 4'-OCHMe$_2$ | 332 | 194 |
| 397 | 1 | 3'-F, 4'-Cl | 326 | 160-164 |
| 398 | 1 | 3'-OMe, 4'-Cl | 338 | 173 (dec.) |
| 399 | 1 | 3',4'-F$_2$, 5'-OMe | 340 | 144-146 |

The substituted meta-heteroaryl-phenyl or ortho-carbocyclic-phenyl compounds, Examples 400-401, of Table 15A were prepared by methods known to one skilled in the art following the general methods of Scheme M using appropriate reactants.

TABLE 15A

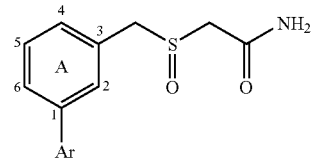

| Ex. No. | q | Ar | MS M + H | MP ° C. |
|---|---|---|---|---|
| 400 | 1 | naphtha-2-yl | 324 | 202-204 |
| 401 | 1 | 3,5-dimethyl-isoxazol-4-yl | 293 | 34-43 |

The substituted para-biphenyl compounds, Examples 402-429, of Table 16 were prepared by methods known to one skilled in the art following the general methods disclosed herein.

TABLE 16

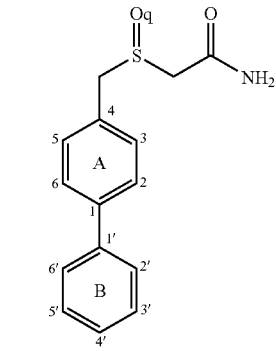

| Ex. No. | q | Substitution | MS M + H | MP ° C. |
|---|---|---|---|---|
| 402 | 1 | 3-F | 292 | 217 |
| 403 | 1 | 2'-Cl | 308 | 149-151 |
| 404 | 1 | 3'-Cl | 308 | 193-196 |
| 405 | 1 | 4'-OMe | 304 | 250-254 |
| 406 | 1 | 3',4'-Methylenedioxy | 317 | 226-229 |
| 407 | 1 | 2',6'-(OMe)$_2$ | 334 | 214-216 |
| 408 | 1 | 4'-Cl | 308 | 237-241 |
| 409 | 1 | 3',4'-(OMe)$_2$ | 334 | 194-197 |
| 410 | 1 | 3'-OMe | 304 | 158-161 |
| 411 | 1 | 4'-CN | 299 | 204-206 |
| 412 | 1 | 2',5'-(OMe)$_2$ | 334 | 134-136 |
| 413 | 1 | 3'-NO$_2$ | 319 | 186-189 |
| 414 | 1 | 3'-Me | 288 | 191-194 |
| 415 | 1 | 2'-OMe | 304 | 105-108 |
| 416 | 1 | 2'-Me, 4'-Cl | 322 | 132 |
| 417 | 1 | 2'-OMe, 4'-Cl | 338 | 147 |
| 418 | 1 | 2',4'-Cl$_2$ | 343 | 168 |
| 419 | 2 | 3',4'-(OMe)$_2$ | 350 | 212-214 |
| 420 | 1 | 3',4'-Cl$_2$ | 342 | 180-191 |
| 421 | 1 | 3-F, 4'-Cl | 326 | 208 |
| 422 | 1 | 3-F, 4'-Me | 306 | 216 |
| 423 | 1 | 4'-Br | 353 | 218-224 |
| 424 | 1 | 3'-Cl, 4'-OMe | 338 | 218-223 |
| 425 | 1 | 3',4',5'-(OMe)$_3$ | 364 | 60-68 |
| 426 | 1 | 3',4'-F$_2$ | 310 | 192-199 |
| 427 | 1 | 3-F, 4'-F | 310 | 215-217 |
| 428 | 2 | 3-F, 4'-F | 326 | 232-235 |
| 429 | 1 | 3-F, 4'-Cl | 310 | 149 |

The substituted para-heteroaryl-phenyl compound, Example 430, of Table 16A was prepared by methods known to one skilled in the art following the general methods disclosed herein.

TABLE 16A

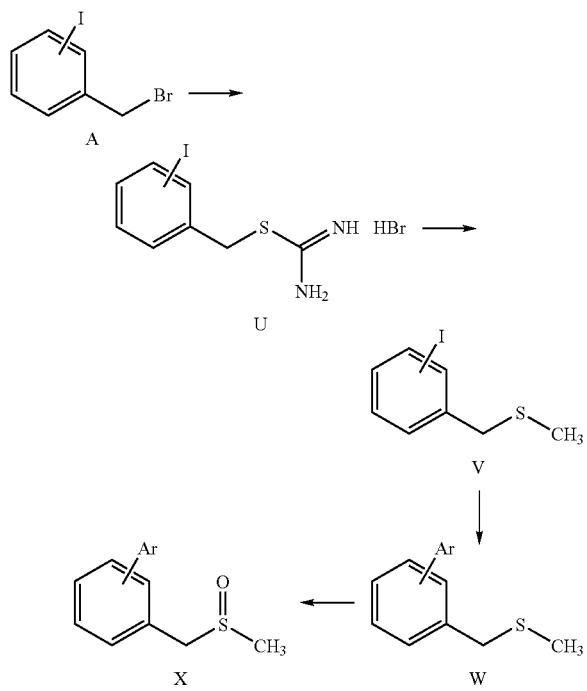

| Ex. No. | q | Ar | MS M + H | MP ° C. |
|---|---|---|---|---|
| 430 | 1 | (3,5-dimethyl)-isoxazol-4-yl | 293 | 27-52 |

Compounds Prepared According to Scheme N

The following Scheme N corresponds to the general synthesis of compounds of the invention wherein $R^1$ is H.

Example 431
2-(2-Methanesulfinylmethyl-phenyl)-benzo[b]thiophene

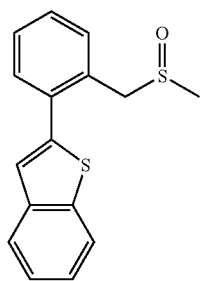

Synthesis of Compound X Wherein Ar=2-benzothienyl; ortho

Compound U (ortho); 2-(2-iodo-benzyl)-isothiourea

To a solution of thiourea (3.04 g, 40 mmol) in water (20 mL) at 60° C. was added compound A, 2-iodo-benzylbromide, (11.88 g, 40 mmol) in one portion. The reaction mixture was then gently heated to reflux for ½ h, cooled and filtered. The residue was washed with water and dried in vacuo to yield compound U (13.53 g, white solid). This compound was directly used in the next step without any further purification. (Yield=90%).

Compound V (ortho); 1-Iodo-2-methylsulfanylmethyl-benzene

To a mixture of 2-(2-iodo-benzyl)-isothiourea (13.53 g, 36.2 mmol) from previous step and a solution of NaOH (22 mL) in water (15 mL) was added dropwise dimethylsulfate (4.1 mL, 43.4 mmol). The reaction mixture was heated to reflux (105° C.) for 2 h, cooled. The resulting oil was then extracted into diethyl oxyde, the organic layer was washed with water, dried over $Na_2SO_4$. On concentration the solution generated a yellow oil that was directly used in the next step without any further purification (8.5 g, yield=89%).

$^1$H-NMR (DMSO) δ (ppm): 7.9 (d, 1H), 7.4 (m, 2H), 7 (dd, 1H), 3.75 (s, 2H), 2 (s, 3H)

Compound W (Ar=2-benzothienyl; ortho)

To a suspension of 1-iodo-2-methylsulfanylmethyl-benzene (2.64 g, 10 mmol) in toluene (39 mL) was added, under nitrogen, tetrakis(triphenylphosphine)palladium (1.16 g, 1 mmol), then a solution of 2-benzothiopheneboronic acid (2.67 g, 15 mmol) in ethanol (69 mL) and at last dropwise a solution of sodium carbonate (6.36 g, 60 mmol) in water (39 mL). The reaction mixture was then heated to reflux 3 h, cooled, concentrated at high vacuum, the residue was diluted with ethyl acetate (100 ml), added with water (50 ml) and hydrochloric acid (pH~2). The organic layer was dried over $Na_2SO_4$ and concentrated to yield compound W (Ar=2-benzothienyl; ortho) (orange brown oil). This compound was directly used in the next step without any further purification. (Yield ~100%). $R_f$(CH$_2$Cl$_2$)=0.95

Synthesis of Compound X: Example 431 (Ar=2-benzothienyl; ortho)

To a cooled solution (ice-bath) of compound W (Ar=2-benzothienyl; ortho) (2.7 g, 10 mmol) in glacial acetic acid (10 mL) was added 35% aqueous hydrogen peroxide (1.34 ml). The ice-bath was removed and the mixture was stirred until no more starting material was detected (HPLC). After 2 h of stirring, the reaction mixture was concentrated at high vacuum, the residue was diluted in water (50 ml), extracted into ethyl acetate (100 ml), the organic layer was washed successively with water (40 ml), aqueous NaHCO$_3$, water (2×30 ml), dried over Na$_2$SO$_4$. On concentration the solution generated a crude product that was purified by column chromatography (CH$_2$Cl$_2$/CH$_3$OH 9.6/0.4). The residue was triturated in diisopropyl oxyde to yield the title compound Example 431 (Ar=2-benzothienyl; ortho) (0.85 g, yield=30%).

$^1$H-NMR (DMSO) δ (ppm): 8 (d, 1H), 7.9 (d, 1H), 7.6 (s, 1H), 7.55-7.4 (m, 6H), 4.25 (q, 2H), 2.5 (s, 3H).

Example 432

3-(2-Methanesulfinylmethyl-phenyl)-thiophene

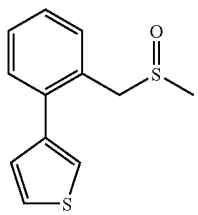

Synthesis of Compound X Wherein Ar=ortho-thien-3-yl

Compound W (Ar=3-thienyl; ortho)

To a suspension of 1-iodo-2-methylsulfanylmethyl-benzene, compound V, (2.64 g, 10 mmol) in toluene (39 mL) was added, under nitrogen, tetrakis(triphenylphosphine)palladium (1.16 g, 1 mmol), then a solution of 3-thiopheneboronic acid (1.92 g, 15 mmol) in ethanol (69 mL) and at last dropwise a solution of sodium carbonate (6.36 g, 60 mmol) in water (39 mL). The reaction mixture was then heated to reflux 3 h, cooled, concentrated at high vacuum, the residue was diluted with ethyl acetate (100 ml), added with water (50 ml) and hydrochloric acid (pH~2). The organic layer was dried over Na$_2$SO$_4$ and concentrated to yield compound W (Ar=3-thienyl; ortho) (brown oil). This compound was directly used in the next step without any further purification. (Yield ~100%). R$_f$(CH$_2$Cl$_2$)=0.95

Synthesis of Compound X: Example 432 (Ar=3-thienyl; ortho)

To a cooled solution (ice-bath) of compound W (Ar=3-thienyl; ortho) (2.2 g, 10 mmol) in glacial acetic acid (10 mL) was added 35% aqueous hydrogen peroxide (1.34 ml). The ice-bath was removed and the mixture was stirred until no more starting material was detected (HPLC). After 2 h of stirring, the reaction mixture was concentrated at high vacuum, the residue was diluted in water (50 ml), extracted into ethyl acetate (100 ml), the organic layer was washed successively with water (40 ml), aqueous NaHCO$_3$, water (2×30 ml), dried over Na$_2$SO$_4$. On concentration the solution generated a crude product that was purified by column chromatography (CH$_2$Cl$_2$/CH$_3$OH 9.8/0.2). A second column chromatography on Cl$_8$ will be necessary (CH$_3$CN/H$_2$O 4/6) to give 1.1 g of Example 432 (Ar=3-thienyl; ortho) (white solid, yield=46%).

$^1$H-NMR (DMSO) δ (ppm): 7.65 (m, 2H), 7.5 (m, 1H), 7.4 (m, 3H), 7.25 (d, 1H), 4.15 (q, 2H), 2.5 (s, 3H).

Example 435

2-Methanesulfinylmethyl-biphenyl

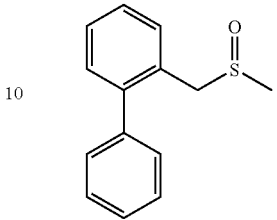

Synthesis of Compound X Wherein Ar=ortho-phenyl

Compound W Wherein Ar=ortho-phenyl

A mixture of biphenyl-2-yl-methanethiol (4 g, 20 mmol) in methanol (27 mL) and sodium methoxide in methanol (0.5 M, 40 mL) was heated at 60° C. for 0.5 h, cooled, treated with methyl iodide (3.7 mL, 60 mmol) and re-heated at 60° C. for 0.5 h. After cooling to room temperature, the reaction mixture was quenched with ice-water, acidified (pH~2) and extracted with ethyl acetate (3×50 mL). Combined organic layer was washed with water (1×50 mL) and brine (1×50 mL), dried (MgSO$_4$), and concentrated to give a crude product that was passed through a bed of silica (solvent: ethyl acetate) to give 3.3 g of 2-methylsulfanylmethyl-biphenyl (yellow oil) that was directly used in the next step.

Example 435

2-Methanesulfinylmethyl-biphenyl; Compound X Wherein Ar=ortho-phenyl

Starting with 2-methylsulfanylmethyl-biphenyl, 2-methanesulfinylmethyl-biphenyl was prepared following a similar procedure as described before for the synthesis of compound T (NR$^{12}$R$^{13}$=NMe$_2$) from compound S(NR$^{12}$R$^{13}$=NMe$_2$); $^1$H-NMR DMSO-d$_6$ δ 7.52-7.26 (m, 9H), 4.01 (q, 2H), 2.40 (s, 3H).

The following Examples 431-435 in Table 17 were prepared using appropriate starting materials and/or reagents, as determined by one skilled in the art, according to the synthetic processes disclosed herein.

TABLE 17

| Ex. No. | Ar | Ar Position | q | R |
|---|---|---|---|---|
| 431 | 2-benzothienyl | ortho | 1 | CH$_3$ |
| 432 | 3-thienyl | ortho | 1 | CH$_3$ |
| 433 | 2-furyl | para | 1 | CH$_3$ |
| 434 | 2-thienyl | para | 1 | CH$_3$ |
| 435 | phenyl | ortho | 1 | CH$_3$ |

The following Table 17A demonstrates the analytical data, by each compound's mass spectrum, for Examples 431-435.

TABLE 17A

| Ex. No. | MF | MS |
|---|---|---|
| 431 | $C_{16}H_{14}OS_2$ | M + H = 287 |
| | | M + Na = 309 |
| 432 | $C_{12}H_{12}OS_2$ | M + H = 237 |
| | | M + Na = 259 |
| | | M + K = 275 |
| | | 2M + Na = 495 |
| 433 | $C_{12}H_{12}O_2S$ | M + Na = 243 |
| | | 2M + Na = 463 |
| 434 | $C_{12}H_{12}OS_2$ | M + Na = 259 |
| | | M + K = 275 |
| | | 2M + H = 473 |
| | | 2M + Na = 495 |
| 435 | $C_{14}H_{14}OS$ | M + H = 231 |

The following Scheme O depicts the synthesis of substituted ortho heteroarylphenyl compounds as listed in Table 18 which can be obtained through the intermediacy of compound L6

Compound PRE7:
(2-Bromo-5-fluoro-phenyl)-methanol

To a solution of 2-bromo-5-fluoro-benzaldehyde (21.34 g, 105 mmole) in methanol (170 mL) was added at 0-5° C. portionwise $NaBH_4$ (3.99 g, 105 mmole). At the end of the addition, the cooling bath was removed and the reaction mixture was stirred at room temperature for 2 h. On concentration, the solution generated a white solid that was added with water, filtered and dried under vacuum to yield compound PRE7 (19.23 g; white powder) (Yield=91 $R_t$: 10.64 min.

Compound PRE8:
(2-Bromo-5-fluoro-benzyl)-isothiourea

To a solution of thiourea (4.9 g, 64.6 mmol) in 48% HBr (32 mL) and $H_2O$ (5.5 mL) at 60° C. was added compound PRE7 (11 g, 53.7 mmol). The reaction mixture was then heated to reflux for 1 h, cooled and filtered. The residue was washed with water and dried under vacuum to generate 17.16 g of (2-bromo-5-fluoro-phenylmethyl)-isothiourea, compound PRE8, that was directly taken into next step without any further purification; $R_t$: 7.33 min; (Yield=93%).

Compound B6:
(2-Bromo-5-fluoro-benzylsulfanyl)-acetic acid

To a mixture of compound PRE8 (17.16 g, 49.88 mmol) in 50% aq. NaOH (24 mL) at 70° C. was added slowly a solution of sodium chloroacetate (59.2 mmol) in 15.5 mL of water. The reaction was then heated to 100° C. for 1 h, cooled, quenched with ice-water and acidified with hydrochloric acid (pH~2). The precipitate was filtered, washed with water and dried under vacuum to generate 13.77 g of compound B6 (Yield=91%; white powder).

$R_f$($CH_2Cl_2/CH_3OH$ 9.5/0.5)=0.40; $R_t$: 11.74 min.

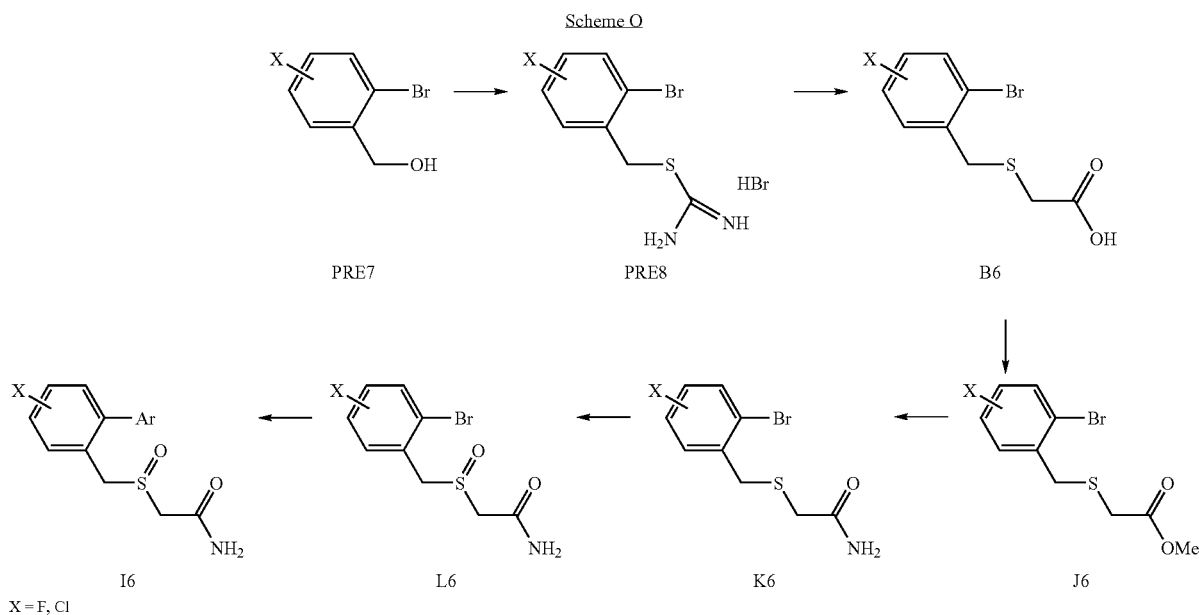

Scheme O

X = F, Cl

Example 437

2-(2-Benzo[b]thiophen-3-yl-phenylmethanesulfinyl)-acetamide

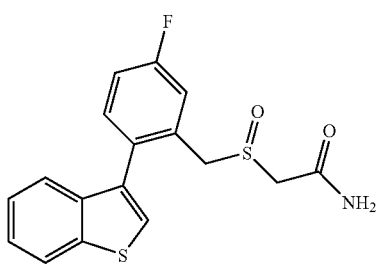

Compound J6: (2-Bromo-5-fluoro-benzylsulfanyl)-acetic acid methyl ester

A solution of compound B6 (17.15 g, 61.4 mmol) in methanol (153 mL) and sulfuric acid (2.1 mL) was heated to reflux for 3 h, cooled and the solvent evaporated. The residue was diluted with diethyl ether (300 mL) and washed with water (100 mL), aqueous $NaHCO_3$, water (100 mL), dried over $Na_2SO_4$ and concentrated to give 17.71 g of compound J6 as a pale yellow oil (Yield=98%).

$R_f(CH_2Cl_2)$=0.85

Compound K6: 2-(2-Bromo-5-fluoro-benzylsulfanyl)-acetamide

A mixture of compound J6 (17.71 g, 60.4 mmol) in methanol (200 mL) and 28% $NH_4OH$ (154 mL) was stirred overnight at room temperature. On concentration, the solution generated a white solid that was filtered, washed with water (3×80 mL) and dried under vacuum to give 13.33 g of compound K6 (Yield=79%).

$R_f(CH_2Cl_2/CH_3OH\ 9/1)$=0.45; $R_t$: 9.88 min.

Compound L6: 2-(2-Bromo-5-fluoro-benzylsulfinyl)-acetamide

To a solution of compound K6 (13.3 g, 47.8 mmol) in glacial acetic acid (48 mL) at room temperature was added 35% aqueous hydrogen peroxide (5 mL). The mixture was stirred until no more starting material was detected (TLC). After 2 h of stirring, the sulfoxide precipitated; the precipitate was filtered, washed with water and diisopropyl oxide successively, dried under vacuum to yield compound L6 (white powder; 12.6 g) (Yield=90%).

$R_f(CH_2Cl_2/CH_3OH\ 9/1)$=0.5; $R_t$: 6.69 min.

Synthesis of Example 437 (Ar=benzothien-3-yl)

To a suspension of 2-(2-bromo-5-fluoro-benzylsulfinyl)-acetamide (compound L6) (2.32 g, 7.88 mmol) in toluene (10 mL) was added, under nitrogen, tetrakis(triphenylphosphine) palladium (0.91 g, 0.79 mmol), then a solution of 3-benzothiopheneboronic acid (2.8 g, 15.76 mmol) in ethanol (10 mL) and at least dropwise aqueous sodium carbonate solution (2M, 8 mL, 16 mmol). The reaction mixture was then heated to 80° C. for 5 h, cooled, concentrated, partitioned between ethyl acetate (100 mL) and water (50 mL) and acidified with hydrochloric acid (pH~2). The organic layer was separated, dried over $Na_2SO_4$ and concentrated to give a crude residue that was purified by flash chromatography (silica, eluting solvent: $CH_2Cl_2/CH_3OH$ 9.6/0.4). The residue was triturated in diisopropyl oxide to yield the title compound Example 437 (1.78 g, yield=65%).

$R_t$: 10.75 min.

$^1$H-NMR (DMSO) δ (ppm): 8.1 (d, 1H) 7.8 (s, 1H), 7.55 (broad s, 1H), 7.45-7.25 (m, 6H), 7.2 (broad s, 1H), 4.05 (q, 2H), 3.45 (q, 2H).

The following Examples 437-444 in Table 18 were prepared using appropriate starting materials and/or reagents, as determined by one skilled in the art, according to the synthetic process disclosed herein.

TABLE 18

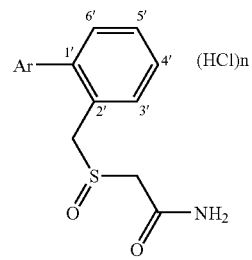

| Ex. No. | Ar | n | MF | MS | SCHEME |
|---|---|---|---|---|---|
| 437 | 4'-fluoro-3-benzothienyl | 0 | $C_{17}H_{14}FNO_2S_2$ | M + Na = 370<br>2M + Na = 717 | O |
| 438 | 4'-fluoro-2-furyl | 0 | $C_{13}H_{12}FNO_3S$ | M + Na = 304<br>2M + Na = 585 | O |
| 439 | 4'-fluoro-3-furyl | 0 | $C_{13}H_{12}FNO_3S$ | M + Na = 304<br>2M + Na = 585 | O |
| 440 | 4'-fluoro-3-pyridyl | 1 | $C_{14}H_{13}FN_2O_2S$ •HCl | M + Na = 315 | O |
| 441 | 4'-fluoro-5-chloro-2-thienyl | 0 | $C_{13}H_{11}ClFNO_2S_2$ | M + Na = 354<br>2M + Na = 685 | O |
| 442 | 5'-chloro-3-pyridyl | 1 | $C_{14}H_{13}ClN_2O_2$ •HCl | M + H = 309<br>M + Na = 331 | O |
| 443 | 4'-fluoro-3-thienyl | 0 | $C_{13}H_{12}FNO_2S_2$ | M + Na = 320<br>2M + Na = 617 | O |
| 444 | 4'-fluoro-5-chloro-2-benzothienyl | 0 | $C_{17}H_{14}FNO_2S_2$ | M + Na = 370<br>2M + Na = 717 | O |

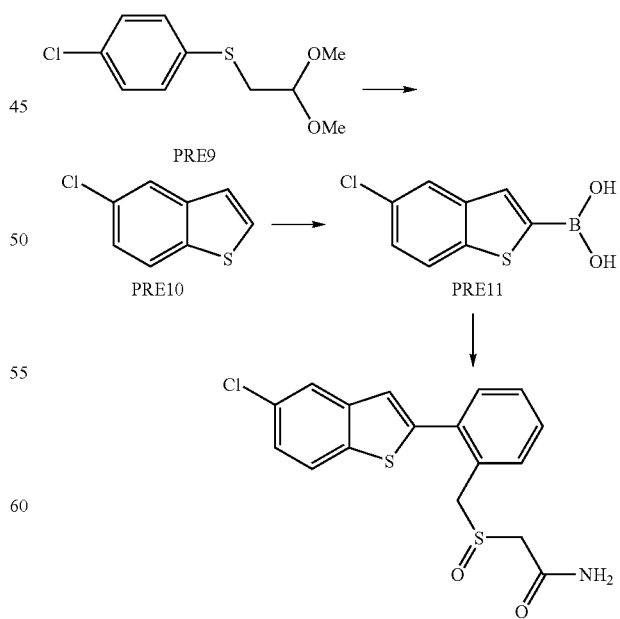

Scheme P

Example 445

Example 445

2-[2-(5-chloro-benzo[b]thiophen-2-yl)-phenyl-methanesulfinyl]-acetamide

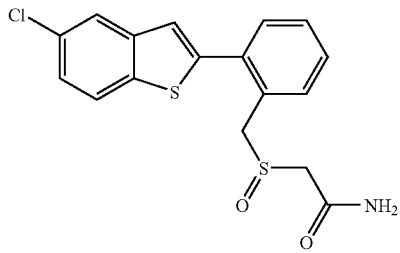

Compound PRE9: 1-Chloro-4-(2,2-dimethoxy-ethyl-sulfanyl)-benzene

To a solution of 4-chlorobenzenethiol (5.78 g; 40 mmol) in anhydrous acetone (50 mL) was added potassium carbonate (5.52 g, 40 mmol) and dropwise at room temperature 2-bromo-1,1-dimethoxy-ethane (4.7 mL, 40 mmol). After 24 h of stirring, the precipitate was filtered, the filtrate concentrated, the residue diluted with water and diethyl ether (150 mL), the organic layer washed successively with water (60 mL), NaOH 4N (30 mL) and water (60 mL), dried over $Na_2SO_4$ and concentrated to give 1-chloro-4-(2,2-dimethoxy-ethylsulfanyl)-benzene (compound PRE9) (9.12 g; orange oil) (Yield=98%).

$R_f$($CH_2Cl_2$)=0.45; $R_t$: 14.84 min.

Compound PRE10: 5-Chloro-benzo[b]thiophene

A mixture of polyphosphoric acid (11.2 g) in chlorobenzene (290 mL) was heated to reflux and added, under nitrogen, dropwise in about one hour 1-chloro-4-(2,2-dimethoxy-ethylsulfanyl)-benzene (compound PRE9; 9.12 g, 39.2 mmol). The reaction mixture was then heated for one night until reaction is complete, cooled, quenched with water (150 mL) and extracted into methylene chloride (200 mL). Combined organic layer was dried over $Na_2SO_4$ and concentrated to give a crude residue that was purified by flash chromatography (silica, eluting solvent: petroleum ether) to give 2.1 g of 5-chloro-benzo[b]thiophene (limpid oil) (Yield=32%).

$R_f$(petroleum ether)=0.6; $R_t$: 15.56 min.

Compound PRE11: (5-Chloro-benzo[b]thiophen-2-yl)-boronic acid

To a solution of 5-chloro-benzo[b]thiophene (compound PRE10) (2.1 g, 12.46 mmol) in anhydrous THF (17 mL) was added dropwise at −60° C. n-BuLi 1.6M in hexane (8.55 mL, 13.69 mmol). After stirring for 30 min at −60° C., was added dropwise triisopropyl borate (3.17 mL, 13.69 mmol). The cooling bath was taken off and the reaction mixture was heated slowly to 0° C. and was added 1N HCl (30 mL) and ethyl acetate (30 mL). The organic layer was dried over $Na_2SO_4$ and concentrated to give 2.15 g of compound dd (white powder; yield=81.5%). $R_t$: 11.75 min.

Synthesis of Example 445

To a suspension of 2-(2-iodo-phenylmethanesulfinyl)-acetamide (compound L) (1.04 g, 3.22 mmol) in toluene (13 mL) was added, under nitrogen, tetrakis(triphenylphosphine) palladium (0.372 g, 0.322 mmol), then a solution of (5-chloro-benzo[b]thiophen-2-yl)-boronic acid (1.02 g, 4.83 mmol) (compound PRE11) in ethanol (23 mL) and at least dropwise aqueous sodium carbonate solution (2.04 g, 19.3 mmol) in water (13 mL). The reaction mixture was then heated to 80° C. for 2 h, cooled, concentrated, partitioned between ethyl acetate (60 mL) and water (30 mL) and acidified with hydrochloric acid (pH~2). An insoluble solid appeared between the two layers. After filtration, the solid residue was purified by flash chromatography (silica, eluting solvent: $CH_2Cl_2/CH_3OH$ 9.3/0.7). The residue was triturated in diisopropyl oxide to yield the title compound Example 445 (0.65 g, yield=55%).

$R_t$: 6.93 min.

$^1$H-NMR (DMSO) δ (ppm): 8.05 (d, 1H), 7.95 (s, 1H), 7.65 (broad s, 1H), 7.65-7.45 (m, 5H), 7.45 (d, 1H), 7.35 (broad s, 1H), 4.3 (q, 2H), 3.65 (q, 2H). Molecular Formula: $C_{17}H_{14}ClNO_2S_2$; Mass Spec.: M+H=364; M+Na=386.

Scheme Q

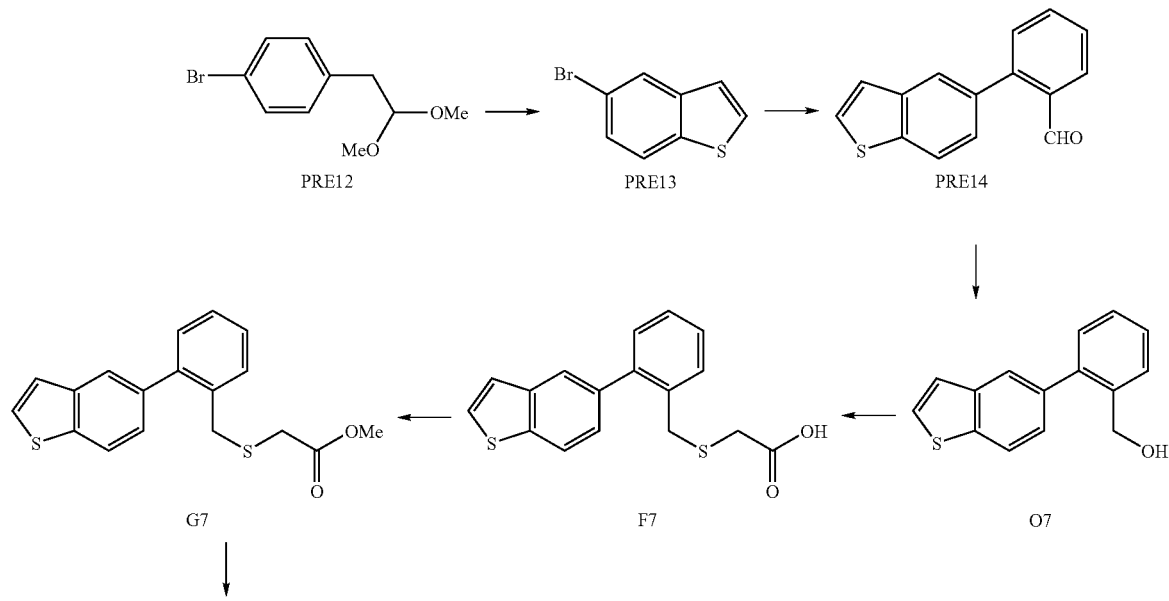

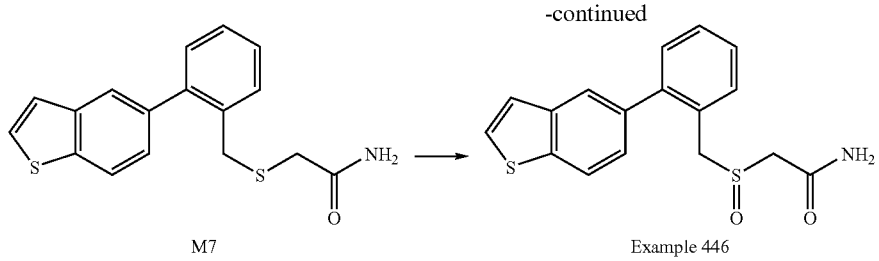

M7 → Example 446

Example 446

2-(2-Benzo[b]thiophen-5-yl-phenylmethanesulfinyl)-acetamide

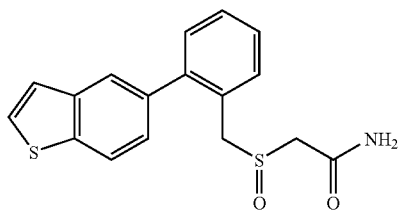

Compound PRE12: 1-Bromo-4-(2,2-dimethoxy-ethylsulfanyl)-benzene

To a solution of 4-bromobenzenethiol (7.56 g; 40 mmol) in anhydrous acetone (50 mL) was added potassium carbonate (5.52 g, 40 mmol) and dropwise at room temperature 2-bromo-1,1-dimethoxy-ethane (4.7 mL, 40 mmol). After 24 h of stirring, the precipitate was filtered, the filtrate concentrated, the residue diluted with water and diethyl ether (150 mL), the organic layer washed successively with water (60 mL), NaOH 4N (30 mL) and water (60 mL), dried over $Na_2SO_4$ and concentrated to give 1-bromo-4-(2,2-dimethoxy-ethylsulfanyl)-benzene (compound PRE12) (9.71 g; orange oil) (Yield=87%).

$R_f(CH_2Cl_2)$=0.45; $R_t$: 15.17 min.

Compound PRE13: 5-Bromo-benzo[b]thiophene

A mixture of polyphosphoric acid (10 g) in chlorobenzene (260 mL) was heated to reflux and added, under nitrogen, dropwise in one hour 1-bromo-4-(2,2-dimethoxy-ethylsulfanyl)-benzene (compound PRE12; 9.71 g, 35 mmol). The reaction mixture was then heated for 4 h until reaction is complete, cooled, quenched with water (150 mL) and extracted into methylene chloride. Combined organic layer was dried over $Na_2SO_4$ and concentrated to give a crude residue that was purified by flash chromatography (silica, eluting solvent: petroleum ether) to give 3.8 g of 5-bromo-benzo[b]thiophene (white solid) (Yield=51%).

$R_f$(petroleum ether)=0.6; $R_t$: 16.31 min.

Compound PRE14: 2-Benzo[b]thiophene-5-yl-benzaldehyde

To a suspension of 5-Bromo-benzo[b]thiophene (compound PRE13) (3.68 g, 17.2 mmol) in toluene (183 mL) was added, under nitrogen, tetrakis(triphenylphosphine)-palladium (1.99 g, 1.72 mmol), then a solution of 2-formylphenylboronic acid (3.87 g, 25.8 mmol) in ethanol (20 mL) and at least dropwise aqueous sodium carbonate solution (3.64 g, 34.4 mmol) in water (20 mL). The reaction mixture was then heated to 80° C. for 3 h, cooled, concentrated, partitioned between ethyl acetate (120 mL) and water (70 mL) and acidified with hydrochloric acid (pH~2). The organic layer was separated, dried over $Na_2SO_4$ and concentrated to give a crude residue that was purified by flash chromatography (silica, eluting solvent: (petroleum ether/AcOEt) 9.2/0.8) to give 3.31 g of compound PRE14 (orange yellow powder; yield=81%).

$R_t$: 15.74 min.

Compound O7: (2-Benzo[b]thiophene-5-yl-phenyl)-methanol

To a suspension of 2-Benzo[b]thiophene-5-yl-benzaldehyde (compound PRE14) (3.31 g, 13.9 mmole) in methanol (30 mL) was added at 0-5° C. portionwise $NaBH_4$ (0.528 g, 13.9 mmole). At the end of the addition, the cooling bath was removed and the reaction mixture was stirred at room temperature for 2 h. After concentration, the residue was diluted with water and diethyl ether, the organic layer dried over $Na_2SO_4$ and concentrated to give 3.13 g of compound O7 as an orange brown oil (Yield=94%).

$R_t$: 13.75 min.

Compound F7: (2-Benzo[b]thiophene-5-yl-benzylsufanyl)-acetic acid

To a solution of thiourea (1.19 g, 15.7 mmol) in 48% HBr (7.6 mL) and $H_2O$ (1.33 mL) at 60° C. was added (2-Benzo[b]thiophene-5-yl-phenyl)-methanol (compound O7) (3.13 g, 13 mmol). The reaction mixture was then heated to reflux for 1 h, cooled and filtered. The residue was washed with water and dried under vacuum to generate 4.57 g of (2-Benzo[b]thiophene-5-yl-benzyl)-isothiourea, that was directly taken into next step without any further purification; $R_t$: 10.66 min.

To a mixture of (2-Benzo[b]thiophene-5-yl-benzyl)-isothiourea (4.57 g, 12 mmol) in 50% aq. NaOH (16 mL) at 70° C. was added slowly a solution of sodium chloroacetate (14.4 mmol) in 1.5 mL of water. The reaction was then heated to 100° C. for 1 h, cooled, quenched with ice-water and acidified with hydrochloric acid (pH~2). The resultant acidic mixture was extracted into diethyl ether (100 mL), dried over $Na_2SO_4$ and concentrated to give 2.1 g of compound F7 as a yellow oil (Yield=51.4%). $R_f$ ($CH_2Cl_2/CH_3OH$ 9/1)=0.50; $R_t$: 14.34 min.

Compound G7: (2-Benzo[b]thiophene-5-yl-benzylsufanyl)-acetic acid methyl ester A solution of compound F7 (2.1 g, 6.69 mmol) in methanol (20 mL) and sulfuric acid (0.23 mL) was heated to reflux for 3 h, cooled and the solvent evaporated. The residue was diluted with diethyl ether (80 mL) and washed with water (30 mL), aqueous NaHCO₃, water (30 mL), dried over Na₂SO₄ and concentrated to give 1.94 g of compound G7 as a pale yellow oil (Yield=88%).

$R_f$(CH₂Cl₂)=0.85; $R_t$: 16.9 min.

Compound M7:
(2-Benzo[b]thiophene-5-yl-benzylsufanyl)-acetamide

A mixture of compound G7 (1.94 g, 5.9 mmol) in methanol (20 mL) and 28% NH₄OH (15 mL) was stirred overnight at room temperature. On concentration, the solution generated a white solid that was filtered, washed with water (3×30 mL) and dried under vacuum to give 1 g of compound M7 (Yield=54.5%).

$R_f$(CH₂Cl₂/CH₃OH 9/1)=0.45; $R_t$: 13.08 min.

Synthesis of Example 446

To a solution of (2-Benzo[b]thiophene-5-yl-benzylsufanyl)-acetamide (compound M7) (1 g, 3.22 mmol) in glacial acetic acid (5 mL) at room temperature was added 35% aqueous hydrogen peroxide (0.35 mL). The mixture was stirred until no more starting material was detected (TLC). After 2 h of stirring, the reaction mixture was concentrated, the resulting oil diluted with water and ethyl acetate (50 mL), the organic layer was washed successively with water (20 mL), aqueous NaHCO₃, water (20 mL) and dried over Na₂SO₄. The residue was triturated with diisopropyl oxide to yield the title compound Example 446 (0.94 g; white powder) (Yield=88%). $R_f$(CH₂Cl₂/CH₃OH 9/1)=0.5; $R_t$: 10.33 min.

¹H-NMR (DMSO) δ (ppm): 8.05 (d, 1H), 7.85 (s, 1H), 7.85 (d, 1H), 7.6 (broad s, 1H), 7.55-7.3 (m, 6H), 7.25 (broad s, 1H), 4.15 (q, 2H), 3.5 (q, 2H).

Molecular Formula: C₁₇H₁₅NO₂S₂; Mass Spec.: M+Na=352, 2M+Na=681.

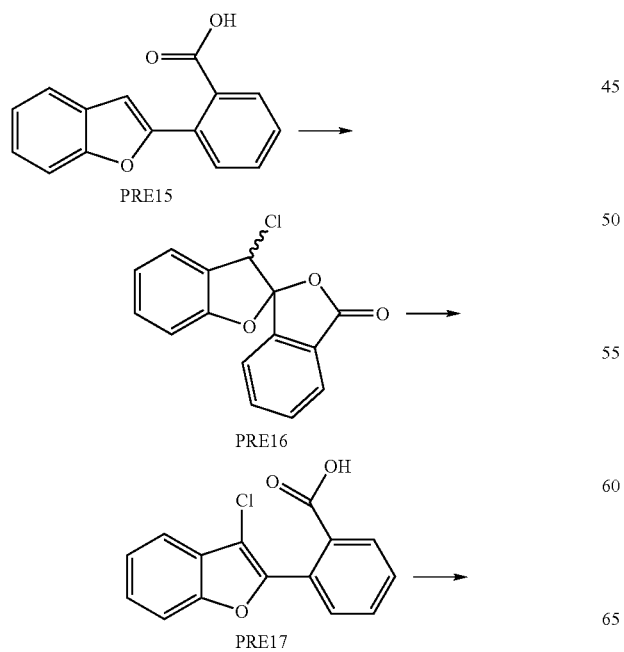

Scheme R

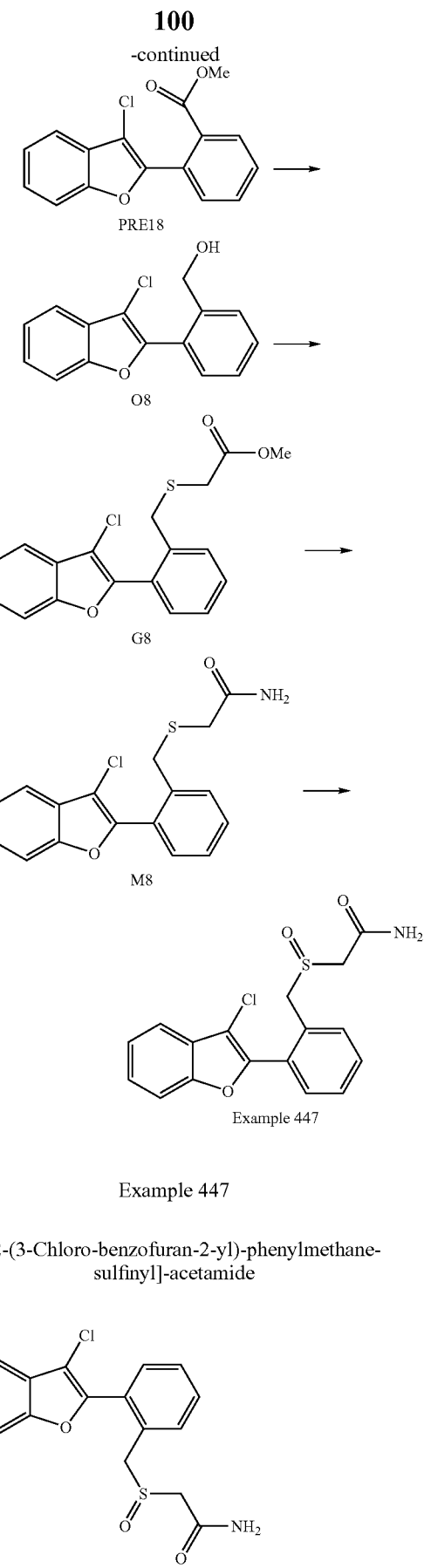

Example 447

2-[2-(3-Chloro-benzofuran-2-yl)-phenylmethane-sulfinyl]-acetamide

Synthesis of Compound PRE16

A mixture of compound PRE15 (5 g, 21 mmole), N-chlorosuccimide (3.58 g, 26.8 mmole) in 100 ml of dioxane and 2 ml of water was heated to reflux for 2 h, then cooled. Ethyl acetate (100 ml) was added, the solution was washed by water, dried over $Na_2SO_4$, evaporated to give a solid which was triturated in methanol to give a suspension. The compound PRE16 (3.83 g) was obtained as a white powder by filtration.

$^1$H NMR (400 MHz, $CHCl_3$) δ 5.03 (1H, s), 7.05 (1H, d), 7.13 (1H, t), 7.37 (1H, t), 7.5 (1H, d), 7.72 (1H, t), 7.8 (1H, t), 7.9 (1H, d), 7.97 (1H, d).

Synthesis of Compound PRE17:
2-(3-chloro-benzofuran-2-yl)-benzoic acid

A mixture of compound PRE16 (17.5 g, 64.3 mmole) and DBU (12 ml, 77.5 mmole) in 650 ml of toluene was heated at reflux for 3 h, and then cooled. The reaction mixture was washed by 2×200 ml 4N HCl, 2×200 ml water, dried over $Na_2SO_4$, evaporated to give compound PRE17 (16.2 g) as a yellowish solid.

$^1$H NMR (400 MHz, $CHCl_3$) δ 7.35 (2H, m), 7.43 (1H, m), 7.57 (1H, t), 7.62 (1H, m), 7.68 (1H, t), 7.8 (1H, d), 8.05 (1H, d).

Synthesis of Compound O8:
[2-(3-chloro-benzofuran-2-yl)-phenyl]-methanol

A mixture of compound PRE17 (16.2 g, 59.6 mmole), EDCI (15 g, 78 mmole), 10 ml methanol and DMAP (1 g) in 250 ml of $CH_2Cl_2$ was stirred at RT for 1 h. The reaction mixture was washed by 100 ml 1N HCl, 200 ml water, dried over $Na_2SO_4$, evaporated to give 16.5 g compound PRE18 as an oil which was pure enough for next step without further purification.

To a solution of compound PRE18 (16.5 g, 58 mmole) in 200 ml THF, LAH (2.2 g, 58 mmole) was added in small portion under nitrogen, the mixture was stirred at RT for 2 h, and then a saturated solution of $NH_4Cl$ was added slowly to give a suspension that was filtered. The filtration was washed by brine, dried over $Na_2SO_4$, evaporated to give 13.1 g compound O8 as a brownish solid.

$^1$H NMR (400 MHz, $CHCl_3$) δ 7.4 (3H, m), 7.5 (2H, d), 7.67 (2H, m), 7.75 (1H, d).

Synthesis of Compound G8: [2-(3-Chloro-benzofuran-2-yl)-benzylsulfanyl]-acetic acid methyl ester A solution of thiourea (11 g, 145 mmole) in 80 ml of aqueous 48% HBr was added to compound O8 (13.1 g, 50.8 mmole) to give a solution which was heated to 100° C. for 20 minutes to give a suspension. The mixture was cooled, filtered, washed by water, and dried in vacuum to give 17 g brownish solid.

To a mixture of the above compound in 35% NaOH (31 ml), was added a solution of sodium chloroacetate (6.2 g, 53.2 mmole) in 50 ml water at 80° C. to give a suspension which was heated to reflux for 1 h, diluted by 300 ml water, acidified to pH2 by concentrated HCl to give an oily solid. The liquid phase was decanted; the solid was dissolved in 200 ml $CH_2Cl_2$, washed by water, dried over $Na_2SO_4$, evaporated to give 13.5 g of the crude sulfanylacetic acid which was esterified directly without further purification.

A mixture of the above crude acid (13.5 g) in 150 ml methanol and 5 ml concentrated $H_2SO_4$ was heated to reflux for 1 h, and then evaporated, the residue was dissolved in 200 ml $CH_2Cl_2$, washed by water, dried $Na_2SO_4$, evaporated to give 13.8 g of compound G8 as a brownish oil which was pure enough for next step without further purification.

Synthesis of Example 447

A solution of compound G8 (9.1 g, 26.3 mmole) in 200 ml of 7N $NH_3$/methanol was stirred at RT for 63 h to give a solution. Solvent was evaporated and the residue was purified by flash chromatography (dichloromethylene/methanol, 20/1) to give 7.2 g of the sulfanylacetamide M8 which was dissolved in 250 ml acetic acid, then 5 ml of 30% $H_2O_2$ added. The mixture was stirred at 45° C. for 1 h, the solvent was evaporated, and the residue was recrystallized in ethanol to give the title compound Example 447 5.4 g as a white crystal.

$^1$H NMR (400 MHz, $CHCl_3$) δ 3.2 (1H, d), 3.53 (1H, d), 4.38 (2H, dd), 5.65 (1H, bs), 6.90 (1H, bs), 7.4 (2H, m), 7.57 (4H, m), 7.64 (1H, d), 7.8 (1H, m).

Molecular Formula: $C_{17}H_{14}ClNO_3S$; Mass Spec.: M+Na=370, 2M+Na=717.

Biological Data

Methodology: Evaluation of Wake Promoting Activity in Rats

The methodology utilized for evaluating wake promoting activity of test compounds is based on that described by Edgar and Seidel, *Journal of Pharmacology and Experimental Therapeutics*, 283:757-769, 1997, and incorporated herein by reference in its entirety by reference.

Animal Surgery. Adult, male Wistar rats (275-320 g from Charles River Laboratories, Wilmington, Mass.) were anesthetized (Nembutal, 45 mg/kg, ip.) and surgically prepared with implants for recording of chronic EEG (encephalographic) and EMG (electromyographic) recording. The EEG implants were made from commercially available components (Plastics One, Roanoke, Va.). EEG signals were recorded from stainless steel screw electrodes: 2 frontal (+3.0 mm AP from bregma, ±2.0 mm ML), and 2 occipital (−4.0 mm AP from bregma, ±2.0 mm ML). Two Teflon-coated stainless steel wires were positioned under the nuchal trapezoid muscles for EMG recording. All electrode leads were inserted into a connector pedestal and the pedestal affixed to the skull by application dental acrylic. Antibiotic was administered post surgically and antibiotic cream was applied to the wound edges to prevent infection. At least one week elapsed between surgery and recording.

Recording environment. Postsurgically, rats were housed in pairs in an isolated room. Food and water were available ad libitum, ambient temperature was 21° C., and humidity was 55%. At least 24 hrs prior to recording, they were placed in Nalgene containers (31×31×31 cm) with a wire-grid top, and entry to the room was prohibited during the day of recording except for dosing. The containers were placed on a rack with two shelves, 4 containers per shelf. Fluorescent overhead room lights were set to a 24 hr. light/dark cycle (on at 7 AM, off at 7 PM). Light levels inside the containers were 38 and 25 lux for the top and bottom shelves respectively. Background white-noise (68 db inside the containers) was present in the room to mask ambient sounds.

Data acquisition. EEG and EMG signals were led via cables to a commutator (Plastics One) and then to pre-amplifiers (model 1700, A-M Systems, Carlsborg, Wash.). EEG and EMG signals were amplified (10K and 1K respectively) and bandpass filtered between 0.3 and 500 Hz for EEG and between 10 and 500 Hz for EMG. These signals were digitized at 128 samples per second using ICELUS sleep research software (M. Opp, U. Texas; see Opp, Physiology and Behavior 63:67-74, 1998, and Imeri, Mancia, and Opp, *Neuroscience* 92:745-749, 1999, incorporated by reference herein in their entirety) running under Labview 5.1 software and data acquisition hardware (PCI-MIO-16E-4; National Instruments, Austin, Tex.). On the day of dosing, data was recorded for 6 to 10 hours beginning at 11 AM.

Drug administration and study design. Compounds were evaluated on groups of from 4 to 8 rats carried out over one or two separate test sessions. Each animal was tested with a different compound or vehicle for up to 10 weeks with at least 7 days between successive tests. A vehicle group was included in all experiments, and each animal received vehicle every $4^{th}$ test. Test compounds were suspended in sterile 0.25% methylcellulose (pH=6.2; Upjohn Co., Kalamazoo, Mich.) at 30 mg/mL. Although compounds can be administered at dosages greater than 100 mg/kg and are expected to be active under the selection criteria of data analysis, unless otherwise noted, compounds were administered at a single dose of 100 mg/kg. Dosing was carried out at noon, while the rats were predominantly asleep. Each rat was lifted out of its container, given an intraperitoneal injection in a volume of 5 mL/kg, and replaced. Dosing required approximately 30 sec per rat.

Sleep/wake scoring. Sleep and wake activity were determined using a procedure involving manual scoring using the ICELUS software, followed by application of an autoscoring program written in Microsoft Excel (Microsoft, Inc., Redmond, Wash.) The ICELUS program displays the EEG and EMG data in blocks of 6 sec along with the EEG frequency spectrum (FFT) amplitudes. Arousal state was scored as awake, rapid eye-movement (REM), or slow-wave or non-REM sleep according to visual analysis of EEG frequency and amplitude characteristics and EMG activity (Opp and Krueger, 1994; Van Gelder, et al., 1991; Edgar, et al., 1991, 1997; Seidel, et al, 1995, incorporated by reference herein in their entirety). Essentially, waking activity consists of relatively low-amplitude EEG activity with relatively lower power in the frequency band from 0.5-6 Hz, accompanied by moderate to high level EMG activity. In a particular waking state ("theta-waking"), EEG power can be relatively focused in the 6-9 Hz (theta) range, but significant EMG activity is always present. NREM sleep is characterized by relative high-amplitude EEG activity with relatively greater power in the low frequency band from 0.5-6 Hz, accompanied by little or no EMG activity. REM sleep is characterized by moderate and constant amplitude EEG focused in the theta (6-9 Hz) range, similar to waking theta, but with no EMG activity.

To convert the raw data to sleep/wake stage scores, normally the first hour of activity (prior to dosing) is manually scored into sleep, wake, or REM states. Subsequent activity is evaluated using a computer algorithm which takes into account FFT amplitudes, theta-band activity, and EMG activity for each 6 second epoch. An iterative procedure is used to adjust 3 different parameter thresholds until the first hour of data scored by the computer algorithm matches as closely as possible with the manual values. These parameter values are then used to score the remaining activity. The data are then reduced to "wake" (wake+waking theta activity) or "sleep" (REM+non-REM) for each 6 sec epoch. The time spent awake was then calculated for each 5 and 30 min interval relative to the specific time of dosing (approximately 12:00 noon).

Data Analysis and Statistics.

Two basic outcome measures were used to ascertain whether a compound exhibited wake-enhancing activity. The first was the percent time spent awake (0-100%) for each 30 min period following dosing. The second was the sum in minutes of the time spent awake for the first 6 half-hour periods following dosing (3 hr AUC; maximum 180 min).

For purposes of ascertaining activity of a test compound, wake activity values were compared against corresponding vehicle values. The vehicle values were of two types. The first type was the corresponding within-experiment vehicle, that is, a value derived from the vehicle group run concurrently with the test compound. A second reference vehicle value was also used for comparison, which consisted of the mean 3 hr AUC value calculated from 234 animals in 59 separate experiments carried out during the same time period as the evaluations of the test compounds (mean±SD=69.22±20.12; 95% confidence limits=66.63-71.81). Two-tailed, unpaired t-tests were performed on the wake time values for drug versus vehicle treated animals, and compounds with $p<0.05$ were deemed significantly wake-promoting. A test compound was considered active as a wake promoting agent if it met one or more of the following three criteria.

(i) The 3 hr AUC value for the test compound was significantly greater ($p<0.05$) than the mean wake value for the reference vehicle group (N=234).

(ii) The 3 hr AUC value for the test compound was significantly greater ($p<0.05$) than the corresponding value for the within-experiment vehicle group.

(iii) One or more of the half-hour wake time values from 0.5 to 2 hrs after dosing were significantly greater ($p<0.05$) in the test compound group compared to the within-experiment vehicle group.

Results.

Compounds of the invention either have demonstrated or are expected to demonstrate utility for wake promoting activity.

References. The following references, to the extent that they provide exemplary procedural or other details supplementary to those set forth herein, are specifically incorporated in their entirety herein by reference:

Touret, et al., *Neuroscience Letters,* 189:43-46, 1995.
Van Gelder, R. N. et al., *Sleep* 14:48-55, 1991.
Edgar, D. M., *J. Pharmacol. Exp. Ther.* 282:420-429, 1997.
Edgar and Seidel, *J. Pharmacol. Exp. Ther.,* 283:757-69, 1997.
Hernant et al., *Psychopharmacology,* 103:28-32, 1991.
Lin et al., *Brain Research,* 591:319-326, 1992.
Opp and Krueger, *American Journal of Physiology* 266: R688-95, 1994
Panckeri et al., *Sleep,* 19(8):626-631, 1996.
Seidel, W. F., et al., *J. Pharmacol. Exp. Ther.* 275:263-273, 1995.
Shelton et al., *Sleep* 18(10):817-826, 1995.
Welsh, D. K., et al., *Physiol. Behav.* 35:533-538, 1985.

Although the present invention has been described in considerable detail, those skilled in the art will appreciate that numerous changes and modifications may be made to the embodiments and preferred embodiments of the invention and that such changes and modifications may be made without departing from the spirit of the invention. It is therefore intended that the appended claims cover all equivalent variations as fall within the scope of the invention.

Utility

The present invention provides a method of treating diseases and conditions in a subject in need thereof comprising administering to said subject a therapeutically effective amount of a compound of formula (I). For example, the compounds of the present invention are use in the treatment of diseases, including treatment of sleepiness, promotion of wakefulness, treatment of Parkinson's disease, cerebral ischemia, stroke, sleep apneas, eating disorders, stimulation of appetite and weight gain, treatment of attention deficit hyperactivity disorder ("ADHD"), enhancing function in disorders associated with hypofunctionality of the cerebral cortex, including, but not limited to, depression, schizophrenia, fatigue, in particular, fatigue associated with neurologic disease, such as multiple sclerosis, chronic fatigue syndrome, and improvement of cognitive dysfunction.

Dosage and Formulation.

The compounds of the present invention can be administered for therapeutic purposes by any means that results in the contact of the active agent with the agent's site of action in a subject. The compounds may be administered by any conventional means available for use in conjunction with pharmaceuticals, either as individual therapeutic agents or in a combination with other therapeutic agents, such as, for example, analgesics, or in combination with antidepressants, including but are not limited to tricyclic antidepressants ("TCAs"), Selective Serotonin Reuptake Inhibitors ("SSRIs"), Serotonin and Noradrenaline Reuptake Inhibitors ("SNRIs"), Dopamine Reuptake Inhibitors ("DRIs"), Noradrenaline Reuptake Inhibitors ("NRUs"), Dopamine, Serotonin and Noradrenaline Reuptake Inhibitors ("DSNRIs") and Monoamine Oxidase Inhibitors ("MAOIs") including reversible inhibitors of monoamine oxidase type A (RIMAs). The compounds of the present invention are preferably administered in therapeutically effective amounts for the treatment of the diseases and disorders described herein.

A therapeutically effective amount can be readily determined by the attending diagnostician, as one skilled in the art, by the use of conventional techniques. The effective dose will vary depending upon a number of factors, including the pharmacodynamics of the active agent, the type and extent of progression of the disease or disorder, the age, weight and health of the particular patient, the formulation of the active and its mode and frequency of administration, and the desired effect with a minimization of side effects. Typically, the compounds are administered at lower dosage levels, with a gradual increase until the desired effect is achieved.

Typical dose ranges are from about 0.01 mg/kg to about 100 mg/kg of body weight per day, with a preferred dose from about 0.01 mg/kg to 10 mg/kg of body weight per day. A typical daily dose for adult humans can range from about 1 to about 1000 mg of the active agent, particularly from about 1 to about 400 mg, and including 25, 50, 85, 100, 150, 170, 200, 255, 250, 255, 340, 400, 425, 500, 600, 700, 750, 800, and 900 mg doses, and equivalent doses for a human child.

The compounds may be administered in one or more unit dose forms, and they may be administered in a single daily dose or in two, three or four doses per day. The unit dose ranges from about 1 to about 1000 mg, particularly from about 1 to about 400 mg, and including 25, 50, 85, 100, 150, 170, 200, 255, 250, 255, 340, 400, 425, 500, 600, 700, 750, 800, and 900 mg unit doses, and equivalent unit doses for a human child. In particular, the unit dosages range from about 1 to about 500 mg administered one to four times a day, preferably from about 10 mg to about 300 mg, two times a day. In an alternate method of describing an effective dose, an oral unit dose is one that is necessary to achieve a blood serum level of about 0.05 to 20 µg/ml in a subject, and preferably about 1 to 20 µg/ml.

The compounds of the present invention may be formulated into pharmaceutical compositions by admixture with one or more pharmaceutically acceptable excipients. The active agent may be present in about 0.5-95% by weight of the composition. The excipients are selected on the basis of the chosen route of administration and standard pharmaceutical practice, as described, for example, in *Remington: The Science and Practice of pharmacy*, 20th ed.; Gennaro, A. R., Ed.; Lippincott Williams & Wilkins: Philadelphia, Pa., 2000.

The compositions can be prepared for administration by oral means, including tablets, pills, powders, capsules, troches and the like; parenteral means, including intravenous, intramuscular, and subcutaneous means; topical or transdermal means, including patches, creams, ointments, lotions, pastes, gels, solutions, suspensions, aerosols, and powders and the like; transmucosal means, including nasal, rectal, vaginal, sublingual and buccal means; ophthalmic or inhalation means. Preferably the compositions are prepared for oral administration, particularly in the form of tablets, capsules or syrups; parenteral administration, particularly in the form of liquid solutions, suspensions or emulsions; intranasal administration, particularly in the form of powders, nasal drops, or aerosols; or for topical use, such as patches, creams, ointments, and lotions.

For oral administration, the tablets, pills, powders, capsules, troches and the like can contain one or more of the following: diluents or fillers such as starch, or cellulose; binders such as microcrystalline cellulose, gelatins, or polyvinylpyrrolidone; disintegrants such as starch or cellulose derivatives; lubricants such as talc or magnesium stearate; glidants such as colloidal silicon dioxide; sweetening agents such as sucrose or saccharin; and flavoring agents such as peppermint or cherry flavoring. Capsules may contain any of the above ingredients, and may also contain a semi-solid or liquid carrier, such as a polyethylene glycol. The solid oral dosage forms may have coatings of sugar, shellac, or enteric agents. Liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as surfactants, suspending agents, emulsifying agents, diluents, sweetening and flavoring agents, dyes and preservatives.

The compositions may also be administered parenterally. The pharmaceutical forms acceptable for injectable use include, for example, sterile aqueous solutions, or suspensions. Aqueous carriers include mixtures of alcohols and water, buffered media, and the like. Nonaqueous solvents include alcohols and glycols, such as ethanol, and polyethylene glycols; oils, such as vegetable oils; fatty acids and fatty acid esters, and the like. Other components can be added including surfactants; such as hydroxypropylcellulose; isotonic agents, such as sodium chloride; fluid and nutrient replenishers; electrolyte replenishers; agents which control the release of the active compounds, such as aluminum monostearate, and various co-polymers; antibacterial agents, such as chlorobutanol, or phenol; buffers; suspending agents; thickening agents; and the like. The parenteral preparations can be enclosed in ampules, disposable syringes or multiple dose vials. Other potentially useful parenteral delivery systems for the active compounds include ethylene-vinyl acetate copolymer particles, osmotic pumps, implantable infusion systems, and liposomes.

Other possible modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for topical use are in the form of an ointment, cream, or gel. Typically these forms include a carrier, such as petrolatum, lanolin, stearyl alcohol, polyethylene glycols, or their combinations, and either an emulsifying agent, such as sodium lauryl sulfate, or a gelling agent, such as tragacanth.

Formulations suitable for transdermal administration can be presented as discrete patches, as in a reservoir or microreservoir system, adhesive diffusion-controlled system or a matrix dispersion-type system. Formulations for buccal administration include, for example lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate.

The compositions of the present invention may be formulated to control and/or delay the release of the active agent(s). Such controlled-, delayed, sustained-, or extended-release compositions are well-known in the art, and may include, for example, reservoir or matrix diffusion products, as well as dissolution systems. Some compositions may utilize, for example biocompatible, biodegradable lactide polymer, lactide/glycolide copolymer, or polyoxyethylene-polyoxypropylene copolymers as excipients.

As those skilled in the art will appreciate, numerous changes and modifications may be made to the embodiments of the invention without departing from the spirit of the invention. It is intended that all such variations fall within the scope of the invention.

What is claimed is:

1. A method of treating sleepiness associated with narcolepsy, obstructive sleep apnea, or shift work disorder; Parkinson's disease; Alzheimer's disease; attention deficit disorder; attention deficit hyperactivity disorder; depression; or fatigue in a mammal comprising administering to said mammal a therapeutically effective amount of a compound of Formula (I):

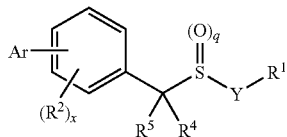

(I)

or a stereoisomeric form, mixture of stereoisomeric forms or pharmaceutically acceptable salt form thereof, wherein:

Ar is $C_6$-$C_{10}$ aryl substituted by 0-5 $R^3$;
$C_5$-$C_{10}$ cycloalkenyl substituted by 0-5 $R^3$; or
5 to 14 membered heteroaryl group substituted by 0-5 $R^3$, wherein said heteroaryl group is selected from phenoxathiinyl, quinolinyl, isoxazolyl, thienyl, benzothienyl, (1,1-dioxo)-benzothienyl, indolyl, furyl, benzofuryl, pyridyl, seleninyl, 1,3-dihydro-isoindolyl, pyrrolyl, imidazopyridinyl, triazolyl, purine and 2-benzo[1,4]dioxine;

Y is $C_1$-$C_6$ alkylene substituted with 0-3 $R^{20A}$;

$R^1$ is selected from H, $C(=O)NR^{12}R^{13}$, $C(=N)NR^{12}R^{13}$, $OC(=O)NR^{12}R^{13}$, $NR^{21}C(=O)NR^{12}R^{13}$, $NR^{21}S(=O)_2NR^{12}R^{13}$, —($C_6$-$C_{10}$ aryl)-$NR^{12}R^{13}$ wherein said aryl is substituted with 0-3 $R^{20}$; $NR^{21}C(=O)R^{14}$, $C(=O)R^{14}$, $C(=O)OR^{11}$, $OC(=O)R^{11}$, and $NR^{21}S(=O)_2R^{11}$;

$R^2$ is selected from H, F, Cl, Br, I, $OR^{16}$, $OR^{25}$, $NR^{17}R^{18}$, NHOH, $NO_2$, CN, $CF_3$, $C_1$-$C_6$ alkyl, $C_2$-$C_6$ alkenyl, $C_2$-$C_6$ alkynyl, $C(=O)R^{16}$, $C(=O)OR^{16}$, $OC(=O)R^{16}$, $C(=O)NR^{17}R^{18}$, $NR^{15}C(=O)R^{16}$, $NR^{15}CO_2R^{16}$, $OC(=O)NR^{17}R^{18}$, $NR^{15}C(=S)R^{16}$, $SR^{16}$, $S(=O)R^{16}$, and $S(=O)_2R^{16}$;

alternatively, two $R^2$ groups may be combined to form a methylenedioxy group, an ethylenedioxy group, or a propylenedioxy group;

$R^3$ is selected from H, F, Cl, Br, I, $OR^{16}$, $OCF_3$, $OR^{25}$, $NR^{17}R^{18}$, NHOH, $NO_2$, CN, $CF_3$, $CH_2OR^{16}$, $C_1$-$C_6$ alkyl, $C_2$-$C_6$ alkenyl, $C_2$-$C_6$ alkynyl, $C_3$-$C_7$ cycloalkyl, phenyl, $C_7$-$C_{10}$ arylalkyl, $C(=O)R^{16}$, $C(=O)OR^{16}$, $OC(=O)R^{16}$, $C(=O)NR^{17}R^{18}$, $NR^{15}C(=O)R^{16}$, $NR^{15}CO_2R^{16}$, $OC(=O)NR^{17}R^{18}$, $NR^{15}C(=S)R^{16}$, $SR^{16}$, $S(=O)R^{16}$, $S(=O)_2R^{16}$, and $NR^{15}S(=O)_2R^{16}$;

alternatively, two $R^3$ groups may be combined to form a methylenedioxy group, an ethylenedioxy group, or a propylenedioxy group;

$R^4$ and $R^5$ at each occurrence are independently selected from H, $C_1$-$C_6$ alkyl, $C_2$-$C_6$ alkenyl, and $C_2$-$C_6$ alkynyl;

alternatively, $R^4$ and $R^5$, together with the carbon atom to which they are attached, form a 3-7 membered spirocyclic ring;

$R^{11}$ at each occurrence is independently selected from H, $C_1$-$C_6$ alkyl substituted with 0-3 $R^{20}$; and $C_6$-$C_{10}$ aryl substituted with 0-3 $R^{20}$;

$R^{12}$ and $R^{13}$ at each occurrence are each independently selected from H, $C_1$-$C_6$ alkyl substituted with 0-3 $R^{20}$; and $C_6$-$C_{10}$ aryl substituted with 0-3 $R^{20}$;

alternatively, $R^{12}$ and $R^{13}$, together with the nitrogen to which they are attached, form a 3-7 membered heterocyclic ring substituted with 0-3 $R^{20}$, wherein said heterocyclic ring is selected from piperazinyl, piperidinyl and pyrrolidinyl;

$R^{14}$ at each occurrence is independently selected from $C_1$-$C_6$ alkyl substituted with 0-3 $R^{20}$; $C_6$-$C_{10}$ aryl substituted with 0-3 $R^{20}$; and $C_7$-$C_{10}$ arylalkyl substituted with 0-3 $R^{20}$;

$R^{15}$ at each occurrence is independently selected from H and $C_1$-$C_6$ alkyl;

$R^{16}$ at each occurrence is independently selected from H, $C_1$-$C_6$ alkyl, and $C_6$-$C_{10}$ aryl;

$R^{17}$ and $R^{18}$ at each occurrence are each independently selected from H, $C_1$-$C_6$ alkyl, and $C_6$-$C_{10}$ aryl, $R^{20}$ at each occurrence is independently selected from F, Cl, Br, I, OH, $OR^{22}$, $OR^{25}$, $NR^{23}R^{24}$, NHOH, $NO_2$, CN, $CF_3$, $C_1$-$C_6$ alkyl, $C_1$-$C_6$ alkyl-OH, $C_2$-$C_6$ alkenyl, $C_2$-$C_6$ alkynyl, $C_3$-$C_7$ cycloalkyl, phenyl substituted by 0-1 $R^{26}$; $C_7$-$C_{10}$ arylalkyl, =O, $C(=O)R^{22}$, $C(=O)OR^{22}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=S)R^{22}$, $SR^{22}$, $S(=O)R^{22}$, and $S(=O)_2R^{22}$;

$R^{20A}$ at each occurrence is independently selected from F, Cl, OH, $C_1$-$C_6$ alkoxy, $CF_3$, $C_1$-$C_6$ alkyl, $C_1$-$C_6$ alkyl-OH, $C_2$-$C_6$ alkenyl, $C_2$-$C_6$ alkynyl, and $C_3$-$C_7$ cycloalkyl;

$R^{21}$ at each occurrence is independently selected from H and $C_1$-$C_6$ alkyl;

$R^{22}$ at each occurrence is independently selected from H, $C_1$-$C_6$ alkyl, $C_1$-$C_6$ alkyl-OH, and $C_6$-$C_{10}$ aryl;

$R^{23}$ and $R^{24}$ at each occurrence are each independently selected from H, $C_1$-$C_6$ alkyl, and $C_6$-$C_{10}$ aryl, $R^{25}$ at each occurrence is independently the residue of an amino acid after the hydroxyl group of the carboxyl group is removed;

$R^{26}$ at each occurrence is independently selected from H, F, Cl, Br, $C_1$-$C_6$ alkyl, and $C_1$-$C_6$ alkoxy;

x is 0, 1, 2, 3, or 4; and q is 1, or 2;

provided
when Y is —$CH_2$—, Ar is phenyl substituted by 0-5 $R^3$, and —$C(R^4)(R^5)$— is —$CH(C_1$-$C_3$ alkyl)-, then Ar is in the ortho or meta position to the —C(R⁴)(R⁵)— substituent on the core phenyl ring;

when Y is —CH$_2$—, $R^1$ is H, C(=O)OR$^{11}$, or C(=O)NR$^{12}$R$^{13}$; Ar is phenyl substituted by 0-2 R$^3$, and R$^3$ is H, F, Cl, Br, I, CH$_3$, OCH$_3$, SCH$_3$, CN, NO$_2$, or methylenedioxyphenyl; then Ar is in the ortho or meta position to the —C(R⁴)(R⁵)— substituent on the core phenyl ring;

when Ar is imidazopyridine substituted by 0-5 R$^3$, Ar is in the ortho or meta position to the —C(R⁴)(R⁵)— substituent on the core phenyl ring;

when Ar is in the meta position to the —C(R⁴)(R⁵)— substituent on the core phenyl ring and Ar is a heteroaryl group attached to the phenyl ring through a nitrogen atom, then Ar is pyrrolyl, indolyl, triazolyl, or 1,3-dihydroisoindolyl;

when Y is —CH$_2$— and Ar is pyridyl substituted by a nitro, a methyl, a second methyl, and a C(=O)OC$_3$H$_7$ group, then $R^1$ is not H;

when Y is —CH$_2$— and Ar is a purine or imidazopyridine substituted by 0-5 R$^3$, then $R^1$ is not H;

when q is 1, Y is butylene and Ar is phenyl, substituted by 0-5 R$^3$, in the para position to the —C(R⁴)(R⁵)— substituent on the core phenyl ring, then $R^1$ is not H;

when q is 1, Y is —CH$_2$— or —CH$_2$CH$_2$—, and Ar is pyrrolyl in the ortho position to the —C(R⁴)(R⁵)— substituent on the core phenyl ring; then $R^1$ is not H;

when q is 1, $R^2$ is OH, and Ar is phenyl or cycloalkenyl; then $R^1$ is not H or C(=O)OR$^{11}$;

when q is 1, Y is —CH$_2$—, R⁴ is H, R⁵ is H, and Ar is phenyl in the ortho position to the —C(R⁴)(R⁵)— substituent on the core phenyl ring, then $R^1$ is not H;

when q is 2, then Ar is in the ortho or meta position to the —C(R⁴)(R⁵)— substituent on the core phenyl ring;

when q is 2, Y is —CH$_2$—, R⁴ is H, R⁵ is H, and Ar is 1,2-(methylenedioxy)-phenyl, then Ar is in the ortho position to the —C(R⁴)(R⁵)— substituent on the core phenyl ring; and when q is 2, and Ar is phenyl in the ortho position to the —C(R⁴)(R⁵)— substituent on the core phenyl ring, then $R^1$ is not H.

2. The method of claim 1, wherein the compound is administered for the treatment of sleepiness associated with narcolepsy.

3. A method for the promotion of wakefulness comprising administering a compound of Formula (I):

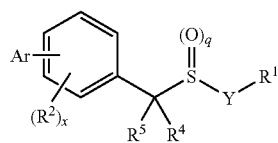

(I)

or a stereoisomeric form, mixture of stereoisomeric forms or pharmaceutically acceptable salt form thereof, wherein:

Ar is C$_6$-C$_{10}$ aryl substituted by 0-5 R$^3$;
C$_5$-C$_{10}$ cycloalkenyl substituted by 0-5 R$^3$; or
5 to 14 membered heteroaryl group substituted by 0-5 R$^3$, wherein said heteroaryl group is selected from phenoxathiinyl, quinolinyl, isoxazolyl, thienyl, benzothienyl, (1,1-dioxo)-benzothienyl, indolyl, furyl, benzofuryl, pyridyl, seleninyl, 1,3-dihydro-isoindolyl, pyrrolyl, imidazopyridinyl, triazolyl, purine and 2-benzo[1,4]dioxine;

Y is C$_1$-C$_6$ alkylene substituted with 0-3 R$^{20A}$;

$R^1$ is selected from H, C(=O)NR$^{12}$R$^{13}$, C(=N)NR$^{12}$R$^{13}$, OC(=O)NR$^{12}$R$^{13}$, NR$^{21}$C(=O)NR$^{12}$R$^{13}$, NR$^{21}$S(=O)$_2$NR$^{12}$R$^{13}$, —(C$_6$-C$_{10}$ aryl)-NR$^{12}$R$^{13}$ wherein said aryl is substituted with 0-3 R$^{20}$; NR$^{21}$C(=O)R$^{14}$, C(=O)R$^{14}$, C(=O)OR$^{11}$, OC(=O)R$^{11}$, and NR$^{21}$S(=O)$_2$R$^{11}$;

$R^2$ is selected from H, F, Cl, Br, I, OR$^{16}$, OR$^{25}$, NR$^{17}$R$^{18}$, NHOH, NO$_2$, CN, CF$_3$, C$_1$-C$_6$ alkyl, C$_2$-C$_6$ alkenyl, C$_2$-C$_6$ alkynyl, C(=O)R$^{16}$, C(=O)OR$^{16}$, OC(=O)R$^{16}$, C(=O)NR$^{17}$R$^{18}$, NR$^{15}$C(=O)R$^{16}$, NR$^{15}$CO$_2$R$^{16}$, OC(=O)NR$^{17}$R$^{18}$, NR$^{15}$C(=S)R$^{16}$, SR$^{16}$, S(=O)R$^{16}$, and S(=O)$_2$R$^{16}$;

alternatively, two R$^2$ groups may be combined to form a methylenedioxy group, an ethylenedioxy group, or a propylenedioxy group;

R$^3$ is selected from H, F, Cl, Br, I, OR$^{16}$, OCF$_3$, OR$^{25}$, NR$^{17}$R$^{18}$, NHOH, NO$_2$, CN, CF$_3$, CH$_2$OR$^{16}$, C$_1$-C$_6$ alkyl, C$_2$-C$_6$ alkenyl, C$_2$-C$_6$ alkynyl, C$_3$-C$_7$ cycloalkyl, phenyl, C$_7$-C$_{10}$ arylalkyl, C(=O)R$^{16}$, C(=O)OR$^{16}$, OC(=O)R$^{16}$, C(=O)NR$^{17}$R$^{18}$, NR$^{15}$C(=O)R$^{16}$, NR$^{15}$CO$_2$R$^{16}$, OC(=O)NR$^{17}$R$^{18}$, NR$^{15}$C(=S)R$^{16}$, SR$^{16}$, S(=O)R$^{16}$, S(=O)$_2$R$^{16}$, and NR$^{15}$S(=O)$_2$R$^{16}$;

alternatively, two R$^3$ groups may be combined to form a methylenedioxy group, an ethylenedioxy group, or a propylenedioxy group;

R⁴ and R⁵ at each occurrence are independently selected from H, C$_1$-C$_6$ alkyl, C$_2$-C$_6$ alkenyl, and C$_2$-C$_6$ alkynyl;

alternatively, R⁴ and R⁵, together with the carbon atom to which they are attached, form a 3-7 membered spirocyclic ring;

R$^{11}$ at each occurrence is independently selected from H, C$_1$-C$_6$ alkyl substituted with 0-3 R$^{20}$; and C$_6$-C$_{10}$ aryl substituted with 0-3 R$^{20}$;

R$^{12}$ and R$^{13}$ at each occurrence are each independently selected from H, C$_1$-C$_6$ alkyl substituted with 0-3 R$^{20}$; and C$_6$-C$_{10}$ aryl substituted with 0-3 R$^{20}$;

alternatively, R$^{12}$ and R$^{13}$, together with the nitrogen to which they are attached, form a 3-7 membered heterocyclic ring substituted with 0-3 R$^{20}$, wherein said heterocyclic ring is selected from piperazinyl, piperidinyl and pyrrolidinyl;

R$^{14}$ at each occurrence is independently selected from C$_1$-C$_6$ alkyl substituted with 0-3 R$^{20}$; C$_6$-C$_{10}$ aryl substituted with 0-3 R$^{20}$; and C$_7$-C$_{10}$ arylalkyl substituted with 0-3 R$^{20}$;

R$^{15}$ at each occurrence is independently selected from H and C$_1$-C$_6$ alkyl;

R$^{16}$ at each occurrence is independently selected from H, C$_1$-C$_6$ alkyl, and C$_6$-C$_{10}$ aryl;

R$^{17}$ and R$^{18}$ at each occurrence are each independently selected from H, C$_1$-C$_6$ alkyl, and C$_6$-C$_{10}$ aryl, R$^{20}$ at each occurrence is independently selected from F, Cl, Br, I, OH, OR$^{22}$, OR$^{25}$, NR$^{23}$R$^{24}$, NHOH, NO$_2$, CN, CF$_3$, C$_1$-C$_6$ alkyl, C$_1$-C$_6$ alkyl-OH, C$_2$-C$_6$ alkenyl, C$_2$-C$_6$ alkynyl, C$_3$-C$_7$ cycloalkyl, phenyl substituted by 0-1 R$^{26}$; C$_7$-C$_{10}$ arylalkyl, =O, C(=O)R$^{22}$, C(=O)OR$^{22}$, OC(=O)R$^{22}$, C(=O)NR$^{23}$R$^{24}$, NR$^{21}$C(=O)R$^{22}$, NR$^{21}$CO$_2$R$^{22}$, OC(=O)NR$^{23}$R$^{24}$, NR$^{21}$C(=S)R$^{22}$, SR$^{22}$, S(=O)R$^{22}$, and S(=O)$_2$R$^{22}$;

R$^{20A}$ at each occurrence is independently selected from F, Cl, OH, C$_1$-C$_6$ alkoxy, CF$_3$, C$_1$-C$_6$ alkyl, C$_1$-C$_6$ alkyl-OH, C$_2$-C$_6$ alkenyl, C$_2$-C$_6$ alkynyl, and C$_3$-C$_7$ cycloalkyl;

$R^{21}$ at each occurrence is independently selected from H and $C_1$-$C_6$ alkyl;

$R^{22}$ at each occurrence is independently selected from H, $C_1$-$C_6$ alkyl, $C_1$-$C_6$ alkyl-OH, and $C_6$-$C_{10}$ aryl;

$R^{23}$ and $R^{24}$ at each occurrence are each independently selected from H, $C_1$-$C_6$ alkyl, and $C_6$-$C_{10}$ aryl;

$R^{25}$ at each occurrence is independently the residue of an amino acid after the hydroxyl group of the carboxyl group is removed;

$R^{26}$ at each occurrence is independently selected from H, F, Cl, Br, $C_1$-$C_6$ alkyl, and $C_1$-$C_6$ alkoxy;

x is 0, 1, 2, 3, or 4; and q is 1, or 2;

provided when Y is —$CH_2$—, Ar is phenyl substituted by 0-5 $R^3$, and —$C(R^4)(R^5)$— is —$CH(C_1$-$C_3$ alkyl)-, then Ar is in the ortho or meta position to the —$C(R^4)(R^5)$— substituent on the core phenyl ring;

when Y is —$CH_2$—, $R^1$ is H, $C(=O)OR^{11}$, or $C(=O)NR^{12}R^{13}$; Ar is phenyl substituted by 0-2 $R^3$, and $R^3$ is H, F, Cl, Br, I, $CH_3$, $OCH_3$, $SCH_3$, CN, $NO_2$, or methylenedioxyphenyl;

then Ar is in the ortho or meta position to the —$C(R^4)(R^5)$— substituent on the core phenyl ring;

when Ar is imidazopyridine substituted by 0-5 $R^3$, Ar is in the ortho or meta position to the —$C(R^4)(R^5)$— substituent on the core phenyl ring;

when Ar is in the meta position to the —$C(R^4)(R^5)$— substituent on the core phenyl ring and Ar is a heteroaryl group attached to the phenyl ring through a nitrogen atom, then Ar is pyrrolyl, indolyl, triazolyl, or 1,3-dihydroisoindolyl;

when Y is —$CH_2$— and Ar is pyridyl substituted by a nitro, a methyl, a second methyl, and a $C(=O)OC_3H_7$ group, then $R^1$ is not H;

when Y is —$CH_2$— and Ar is a purine or imidazopyridine substituted by 0-5 $R^3$, then $R^1$ is not H;

when q is 1, Y is butylene and Ar is phenyl, substituted by 0-5 $R^3$, in the para position to the —$C(R^4)(R^5)$— substituent on the core phenyl ring, then $R^1$ is not H;

when q is 1, Y is —$CH_2$— or —$CH_2CH_2$—, and Ar is pyrrolyl in the ortho position to the —$C(R^4)(R^5)$— substituent on the core phenyl ring; then $R^1$ is not H;

when q is 1, $R^2$ is OH, and Ar is phenyl or cycloalkenyl; then $R^1$ is not H or $C(=O)OR^{11}$;

when q is 1, Y is —$CH_2$—, $R^4$ is H, $R^5$ is H, and Ar is phenyl in the ortho position to the —$C(R^4)(R^5)$— substituent on the core phenyl ring, then $R^1$ is not H;

when q is 2, then Ar is in the ortho or meta position to the —$C(R^4)(R^5)$— substituent on the core phenyl ring;

when q is 2, Y is —$CH_2$—, $R^4$ is H, $R^5$ is H, and Ar is 1,2-(methylenedioxy)-phenyl, then Ar is in the ortho position to the —$C(R^4)(R^5)$— substituent on the core phenyl ring; and when q is 2, and Ar is phenyl in the ortho position to the —$C(R^4)(R^5)$— substituent on the core phenyl ring, then $R^1$ is not H.

4. The method of claim 1 or 3 wherein the compound of Formula I has the following structure:

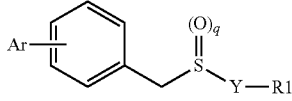

and is selected from the following:

| Ex. No. | Ar | Ar Position | q | Y-$R^1$ |
| --- | --- | --- | --- | --- |
| 1 | 3-thienyl | ortho | 1 | $CH_2CONH_2$ |
| 2 | 3-thienyl | ortho | 1 | $CH_2CO$-N-pyrrolidinyl |
| 3 | 3-thienyl | ortho | 1 | $CH_2CON(CH_3)_2$ |
| 4 | 3-thienyl | ortho | 1 | $CH_2CONHCH(CH_3)_2$ |
| 5 | 3-thienyl | ortho | 1 | $CH_2CO$-1-(4-acetyl)-piperazinyl |
| 6 | 3-thienyl | ortho | 1 | $CH_2CONH(CH_2)_2OH$ |
| 7 | 3-thienyl | ortho | 1 | $CH_2CO$-1-(4-hydroxy)-piperidinyl |
| 9 | 3-thienyl | ortho | 1 | $CH_2CO$-1-(4-ethylcarboxamide)-piperazinyl |
| 10 | 3-thienyl | ortho | 1 | $CH_2CO$-1-(4-carboxamide)-piperazinyl |
| 11 | 3-thienyl | ortho | 1 | $CH_2CO$-1-(4-phenylcarboxamide)-piperazinyl |
| 12 | 3-thienyl | ortho | 1 | $CH_2CO$-N-piperazinyl |
| 13 | 3-thienyl | ortho | 1 | $CH_2CO$-1-(4-ethylcarboxylate)-piperazinyl |
| 14 | 3-thienyl | ortho | 1 | $CH_2CO$-1-(4-methyl)-piperazinyl |
| 15 | 3-thienyl | ortho | 1 | $CH_2COOH$ |
| 16 | 3-thienyl | ortho | 2 | $CH_2CO$-1-(4-acetyl)-piperazinyl |
| 17 | 5-chloro-2-thienyl | ortho | 1 | $CH_2CONH_2$ |
| 18 | 4-methyl-3-thienyl | ortho | 1 | $CH_2CONH_2$ |
| 19 | 3-thienyl | meta | 1 | $CH_2CONH_2$ |
| 20 | 3-thienyl | meta | 1 | $CH_2CO$-N-pyrrolidinyl |
| 21 | 3-thienyl | meta | 1 | $CH_2CON(CH_3)_2$ |
| 22 | 3-thienyl | meta | 1 | $CH_2CONHCH(CH_3)_2$ |
| 23 | 3-thienyl | meta | 1 | $CH_2CO$-1-(4-acetyl)-piperazinyl |
| 24 | 3-thienyl | meta | 1 | $CH_2CONH(CH_2)_2OH$ |
| 25 | 3-thienyl | meta | 1 | $CH_2CO$-1-(4-hydroxy)-piperidinyl |
| 26 | 3-thienyl | meta | 1 | $CH_2CO$-1-(4-phenyl)-piperazinyl |
| 27 | 3-thienyl | meta | 1 | $CH_2CO$-1-(4-ethylcarboxylate)-piperazinyl |
| 28 | 3-thienyl | meta | 1 | $CH_2CO$-1-(4-methyl)-piperazinyl |
| 29 | 3-thienyl | meta | 1 | $CH_2CO$-N-piperazinyl |
| 30 | 3-thienyl | meta | 1 | $CH_2CO$-1-(4-carboxamide)-piperazinyl |
| 31 | 3-thienyl | meta | 1 | $CH_2CO$-1-(4-propylphenyl)-piperazinyl |
| 32 | 3-thienyl | meta | 1 | $CH_2CO$-1-(4-propyl)-piperazinyl |
| 33 | 5-chloro-2-thienyl | meta | 1 | $CH_2CONH_2$ |
| 34 | 3-thienyl | para | 1 | $CH_2CO$-N-pyrrolidinyl |
| 35 | 3-thienyl | para | 1 | $CH_2CONH_2$ |
| 36 | 3-thienyl | para | 1 | $CH_2CON(CH_3)_2$ |
| 37 | 3-thienyl | para | 1 | $CH_2CONHCH(CH_3)_2$ |
| 38 | 3-thienyl | para | 1 | $CH_2CONHCH_2CN$ |
| 39 | 3-thienyl | para | 1 | $CH_2CO$-1-(4-acetyl)-piperazinyl |
| 40 | 3-thienyl | para | 1 | $CH_2CO$-1-(4-hydroxy)-piperidinyl |
| 41 | 3-thienyl | para | 1 | $CH_2CO$-1-(4-methyl)-piperazinyl |
| 42 | 3-thienyl | para | 1 | $CH_2CO$-1-(4-cyclohexyl)-piperazinyl |
| 43 | 3-thienyl | para | 1 | $CH_2CO$-1-(4-ethylcarboxylate)-piperazinyl |
| 44 | 3-thienyl | para | 1 | $CH_2CO$-1-(4-carboxamide)-piperazinyl |
| 45 | 3-thienyl | para | 1 | $CH_2CO$-N-piperazinyl |
| 46 | 3-thienyl | para | 1 | $CH_2CO$-1-(4-ethylcarboxamide)-piperazinyl |
| 47 | 2-benzothienyl | ortho | 1 | $CH_2CONH_2$ |
| 48 | 2-benzothienyl | ortho | 1 | $CH_2CO$-1-(4-acetyl)-piperazinyl |
| 49 | 2-benzothienyl | ortho | 1 | $CH_2CO$-1-(4-ethylcarboxylate)-piperazinyl |
| 50 | 2-benzothienyl | ortho | 1 | $CH_2CO$-N-piperazinyl |
| 51 | 2-benzothienyl | ortho | 1 | $CH_2CO$-1-(4-carboxamide)-piperazinyl |
| 52 | 2-benzothienyl | ortho | 1 | $CH_2CO$-1-(4-ethylcarboxamide)-piperazinyl |
| 53 | 2-benzothienyl | ortho | 1 | $CH_2CO$-1-(4-phenylcarboxamide)-piperazinyl |
| 55 | 2-benzothienyl | ortho | 1 | $(CH_2)_2CONH_2$ |

| Ex. No. | Ar | Ar Position | q | Y-R$^1$ |
|---|---|---|---|---|
| 56 | 2-benzothienyl | ortho | 1 | $(CH_2)_2$CO-1-(4-methyl)-piperazinyl |
| 57 | 2-benzothienyl | ortho | 1 | $CH_2$COOH |
| 58 | 2-benzothienyl | ortho | 2 | $CH_2CONH_2$ |
| 59 | 2-(1,1-dioxo)-benzothienyl | ortho | 2 | $CH_2CONH_2$ |
| 60 | 2-benzothienyl | ortho | 1 | $CH_2$CO-1-(4-methyl)-piperazinyl |
| 61 | 3-benzothienyl | ortho | 1 | $CH_2CONH_2$ |
| 63 | 3-benzothienyl | ortho | 1 | $(CH_2)_2$CO-1-(4-methyl)-piperazinyl |
| 64 | 3-benzothienyl | ortho | 1 | $CH_2$CO-1-(4-acetyl)-piperazinyl |
| 65 | 3-benzothienyl | ortho | 1 | $CH_2$CO-1-(4-ethylcarboxylate)-piperazinyl |
| 66 | 3-benzothienyl | ortho | 1 | $CH_2$CO-1-(4-hydroxyethyl)-piperazinyl |
| 67 | 2-benzothienyl | meta | 1 | $CH_2CONH_2$ |
| 68 | 2-benzothienyl | meta | 1 | $CH_2$CO-1-(4-acetyl)-piperazinyl |
| 69 | 2-benzothienyl | meta | 1 | $CH_2$CO-1-(4-methyl)-piperazinyl |
| 70 | 2-benzothienyl | meta | 1 | $CH_2CONHCH(CH_3)_2$ |
| 72 | 2-benzothienyl | meta | 1 | $CH_2$CO-1-(4-ethylcarboxylate)-piperazinyl |
| 73 | 2-benzothienyl | meta | 1 | $CH_2CON(C_2H_5)_2$ |
| 74 | 2-benzothienyl | para | 1 | $CH_2CONH_2$ |
| 75 | 2-benzothienyl | para | 1 | $CH_2$CO-1-(4-acetyl)-piperazinyl |
| 76 | 2-benzothienyl | meta | 1 | $CH_2$CO-1-(4-hydroxyethyl)-piperazinyl |
| 77 | 3-benzothienyl | meta | 1 | $CH_2CONH_2$ |
| 78 | 3-benzothienyl | meta | 1 | $CH_2$CO-1-(4-acetyl)-piperazinyl |
| 79 | 3-benzothienyl | meta | 1 | $CH_2$CO-1-(4-methyl)-piperazinyl |
| 80 | 3-benzothienyl | meta | 1 | $CH_2$CO-1-(4-hydroxyethyl)-piperazinyl |
| 81 | 3-benzothienyl | meta | 1 | $CH_2$CO-1-(4-ethylcarboxylate)-piperazinyl |
| 82 | 2-benzothienyl | para | 1 | $CH_2$CO-1-(4-methyl)-piperazinyl |
| 83 | 2-benzothienyl | para | 1 | $CH_2$CO-1-(4-hydroxyethyl)-piperazinyl |
| 84 | 3-benzothienyl | para | 1 | $CH_2CONH_2$ |
| 85 | 2-indolyl | ortho | 1 | $CH_2CONH_2$ |
| 86 | 3-furyl | ortho | 1 | $CH_2$CO-1-(4-acetyl)-piperazinyl |
| 87 | 3-furyl | ortho | 1 | $CH_2$CO-1-(4-methyl)-piperazinyl |
| 88 | 3-furyl | ortho | 1 | $CH_2CONH_2$ |
| 89 | 3-pyridyl | ortho | 1 | $CH_2CONH$(isopropyl) |
| 90 | 3-pyridyl | ortho | 1 | $CH_2CONH(CH_2)_2OH$ |
| 91 | 3-pyridyl | ortho | 1 | $CH_2CONH_2$ |
| 92 | 3-pyridyl | ortho | 1 | $CH_2CONH_2$ |
| 93 | 3-pyridyl | meta | 1 | $CH_2CONH_2$ |
| 94 | 3-pyridyl | meta | 1 | $CH_2$CO-1-(4-acety)piperazinyl |
| 95 | 3-pyridyl | meta | 1 | $CH_2CONH(CH_2)_2OH$ |
| 96 | 3-pyridyl | meta | 1 | $CH_2$CO-N-piperazinyl |
| 97 | 3-pyridyl | meta | 1 | $CH_2CONH_2$ |
| 98 | 3-pyridyl | para | 1 | $CH_2CONH_2$ |
| 99 | 3-pyridyl | para | 1 | $CH_2$CO-1-(4-acetyl)piperazinyl |
| 100 | 3-pyridyl | para | 1 | $CH_2$CO-N-piperazinyl |
| 101 | 3-pyridyl | para | 1 | $CH_2CONH(CH_2)_2OH$ |
| 102 | 3-pyridyl | para | 1 | $CH_2CONH_2$ |
| 103 | 2-furyl | ortho | 1 | $CH_2CON(CH_3)_2$ |
| 104 | 2-furyl | ortho | 1 | $CH_2CONHCH_2CN$ |
| 105 | 2-furyl | ortho | 1 | $CH_2CONH$(isopropyl) |
| 106 | 2-furyl | ortho | 1 | $CH_2CONH_2$ |
| 107 | 2-furyl | ortho | 1 | $CH(OCH_3)CONH_2$ |
| 108 | 2-furyl | ortho | 1 | $CH_2CONH(CH_2)_2OH$ |
| 109 | 2-furyl | ortho | 1 | $CH_2$CO-1-(4-acetyl)piperazinyl |
| 110 | 2-furyl | ortho | 1 | $CH_2$COOH |
| 111 | 2-furyl | meta | 1 | $CH_2$CO-N-pyrrolidinyl |
| 112 | 2-furyl | meta | 1 | $CH_2CON(CH_3)_2$ |
| 113 | 2-furyl | meta | 1 | $CH_2CONH$(isopropyl) |
| 114 | 2-furyl | meta | 1 | $CH_2CONHCH_2CN$ |
| 115 | 2-furyl | meta | 1 | $CH_2$CO-1-(4-acetyl)piperazinyl |
| 116 | 2-furyl | meta | 1 | $CH_2CONH(CH_2)_2OH$ |
| 117 | 2-furyl | meta | 1 | $CH_2$CO-N-(4-piperidinol) |
| 118 | 2-furyl | meta | 1 | $CH_2$CO-N-piperazinyl |
| 119 | 2-furyl | meta | 1 | $CH_2CONH_2$ |
| 120 | 2-furyl | meta | 1 | $CH_2$CO-1-[4-(2-methoxyphenyl)]-piperazinyl |
| 121 | 2-furyl | meta | 1 | $CH_2$CO-1-[4-(4-fluorophenyl)]-piperazinyl |
| 122 | 2-furyl | meta | 1 | $CH_2$CO-1-(4-phenyl)piperazinyl |
| 123 | 2-furyl | meta | 1 | $CH_2CONH_2$ |
| 124 | 2-seleninyl[[1]] | meta | 1 | $CH_2$CO-1-(4-acetyl)piperazinyl |
| 125 | 2-hydroxyphenyl | meta | 1 | $CH_2$CO-1-(4-acetyl)piperazinyl |
| 126 | 2-benzofuryl | meta | 1 | $CH_2$CO-1-(4-acetyl)piperazinyl |
| 127 | 2-benzofuryl | meta | 1 | $CH_2CONH(CH_2)_2OH$ |
| 128 | 2-furyl | para | 1 | $CH_2CONH_2$ |
| 129 | 2-furyl | para | 1 | $CH_2CONH$(isopropyl) |
| 130 | 2-furyl | para | 1 | $CH_2CONHCH_2CN$ |
| 131 | 2-furyl | para | 1 | $CH_2CON(CH_3)_2$ |
| 132 | 2-furyl | para | 1 | $CH_2$CO-1-(4-acetyl)piperazinyl |
| 133 | 2-furyl | para | 1 | $CH_2CONH(CH_2)_2OH$ |
| 134 | 2-furyl | para | 1 | $CH_2$CO-N-piperazinyl |
| 135 | 2-thienyl | ortho | 1 | $CH_2$CO-N-pyrrolidinyl |
| 136 | 2-(5-bromo)-thienyl | ortho | 1 | $CH_2$CO-N-pyrrolidinyl |
| 137 | 2-thienyl | ortho | 1 | $CH_2CON(CH_3)_2$ |
| 138 | 2-(5-bromo)-thienyl | ortho | 1 | $CH_2CON(CH_3)_2$ |
| 139 | 2-thienyl | ortho | 1 | $CH_2CONH_2$ |
| 140 | 2-thienyl | ortho | 1 | $CH_2CONH(CH_2)_2OH$ |
| 141 | 2-thienyl | ortho | 1 | $CH_2$CO-N-piperazinyl |
| 142 | 2-thienyl | ortho | 1 | $CH_2$CO-1-(4-acetyl)piperazinyl |
| 143 | 2-thienyl | ortho | 1 | $CH_2CONH$(isopropyl) |
| 144 | 2-thienyl | meta | 1 | $CH_2$CO-N-pyrrolidinyl |
| 145 | 2-thienyl | meta | 1 | $CH_2CON(CH_3)_2$ |
| 146 | 2-thienyl | meta | 1 | $CH_2CONH_2$ |
| 147 | 2-thienyl | meta | 1 | $CH_2CONH(CH_2)_2OH$ |
| 148 | 2-thienyl | meta | 1 | $CH_2$CO-N-piperazinyl |
| 149 | 2-thienyl | meta | 1 | $CH_2$CO-1-(4-acetyl)piperazinyl |
| 150 | 2-thienyl | para | 1 | $CH_2$CO-N-pyrrolidinyl |
| 151 | 2-(5-bromo)-thienyl | para | 1 | $CH_2$CO-N-pyrrolidinyl |
| 152 | 2-thienyl | para | 1 | $CH_2CON(CH_3)_2$ |
| 153 | 2-(5-bromo)-thienyl | para | 1 | $CH_2CON(CH_3)_2$ |
| 154 | 2-thienyl | para | 1 | $CH_2CONH_2$ |
| 155 | 2-thienyl | para | 1 | $CH_2CONHCH_2CN$ |
| 156 | 2-thienyl | para | 1 | $CH_2CONH$(isopropyl) |
| 157 | 2-thienyl | para | 1 | $CH_2$CO-1-(4-acetyl)piperazinyl |
| 158 | 2-thienyl | para | 1 | $CH_2CONH(CH_2)_2OH$ |
| 159 | 2-thienyl | para | 1 | $CH_2$CO-N-pyrrolidinyl |
| 436 | 2-furyl | ortho | 2 | $CH_2$CO-1-(4-acetyl)piperazinyl |
| 160 | 1,3-Dihydro-isoindol-2-yl | ortho | 1 | $CH_2$CO-N-pyrrolidinyl |
| 161 | 1,3-Dihydro-isoindol-2-yl | ortho | 1 | $CH_2CONMe_2$ |
| 162 | 1,3-Dihydro-isoindol-2-yl | meta | 1 | $CH_2$CO-N-pyrrolidinyl |
| 163 | 1,3-Dihydro-isoindol-2-yl | meta | 1 | $CH_2CONMe_2$ |

| Ex. No. | Ar | Ar Position | q | Y-R¹ |
|---|---|---|---|---|
| 164 | 1,3-Dihydro-isoindol-2-yl | meta | 1 | CH$_2$CONHCHMe$_2$ |
| 165 | 1,3-Dihydro-isoindol-2-yl | meta | 1 | CH$_2$CONHCH$_{2CN}$ |
| 166 | 2-Benzofuryl | Ortho | 1 | CH$_2$CO-1-piperazinyl |
| 167 | 2-Benzofuryl | Ortho | 1 | CH$_2$CO-1-(4-acetyl)-piperazinyl |
| 168 | 2-benzo[1,4]dioxine | Ortho | 1 | CH$_2$CO-1-(4-acetyl)-piperazinyl |
| 169 | 2-benzo[1,4]dioxine | Ortho | 1 | CH$_2$CO-1-(4-methyl)-piperazinyl |
| 170 | 2-benzo[1,4]dioxine | Ortho | 1 | CH$_2$CONHCH(CH$_3$)$_2$ |
| 171 | Pyrrol-1-yl | meta | 1 | CH$_2$CONH(CH$_2$)$_2$OH |
| 172 | Pyrrol-1-yl | meta | 1 | CH$_2$CO-1-(4-hydroxy)-piperidinyl |
| 173 | Pyrrol-1-yl | meta | 1 | CH$_2$CO-1-(4-acetyl)-piperazinyl |
| 174 | Pyrrol-1-yl | ortho | 1 | CH$_2$CONH(CH$_2$)$_2$OH |
| 175 | Pyrrol-1-yl | ortho | 1 | CH$_2$CO-1-(4-hydroxy)-piperidinyl |
| 176 | Pyrrol-1-yl | ortho | 1 | CH$_2$CONH(CH$_2$)$_2$O(CH$_2$)$_2$OH |
| 177 | Pyrrol-1-yl | ortho | 1 | CH$_2$CO-N-pyrrolidinyl |
| 178 | Pyrrol-1-yl | ortho | 1 | CH$_2$CONMe$_2$ |
| 179 | Pyrrol-1-yl | ortho | 1 | CH$_2$CONHCHMe$_2$ |
| 180 | Pyrrol-1-yl | ortho | 1 | CH$_2$CO-1-(4-acetyl)-piperazinyl |
| 181 | Pyrrol-1-yl | meta | 1 | CH$_2$CONHCH$_2$CN |
| 182 | Pyrrol-1-yl | meta | 1 | CH$_2$CONHCHMe$_2$ |
| 183 | Pyrrol-1-yl | meta | 1 | CH$_2$CONMe$_2$ |
| 184 | 2-Benzofuryl | Ortho | 1 | CH$_2$CON(CH$_3$)$_2$ |
| 185 | 2-Benzofuryl | Ortho | 1 | CH$_2$CONHCH(CH$_3$)$_2$ |
| 186 | Pyrrol-1-yl | ortho | 1 | CH$_2$CONH$_2$ |
| 187 | Pyrrol-1-yl | meta | 1 | CH$_2$CONH$_2$ |
| 188 | Pyrrol-1-yl | para | 1 | CH$_2$CONH$_2$ |
| 190 | 2-benzo[1,4]-dioxine | ortho | 1 | CH$_2$CONH$_2$ |
| 191 | 2-Benzofuryl | Ortho | 1 | CH$_2$CONH$_2$ |
| 192 | 1,3-Dihydro-isoindol-2-yl | ortho | 1 | CH$_2$CONH$_2$ |
| 193 | 1,3-Dihydro-isoindol-2-yl | meta | 1 | CH$_2$CONH$_2$ |
| 194 | phenyl | ortho | 1 | CH$_2$CON(CH$_3$)$_2$ |
| 195 | phenyl | ortho | 1 | CH$_2$CONH$_2$ |
| 196 | phenyl | ortho | 1 | CH$_2$CONHCH$_3$ |
| 197 | phenyl | ortho | 1 | CH$_2$CONH(C$_2$H$_5$)$_2$ |
| 198 | phenyl | ortho | 1 | CH$_2$CONH(CH$_2$)$_2$OH |
| 199 | phenyl | ortho | 1 | CH$_2$CONHCH$_2$-($_3$-pyridyl) |
| 200 | phenyl | ortho | 1 | CH$_2$CONH(cyclobutyl) |
| 201 | phenyl | ortho | 1 | CH$_2$CONH-(cyclopentyl) |
| 202 | phenyl | ortho | 1 | CH$_2$CO-N-pyrrolidinyl |
| 203 | phenyl | ortho | 1 | CH$_2$CO-N-(2-carboxamide)-pyrrolidinyl |
| 205 | phenyl | ortho | 1 | CH$_2$CO-N-piperazinyl |
| 206 | phenyl | ortho | 1 | CH$_2$CO-N-1-(4-t-butylcarboxylate)-piperazinyl |
| 207 | phenyl | ortho | 1 | CH$_2$CONHCH$_2$CN |
| 208 | phenyl | ortho | 1 | CH$_2$CO NHCH$_2$CF$_3$ |
| 210 | phenyl | ortho | 1 | CH$_2$CONHCH(CH$_3$)$_2$ |
| 211 | phenyl | para | 1 | CH$_2$CO NH$_2$ |
| 212 | phenyl | para | 1 | CH$_2$CO-N-pyrrolidinyl |
| 213 | phenyl | para | 1 | CH$_2$CO N(CH$_3$)$_2$ |
| 215 | phenyl | Para | 1 | CH$_2$CO-N-piperidinyl |
| 216 | phenyl | para | 1 | CH$_2$CONH(CH$_2$)$_2$-($_2$-pyridyl) |
| 217 | phenyl | para | 1 | CH$_2$CONHCH$_2$-($_3$-pyridyl) |
| 218 | phenyl | Para | 1 | CH$_2$CONHCH(CH$_3$)$_2$ |
| 219 | phenyl | Meta | 1 | CH$_2$CONH$_2$ |
| 220 | phenyl | Meta | 1 | CH$_2$CON(CH$_3$)$_2$ |
| 221 | phenyl | Meta | 1 | CH$_2$CO-N-pyrrolidinyl |
| 222 | phenyl | Meta | 1 | CH$_2$CONHCH(CH$_3$)$_2$ |

| Ex. No. | Q | Ar | Y-R¹ | Ar position |
|---|---|---|---|---|
| 353 | 1 | cyclohexen-1-yl | CH$_2$CONH$_2$ | ortho |
| 354 | 1 | cyclopenten-1-yl | CH$_2$CONH$_2$ | ortho |
| 355 | 1 | cyclohepten-1-yl | CH$_2$CONH$_2$ | ortho |
| 356 | 1 | Naphth-2-yl | CH$_2$CONH$_2$ | ortho |
| 357 | 1 | phenoxathiin-4-yl | CH$_2$CONH$_2$ | ortho |
| 358 | 1 | Quinolin-3-yl | CH$_2$CONH$_2$ | ortho |
| 359 | 1 | 3,5-dimethyl-isoxazol-4-yl | CH$_2$CONH$_2$ | ortho |

| Ex. No. | q | Ar | Ar position | Y-R¹ |
|---|---|---|---|---|
| 400 | 1 | naphtha-2-yl | meta | CH$_2$CONH$_2$ |
| 401 | 1 | 3,5-dimethyl-isoxazol-4-yl | meta | CH$_2$CONH$_2$ |

| Ex. No. | q | Ar | Ar position | Y-R¹ |
|---|---|---|---|---|
| 430 | 1 | (3,5-dimethyl)-isoxazol-4-yl | para | CH$^2$CONH$^2$ |

| Ex. No. | Ar | Ar Position | q | Y-R¹ |
|---|---|---|---|---|
| 431 | 2-benzothienyl | ortho | 1 | CH$_3$ |
| 432 | 3-thienyl | ortho | 1 | CH$_3$ |
| 433 | 2-furyl | para | 1 | CH$_3$ |
| 434 | 2-thienyl | para | 1 | CH$_3$ |
| 435 | phenyl | ortho | 1 | CH$_3$ | or a stereoisomeric form, mixture of stereoisomeric forms or a pharmaceutically acceptable salt thereof.

5. The method of claim 1 or 3 wherein the compound is 2-[2-(5-chloro-benzo[b]thiophen-2-yl)-phenylmethanesulfinyl]-acetamide, 2-(2-benzo[b]thiophen-5-yl-phenylmethanesulfinyl)-acetamide, 2-[2-(3-chloro-benzofuran-2-yl)-phenylmethanesulfinyl]-acetamide, or a stereoisomeric form, mixture of stereoisomeric forms or a pharmaceutically acceptable salt thereof or is a compound of selected from the following:

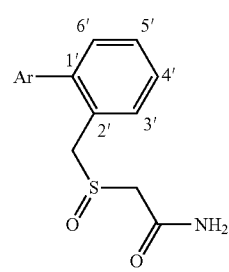

selected from

| Ex. No. | Ar |
|---|---|
| 437 | 4'-fluoro-3-benzothienyl |
| 438 | 4'-fluoro-2-furyl |
| 439 | 4'-fluoro-3-furyl |
| 440 | 4'-fluoro-3-pyridyl |
| 441 | 4'-fluoro-5-chloro-2-thienyl |
| 442 | 5'-chloro-3-pyridyl |
| 443 | 4'-fluoro-3-thienyl |
| 444 | 4'-fluoro-5-chloro-2-benzothienyl | or a stereoisomeric form, mixture of stereoisomeric forms, or a pharmaceutically acceptable salt thereof.

6. The method of claim 1 or 3 wherein the compound of Formula I has the following structure:

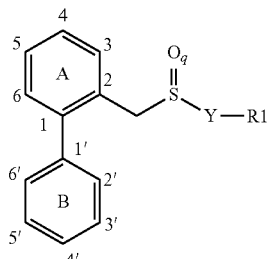

and is selected from the following:

| Ex. No. | q | Substitution on Biphenyl Moiety | Y-R$^1$ |
|---|---|---|---|
| 223 | 1 | 4'-COCH$_3$ | CH$_2$CONH$_2$ |
| 224 | 1 | 4'-F | CH$_2$CONH$_2$ |
| 225 | 1 | 4'-CH3 | CH$_2$CONH$_2$ |
| 226 | 1 | 2'-CH3 | CH$_2$CONH$_2$ |
| 227 | 1 | 3',5'-Difluoro | CH$_2$CONH$_2$ |
| 228 | 1 | 3',5'-Dimethyl | CH$_2$CONH$_2$ |
| 229 | 1 | 3'-F | CH$_2$CONH$_2$ |
| 230 | 1 | 2'-F | CH$_2$CONH$_2$ |
| 231 | 1 | 2'-OEt | CH$_2$CONH$_2$ |
| 232 | 1 | 3'-F,4'-Ph | CH$_2$CONH$_2$ |
| 233 | 1 | 2'-OMe, 5'-F | CH$_2$CONH$_2$ |
| 234 | 1 | 4'-OMe | CH$_2$CONH$_2$ |
| 235 | 1 | 4'-OPh | CH$_2$CONH$_2$ |
| 236 | 1 | 3'-CN | CH$_2$CONH$_2$ |
| 237 | 1 | 3'CONH$_2$ | CH$_2$CONH$_2$ |
| 238 | 1 | 3',5'-Dichloro | CH$_2$CONH$_2$ |
| 239 | 1 | 3'-CF$_3$ | CH$_2$CONH$_2$ |
| 240 | 1 | 3'-SCH$_3$ | CH$_2$CONH$_2$ |
| 241 | 1 | 3'-SOMe | CH$_2$CONH$_2$ |
| 242 | 1 | 3'-OCF$_3$ | CH$_2$CONH$_2$ |
| 243 | 1 | 3'-CONMe$_2$ | CH$_2$CONH$_2$ |
| 244 | 1 | 4'-OCF$_3$ | CH$_2$CONH$_2$ |
| 245 | 1 | 4'-CF$_3$ | CH$_2$CONH$_2$ |
| 246 | 1 | 4'-SCH$_3$ | CH$_2$CONH$_2$ |
| 247 | 1 | 4'-SOCH$_3$ | CH$_2$CONH$_2$ |
| 248 | 1 | 2'-Cl | CH$_2$CONH$_2$ |
| 249 | 1 | 3'-Cl | CH$_2$CONH$_2$ |
| 250 | 1 | 4'-Cl | CH$_2$CONH$_2$ |
| 251 | 1 | 2'-OMe | CH$_2$CONH$_2$ |
| 252 | 1 | 3'-OMe | CH$_2$CONH$_2$ |
| 253 | 1 | 3',4'-Dimethoxy | CH$_2$CONH$_2$ |
| 254 | 1 | 3',4'-Methylenedioxy | CH$_2$CONH$_2$ |
| 255 | 1 | 3',4'-Ethylenedioxy | CH$_2$CONH$_2$ |
| 256 | 1 | 3',4'-Propylenedioxy | CH$_2$CONH$_2$ |
| 257 | 1 | 2',6'-Dimethoxy | CH$_2$CONH$_2$ |
| 258 | 1 | 2',5'-Dimethoxy | CH$_2$CONH$_2$ |
| 259 | 1 | 3'-NO$_2$ | CH$_2$CONH$_2$ |
| 260 | 1 | 2'-OH | CH$_2$CONH$_2$ |
| 261 | 1 | 3'-OH | CH$_2$CONH$_2$ |
| 262 | 1 | 4'-OH | CH$_2$CONH$_2$ |
| 263 | 1 | 4'-CN | CH$_2$CONH$_2$ |
| 264 | 1 | 3'-Me | CH$_2$CONH$_2$ |
| 265 | 1 | 2'-OCF$_3$ | CH$_2$CONH$_2$ |
| 266 | 1 | 3'-Me, 4'-F | CH$_2$CONH$_2$ |
| 267 | 1 | 2'-SMe | CH$_2$CONH$_2$ |
| 268 | 1 | 3-Cl, 4'-F | CH$_2$CONH$_2$ |
| 269 | 1 | 2'-OMe, 5'-Cl | CH$_2$CONH$_2$ |
| 270 | 1 | 2'-SOMe | CH$_2$CONH$_2$ |
| 271 | 1 | 4,5-(OMe)$_2$ | CH$_2$CONH$_2$ |
| 272 | 1 | 4'-Br | CH$_2$CONH$_2$ |
| 273 | 1 | 2'-OMe, 4'-Cl | CH$_2$CONH$_2$ |
| 274 | 1 | 2'-Me, 4'-Cl | CH$_2$CONH$_2$ |
| 275 | 1 | 2'-Cl, 4'-Cl | CH$_2$CONH$_2$ |
| 276 | 1 | 2'-CF$_3$ | CH$_2$CONH$_2$ |
| 277 | 1 | 2'-F, 4'-Br | CH$_2$CONH$_2$ |
| 278 | 2 | 4'-Cl | CH$_2$CONH$_2$ |
| 279 | 1 | 4'-CHMe$_2$ | CH$_2$CONH$_2$ |
| 280 | 1 | 4'-CMe$_3$ | CH$_2$CONH$_2$ |
| 281 | 2 | 4'-Me | CH$_2$CONH$_2$ |
| 282 | 2 | 4'-F | CH$_2$CONH$_2$ |
| 283 | 1 | 4'-Cl | (CH$_2$)$_2$OH |
| 284 | 1 | 3'-Br | CH$_2$CONH$_2$ |
| 285 | 1 | 2'-Br | CH$_2$CONH$_2$ |
| 286 | 1 | 4'-Cl | CH$_2$CO-N-pyrrolidinyl |
| 287 | 1 | 4'-NMe$_2$ | CH$_2$CONH$_2$ |
| 288 | 1 | 4'-CH=CH$_2$ | CH$_2$CONH$_2$ |
| 289 | 1 | 4'-Cl | CH$_2$CO-4-acetylpiperazinyl |
| 290 | 1 | 4'-SO$_2$Me | CH$_2$CONH$_2$ |
| 291 | 1 | 3',4'-Cl$_2$ | CH$_2$CONH$_2$ |
| 292 | 1 | 4'-Et | CH$_2$CONH$_2$ |
| 293 | 1 | 4'-CH$_2$OMe | CH$_2$CONH$_2$ |
| 294 | 1 | 4'-CO-N-(4-oxo)piperidinyl | CH$_2$CONH$_2$ |
| 295 | 1 | 4'-NHSO$_2$Me | CH$_2$CONH$_2$ |
| 296 | 1 | 4'-CONMe$_2$ | CH$_2$CONH$_2$ |
| 298 | 1 | 4'-Cyclohexyl | CH$_2$CONH$_2$ |
| 299 | 1 | 3',4'-F$_2$ | CH$_2$CONH$_2$ |
| 300 | 1 | 3',4',5'-OMe$_3$ | CH$_2$CONH$_2$ |
| 302 | 1 | 4'-Cl | (CH$_2$)$_2$CONH$_2$ |
| 303 | 1 | 3'-NMe$_2$ | CH$_2$CONH$_2$ |
| 304 | 1 | 4'-CH$_2$CHMe$_2$ | CH$_2$CONH$_2$ |
| 305 | 1 | 5-F, 4'-Cl | CH$_2$CONH$_2$ |
| 306 | 1 | 3'-F, 4'-Cl | CH$_2$CONH$_2$ |
| 307 | 1 | 5-F, 4'-Me | CH$_2$CONH$_2$ |
| 308 | 1 | 5-F, 4'-F | CH$_2$CONH$_2$ |
| 309 | 1 | 5-F, 4'-NMe$_2$ | CH$_2$CONH$_2$ |
| 310 | 1 | 3'-OMe, 4'-Cl | CH$_2$CONH$_2$ |
| 311 | 1 | 3',4'-F$_2$, 5'-OMe | CH$_2$CONH$_2$ |
| 312 | 1 | 3'-CF$_3$, 4'-Cl | CH$_2$CONH$_2$ |
| 313 | 1 | 4'-OCH$_2$CHMe$_2$ | CH$_2$CONH$_2$ |
| 314 | 1 | 4'-COOMe | CH$_2$CONH$_2$ |
| 315 | 1 | 4'-CH$_2$OH | CH$_2$CONH$_2$ |
| 316 | 1 | 4'-COOtBu | CH$_2$CONH$_2$ |
| 317 | 1 | 3',4'-Me$_2$ | CH$_2$CONH$_2$ |
| 318 | 1 | 3'-CF$_3$, 4'-F | CH$_2$CONH$_2$ |
| 319 | 1 | 3'-F, 4'-Me | CH$_2$CONH$_2$ |
| 320 | 1 | 3'-Cl, 4'-Me | CH$_2$CONH$_2$ |
| 321 | 1 | 3'-Me, 4'-Cl | CH$_2$CONH$_2$ |
| 322 | 1 | 4,5-O-CH$_2$-O, 4'-Cl | CH$_2$CONH$_2$ |
| 323 | 1 | 4,5-OMe$_2$, 4'-Cl | CH$_2$CONH$_2$ |
| 324 | 1 | 4,5-O-CH$_2$-O, 4'-F | CH$_2$CONH$_2$ |
| 325 | 1 | 5-F, 3', 4'-F$_2$ | CH$_2$CONH$_2$ |
| 326 | 1 | 4,5-O-CH$_2$-O, 4'-Me | CH$_2$CONH$_2$ |
| 327 | 1 | 4,5-O-CH$_2$-O, 3', 4'-F$_2$ | CH$_2$CONH$_2$ |
| 328 | 1 | 4,5-OMe$_2$, 4'-F | CH$_2$CONH$_2$ |
| 329 | 1 | 4,5-OMe$_2$, 4'-Me | CH$_2$CONH$_2$ |
| 330 | 1 | 4,5-OMe$_2$, 3', 4'-F$_2$ | CH$_2$CONH$_2$ |
| 331 | 1 | 3'-Me, 4'-OMe | CH$_2$CONH$_2$ |
| 332 | 1 | 5-Cl, 4'-Cl | CH$_2$CONH$_2$ |
| 333 | 1 | 3',5'-Me$_2$, 4'-Cl | CH$_2$CONH$_2$ |

| Ex. No. | q | Substitution on Biphenyl Moiety | Y-R$^1$ |
|---|---|---|---|
| 334 | 1 | 5-Cl, 4'-F | CH$_2$CONH$_2$ |
| 335 | 1 | 3'-CF$_3$, 4'-Me | CH$_2$CONH$_2$ |
| 336 | 1 | 3'-NO$_2$, 4'-Cl | CH$_2$CONH$_2$ |
| 337 | 1 | 4-F, 4'-Cl | CH$_2$CONH$_2$ |
| 338 | 1 | 5-Cl, 3',4'-F$_2$ | CH$_2$CONH$_2$ |
| 339 | 2 | 5-F, 4'-Cl | CH$_2$CONH$_2$ |
| 340 | 1 | 4'-F | (CH$_2$)$_2$CONH$_2$ |
| 341 | 1 | 4-F, 4'-F | CH$_2$CONH$_2$ |
| 342 | 1 | 4-F, 4'-Me | CH$_2$CONH$_2$ |
| 343 | 1 | 4-F, 3', 4'-F$_2$ | CH$_2$CONH$_2$ |
| 344 | 2 | 3', 4'-F$_2$ | CH$_2$CONH$_2$ |
| 345 | 1 | 5-Cl, 4'-Me | CH$_2$CONH$_2$ |
| 346 | 1 | 4-OMe, 4'-Cl | CH$_2$CONH$_2$ |
| 347 | 1 | 6-Me, 4'-Cl | CH$_2$CONH$_2$ |
| 348 | 1 | 6-Me, 3',4'-Cl$_2$ | CH$_2$CONH$_2$ |
| 349 | 1 | 4-OMe, 3',4'-Cl$_2$ | CH$_2$CONH$_2$ |
| 350 | 1 | 4-Cl, 4'-Cl | CH$_2$CONH$_2$ |
| 351 | 1 | 4-F, 3',4'-Cl$_2$ | CH$_2$CONH$_2$ |
| 352 | 1 | 6-Me, 3'-F, 4'-Cl | CH$_2$CONH$_2$ |
| 402 | 1 | 3-F | CH$_2$CONH$_2$ |
| 403 | 1 | 2'-Cl | CH$_2$CONH$_2$ |
| 404 | 1 | 3'-Cl | CH$_2$CONH$_2$ |
| 405 | 1 | 4'-OMe | CH$_2$CONH$_2$ |
| 406 | 1 | 3',4'-Methylenedioxy | CH$_2$CONH$_2$ |
| 407 | 1 | 2',6'-(OMe)$_2$ | CH$_2$CONH$_2$ |
| 408 | 1 | 4'-Cl | CH$_2$CONH$_2$ |
| 409 | 1 | 3',4'-(OMe)$_2$ | CH$_2$CONH$_2$ |
| 410 | 1 | 3'-OMe | CH$_2$CONH$_2$ |
| 411 | 1 | 4'-CN | CH$_2$CONH$_2$ |
| 412 | 1 | 2',5'-(OMe)$_2$ | CH$_2$CONH$_2$ |
| 413 | 1 | 3'-NO$_2$ | CH$_2$CONH$_2$ |
| 414 | 1 | 3'-Me | CH$_2$CONH$_2$ |
| 415 | 1 | 2'-OMe | CH$_2$CONH$_2$ |
| 416 | 1 | 2'-Me, 4'-Cl | CH$_2$CONH$_2$ |
| 417 | 1 | 2'-OMe, 4'-Cl | CH$_2$CONH$_2$ |
| 418 | 1 | 2', 4'-Cl$_2$ | CH$_2$CONH$_2$ |
| 419 | 2 | 3',4'-(OMe)$_2$ | CH$_2$CONH$_2$ |
| 420 | 1 | 3',4'-Cl$_2$ | CH$_2$CONH$_2$ |
| 421 | 1 | 3-F, 4'-Cl | CH$_2$CONH$_2$ |
| 422 | 1 | 3-F, 4'-Me | CH$_2$CONH$_2$ |
| 423 | 1 | 4'-Br | CH$_2$CONH$_2$ |
| 424 | 1 | 3'-Cl, 4'-OMe | CH$_2$CONH$_2$ |
| 425 | 1 | 3',4',5'-(OMe)$_3$ | CH$_2$CONH$_2$ |
| 426 | 1 | 3',4'-F$_2$ | CH$_2$CONH$_2$ |
| 427 | 1 | 3-F, 4'-F | CH$_2$CONH$_2$ |
| 428 | 2 | 3-F, 4'-F | CH$_2$CONH$_2$ |
| 429 | 1 | 3-F, 4'-Cl | CH$_2$CONH$_2$ | or a stereoisomeric form, mixture of stereoisomeric forms, or a pharmaceutically acceptable salt thereof.

\* \* \* \* \*